United States Patent
Genovese et al.

(10) Patent No.: US 11,479,792 B2
(45) Date of Patent: Oct. 25, 2022

(54) COMPOSITIONS AND METHODS FOR INCREASING THE EFFICIENCY OF CELL CULTURES USED FOR FOOD PRODUCTION

(71) Applicant: Upside Foods, Inc., Berkeley, CA (US)

(72) Inventors: Nicholas J. Genovese, Hayward, CA (US); Eric N. Schulze, San Francisco, CA (US); Danielle N. Desmet, Berkeley, CA (US)

(73) Assignee: Upside Foods, Inc., Berkeley, CA (US)

( * ) Notice: Subject to any disclaimer, the term of this patent is extended or adjusted under 35 U.S.C. 154(b) by 398 days.

(21) Appl. No.: 16/630,404

(22) PCT Filed: Jul. 13, 2018

(86) PCT No.: PCT/US2018/042187
§ 371 (c)(1),
(2) Date: Jan. 10, 2020

(87) PCT Pub. No.: WO2019/014652
PCT Pub. Date: Jan. 17, 2019

(65) Prior Publication Data
US 2021/0340570 A1  Nov. 4, 2021

Related U.S. Application Data

(60) Provisional application No. 62/532,345, filed on Jul. 13, 2017.

(51) Int. Cl.
| | |
|---|---|
| *C12N 15/87* | (2006.01) |
| *C07K 14/65* | (2006.01) |
| *C07K 14/76* | (2006.01) |
| *C12N 5/071* | (2010.01) |
| *C12N 9/12* | (2006.01) |
| *C12N 9/00* | (2006.01) |
| *A23L 35/00* | (2016.01) |

(52) U.S. Cl.
CPC .............. *C12N 15/87* (2013.01); *C07K 14/65* (2013.01); *C07K 14/76* (2013.01); *C12N 5/0602* (2013.01); *C12N 9/1276* (2013.01); *C12N 9/93* (2013.01); *A23L 35/00* (2016.08); *C12N 2501/60* (2013.01); *C12Y 603/01002* (2013.01)

(58) Field of Classification Search
CPC .. C12P 21/00; C12N 9/00; C12N 9/92; C12N 15/67; C12N 15/87
See application file for complete search history.

(56) References Cited

U.S. PATENT DOCUMENTS

| | | | |
|---|---|---|---|
| 5,624,840 A | 4/1997 | Naughton et al. | |
| 6,593,275 B1 | 7/2003 | Unkefer et al. | |
| 6,767,719 B1 | 7/2004 | Morin et al. | |
| 6,835,390 B1 | 12/2004 | Vein | |
| 7,033,744 B2 * | 4/2006 | Kobayashi | A61P 1/16 435/1.1 |
| 7,147,871 B2 | 12/2006 | Voytik-Harbin et al. | |
| 7,270,829 B2 | 9/2007 | Van Eelen | |
| 8,105,575 B2 | 1/2012 | Kim et al. | |
| 8,703,216 B2 | 4/2014 | Forgacs et al. | |
| 8,883,502 B2 | 11/2014 | Kumar | |
| 9,102,739 B2 | 8/2015 | Lazar et al. | |
| 2002/0068706 A1 | 6/2002 | Gyuris et al. | |
| 2005/0260748 A1 | 11/2005 | Chang et al. | |
| 2006/0121006 A1 | 6/2006 | Chancellor et al. | |
| 2007/0248716 A1 | 10/2007 | Kruse et al. | |
| 2010/0319079 A1 | 12/2010 | Kruse et al. | |
| 2011/0091604 A1 | 4/2011 | Miller | |
| 2011/0191871 A1 | 8/2011 | Walsh et al. | |
| 2011/0225664 A1 | 9/2011 | Smith | |
| 2011/0301249 A1 | 12/2011 | Challakere | |
| 2013/0004466 A1 | 1/2013 | Tremblay et al. | |
| 2013/0029008 A1 | 1/2013 | Forgacs et al. | |
| 2013/0171731 A1 | 7/2013 | Ivashchenko et al. | |
| 2013/0224855 A1 | 8/2013 | Gupta et al. | |
| 2013/0255003 A1 | 10/2013 | Forgacs et al. | |
| 2014/0093618 A1 | 4/2014 | Forgacs et al. | |
| 2014/0242155 A1 | 8/2014 | Ramunas et al. | |
| 2014/0370537 A1 | 12/2014 | Sakurai et al. | |
| 2015/0025128 A1 | 1/2015 | Cain et al. | |
| 2015/0079238 A1 | 3/2015 | Marga et al. | |
| 2015/0087532 A1 | 3/2015 | Brown et al. | |
| 2015/0133520 A1 | 5/2015 | Czech et al. | |
| 2015/0216216 A1 | 8/2015 | Marga | |
| 2015/0231209 A1 | 8/2015 | Hsueh et al. | |
| 2015/0289541 A1 | 10/2015 | Brown et al. | |
| 2015/0296834 A1 | 10/2015 | Geistlinger | |
| 2015/0296835 A1 | 10/2015 | Anderson et al. | |

(Continued)

FOREIGN PATENT DOCUMENTS

| | | |
|---|---|---|
| CA | 2333966 C | 12/1999 |
| CA | 2780087 A1 | 12/2012 |

(Continued)

OTHER PUBLICATIONS

Animal Sake Farm Animals List, downloaded May 24, 2022; on the web atanimalsake.com/farm-animals-list. pp. 1-10.*
Cox et al. Jan. 18, 2017; Yap reprograms glutamine metabolism to increase nucleotide biosynthesis and enable liver growth. Nat. Cell. Biol. 18(8): 886-896.*
Kanzaki et al. 2002; Telomerase rescues the expression levels of keratinocyte growth factor and insulin-like growth factor-II in senescent human fibroblasts. Environmental Cell Research. 279: 321-329.*

(Continued)

*Primary Examiner* — Karen Cochrane Carlson
(74) *Attorney, Agent, or Firm* — Fenwick & West LLP

(57) ABSTRACT

Provided herein are compositions and methods to make and use engineered cells, for the purpose of increasing the cell density of a culture comprising metazoan cells and for the production of a cultured edible product.

18 Claims, 12 Drawing Sheets
Specification includes a Sequence Listing.

(56) References Cited

U.S. PATENT DOCUMENTS

| | | |
|---|---|---|
| 2015/0305361 A1 | 10/2015 | Holtz-Schietinger et al. |
| 2015/0305390 A1 | 10/2015 | Vrljic et al. |
| 2016/0227830 A1 | 8/2016 | Genovese et al. |
| 2016/0251625 A1 | 9/2016 | Genovese et al. |
| 2017/0101629 A1 | 4/2017 | Minshull et al. |
| 2017/0114382 A1 | 4/2017 | Follit et al. |
| 2017/0369849 A1 | 12/2017 | Hanson et al. |
| 2019/0024079 A1 | 1/2019 | Genovese et al. |
| 2020/0190524 A1 | 6/2020 | Minshull et al. |
| 2021/0106032 A1 | 4/2021 | Leung et al. |
| 2021/0145031 A1 | 5/2021 | Leung et al. |

FOREIGN PATENT DOCUMENTS

| | | | |
|---|---|---|---|
| CN | 1942576 A | 4/2007 | |
| CN | 101624570 A | 1/2010 | |
| EP | 0435617 A1 | 7/1991 | |
| EP | 1037966 B1 | 5/2003 | |
| JP | 2013-81783 | 5/2013 | |
| WO | WO-1993/009236 A1 | 5/1993 | |
| WO | WO-1999/031222 A1 | 6/1999 | |
| WO | WO-1999-031223 A1 | 6/1999 | |
| WO | WO-2006/041429 A2 | 4/2006 | |
| WO | WO-2007071339 A1 * | 6/2007 | ............ A61K 35/28 |
| WO | WO-2010-068897 A2 | 6/2010 | |
| WO | WO-2012/095514 A1 | 7/2012 | |
| WO | WO-2012/170995 A2 | 12/2012 | |
| WO | WO-2012/176023 A1 | 12/2012 | |
| WO | WO-2013/007656 A1 | 1/2013 | |
| WO | WO-2013/016547 A2 | 1/2013 | |
| WO | WO-2013/073246 A1 | 5/2013 | |
| WO | WO 2015/038988 A1 | 3/2015 | |
| WO | WO-2015/066377 A1 | 5/2015 | |
| WO | WO 2015/120174 A1 | 8/2015 | |
| WO | WO-2015/167959 A1 | 11/2015 | |
| WO | WO 2016/052472 A1 | 4/2016 | |
| WO | WO 2017/019125 A1 | 2/2017 | |
| WO | WO-2017/120089 A1 | 7/2017 | |
| WO | WO-2017/124100 A1 | 7/2017 | |
| WO | WO-2018/208628 A1 | 11/2018 | |
| WO | WO-2019/014652 A1 | 1/2019 | |

OTHER PUBLICATIONS

Bhat, Z.F. et al., "Prospectus of cultured meat—Advancing meat alternatives," Journal of Food Science and Technology 48(2), Apr. 2010, pp. 125-140.

European Patent Office, Extended European Search Report and Opinion, EP Patent Application No. 18832585.6, dated Apr. 9, 2021, nine pages.

Fan, L. et al., "The use of glutamine synthetase as a selection marker: recent advances in Chinese hamster ovary cell line generation processes," Pharmaceutical Bioprocessing 1(15), 2013, pp. 487-502.

Kadim, I.T. et al., "Cultured meat from muscle stem cells: A review of challenges and prospects," Journal of Integrative Agriculture 14(2), Feb. 2015, pp. 222-233.

Paredes, C. et al., "Modification of glucose and glutamine metabolism in hybridoma cells through metabolic engineering," Cytotechnology, vol. 30, Jul. 1999, pp. 85-93.

Zhu, C-H. et al. "Cellular Senescence in Human Myoblasts is Overcome by Human Telomerase Reverse Transcriptase and Cyclin-Dependent Kinase 4: Consequences in Aging Muscle and Therapeutic Strategies for Muscular Dystrophies." Aging Cell, vol. 6, No. 4, Aug. 2007, pp. 515-523.

Albini, S., et al., "Epigenetic Reprogramming of Human Embryonic Stem Cells into Skeletal Muscle Cells and Generation of Contractile Myospheres," Cell Reports 3:661-670 (2013).

Barberi, T., et al., "Derivation of engraftable skeletal myoblasts from human embryonic stem cells," Nature Medicine 13(5):642-648(2007).

Bartholet, J., "Inside The Meat Lab A Handful Of Scientists Aim to Satisfy the World's Growing Appetite for Steak Without Wrecking The Planet. The First Step: Grab a Petri Dish," Scientific American, pp. 65-69 (2011).

Benjaminson, M., et al.,"In Vitro Edible Muscle Protein Production System (MPPS): Stage 1, FISH," Acta Astronautica 51(12):879-889 (2002).

Bentzinger, C., et al., "Building Muscle: Molecular Regulation of Myogenesism," Cold Spring Harb Perspect Biol 4(2):1-16 (2012).

Bhagavati and Xu., "Generation Of Skeletal Muscle from Transplanted Embryonic Stem Cells in Dystrophic Mice," Biochemical and Biophysical Research Communications 333:644-649 (2005).

Bhat and Bhat, "Animal-Free Meat Biofabrication," American Journal of Food Technology 6(6):441-459, (2011).

Boonen and Post, "The Muscle Stem Cell Niche: Regulation of Satellite Cells During Regeneration," Tissue Engineering—Part B: Reviews 14(4):419-431 (2008).

Cenciarelli et al., "Critical Role Played by Cyclin D3 in the Myod-Mediated Arrest of Cell Cycle During Myoblast Differentiation," Molecular and Cellular Biology 19(7):5203-5217 (1999).

Chang, et al., "Generation of Transplantable, Functional Satellite-Like Cells from Mouse Embryonic Stem Cells," FASEB J. 23, 1907-1919 (2009).

Chen et al., "Potentiation of MyoD1 Activity By 5-Aza-2'-Deoxycytidine," Cell Growth & Differentiation, 1:383-392 (1990).

Chiu and Blau,"5-5Azacytidine Permits Gene Activation in a Previously Noninducible Cell Type," Cell, vol. 40, 417-424 (1985).

Darabi, R., et al., "Assessment of the Myogenic Stem Cell Compartment Following Transplantation of Pax3/Pax7-Induced Embryonic Stem Cell-Derived Progenitors," Lillehei Heart Institute, Department of Medicine, University of Minnesota, Minneapolis, MN, USA, 27 pages (2011).

Darabi, R., et al., Functional Skeletal Muscle Regeneration From Differentiating Embryonic Stem Cells, Nature and Medicine 14(2):134-143 (2008).

Datar and Betti, "Possibilities for an In Vitro Meat Production System," Innovative Food Science & Emerging Technologies 11(1):13-22(2010).

Davis, R., et al., "Expression of a Single Transfected cDNA Converts Fibmblasts to Myoblasts," Cell, vol. 51. 987-1000 (1987).

Dekel, I., et al., "Conditional Conversion of ES Cells to Skeletal Muscle by an Exogenous MyoDI Gene," (1992).

Edelman, P. et al., "In Vitro-Cultured Meat Production," Tissue Engineering 11(5/6):659-662 (2005).

Genovese et al.,"Enhanced Development of Skeletal Myotubes form Porcine Induced Pluripotent Stem Cells," Scientific Reports, vol. 7, 12 pages (2017).

Gianakopoulos, P., et al., "MyoD Directly Up-regulates Premyogenic Mesoderm Factors during Induction of Skeletal Myogenesis in Stem Cells," The Journal of Biological Chemistry 286(4):2517-2525 (2011).

Goudenege, S., et al., "Myoblasts Derived From Normal hESCs and Dystrophic hiPSCs Efficiently Fuse With Existing Muscle Fibers Following Transplantation," Molecular Therapy 20(11):2153-2167 Nov. 2012 (2012).

Hollenberg, S., et al., "Use of a conditional MyoD transcription factor in studies of MyoD trans-activation and muscle determination," Proc. Natl. Acad. Sci. USA vol. 90, pp. 8028-8032 (1993).

Hopkins and Dacey, "Vegetarian meat: Could Technology Save Animals And Satisfy Meat Eaters?" Journal of Agricultural and Environmental Ethics 21(6):579-596 (2008).

Hwang, Y., et al., "Directed In Vitro Myogenesis of Human Embryonic Stem Cells and Their In Vivo Engraftment," PLOS ONE e72023 8(8):1-10 (2013).

Iacovino, M., et al., "Inducible Cassette Exchange: A Rapid and Efficient System Enabling Conditional Gene Expression in Embryonic Stem and Primary Cells," Stem Cells 2011;29:1580-1587 (2011).

Jones, N., "A Taste of Things to Come?" Nature 468:752-753 (2010).

Langelaan, et al., "Meet The New Meat: Tissue Engineered Skeletal Muscle," Trends in Food Science & Technology 21(2):59-66 (2010).

(56) References Cited

OTHER PUBLICATIONS

Lassar, A., et al., "Transfection of a DNA Locus That Mediates the Conversion of IOTV2 Fibroblasts to Myoblasts," Cell 47:649-656 (1986).
Lavial et al., "Chicken Embryonic Stem Cells As A Non-Mammalian Embryonic Stem Cell Model," Development, Growth & Differentiation 52:101-1114 (2010).
Leung, M., et al., "Nanofiber-Based in Vitro System for High Myogenic Differentiation of Human Embryonic Stem Cells," Biomacromolecules 14:4207-4216 (2013).
Li et al., "Short-Term Serum-Free Culture Reveals That Inhibition of Gsk3beta Induces the Tumor-Like Growth of Mouse Embryonic Stem Cells," 6(6):1/10-10/10 (2011).
Lian et al., Directed Cardiomyocyte Differentiation From Human Pluripotent Stem Cells by Modulating Wnt/Beta-Catenin Signaling Under Fully Defined Conditions. Nature Protocols, 8(1):162-175 (2013).
Maak et al., "Identification and Analysis of Putative Regulatory Sequences for the MYF5/MYF6 Locus in Different Vertebrate Species," Gene, 379:141-147 (2006).
Mahmood, A., Enhanced Differentiation of Human Embryonic Stem Cells to Mesenchymal Progenitors by Inhibition of TGF-beta/Activin/Nodal Signaling Using SB-431542 Journal of Bone and Mineral Research 25(6):1216-1233 (2010).
Mcfarlane et al., "Myostatin Signals Through Pax7 To Regulate Satellite Cell Self-Renewal," Experimental Cell Research 314:317-329 (2008), available online Sep. 2007.
Minzuno, Y., et al., "Generation of Skeleta Muscle Stem/Progenitor Cells from Murine Induced Pluripotent Stem Cells," The FASEB Journal 24:2245-2243 (2010).
Ozasa et al., "Efficient Conversion Of ES Cells into Myogenic Lineage Using the Gene-Inducible System," Biochemical and Biophysical Research Communications 357: 957-963 (2007).
Post, M., "Cultured beef: Medical Technology to Produce Food," Journal of the Science of Food and Agriculture 94(6): 1039-1041 (2014).
Post, M., "Cultured Meat From Stem Cells: Challenges and Prospects," Meat Sci. 92(3):297-301 (2012).
Rohwedel, J., et al., "Muscle Cell Differentiation of Embryonic Stem Cells Reflects Myogenesis In Vivo: Developmentally Regulated Expression of Myogenic Determination Genes and Functional Expression of Ionic Currents.," Dev Biol. 164(1):87-101 (1994). (Abstract).
Rommel, C., "Mediation of IGF-1-Induced Skeletal Myotube Hypertrophy by PI(3)K/Akt/mTOR and PI(3)K/Akt/GSK3 Pathways," Nature Cell Biology 3:1009-1013 (2001).
Ryan, T., "Retinoic Acid Enhances Skeletal Myogenesis in Human Embryonic Stem Cells by Expanding the Premyogenic Progenitor Population,"Stem Cell Rev and Rep 8:482-493 (2012).
Sakurai, H., et al., "Paraxial Mesodermal Progenitors Derived from Mouse Embryonic Stem Cells Contribute to Muscle Regeneration via Differentiation into Muscle Satellite Cells," Stem Cells 26:1865-1873 (2008).
Sakurai, H., et al., "Bidirectional Induction Toward Paraxial Mesodermal Derivatives from Mouse ES Cells In Chemically Defined Medium," Stem Cell Research 3:157-169 (2009).
Salani, S., et al., "Generation Of Skeletal Muscle Cells from Embryonic and Induced Pluripotent Stem Cells As An In Vitro Model and for Therapy of Muscular Dystrophies," J. Cell. Mol. Med. 16(7):1353-1364 (2012).
Sasaki, T., et al., "Generation of a Multi-Layer Muscle Fiber Sheet from Mouse ES Cells by the Spermine Action At Specific Timing and Concentration," Differentiation 76:1023-1030(2008).
Tan et al., "Efficient Derivation Of Lateral Plate and Paraxial Mseoderm Subtypes From Human Embryonic Stem Cells Through GS Kimediated Differentiation," Stem Cells and Development 22(13):1893-1906 (2013).
Tanaka, et al., "Efficient and Reproducible Myogenic Differentiation from Human iPS Cells: Prospects for Modeling Miyoshi Myopathy In Vitro," PLOS ONE e61540 8(4):1-14 (2013).
Taylor et al. "Multiple new phenotypes induced in 10T1/2 and 3T3 cells treated with 5-azacytidine," Cell 17:771-779 (1979).
Telugu, B., et al., "Lif-Dependent, Pluripotent Stem Cells Established From Inner Cell Mass of Porcine Embryos," The American Society for Biochemistry and Molecular Biology, Inc., Downloaded from www.jbc.org at University of Missouri-Columbia, on Jul. 15, 2011 (2011).
Telugu, B., et al., "Leukemia Inhibitory Factor (LIF)-dependent, Pluripotent Stem Cells Established from Inner Cell Mass of Porcine Embryos," Journal of Biological Chemistry, 2011, 286(33):28948-28953.
Tuomisto, et al., "Environmental Impacts of Cultured Meat Production," Environ. Sci. Technol. 45(14):6117-6123 (2011).
Van der Schaft, D., et al., "Engineering Skeletal Muscle Tissues From Murine Myoblast Progenitor Cells and Application of Electrical Stimulation," J. Vis. Exp. 73:1-6 (2013)).
Van der Velden, J., et al., "Inhibition of Glycogen Synthase Kinase-3beta-activity is Sufficient To Stimulate Myogenic Differentiation," Am J Physiol Cell Physiol 290: C453-C462, (2006).
Van Der Weele, C., "In Vitro Meat," Encyclopedia of Food and Agricultural Ethics, pp. 1-8 (2014).
Van Der Weele, C., "In Vitro Meat: Promises and Responses: Cooperation Between Science, Social Research And Ethics," Global Food Security: Ethical and Legal Challenges: EurSafe 2010 Bilbao, Spain Sep. 16-18, 2010, pp. 507-512.
Vyas, D., et al., "GSK-3 Negatively Regulates Skeletal Myotube Hypertrophy," Am J Physiol Cell Physiol 283: C545-C551 (2002).
Wagers, A., "Wnt Not, Waste Not," Cell Stem Cell 2:6-7 (2008).
Wilschut, K., et al., "Extracellular Matrix Components Direct Porcine Muscle Stem Cell Behavior," Experimental Cell Research 316:341-352 (2010).
Wilschut, K., et al., "Isolation and Characterization of Porcine Adult Muscle-Derived Progenitor Cells," Journal of Cellular Biochemistry 105:1228-1239 (2008).
Wu, G., et al., "Production and Supply of High-Quality Food Protein for Human Consumption: Sustainability, Challenges, and Innovations," Annals of the New York Academy of Sciences 1321(1):1-19 (2014).
Yokoyama et al., "The Myogenic Transcriptional Network," Cellular and Molecular Life Sciences 68:1843-1849 (2011).
Zheng, J., K., et al., "Skeletal Myogenesis by Human Embryonic Stem Cells," Cell Research 713-722 (2006).
International Search Report and Written Opinion issued by The International Searching Authority for Application No. PCT/US14/63250, dated Jan. 21, 2015, 9 pages.
Non-Final Office Action dated Dec. 13, 2016 from The United States Patent and Trademark Office for U.S. Appl. No. 15/134,252, filed Apr. 30, 2016, 28 pages.
Extended European Search Report dated May 19, 2017, from the European patent Office for Application No. 14858383.4, filed Oct. 30, 2014, 10 pages.
Final Office Action dated Jul. 13, 2017, from The United States Patent and Trademark Office for U.S. Appl. No. 15/134,252, filed Apr. 30, 2016, 28 pages.
Baquero-Perez et al., "A Simplified but Robust Method for the Isolation of Avaian and Mammalian Satellite cells," BMC Cell Biology 13(16):1/11-11/11 (2012).
Rezanejad et al., Induced pluripotent stem cells: Progress and future perspectives in the stem cell world. Cellular Reprogramming 14(6):459-470 (2012).
Weintraub et al. Activation of muscle-specific genes in pigment, nerve, fat, liver and fibroblast cell lines by forced expression of MyoD. Proceedings of the National Academy of Sciences, USA, 86:5434-5438 (1989).
Hanas et al. Potentiation of myogenesis by 5-azacytidine. Journal of Cell Biology, vol. 91, No. 2, p. 27, Abstract 1051, Nov. 1981.
Non-Final Office Action dated Mar. 12, 2018 from The United States Patent and Trademark Office for U.S. Appl. No. 15/134,252, filed Apr. 20, 2016, 28 pages.
Rinkevich, B. Cell cultures from marine invertebrates: New insights for capturing endless sternness. Marine Biotechnology (New York, N.Y.), vol. 13, No. 3, pp. 345-354, Jun. 2011, Epub Jan. 7, 2011. (Year: 2011).

(56) References Cited

OTHER PUBLICATIONS

Nowak-Imialek et al. Pluripotent cells in farm animals: state of the art and future perspectives. Reproduction, Fertility and Development, vol. 25, No. 1, pp. 103-108, 2012. (Year: 2012).
Blomberg et al. Twenty years of embryonic stem cell research in farm animals. Reproduction in Domestic Animals, vol. 47, Suppl. 4, pp. 80-85, Aug. 2012. (Year: 2012).
Molkentin et al. Cooperative activation of muscle gene expression by MEF2 and myogenic bHLH proteins. Cell, vol. 83, pp. 1125-1136, Dec. 1995. (Year: 1995).
Hupkes et al. Epigenetics: DNA demethylation promotes skeletal myyotube maturation. The FASEB Journal, vol. 25, No. 11, pp. 3861-3872, Nov. 2011. (Year: 2011).
Chen et al. DNA methyltransferase inhibitor CDA-11 inhibits myogenic differentiation. Biochemical and Biophysical Research Communications, vol. 422, pp. 522-526, May 22, 2012. (Year: 2012).
Hu, Yang "Exercise molecule biology," Beijing Sport University press, pp. 152-157 (2013).
A. The English translation of paragraph 2 on p. 152 to paragraph 1 on p. 157 of Ref 145.
Yu et al., "Chinese Disease Signal Pathway and Targeted Therapy," Anhui Science and Technology Press, p. 372 (2013).
B. The English translation of paragraphs 4-8 on p. 372 of Ref 147.
Nagashima et al., "The Hippo Pathway as Drug Targets in Cancer Therapy and Regenerative Medicine," Current Drug Targets, (2017), vol. 18, pp. 447-454.
International Search Report and Written Opinion issued by The International Searching Authority for Application No. PCT/US2018/031276, dated Sep. 10, 2018, 10 pages.
Wang et. al., "Immortalization of chicken preadipocytes by retroviral transduction of chicken TERT and TR," (2017), PLoS ONE 12(5): e0177348. retrieved May 9, 2017 at https://doi.org/10.1371/journal.pone.0177348.
Jesus et. al., "The telomerase activator TA-65 elongates short telomeres and increases health span of adult/old mice without increasing cancer incidence," Aging Cell 10:604-621 (2011).
Bell et al., "Understanding TERT Promoter Mutations: A Common Path to Immortality," Mol Cancer Res 14:315-323 (2016). Published OnlineFirst Mar. 3, 2016, retrieved Jul. 6, 2017 from mcr.aacrjournals.org, 10 pages.
Dominguez et al., "Beyond editing: repurposing CRISPR-Cas9 for precision genome regulation and interrogation," Nature Reviews Molecular Cell Biology 17:5-15 (2016).
Liu et. al., "Linking Telomere Regulation to Stem Cell Pluripotency," Trends in Genetics 33(1): 16-33 (2017).
International Search Report and Written Opinion issued by the International Searching Authority for Application No. PCT/US2017/13782, dated Apr. 10, 2017, 7 pages.
Pandurangan, et al. A novel approach for in vitro meat production. Appl Microbiol Biotechnol. Jul. 2015; 99(13):5391-5395. doi: 10.1007/s00253-015-6671-5. Epub May 14, 2015.
Munro, et al. Histone deacetylase inh1b1tors induce a senescence-like state in human cells by a p16-dependent mechanism that is independent of a mitotic clock. Exp Cell Res. 2004 295(2):525-538.
Sharpless, et al. Forging a signature of in vivo senescence. Nature Reviews Cancer 2015, 15(7):397-408.
Harley, "Telomerase is not an oncogene," Oncogene 2002, 21(4):494-502.
Garrels et al. Ectopic expression of human telomerase KNA component results 1n increased telomerase activity and elongated telomeres in bovine blastocysts. Biol Reprod. 2012, 87(4):95, 1-7.
Barnes, et al., Advances in animal cell recombinant protein production: GS-NS0 expression system, Cytotechnology 2000, vol. 32, pp. 109-123.
Final Office Action dated Nov. 27, 2018 from The United States Patent and Trademark Office for U.S. Appl. No. 15/134,252, filed Apr. 30, 2016, 24 pages.

George et al. "Exploiting Expression of Hippo Effector, Yap, for Expansion of Functional Islet Mass," Molecular Endocrinology. Sep. 17, 2015 (Sep. 17, 2015), vol. 29, Iss. 11, pp. 1594-1607. entire document.
Watt et al. "Regulation of Tissue Growth by the Mammalian Hippo Signaling Pathway," Frontiers in Physiology. Nov. 24, 2017 (Nov. 14, 2017), vol. B, Article 942, pp. 1-12. entire document.
Huang et al. "Zfp423 Promotes Adipogenic Differentiation of Bovine Stromal Vascular Cells," PLOS ONE, Oct. 2012, vol. 7, Issue 10, 10 pages.
Van Der Weele et al. Cultured meat: every village its own factory?, Trends in Biotechnology, Jun. 2014, vol. 32, No. 6, 3 pages.
Wooton et al. "Telomerase Alone Extends the Replicative Life Span of Human Skeletal Muscle Cells Without Compromising Genomic Stability," Human Gene Therapy, vol. 14, No. 15, Oct. 10, 2003, 15 pages.
Lee et al. "Establishment of an immortal chicken embryo liver-derived cell line," 2013 Poultry Science, vol. 92, No. 6, 9 pages.
International Search Report and Written Opinion issued by the International Searching Authority for Application No. PCT/US2018/042187, dated Nov. 1, 2018, 15 pages.
Xu et al., "Effects of glutamine and asparagine on recombinant antibody production using CHO-GS cell lines," Biotechnol Prog. Nov.-Dec. 2014;30(6):1457-68.
Noh et al., "Reduction of ammonia and lactate through the coupling of glutamine synthetase selection and downregulation of lactate dehydrogenase-A in CHO cells," Appl Microbiol Biotechnol. Feb. 2017;101(3):1035-1045.
Knox et al., "A streamlined implementation of the glutamine synthetase-based protein expression system," BMC Biotechnol. Sep. 24, 2013;13:74, 10 pages.
Addgene. "pBABE-hygro-hTERT." Plasmid #1773, Dec. 1998, 6 pages, [Online] [Retrieved Dec. 3, 2020], Retrieved from the Internet <URL:https://www.addgene.org/1773/>.
Addgene. "pBABE-neo-hTERT." Plasmid #1774, Dec. 1998, 5 pages, [Online] [Retrieved Dec. 4, 2020], Retrieved from the Internet <URL:https://www.addgene.org/1774/>.
Black, Brian L., and Eric N. Olson. "Transcriptional control of muscle development by myocyte enhancer factor-2 (MEF2) proteins" Annual review of cell and developmental biology 14.1 (1998): 167-196.
Canizo et al., "Exogenous human OKSM factors maintain pluripotency gene expression of bovine and porcine iPS-like cells obtained with STEMCCA delivery system," BMC Research Notes vol. 11, Article No. 509 (2018), 8 pages.
Chen, et al., Homeostatic control of Hippo signaling activity revealed by an endogenous activating mutation in YAP, Genes & Development, 29: 1285-1297. (Year: 2015).
Choi, Sang-Woon, and Simonetta Friso. "Epigenetics: a new bridge between nutrition and health" Advances in nutrition 1.1 (2010): 8-16.
Darabi, R., et al, "Perspective Lineage-Specific Reprogramming as a Strategy for Cell Therapy," Cell Cycle 7(12):1732-1737 (2008).
Delany, M. E. et al. "Telomeres in the Chicken: Genome Stability and Chromosome Ends." Poultry Science, vol. 82, No. 6, Jun. 1, 2003, pp. 917-926.
Desbois-Mouthon, Christele, et al. "Insulin and IGF-1 stimulate the .beta.-catenin pathway through two signalling cascades involving GSK-3.beta. inhibition and Ras activation" Oncogene 20.2 (2001): 252-259.
Ding, Vanessa MY, et al. "FGF-2 modulates Wnt signaling in undifferentiated hESC and iPS cells through activated PI3-K/GSK3.beta. signaling" Journal of cellular physiology 225.2 (2010): 417-428.
Dong, J. et al. "Elucidation of a Universal Size-Control Mechanism in *Drosophila* and Mammals," Cell, vol. 130, No. 6, pp. 1120-1133, Sep. 21, 2007.
European Patent Office, Extended European Search Report and Opinion, EP Patent Application No. 18797874.7, dated May 21, 2021, 15 pages.
Genbank. "Bos Taurus Cyclin-Dependent Kinase 4, mRNA (cDNA Clone MGC:133903 IMAGE:8041087), Complete CDS." NCBI, GenBank: BC109858.1, Nov. 2005, 2 pages, [Online] [Retrieved

(56) References Cited

OTHER PUBLICATIONS

Dec. 7, 2020], Retrieved from the Internet <URL:https://www.ncbi.nlm.nih.gov/nuccore/BC109858>.
Genbank. "Gallus Gallus Gallus Telomerase Reverse Transcriptase (TERT) mRNA, Complete CDS." GenBank: NCBI, AY502592.1, 2004, 3 pages, [Online] [Retrieved Dec. 7, 2020], Retrieved from the Internet <URL:https://www.ncbi.nlm.nih.gov/nuccore/AY502592>.
He Rong et al., "Expression and clinical significance of p15 protein, mRNA in nasopharyngeal carcinoma," Chinese Journal of Laboratory Diagnosis, vol. 13, No. 5, Jun. 19, 2009, pp. 618-622, (with English abstract).
Hupkes, Marlinda, et al. "DNA methylation restricts spontaneous multi-lineage differentiation of mesenchymal progenitor cells, but is stable during growth factor-induced terminal differentiation" Biochimica et Biophysica Acta (BBA)—Molecular Cell Research 1813.5 (2011): 839-849.
International Preliminary Report on Patentability in corresponding PCT Application No. PCT/US2014/063250, dated May 3, 2016.
Kucharczak, J. et al., "R-Cadherin Expression Inhibits Myogenesis and Induces Myoblast Transformation via Rac1 GTPase," Cancer Research, vol. 68, No. 16, Aug. 15, 2008, pp. 6559-6568.
Lei, et al., TAZ promotes cell proliferation and epithelial-mesenchymal transition and is inhibited by the hippo pathway, Molecular and Cellular Biology, 28(7): 2426-2436. (Year: 2008).
Iemata, M., et al., "Suppression by Glutamate of Proliferative Activity Through Glutathione Depletion Mediated by the Cystine/Glutamate Anti porter in Mesenchymal C3H10T1/2 Stem Cells," Journal of Cellular Physiology 213:721-729 (2007).
Mannaerts et al. The Hippo pathway effector YAP controls mouse hepatic stellate cell activation, Journal of Hepatology, 63: 679-688 (Year: 2015).
Mckinnon, T. et al., "Kras activation in p53-deficient myoblasts results in high-grade sarcoma formation with impaired myogenic differentiation," Oncotarget, vol. 6, No. 16, Jun. 10, 2015, pp. 14220-14232.
Minniti, C.P. et al., "Insulin-like growth factor II overexpression in myoblasts induces phenotypic changes typical of the malignant phenotype," Cell Growth & Differentiation, vol. 6, Mar. 1995, pp. 263-269.
Miranda, A.F. et al., "Transformation of human skeletal muscle cells by simian virus 40," PNAS, vol. 80, Nov. 1983, pp. 6581-6585.
Nguyen, H.T. et al., "Viral Small T Oncoproteins Transform Cells by Alleviating Hippo-Pathway-Mediated Inhibition of the YAP Proto-oncogene," Cell Reports, vol. 8, No. 3, Aug. 7, 2014, pp. 707-713.
Overholtzer, M. et al., "Transforming properties of YAP, a candidate oncogene on the chromosome 11a22 amplicon," PNAS, vol. 103, No. 33, Aug. 15, 2006, pp. 12405-12410.
Park et al. "Generation of porcine induced pluripotent stem cells and evaluation of their major histocompatibility complex protein expression in vitro." Veterinary Research Communications, vol. 37, No. 4, pp. 293-301, Dec. 2013, published online Aug. 23, 2013. (Year: 2013).
Poon et al., The sterile 20-like kinase Tao-1 controls tissue growth by regulating the Salvador-Warts-Hippo pathway, Developmental Cell, 21: 896-906. (Year: 2011).
Rao, L., et al., "Highly Efficient Derivation of Skeletal Myotubes from Human Embryonic Stem Cells," Stem Cell Rev and Rep 8:1109-1119 (2012).
Schnapp, Esther, et al. "Induced early expression of mrf4 but not myog rescues myogenesis in the myod/myf5 double-morphant zebrafish embryo" Journal of Cell Science 122.4 (2009): 481-488.
Schutte, U. et al., "Hippo Signaling Mediates Proliferation, Invasiveness, and Metastatic Potential of Clear Cell Renal Cell Carcinoma," Translational Oncology, vol. 7, Iss. 2, Apr. 2014, pp. 309-321.
Stadler, G. et al. "Establishment of Clonal Myogenic Cell Lines from Severely Affected Dystrophic Muscles—CDK4 Maintains the Myogenic Population." Skeletal Muscle, vol. 1, Article 12, Mar. 2011, pp. 1-10.
Tako, E. et al. "Using the Domestic Chicken (*Gallus gallus*) as an In Vivo Model for Iron Bioavailability." Poultry Science, vol. 89, No. 3, Mar. 1, 2010, pp. 514-521.
Tseng et al. The GSK-3 inhibitor BIO promotes proliferation in mammalian cardiomyocytes. Chemistry & Biology, vol. 13, pp. 957-963, Sep. 2006. (Year: 2006).
United States Office Action, U.S. Appl. No. 15/134,252, dated Dec. 13, 2016, 31 pages.
United States Office Action, U.S. Appl. No. 15/134,252, dated Jul. 13, 2017, 43 pages.
United States Office Action, U.S. Appl. No. 15/134,252, dated Mar. 12, 2018, 28 pages.
United States Office Action, U.S. Appl. No. 15/134,252, dated Mar. 3, 2020, 18 pages.
United States Office Action, U.S. Appl. No. 15/134,252, dated Nov. 27, 2018, 21 pages.
United States Office Action, U.S. Appl. No. 16/070,251, dated Jan. 8, 2021, 31 pages.
United States Office Action, U.S. Appl. No. 16/070,251, dated Jul. 9, 2021, 21 pages.
West et al. Porcine induced pluripotent stem cells produce chimeric offspring. Stem Cells and Development, vol. 19, No. 8, 2010, pp. 1211-1220, 2010. (Year: 2010).
Wilschut, K., et al., "Alpha 6 Integrin is Important for Myogenic Stem Cell Differentiation," Stem Cell Research 7:112-123 (2011).
Yu et al., "Chinese Disease Signal Pathway and Targeted Therapy," Anhui Science and Technology Press, p. 372 (2013), (English translation not available).
Zeng, Q. et al., "The Emerging Role of the Hippo Pathway in Cell Contact Inhibition, Organ Size Control, and Cancer Development in Mammals," Cancer Cell, vol. 13, Mar. 2008, pp. 188-192.
Zhao, B. et al., "Cell detachment activates the Hippo pathway via cytoskeleton reorganization to induce anoikis," Genes & Development, vol. 26, Jan. 2012, pp. 54-68.

\* cited by examiner

SEQUENCE LISTING

<160> NUMBER OF SEQ ID NOS: 58

<210> SEQ ID NO 1
<211> LENGTH: 465
<212> TYPE: DNA
<213> ORGANISM: Artificial Sequence
<220> FEATURE:
<223> OTHER INFORMATION: bovine IGF1 and porcine albumin signal peptide

<400> SEQUENCE: 1

```
atgaagtggg tgactttat ttcccttctc tttctcttca gctctgctta ttccttcttg      60
aagcaggtga agatgcccat cacatcctcc tcgcatctct tctatctggc cctgtgcttg     120
ctcgccttca ccagctctgc cacggcggga cccgagaccc tctgcggggc tgagttggtg     180
gatgctctcc agttcgtgtg cggagacagg ggcttttatt tcaacaagcc cacggggtat     240
ggctcgagca gtcggagggc gccccagaca ggaatcgtgg atgagtgctg cttccggagc     300
tgtgatctga ggaggctgga gatgtactgc gcgcctctca gcccgccaa gtcggcccgc      360 tcagtccgtg cccagcgcca ccgacatg cccaaggctc agaaggaagt acatttgaag       420
aacacaagta gagggagtgc aggaaacaag aactacagaa tgtag                     465

<210> SEQ ID NO 2
<211> LENGTH: 462
<212> TYPE: DNA
<213> ORGANISM: Artificial Sequence
<220> FEATURE:
<223> OTHER INFORMATION: chicken IGF1 and porcine albumin signal peptide

<400> SEQUENCE: 2
atgaagtggg tgactttat ttcccttctc tttctcttca gctctgctta ttccttcttg      60
aaggtgaaga tgcacactgt gtcctacatt catttcttct accttggcct gtgtttgctt     120
accttaacca gttctgctgc tgccggccca gaaacactgt gtggtgctga gctggttgat     180
gctcttcagt tcgtatgtgg agacagaggc ttctacttca gtaagcctac agggtatgga     240
tccagcagta gacgcttaca ccacaaggga atagtggatg aatgctgctt ccagagttgt     300
gacctgagga ggctggagat gtactgtgct ccaataaagc cacctaaatc tgcacgctct     360
gtacgtgctc agcgccacac tgatatgcca aaagcacaaa aggaagtgca tttgaagaat     420
acaagtagag ggaacacagg aaacagaaac tacagaatgt aa                       462

<210> SEQ ID NO 3
<211> LENGTH: 414
<212> TYPE: DNA
<213> ORGANISM: Artificial Sequence
<220> FEATURE:
<223> OTHER INFORMATION: porcine IGF1 and porcine albumin signal peptide

<400> SEQUENCE: 3
atgaagtggg tgactttat ttcccttctc tttctcttca gctctgctta ttccttggcc      60
ctgtgcttgc tctccttcac cagctctgcc acggctggac tgagaccct ctgtggggct      120 gagctggtgg acgctcttca gttcgtgtgc ggagacaggg gcttttattt caacaagccc     180
acagggtacg gctccagcag tcggagggcg ccacagacgg gcatcgtgga tgagtgctgc     240
ttccggagct gtgatctgag gaggctggag atgtactgtg caccctcaa gcctgccaag      300 tcggcccgct ccgtccgtgc ccagcgccac acggacatgc ccaaggctca gaaggaagta     360
catttgaaga acacaagtag agggagttca ggaaacaaga actacagaat gtag           414

<210> SEQ ID NO 4
<211> LENGTH: 462
<212> TYPE: DNA
<213> ORGANISM: Gallus gallus

<400> SEQUENCE: 4
atggaaaaaa tcaacagtct ttcaacacaa ttagttaagt gctgcttttg tgatttcttg      60
aaggtgaaga tgcacactgt gtcctacatt catttcttct accttggcct gtgtttgctt     120
```

```
accttaacca gttctgctgc tgccggccca gaaacactgt gtggtgctga gctggttgat      180
gctcttcagt tcgtatgtgg agacagaggc ttctacttca gtaagcctac agggtatgga      240
tccagcagta gacgcttaca ccacaaggga atagtggatg aatgctgctt ccagagttgt      300
gacctgagga ggctggagat gtactgtgct ccaataaagc cacctaaatc tgcacgctct      360
gtacgtgctc agcgccacac tgatatgcca aaagcacaaa aggaagtgca tttgaagaat      420
acaagtagag ggaacacagg aaacagaaac tacagaatgt aa                        462

<210> SEQ ID NO 5
<211> LENGTH: 465
<212> TYPE: DNA
<213> ORGANISM: Bos taurus

<400> SEQUENCE: 5
atgggaaaaa tcagcagtct tccaacccaa ttatttaagt gctgcttttg tgatttcttg       60
aagcaggtga agatgcccat cacatcctcc tcgcatctct tctatctggc cctgtgcttg      120
ctcgccttca ccagctctgc cacggcggga cccgagaccc tctgcggggc tgagttggtg      180
gatgctctcc agttcgtgtg cggagacagg ggcttttatt tcaacaagcc cacggggtat      240
ggctcgagca gtcggagggc gccccagaca ggaatcgtgg atgagtgctg cttccggagc      300
tgtgatctga ggaggctgga gatgtactgc gcgcctctca gcccgccaa gtcggcccgc       360 tcagtccgtg cccagcgcca caccgacatg cccaaggctc agaaggaagt acatttgaag      420
aacacaagta gagggagtgc aggaaacaag aactacagaa tgtag                     465

<210> SEQ ID NO 6
<211> LENGTH: 393
<212> TYPE: DNA
<213> ORGANISM: Sus scrofa

<400> SEQUENCE: 6
atgcacatca catcctcttc gcatctcttc tacttggccc tgtgcttgct ctccttcacc       60
agctctgcca cggctggacc tgagaccctc tgtggggctg agctggtgga cgctcttcag      120
ttcgtgtgcg agacaggggg cttttatttc aacaagccca gggtacgg ctccagcagt       180 cggagggcgc cacagacggg catcgtggat gagtgctgct tccggagctg tgatctgagg      240
aggctggaga tgtactgtgc acccctcaag cctgccaagt cggcccgctc cgtccgtgcc      300
cagcgccaca cggacatgcc caaggctcag aaggaagtac atttgaagaa cacaagtaga      360
gggagttcag gaaacaagaa ctacagaatg tag                                  393

<210> SEQ ID NO 7
<211> LENGTH: 1824
<212> TYPE: DNA
<213> ORGANISM: Artificial Sequence
<220> FEATURE:
<223> OTHER INFORMATION: bovine albumin and porcine albumin signal
      peptide

<400> SEQUENCE: 7
atgaagtggg tgacttttat ttcccttctc tttctcttca gctctgctta ttccaggggt       60
gtgtttcgtc gagatacaca caagagtgag attgctcatc ggtttaaaga tttgggagaa      120
gaacatttta aaggcctggt actgattgcc ttttctcagt atctccagca gtgtccattt      180
gatgagcatg taaaattagt gaacgaacta actgagtttg caaaaacatg tgttgctgat      240
gagtcccatg ccggctgtga aagtcacttc acactctctt tggagatgaa ttgtgtaaa       300
```

```
gttgcatccc ttcgtgaaac ctatggtgac atggctgact gctgtgagaa acaagaacct      360
gagagaaatg aatgcttctt gtcacacaaa gatgatagcc ctgatctacc taaactcaaa      420
cctgacccca atactttgtg tgacgagttt aaggccgatg aaaagaagtt ttggggaaaa      480
tacctatacg aaattgctag aagacatccc tacttttatg caccagaact cctttactat      540
gctaataaat ataatggagt ttttcaagaa tgctgccaag ctgaagataa aggtgcctgc      600
ctgctaccaa agattgaaac tatgagggaa aaggtactga cttcatctgc cagacagaga      660
ctcaggtgtg ccagtattca aaaatttgga gaaagagctt taaaagcatg gtcagtagct      720
cgcctgagcc agaaatttcc caaggctgag tttgtagaag ttaccaagct agtgacagat      780
ctcacaaaag tgcacaagga atgctgccat ggagacctac ttgaatgcgc agatgacagg      840
gcggaccttg ccaagtacat atgtgataat caagatacaa tctccagtaa actgaaggaa      900
tgctgtgata agccttttgtt ggaaaaatcc cactgcattg ctgaggtaga aaaagatgcc      960
atacctgaaa acttgccccc attaactgct gactttgctg aagataagga tgtatgcaaa     1020
aactatcaag aagcaaagga tgccttcctg ggctcatttc tttatgaata ttcaagaagg     1080
catcctgaat atgctgtctc agtgctattg agacttgcca aggaatatga agccacactg     1140
gaggaatgct gtgccaaaga tgatccacat gcatgctatt ccacagtgtt tgacaaactt     1200
aagcatcttg tggatgagcc tcagaattta attaaacaaa actgtgacca attcgaaaaa     1260
cttggagagt atggattcca aaatgcgctc atagttcgtt acaccaggaa agtaccccaa     1320
gtgtcaactc caactctcgt ggaggtttca agaagcctag gaaaagtggg tactaggtgt     1380
tgtacaaaac cggaatcaga aagaatgccc tgtacagaag actatctgag cttgatcctg     1440
aaccggttgt gcgtgctgca tgagaagaca ccagtgagtg aaaaagtcac caagtgctgc     1500
acagagtcat tggtgaacag acggccatgt ttctctgctc tgacacctga tgaaacatat     1560
gtacccaaag ccttttgatga gaaattgttc accttccatg cagatatatg cacacttccc     1620
gatactgaga aacaaatcaa gaaacaaact gcacttgttg agctgttgaa acacaagccc     1680
aaggcaacag aggaacaact gaaaaccgtc atggagaatt ttgtggcttt tgtagacaag     1740
tgctgcgcag ctgatgacaa agaagcctgc tttgctgtgg agggtccaaa acttgttgtt     1800
tcaactcaaa cagccttagc ctaa                                           1824
```

<210> SEQ ID NO 8
<211> LENGTH: 1848
<212> TYPE: DNA
<213> ORGANISM: Artificial Sequence
<220> FEATURE:
<223> OTHER INFORMATION: chicken albumin and porcine albumin signal
      peptide

<400> SEQUENCE: 8

```
atgaagtggg tgacttttat ttcccttctc tttctcttca gctctgctta ttccaggaat       60
ctgcaaagat tgctcgtga tgcagagcac aagagtgaaa ttgcccatcg ctacaatgat      120
ttgaaagaag aaacatttaa ggcagttgcc atgatcacat ttgcccagta tctccagagg      180
tgctcttatg aaggactgtc taagcttgtg aaggatgttg ttgatctggc acaaaaatgt      240
gtagccaatg aagatgctcc tgaatgctca aaaccactgc cttccattat cctggatgaa      300
atctgccaag tggaaaagct ccgtgactct tatggtgcaa tggccgactg ctgtagcaaa      360
gctgatcctg aaagaaatga gtgtttcctg tcatttaaag tttcccaacc agacttcgtt      420
cagccatacc aaagaccagc ttctgatgtg atatgccagg aataccagga caacagagtg      480
```

```
tcatttctgg gacatttcat ctattctgtt gcaagaagac accccttctt gtatgcccct      540
gcaatcctta gttttgctgt tgattttgaa catgcacttc aaagctgttg caaagagagt      600
gatgtcggtg cttgcctgga caccaaggaa attgttatga gagaaaaagc caagggagta      660
agtgtgaagc agcagtattt tgtggaatc ttgaagcagt tcggagatag agttttccaa       720
gcacgacaac ttatttacct aagccaaaaa taccccaagg ctccattctc agaggtttct      780
aaatttgtac atgattctat cggcgtccac aaagagtgct gtgaagggga catggtggag      840
tgcatggatg acatggcacg tatgatgagc aatctgtgct ctcaacaaga tgttttctca      900
ggtaaaatca aagactgctg tgagaagcct attgtggaac gaagccagtg cattatggag      960
gcagaatttg atgagaaacc tgcagatctt ccttcattag ttgaaaagta catagaagat     1020
aaggaagtgt gtaaaagttt tgaagcaggc acgatgcat tcatggcaga gttcgtttat      1080
gaatactcac gaagacaccc tgagttctcc atacagctta ttatgagaat tgccaaagga     1140
tatgaatcac ttctggaaaa gtgctgcaaa actgataacc ctgctgagtg ctacgcaaat     1200
gctcaagagc aactgaacca acatatcaaa gaaactcagg atgttgtgaa gacaaactgt     1260
gatcttctcc atgaccatgg cgaggcagac ttcctcaagt ccatcctgat ccgctacact     1320
aagaaaatgc ctcaagtacc aactgatctc ctgcttgaaa ctggaaagaa atgacaact     1380 attggtacta agtgctgcca gcttcctgaa gacagacgca tggcttgttc tgagggttat     1440
ctgagcattg tgattcatga tacgtgcagg aaacaggaga ccacacctat aaatgacaac     1500
gtttcacaat gctgcagcag ctcctatgct aacagaagac catgtttcac tgctatggga     1560
gtagatacca aatatgttcc tccaccattt aatcctgata tgttcagctt tgatgaaaaa     1620
ttgtgcagtg ctcctgctga gaacgagaa gtaggccaga tgaaattgct aatcaacctc      1680
attaaacgca agccccagat gacagaagaa caaataaaga caattgctga tggtttcact     1740
gccatggttg acaagtgctg caagcagtcg gacatcaata catgctttgg agaagagggt     1800
gccaacctaa tagtccaaag cagagccaca ttaggaattg gtgcttaa                  1848
```

<210> SEQ ID NO 9
<211> LENGTH: 1824
<212> TYPE: DNA
<213> ORGANISM: Sus scrofa

<400> SEQUENCE: 9

```
atgaagtggg tgactttat ttcccttctc tttctcttca gctctgctta ttccagggt       60 gtgtttcgtc gagatacata caagagtgaa attgctcatc ggtttaaaga tttgggagaa     120
caatatttca aaggcctagt gctgattgcc ttttctcagc atctccagca atgcccatat     180 gaaagagcatg tgaaattagt gagggaagta actgagtttg caaaaacatg tgttgctgat     240
gagtcagctg aaaattgtga caagtcaatt cacactctct ttggagataa attatgtgca     300
attccatccc ttcgtgaaca ctatggtgac ttggctgact gctgtgaaaa agaagagcct     360
gagagaaacg aatgcttcct ccaacacaaa atgataacc cgacatccc taaattgaaa       420 ccagaccctg ttgctttatg cgctgacttc aggaagatg aacagaagtt tgggaaaa       480 tacctatatg aaattgccag aagacatccc tatttctacg ccccagaact cctttattat    540
gccattatat ataaagatgt tttttcagaa tgctgccaag ctgctgataa agctgcctgc    600
ctgttaccaa agattgagca tctgagagaa aaagtactga cttccgccgc caaacagaga   660
cttaagtgtg ccagtatcca aaaattcgga gagagagctt tcaaagcatg gtcattagct   720
cgcctgagcc agagatttcc caaggctgac tttacagaga tttccaagat agtgacagat   780
```

```
cttgcaaaag tccacaagga atgctgccat ggtgacctgc ttgaatgtgc agatgacagg    840
gcggatcttg ccaaatatat atgtgaaaat caagacacaa tctccactaa actgaaggaa    900
tgctgtgata agcctctgtt ggaaaaatcc cactgcattg ctgaggcaaa agagatgaa     960 ttgcctgcag acctgaaccc attagaacat gattttgttg aagataagga agtttgtaaa   1020
aactataaag aagcaaagca tgtcttcctg ggcacgtttt tgtatgagta ttcaagaagg   1080
cacccagact actctgtctc attgctgctg agaattgcca agatatatga agccacactg   1140
gaggactgct gtgccaaaga ggatcctccg gcatgctatg ccacagtgtt tgataaattt   1200
cagcctcttg tggatgagcc taagaattta atcaaacaaa actgtgaact ttttgaaaaa   1260
cttggagagt atggattcca aaatgcgctc atagttcgtt acaccaagaa agtacccaa    1320 gtgtcaactc caactcttgt ggaggtcgca agaaaactag gactagtggg ctctaggtgt   1380
tgtaagcgtc ctgaagaaga aagactgtcc tgtgctgaag actatctgtc cctggtcctg   1440
aaccggttgt gcgtgttgca cgagaagaca ccagtgagcg aaaaagttac caaatgctgc   1500
acagagtcct tggtgaacag acggccttgc ttttctgctc tgacaccaga cgaaacatac   1560
aaacccaaag aatttgttga gggaaccttc accttccatg cagacctatg cacacttcct   1620
gaggatgaga acaaatcaa gaagcaaact gcactcgttg agttgttgaa acacaagcct    1680
catgcaacag aggaacaact gagaactgtc ctgggcaact ttgcagcctt tgtacaaaag   1740
tgctgcgccg ctcctgacca tgaggcctgc tttgctgtgg agggtccgaa atttgttatt   1800
gaaattcgag ggatcttagc ctaa                                          1824

<210> SEQ ID NO 10
<211> LENGTH: 1848
<212> TYPE: DNA
<213> ORGANISM: Gallus gallus

<400> SEQUENCE: 10
atgaagtggg taacattaat ttcattcatt ttcctcttca gttcagcaac atccaggaat     60
ctgcaaagat tgctcgtga tgcagagcac aagagtgaaa ttgcccatcg ctacaatgat    120
ttgaaagaag aaacatttaa ggcagttgcc atgatcacat ttgcccagta tctccagagg    180
tgctcttatg aaggactgtc taagcttgtg aaggatgttg ttgatctggc acaaaaatgt    240
gtagccaatg aagatgctcc tgaatgctca aaaccactgc cttccattat cctggatgaa    300
atctgccaag tggaaaagct ccgtgactct tatggtgcaa tggccgactg ctgtagcaaa    360
gctgatcctg aaagaaatga gtgtttcctg tcatttaaag tttcccaacc agacttcgtt    420
cagccatacc aaagaccagc ttctgatgtg atatgccagg ataccaggga acagagtg     480 tcatttctgg acatttcat ctattctgtt gcaagaagac acccttctt gtatgcccct     540 gcaatcctta gttttgctgt tgattttgaa catgcacttc aaagctgttg caaagagagt    600
gatgtcggtc cttgcctgga caccaaggaa attgttatga gagaaaagc caagggagta    660 agtgtgaagc agcagtattt tgtggaatc ttgaagcagt tcggagatag agttttccaa     720
gcacgacaac ttatttaacct aagccaaaaa taccccaagg ctccattctc agaggttct    780 aaatttgtac atgattctat cggcgtccac aaagagtgct gtgaaggga catggtggag    840 tgcatggatg acatggcacg tatgatgagc aatctgtgct ctcaacaaga tgttttctca    900
ggtaaaatca aagactgctg tgagaagcct attgtggaac gaagccagtg cattatggag    960
gcagaatttg atgagaaacc tgcagatctt ccttcattag ttgaaaagta catagaagat   1020
```

```
aaggaagtgt gtaaaagttt tgaagcaggc cacgatgcat tcatggcaga gttcgtttat    1080
gaatactcac gaagacaccc tgagttctcc atacagctta ttatgagaat tgccaaagga    1140
tatgaatcac ttctggaaaa gtgctgcaaa actgataacc ctgctgagtg ctacgcaaat    1200
gctcaagagc aactgaacca acatatcaaa gaaactcagg atgttgtgaa gacaaactgt    1260
gatcttctcc atgaccatgg cgaggcagac ttcctcaagt ccatcctgat ccgctacact    1320
aagaaaatgc tcaagtacc aactgatctc ctgcttgaaa ctggaaagaa atgacaact     1380 attggtacta agtgctgcca gcttcctgaa gacagacgca tggcttgttc tgagggttat    1440
ctgagcattg tgattcatga tacgtgcagg aaacaggaga ccacacctat aaatgacaac    1500
gtttcacaat gctgcagcag ctcctatgct aacagaagac catgtttcac tgctatggga    1560
gtagatacca aatatgttcc tccaccattt aatcctgata tgttcagctt tgatgaaaaa    1620
ttgtgcagtg ctcctgctga agaacgagaa gtaggccaga tgaaattgct aatcaacctc    1680
attaaacgca agccccagat gacagaagaa caaataaaga caattgctga tggtttcact    1740
gccatggttg acaagtgctg caagcagtcg gacatcaata catgctttgg agaagagggt    1800
gccaacctaa tagtccaaag cagagccaca ttaggaattg gtgcttaa                 1848

<210> SEQ ID NO 11
<211> LENGTH: 1824
<212> TYPE: DNA
<213> ORGANISM: Bos taurus

<400> SEQUENCE: 11
atgaagtggg tgactttttat ttctcttctc cttctcttca gctctgctta ttccaggggt      60
gtgtttcgtc gagatacaca caagagtgag attgctcatc ggtttaaaga tttgggagaa    120
gaacatttta aaggcctggt actgattgcc ttttctcagt atctccagca gtgtccattt    180
gatgagcatg taaaattagt gaacgaacta actgagtttg caaaaacatg tgttgctgat    240
gagtcccatg ccggctgtga aagtcactt cacactctct ttggagatga attgtgtaaa     300
gttgcatccc ttcgtgaaac ctatggtgac atggctgact gctgtgagaa acaagaacct    360
gagagaaatg aatgcttctt gtcacacaaa gatgatagcc ctgatctacc taaactcaaa    420 cctgaccca atactttgtg tgacgagttt aaggccgatg aaaagaagtt ttggggaaaa     480
taactatacg aaattgctag aagacatccc tactttatg caccagaact cctttactat     540
gctaataaat ataatggagt ttttcaagaa tgctgccaag ctgaagataa aggtgcctgc    600
ctgctaccaa agattgaaac tatgagggaa aaggtactga cttcatctgc cagacagaga    660
ctcaggtgtg ccagtattca aaaatttgga gaaagagctt aaaagcatg gtcagtagct     720 cgcctgagcc agaaatttcc caaggctgag tttgtagaag ttaccaagct agtgacagat    780
ctcacaaaag tgcacaagga atgctgccat ggagacctac ttgaatgcgc agatgacagg    840
gcggaccttg ccaagtacat atgtgataat caagatacaa tctccagtaa actgaaggaa    900
tgctgtgata agcctttgtt ggaaaaatcc cactgcattg ctgaggtaga aaaagatgcc    960
atacctgaaa acttgccccc attaactgct gactttgctg aagataagga tgtatgcaaa    1020
aactatcaag aagcaaagga tgccttcctg ggctcatttc tttatgaata ttcaagaagg    1080
catcctgaat atgctgtctc agtgctattg agacttgcca aggaatatga agccacactg    1140
gaggaatgct gtgccaaaga tgatccacat gcatgctatt ccacagtgtt tgacaaactt    1200
aagcatcttg tggatgagcc tcagaattta attaaacaaa actgtgacca attcgaaaaa    1260
cttggagagt atggattcca aaatgcgctc atagttcgtt acaccaggaa agtaccccaa    1320
```

```
gtgtcaactc caactctcgt ggaggtttca agaagcctag gaaaagtggg tactaggtgt    1380
tgtacaaaac cggaatcaga aagaatgccc tgtacagaag actatctgag cttgatcctg    1440
aaccggttgt gcgtgctgca tgagaagaca ccagtgagtg aaaaagtcac caagtgctgc    1500
acagagtcat tggtgaacag acggccatgt ttctctgctc tgacacctga tgaaacatat    1560
gtacccaaag cctttgatga gaaattgttc accttccatg cagatatatg cacacttccc    1620
gatactgaga aacaaatcaa gaaacaaact gcacttgttg agctgttgaa acacaagccc    1680
aaggcaacag aggaacaact gaaaaccgtc atggagaatt tgtggctttt gtagacaag     1740 tgctgcgcag ctgatgacaa agaagcctgc tttgctgtgg agggtccaaa acttgttgtt    1800
tcaactcaaa cagccttagc ctaa                                           1824
```

<210> SEQ ID NO 12
<211> LENGTH: 4041
<212> TYPE: DNA
<213> ORGANISM: Artificial Sequence
<220> FEATURE:
<223> OTHER INFORMATION: Gallus gallus telomerase reverse transcriptase
    T2667C mutant

<400> SEQUENCE: 12

```
atggagcgcg gggctcagcc gggagtcggt gtgcggcggc tccgcaatgt agcgcgggag    60
gagcccttcg ccgcggtcct gggcgcgctg cggggctgct acgccgaggc cacgccgctg    120
gaggccttcg tccggcggct gcaggagggt ggcaccgggg aggtcgaggt gctgcgaggc    180
gacgacgctc agtgctaccg gaccttcgtg tcgcagtgcg tggtgtgcgt cccccgcggt    240
gctcgcgcca tcccccggcc catctgcttc cagcagttat ccagtcagag cgaagtcatc    300
acaagaatcg ttcagaggct gtgtgaaaag aaaaagaaga acatccttgc gtatggatac    360
tccttgctgg atgagaacag ttgtcacttc agagttttgc catcttcgtg tatatacagc    420
tatctgtcca atactgtaac agaaacgatt cgcatcagtg gcctctggga gatactgctg    480
agtaggatag gggacgacgt gatgatgtac ctgctggagc actgtgcact cttcatgctg    540
gttcccccaa gtaactgtta ccaggtctgc gggcaaccaa tttatgaact tatttcgcgt    600
aacgtagggc catccccagg gttttgttaga cgacggtact caaggtttaa acataatagc    660
ttgcttgact atgtgcgaaa aaggcttgtg tttcacaggc actatctttc caagtcgcag    720
tggtggaagt gcaggccgag acgtcgaggt cgtgtctcca gcaggagaaa aagaaggagc    780
cataggatac aaagcctaag gtctggttat cagccttctg caaaagtgaa ctttcaagca    840
ggtaggcaga tcagcacagt tactgcacgt ctggaaaaac agagctgctc cagtttatgt    900
ttgccagcta gagcaccatc tttaaaaagg aagcgtgatg gagaacaggt tgaaatcaca    960
gctaagagag tgaaaataat ggagaaagag atagaggaac aggcttgtag tatcgttcct    1020
gatgtaaacc aaagtagctc ccagaggcat ggaacctcct ggcatgtagc accacgtgct    1080
gtaggtctta ttaaagaaca ttacatttct gaaagaagta acagtgagat gtctggtcct    1140
tctgtagttc acagatctca ccctgggaag aggcctgtgg cagacaaaag ctcttttcca    1200
caaggagttc agggtaacaa acgcataaag accggtgcag aaaaacgagc agaatccaat    1260 agaagggggca tagagatgta tataaaccca atccataaac ccaatagaag gggcatagag    1320
aggcgtataa atccaaccca caaacctgag ttgaattctg tacaaactga accaatggaa    1380
ggtgcttctt caggggacag aaagcaggaa aatcccccag ctcatttggc aaagcagtta    1440
ccaaatacat tgtcgcgctc tacagtgtac tttgagaaga aatttcttct gtattcccgc    1500
```

```
agttaccaag aatattttcc taaatcgttc atactgagcc gcctgcaggg ttgtcaggca    1560
ggtggaaggc ggcttataga aactatattc ttaagccaaa acccattaaa ggaacagcag    1620
aaccaaagcc taccacagca aaagtggcga agaagaggt tgcccaaacg ctactggcaa     1680
atgagagaga tatttcagaa gctggtaaag aaccatgaga agtgcccta tttagttttc     1740 ttgaggaaaa attgccctgt tttgctttct gaagcatgtt tgaaaaagac ggagctgacc    1800
ttgcaggcgg ctctgcctgg ggaagcaaag gttcacaagc acacagaaca tgggaaagag    1860
tccactgagg gtactgcacc gaacagcttc ctcgctcctc cctcagtgct agcatgtggg    1920
cagccagaga gaggggaaca gcaccctgca gaggggagtg atccgctcct cagggagctg    1980
ctcaggcagc acagcagcca ctggcaggtg tatggctttg tgagggagtg cctggagcgg    2040
gtgatccctg ctgagctgtg gggttcaagc cataacaaat gccggttctt taaaaacgtg    2100
aaagcattca tttccatggg gaagtatgct aagctttcat tgcagcagct gatgtggaag    2160
atgagagtga atgactgcgt atggcttcgt ctggccaaag gtaatcactc tgttcctgcc    2220
tatgaacatt gttaccgtga agaaattctg gcaaaattcc tatactggct gatggattcc    2280
tatgttatcg agttgctcaa atcatttttc tatatcaccg agaccatgtt ccagaaaaac    2340
atgcttttct actaccgaaa gtttatctgg ggcaagttac agaacattgg aattagagac    2400
cattttgcca agtacatct acgtgccttg tcttcagagg agatggaagt gatccgtcaa    2460
aaaaagtatt ttcctattgc atcaaggctc cggttcattc ctaaaatgaa tggtttaaga    2520
cccgtagtaa gactaagccg tgttgttgaa ggacagaaac tcagcaagga agcagagaa    2580 aagaagatac agcgctataa cactcagcta aaaaatctat ttagtgtttt aaactatgaa    2640
cgaactgtaa acaccagtat cattggctcc tcagtattcg ggagagatga tatctacagg    2700
aagtggaagg agtttgttac aaaggttttt gaatcaggtg gtgaaatgcc tcatttctac    2760
tttgtaaagg gtgatgtatc cagagctttt gataccattc ctcacaagaa acttgtggaa    2820
gtgatatcac aggtcttgaa acctgagagc caaactgtct atggaataag gtggtatgca    2880
gtgattatga ttaccccaac tggaaaagcc aggaaactct ataagagaca tgtttctact    2940
ttcgaggatt ttattccaga catgaagcag tttgtgtcca gcttcaaga gagaacttca    3000 ttacgaaatg caatagtagt tgaacagtgc ttaacttta atgagaacag ttccaccctg    3060
tttactttct ttcttcaaat gttacataat aacatcctgg agattgggca caggtactat    3120
atacagtgct ctggaatccc acagggctcc attttgtcaa ccttactttg cagcttatgc    3180 tacgagaca tggaaaacaa attactctgt gggatccaga aggatggagt cctaatacgt    3240
cttattgatg acttttttgct ggttacgcca catttaatgc aggcaagaac ttttctaagg    3300
actatagcag caggtattcc tgagtatggc ttttttaataa atgccaagaa gactgtggtg    3360
aattttcctg ttgatgatat cccgggatgt tccaagttca acatctgcc agattgtcgt    3420 ttgatctcat ggtgtggttt attattggat gtgcagacac ttgaggttta ttgtgattac    3480
tccagttatg cctttactc tatcagatca agtctttcct tcaattcaag tagaatagct    3540
gggaaaaaca tgaaatgcaa attgactgca gtcctcaaac tgaaatgcca tccttactt    3600 cttgacttaa agatcaacag ccttcagaca gttctaatta acatctacaa gatattttta    3660
cttcaggctt acaggttcca tgcctgtgtt cttcagcttc cattcaacca gaaagttagg    3720
aataatcctg atttcttcct aaggatcatc tctgatactg cttcatgctg ctattttatc    3780
ctgaaagcta aaaatccagg agtttcttta ggtagcaaag atgcatctgg catgttccct    3840
```

|  |  |
|---|---:|
| tttgaggcag cagaatggct gtgctaccat gccttcattg tcaaactgtc caaccacaaa | 3900 |
| gttatttaca aatgcttact taagccccctt aaagtctata agatgcatct gtttgggaag | 3960 |
| atcccaaggg atactatgga actgctgaag acggtgacgg aaccatcgct ttgtcaagat | 4020 |
| ttcaaaacta tactggacta a | 4041 |

<210> SEQ ID NO 13
<211> LENGTH: 1854
<212> TYPE: DNA
<213> ORGANISM: Artificial Sequence
<220> FEATURE:
<223> OTHER INFORMATION: chicken cMyoDER

<400> SEQUENCE: 13

|  |  |
|---|---:|
| atggacttac tgggccccat ggaaatgacg gagggctccc tctgctcctt cacggccgcc | 60 |
| gatgacttct atgacgaccc gtgcttcaac acgtcggaca tgcacttctt cgaggacctg | 120 |
| gaccccggc tggtgcacgt gggcgggctg ctgaagcccg aggagcaccc gcaccaccac | 180 |
| gggcaccacc acgggaaccc acacgaggag gagcacgtgc gggcgccag tgggcaccac | 240 |
| caggccggcc gctgcctgct gtgggcgtgc aaggcctgca agaggaagac caccaacgct | 300 |
| gaccgccgca agccgccac catgagggaa cggcggcggc tcagcaaggt caacgaggcc | 360 |
| ttcgagaccc tcaagcgctg cacttccacc aaccccaacc agcgcctgcc caaggtggag | 420 |
| atcctgcgca acgccatccg ctacatcgag agcctgcagg ccctgctgcg tgagcaggag | 480 |
| ggcgattctt ctacagagct gcgagctcca acccttggga caagtccact ggtggttaaa | 540 |
| cataacaaga gaacagtcc ggctctgtct ctgacagcag aacagatggt cagtgccttg | 600 |
| ctggaagctg agccacctat agtttattct gaatatgacc ccaatagacc attcaacgaa | 660 |
| gcatctatga tgaccctgtt gaccaacctt gcagacagaa aattagtgca catgatcaac | 720 |
| tgggcaaaga gagttccagg atttgtggat ttaacactcc atgatcaggt ccatctgctg | 780 |
| gaatgtgcct ggttagagat attgatgatc ggcttagtct ggcgctccat ggaacaccca | 840 |
| ggaaagcttt tatttgcacc taatctatta ctggacagga tcaagggaa atgtgtagag | 900 |
| ggcatggtgg aaatctttga catgctactg gctactgctg ctcggtttcg gatgatgaac | 960 |
| cttcaagggg aggaatttgt gtgccttaag tccatcatcc tgctcaattc tggtgtgtac | 1020 |
| acttttcttt ctagcacctt gaaatctctg gaagagaggg actatatcca ccgtgttctg | 1080 |
| gacaaaatca cagatactct gatacaccta atggcaaagt caggtctttc tctgcagcag | 1140 |
| caacaccggc gactagctca gctcctcctt atcctctctc acatcaggca tatgagcaac | 1200 |
| aaaggaatgg agcacctgta caatatgaag tgtaaaaatg tagttccgct ctacgacctc | 1260 |
| ttactggaga tgctggacgc tcaccgccta catgcaccgg cagccaggag tgctgcacca | 1320 |
| atggaagagg agaaccgaaa ccaactgaca accgcaccag cttcatctca ttccctgcag | 1380 |
| tcctttttaca ttaacagcaa agaagaggag agtatgcaga atacagctat cgccgatgca | 1440 |
| tactacccag tgctggagca ctacagcggg gagtcagatg cctccagccc tcgctccaac | 1500 |
| tgctccgacg gcatgatgga gtacagcggg ccgcctgta gctctcgcag gagaaacagc | 1560 |
| tacgacagca gctactacac ggaatcacca aatgacccaa gcatgggaa gagttctgtt | 1620 |
| gtttccagcc tcgactgcct ctcaagcatt gtggagagga tttccacaga caactccaca | 1680 |
| tgtcccatac tgcctccagc tgaagctgta gctgaaggga gtccctgttc ccccaggaa | 1740 |
| ggagcaaacc tgagtgacag tggagcccag attccttccc ccaccaactg caccctctct | 1800 |
| ccccaggaaa gcagcagcag cagcagcagc aatccaatct accaagtgct ataa | 1854 |

<210> SEQ ID NO 14
<211> LENGTH: 8
<212> TYPE: PRT
<213> ORGANISM: Unknown
<220> FEATURE:
<223> OTHER INFORMATION: FLAG-tag peptide

<400> SEQUENCE: 14

Asp Tyr Lys Asp Asp Asp Asp Lys
1               5

<210> SEQ ID NO 15
<211> LENGTH: 540
<212> TYPE: DNA
<213> ORGANISM: Bos taurus

<400> SEQUENCE: 15

| | | | | | |
|---|---|---|---|---|---|
| atggggatca | cagcaggaaa | gtcggtgctg | gtgcttcttg | ccttcttggc | cttcgcctcg | 60 |
| tgctgctatg | ctgcttaccg | ccccagcgag | actctgtgcg | gcggggagct | ggtggacacc | 120 |
| ctccagtttg | tctgtgggga | ccgcggcttc | tacttcagcc | gaccatccag | ccgcataaac | 180 |
| cgacgcagcc | gtggcatcgt | ggaagagtgt | tgcttccgaa | gctgcgacct | ggccctgctg | 240 |
| gagacttact | gtgccacccc | cgccaagtcc | gagagggatg | tgtctgcctc | tacgaccgtg | 300 |
| cttccggacg | acgtcaccgc | ataccccgtg | ggcaagttct | tccaatatga | catctggaag | 360 |
| cagtccaccc | agcgcctgcg | caggggcctg | cccgccttcc | tgcgagcacg | ccggggtcgc | 420 |
| acgctcgcca | aggagctgga | ggcgctcaga | gaggccaaga | gtcaccgtcc | gctgatcgcc | 480 |
| ctgcccaccc | aggaccctgc | cacccacggg | ggcgcctctt | ccaaggcatc | cagcgattag | 540 |

<210> SEQ ID NO 16
<211> LENGTH: 486
<212> TYPE: DNA
<213> ORGANISM: Danio rerio

<400> SEQUENCE: 16

| | | | | | |
|---|---|---|---|---|---|
| atgtctagcg | gtcatttctt | ccaggggcat | tggtgtgatg | tctttaagtg | taccatgcgc | 60 |
| tgtctcccga | gtacccacac | cctctcactg | gtgctgtgcg | tcctcgcgtt | gactcccgcg | 120 |
| actctggagg | cggggccgga | gacgctgtgc | ggggcggagc | ttgtagacac | gctgcagttt | 180 |
| gtgtgtggag | acagggggctt | ttatttcagc | aaaccgacag | gatatggacc | tagttcaaga | 240 |
| aggtcacaca | accgtggcat | cgtggacgaa | tgctgctttc | agagctgtga | gctacggcgc | 300 |
| ctcgagatgt | attgtgcgcc | tgtgaagaca | ggcaaatctc | cacgatctct | acgagcacaa | 360 |
| cgacacacag | atattcccag | gacaccaaag | aaacctatat | ctgggcatag | ccactcttcc | 420 |
| tgtaaggagg | ttcatcagaa | gaactcgagc | cgaggaaaca | caggggggcag | aaactatcgc | 480 |
| atgtag | | | | | | 486 |

<210> SEQ ID NO 17
<211> LENGTH: 312
<212> TYPE: DNA
<213> ORGANISM: Oncorhynchus mykiss

<400> SEQUENCE: 17

| | | | | | |
|---|---|---|---|---|---|
| atgaggagac | cctgtatcct | ggccatccag | cctgacacgg | agttcatgcc | cccagagctg | 60 |
| gatgccagca | acttccacat | gggccctgag | ctctgcacca | aggacagcaa | ggagctgctg | 120 |
| ctctctggga | agaaactact | gtatggtgtg | gtcagacata | agaccaccat | cactgaggag | 180 |

| | |
|---|---|
| cagctgaagt ccatctctac taaatatcac agtatgaagg agaagtgctg tgctgctgag | 240 |
| gaccaagcag catgcttcac tgaggaggca cccaagctgg ttgctgagag tgcagagctg | 300 |
| gtcaaggctt aa | 312 |

<210> SEQ ID NO 18
<211> LENGTH: 1116
<212> TYPE: DNA
<213> ORGANISM: Oreochromis niloticus

<400> SEQUENCE: 18

| | |
|---|---|
| atggctacat ccgccagcgc cagcttgagt aaagctgtca agcagcagta catggagctc | 60 |
| cctcaggggg acaaagtcca ggccatgtac atctggatcg acggaaccgg agaggggctc | 120 |
| cgatgcaaaa ccaggacgct tgattctgag cccaaaagca tcgaagatct tcctgaatgg | 180 |
| aactttgacg gatccagtac ctaccagtcc gaaggctcca acagcgacat gtatctgatc | 240 |
| ccctcagcca tgttccgcga tccattccgc aaagacccca caagctggt gctgtgtgaa | 300 |
| gtcctgaagt acaaccgtaa acctacagaa accaaccttc ggctcacctg taagaaagtg | 360 |
| atggatatgg tggcggatca gcatccttgg tttggcatgg agcaggagta caccatcctt | 420 |
| ggaacggacg ggcatccatt tggctggcca tctaatggtt tccccggacc acaggggccg | 480 |
| tactactgtg tgttggagc tgacaaagcc tatggcaggg acgtagtcga ggcccattac | 540 |
| aaagcttgtt tgtacgctgg agtccagatt tgtggcacaa atgctgaagt aatgcctgct | 600 |
| cagtgggagt tccaggtcgg accttgcgaa ggcattgaca tgggcgatca tttgtgggta | 660 |
| gcgcgcttca tcctgcaccg tgtctgtgag gatttggcg tcgtcgcctc atttgatccc | 720 |
| aagccaatcc ctggaaactg gaacggtgct ggctgccata caaacttcag cacgaaagag | 780 |
| atgagggaag acggtggatt gaaagctatt gaggattcca ttgagaagct tggaaagagg | 840 |
| cacagctacc acattcgtgc ctacgacccc aaagggggc tcgacaacgc cgccgtctc | 900 |
| actggccgcc atgaaacctc aaacatcaac gaattctctg ctggtgtggc caaccgtggt | 960 |
| gccagcattc gcattcctcg taatgttggt caggagaaga aaggctactt cgaagaccgt | 1020 |
| cgcccttcag ccaactgtga cccgtacagt gtgaccgagg ccctgatccg cacctgtctg | 1080 |
| ctgaacgagg aaggagatga acccgcggat tactaa | 1116 |

<210> SEQ ID NO 19
<211> LENGTH: 645
<212> TYPE: DNA
<213> ORGANISM: Oncorhynchus mykiss

<400> SEQUENCE: 19

| | |
|---|---|
| atggaaaccc agaaaagaca cgaataccac tcagtttgtc acacctgccg gagaacggaa | 60 |
| aacacaagaa tgaaggtcaa gatgatgtct tcgtcaaatc gagtgctggt cattgcgctg | 120 |
| gcacttactc tgtacattgt tgaagtggct tcggcagaaa cgctatgtgg aggagaactg | 180 |
| gtggacgcgc tgcagttcgt ctgtgaagat agaggattct atttcagtag ccaaccagc | 240 |
| aggtctaaca gcagacgctc ccagaaccgt ggtatcgtgg aggagtgttg tttccgtagc | 300 |
| tgtgacctca acctgttgga gcagtactgt gccaaacctg ccaagtcaga gagggacgtg | 360 |
| tcggccacct ctctacagat cattcccatg gtgcccacaa tcaaacagga tgtcccaaga | 420 |
| aaacatgtga ctgtgaagta ttccaaatat gaggcgtggc agaggaaggc tgctcagcgg | 480 |
| ctccggaggg gcgtcccggc catcctcagg gcccggaagt tccggaggca ggcggtgaag | 540 |

| | |
|---|---|
| atcaaggccc aagagcaggc gatgttccac cggcctctga tcaccctgcc cagcaagctt | 600 |
| cccccagtcc tgcccccac ggacaactac gtcagccaca attga | 645 |

<210> SEQ ID NO 20
<211> LENGTH: 462
<212> TYPE: DNA
<213> ORGANISM: Xenopus tropicalis

<400> SEQUENCE: 20

| | |
|---|---|
| atggaaaaaa acaacagtct ttcaacacaa ttatttaagt gctacttttg tgatttctta | 60 |
| aagctgaaga tgcacaaaat gtcctacatt catctgctct acctggcttt gtgtttcctg | 120 |
| actttaaccc attcagcagc tgctggacca gagaccctct gtggagccga actggtagac | 180 |
| actcttcagt ttgtatgtgg agacagaggc ttctatttta gcaagccaac agggtacgga | 240 |
| tccagcaatc gaagatcgca tcacagagga atagtagatg agtgctgttt ccaaagctgt | 300 |
| gatttcagaa ggctggagat gtactgcgct cctgccaagc cagccaaatc agcacgttct | 360 |
| gtacgtgctc aacgtcacac tgacatgcca aaagcccaga aggaagtaca cctaaagaat | 420 |
| gcaagtcgag gaaacacagg gagtcgagga ttccgaatgt aa | 462 |

<210> SEQ ID NO 21
<211> LENGTH: 1122
<212> TYPE: DNA
<213> ORGANISM: Xenopus tropicalis

<400> SEQUENCE: 21

| | |
|---|---|
| atggcaacct ccgccagtgc tcagttgagt aaggccataa agcagatgta tctggaactg | 60 |
| ccacagggag ataaggtgca ggctatgtac atctgggttg atgggaccgg ggagggtctt | 120 |
| cgctgcaaga ctcgcactct ggacagtgaa cccaagacca tagaagatct tcctgaatgg | 180 |
| aacttcgatg gatctagcac ataccaatcc gagggttcca acagtgacat gtacctgatt | 240 |
| ccagttgcaa tgtttagaga ccctttcga agggacccca acaagctggt actctgcgag | 300 |
| gtgctcaaat acaaccgaaa aacagctgaa acaaacttgc gtcatacatg taaccagata | 360 |
| atggacatga tggccaatga gcatccatgg tttggcatgg aacaggaata cacattgctg | 420 |
| ggtatggatg acacccttt tggctggcct tcaaatggct tcccaggacc acaaggtccc | 480 |
| tattactgtg gagtgggtgc agataaggca tatggtcggg atattgtgga ggctcattat | 540 |
| cgggcttgcc tttatgctgg tgtgaaaatt gcaggaacaa atgcagaagt tatgccagca | 600 |
| cagtgggagt tccaaattgg gccatgtgag ggaatagaaa tgggagatca cctttggatt | 660 |
| gctcgattta tactgcatag aatttgtgag gattttggga tcattgtttc gtttgaccca | 720 |
| aagcccataa ctggaaactg gaatggagct ggatgtcaca ccaatttcag cacaaagtca | 780 |
| atgcgtgaag aaggaggcct taaggacata gaagaatcca ttgaacgtct aagcaaacgt | 840 |
| catgattatc acatcagaat gtatgaccca aggggtggta agacaatgc ccgtcgtctc | 900 |
| acaggtttcc atgagacctc cagcatccat gagttctctg caggagtggc aaaccgtggt | 960 |
| gccagtatcc gcattccccg cagtgtaggc caggagaaga aaggctattt tgaagatcgt | 1020 |
| cgtccatcag ccaactgtga tccctatgct gtgacagaag ctatgatcag aacctgccta | 1080 |
| ctgaatgaaa ctggagacga acctcttgaa tacaagaact aa | 1122 |

<210> SEQ ID NO 22
<211> LENGTH: 1719
<212> TYPE: DNA
<213> ORGANISM: Xenopus tropicalis

<400> SEQUENCE: 22

| | | | | | |
|---|---|---|---|---|---|
| atgaacgcgt | tgatgcggcg | tgcctgctgc | ggggcgctat | tccccctctc | attccgactg | 60 |
| gccgcgctga | gccctatgaa | gggagctagt | aactttagct | gcggtaacgt | gtgcgcctct | 120 |
| cctgccggat | gttgggcgcc | accaagtgga | cacgacacgg | ggataaaagt | gtacaacagc | 180 |
| cttactagga | ggaaggatcc | acttattctg | gcagatccga | cagtagcgac | atggtatagc | 240 |
| tgtggaccta | cagtttatga | ccatgcacat | cttggacatg | catgttctta | tgttagattt | 300 |
| gacataattc | gaaggattct | gctcaaggtt | tttgggattg | atacagtcgt | ggtgatggta | 360 |
| gtcacagaca | ttgatgataa | gataatcaag | agagcaaagg | agctcaatat | atctcctgtg | 420 |
| gccttagctc | gtacttacga | acaggatttt | aaacaagaca | tgactgcgtt | gaaggtcctt | 480 |
| ccaccaacag | tatacatgag | agttactgaa | atattccac | agatcatatc | atttattgaa | 540 |
| cacataattg | ccaatggata | tgcatatgct | acctcacaag | gaaatgttta | ttttgatgtt | 600 |
| cagtcgattg | gagagcgata | tgggaaattt | aatgattctt | tcagtgatac | agccagcgaa | 660 |
| tcagcatcac | aagataaaag | gcatatccga | gattttgctt | tgtggaaaac | atccaagcct | 720 |
| gaggagcctt | actgggcttc | tccttggggc | aagggaagac | ctggctggca | catagagtgt | 780 |
| tccacaattg | caagttctgt | atttggcaaa | catctagaca | ttcacactgg | tgggattgac | 840 |
| cttgctttcc | ctcatcatga | aaatgaaatt | gctcagtgtg | aggcatatca | ccagagcaca | 900 |
| cagtggggaa | actatttcct | tcatactgga | catttacatt | tgaagggaa | tgaagaaaaa | 960 |
| atgtcaaaat | ccctgagaaa | ctatctgaca | gttaaggagt | ttttaaagtc | cttttccccct | 1020 |
| gaccagttta | gaatgttttg | tctgcgctca | aaatataaat | cagccgtgga | atacagcaac | 1080 |
| gggtccatgc | atgatgcagt | aaatacccta | cacaccatct | cttcgtttgt | cgatgatgca | 1140 |
| aaagcctata | tgaaaggtca | gctgatttgc | caaccagtgc | aggaggcttt | actctggcaa | 1200 |
| aggctgaatg | aaacaaaagt | aaatgttaag | gctgcgtttt | cagatgactt | tgacacccca | 1260 |
| cgagcagttg | atgcagttat | ggacctcatt | caccatggca | acagacagct | taaggctgtt | 1320 |
| tccaaggagt | caaactctcc | caggagctct | gtagtttatg | gtgccatgat | ctcttacatt | 1380 |
| gaacaatttc | tggagatatt | gggaatttcc | ttgagccaaa | accaggtcgc | tgcagaagat | 1440 |
| agacactcgg | ctgttctctt | taatgtagta | gaagaaatga | tcagttttag | aagtaaggtg | 1500 |
| cggaattacg | ccctggctgc | agatgaatca | ccaaatgcaa | taggacaaga | ggaaaaacag | 1560 |
| caatacaagg | agaggagaag | gcagttgtta | ctggaaaggg | aaccactcct | acaggcttgt | 1620 |
| gacataatgc | gccaacatct | ggctgtatat | ggcataaatg | taaggatcg | tggaaataca | 1680 |
| tcaacatggg | aactacttga | ccgcaaagaa | gaaacctag | | | 1719 |

<210> SEQ ID NO 23
<211> LENGTH: 549
<212> TYPE: DNA
<213> ORGANISM: Xenopus tropicalis

<400> SEQUENCE: 23

| | | | | | |
|---|---|---|---|---|---|
| atgaggcatc | tcctcctcct | ctctatcacc | ttcctggtat | acacgctaga | ctctgctaaa | 60 |
| gcctatggag | caacggagac | cctgtgcggt | ggggagctgg | tggacaccct | gcagtttgtt | 120 |
| tgtggagaca | ggggcttcta | tttcagcagg | aataatggcc | gctccaaccg | cagggctaac | 180 |
| aggggggattg | tggaagaatg | ttgcttccgg | agctgtgatt | tggaactgtt | ggaaacgtac | 240 |
| tgcgcaaagc | cagctaagaa | cgagagggat | gtctccactg | caccctccac | agcaatacca | 300 |

```
ccactgaaca agcaggacct gtaccacaaa catcaccaca caaagagctc caagtatgac    360
atttggcaga ggaagtctat ccatcggctg cggagaggag tccctgccat tgtacgtgct    420
aggcagtatc gattgctaat gcagcaggct gaagaatcag agcaggcact atcacatcgg    480
ccccttacca ccttacccat aacgcggcct ctccatctgc aacaaacctc agaaccttcc    540
ctcaattga                                                            549
```

```
<210> SEQ ID NO 24
<211> LENGTH: 1122
<212> TYPE: DNA
<213> ORGANISM: Gallus gallus

<400> SEQUENCE: 24
atggccacct cggcgagctc ccacctgagc aaagccatca agcacatgta catgaagctg     60
ccgcagggtg agaaggtcca agccatgtac atctggatcg acgggactgg ggagcacctc    120
cgctgcaaaa cccgcactct ggaccacgaa cccaagagcc tggaagatct ccccgagtgg    180
aactttgatg gctccagcac cttccaagcc gaaggctcca cagcgacat gtacctgcga     240 cctgctgcca tgttccggga cccttttcgc aaggatccca acaaattagt tctctgtgag    300
gtcttcaaat acaaccgcca gtctgcagac acaaatcttc ggcacacctg taggcggatt    360
atggatatgg tgtccaacca gcaccctg tttgggatgg agcaggagta caccttctg     420 ggaacagatg gtcatccgtt tggctggcct tccaattgct ccctggacc caaggtccg     480 tactactgcg gtgtaggagc tgacaaagcc tatggcagag acattgtgga ggcccactac    540
cgagcgtgcc tgtatgctgg tgtgaaaatt ggaggaacca acgcagaagt gatgccagcc    600
cagtgggagt tccaggtggg accgtgcgaa gggattgaga tggggatca cctctggata    660 gcacgtttca tcctccaccg ggtgtgcgaa gactttggtg tcattgtgtc cttcgatccc    720
aaacccatcc ctgggaactg gaacggtgct ggctgtcaca ccaacttcag caccaagaac    780
atgagggaag atggaggtct caagcacatc gaggaggcca tcgagaagct gagcaagcgc    840
caccagtacc acatccgtgc ctacgacccc aaaggagggc tggacaacgc ccggcgcctg    900
acgggcttcc acgagacgtc cagcatccac gagttctccg ccggcgtggc caaccgcggc    960
gccagcatcc gcatcccacg caacgtgggc catgagaaga aaggctactt cgaggaccgc   1020
gggccttcag ccaactgcga tccctacgcc gtgacggagg ccctggtccg tacgtgtctc   1080
ctcaacgaaa ccgggacga gccttttgag tacaagaact aa                       1122
```

```
<210> SEQ ID NO 25
<211> LENGTH: 564
<212> TYPE: DNA
<213> ORGANISM: Gallus gallus

<400> SEQUENCE: 25
atgtgtgctg ccaggcagat actgctgcta ctgctggcct tcctggccta tgcgttggat     60
tcagctgcgg cgtatggcac ggcggagacc ctctgcggtg gggagctggt ggacacactg    120
cagttcgtct gtggggacag gggcttctac ttcagtagac cagtgggacg aaataacagg    180
aggatcaacc gtggcattgt ggaggagtgc tgctttcgga gctgtgacct ggctctgctg    240
gaaacctact gtgccaagtc cgtcaagtca gagcgtgacc tctccgccac ctccctcgcg    300
ggcctcccag ccctcaacaa ggagagcttc cagaagccat tcatgccaa gtactccaag     360 tacaacgtgt ggcagaagaa gagctcgcag cggctgcagc gggaggtgcc aggcatcctg    420
cgtgcccgtc ggtaccggtg gcaggcggag gggctgcaag cagctgagga agccagggcg    480
```

```
atgcatcgtc cctcatctc cttgcccagt cagcggcccc cagcgccgcg ggcatcccct    540
gaagcgaccg gcccccagga atga                                          564
```

<210> SEQ ID NO 26
<211> LENGTH: 179
<212> TYPE: PRT
<213> ORGANISM: Bos taurus

<400> SEQUENCE: 26

```
Met Gly Ile Thr Ala Gly Lys Ser Val Leu Val Leu Leu Ala Phe Leu
1               5                   10                  15

Ala Phe Ala Ser Cys Cys Tyr Ala Ala Tyr Arg Pro Ser Glu Thr Leu
            20                  25                  30

Cys Gly Gly Glu Leu Val Asp Thr Leu Gln Phe Val Cys Gly Asp Arg
        35                  40                  45

Gly Phe Tyr Phe Ser Arg Pro Ser Ser Arg Ile Asn Arg Arg Ser Arg
    50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Ala
                85                  90                  95

Ser Thr Thr Val Leu Pro Asp Asp Val Thr Ala Tyr Pro Val Gly Lys
            100                 105                 110

Phe Phe Gln Tyr Asp Ile Trp Lys Gln Ser Thr Gln Arg Leu Arg Arg
        115                 120                 125

Gly Leu Pro Ala Phe Leu Arg Ala Arg Arg Gly Arg Thr Leu Ala Lys
    130                 135                 140

Glu Leu Glu Ala Leu Arg Glu Ala Lys Ser His Arg Pro Leu Ile Ala
145                 150                 155                 160

Leu Pro Thr Gln Asp Pro Ala Thr His Gly Gly Ala Ser Ser Lys Ala
                165                 170                 175

Ser Ser Asp
```

<210> SEQ ID NO 27
<211> LENGTH: 161
<212> TYPE: PRT
<213> ORGANISM: Danio rerio

<400> SEQUENCE: 27

```
Met Ser Ser Gly His Phe Phe Gln Gly His Trp Cys Asp Val Phe Lys
1               5                   10                  15

Cys Thr Met Arg Cys Leu Pro Ser Thr His Thr Leu Ser Leu Val Leu
            20                  25                  30

Cys Val Leu Ala Leu Thr Pro Ala Thr Leu Glu Ala Gly Pro Glu Thr
        35                  40                  45

Leu Cys Gly Ala Glu Leu Val Asp Thr Leu Gln Phe Val Cys Gly Asp
    50                  55                  60

Arg Gly Phe Tyr Phe Ser Lys Pro Thr Gly Tyr Gly Pro Ser Ser Arg
65                  70                  75                  80

Arg Ser His Asn Arg Gly Ile Val Asp Glu Cys Cys Phe Gln Ser Cys
                85                  90                  95

Glu Leu Arg Arg Leu Glu Met Tyr Cys Ala Pro Val Lys Thr Gly Lys
            100                 105                 110

Ser Pro Arg Ser Leu Arg Ala Gln Arg His Thr Asp Ile Pro Arg Thr
        115                 120                 125
```

```
Pro Lys Lys Pro Ile Ser Gly His Ser His Ser Ser Cys Lys Glu Val
            130                 135                 140

His Gln Lys Asn Ser Ser Arg Gly Asn Thr Gly Gly Arg Asn Tyr Arg
145                 150                 155                 160

Met

<210> SEQ ID NO 28
<211> LENGTH: 103
<212> TYPE: PRT
<213> ORGANISM: Oncorhynchus mykiss

<400> SEQUENCE: 28

Met Arg Arg Pro Cys Ile Leu Ala Ile Gln Pro Asp Thr Glu Phe Met
1               5                   10                  15

Pro Pro Glu Leu Asp Ala Ser Asn Phe His Met Gly Pro Glu Leu Cys
            20                  25                  30

Thr Lys Asp Ser Lys Glu Leu Leu Leu Ser Gly Lys Lys Leu Leu Tyr
        35                  40                  45

Gly Val Val Arg His Lys Thr Thr Ile Thr Glu Glu Gln Leu Lys Ser
50                  55                  60

Ile Ser Thr Lys Tyr His Ser Met Lys Glu Lys Cys Cys Ala Ala Glu
65                  70                  75                  80

Asp Gln Ala Ala Cys Phe Thr Glu Glu Ala Pro Lys Leu Val Ala Glu
                85                  90                  95

Ser Ala Glu Leu Val Lys Ala
            100

<210> SEQ ID NO 29
<211> LENGTH: 371
<212> TYPE: PRT
<213> ORGANISM: Oreochromis niloticus

<400> SEQUENCE: 29

Met Ala Thr Ser Ala Ser Ala Ser Leu Ser Lys Ala Val Lys Gln Gln
1               5                   10                  15

Tyr Met Glu Leu Pro Gln Gly Asp Lys Val Gln Ala Met Tyr Ile Trp
            20                  25                  30

Ile Asp Gly Thr Gly Glu Gly Leu Arg Cys Lys Thr Arg Thr Leu Asp
        35                  40                  45

Ser Glu Pro Lys Ser Ile Glu Asp Leu Pro Glu Trp Asn Phe Asp Gly
50                  55                  60

Ser Ser Thr Tyr Gln Ser Glu Gly Ser Asn Ser Asp Met Tyr Leu Ile
65                  70                  75                  80

Pro Ser Ala Met Phe Arg Asp Pro Phe Arg Lys Asp Pro Asn Lys Leu
                85                  90                  95

Val Leu Cys Glu Val Leu Lys Tyr Asn Arg Lys Pro Thr Glu Thr Asn
            100                 105                 110

Leu Arg Leu Thr Cys Lys Lys Val Met Asp Met Val Ala Asp Gln His
        115                 120                 125

Pro Trp Phe Gly Met Glu Gln Glu Tyr Thr Ile Leu Gly Thr Asp Gly
130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Val Val
                165                 170                 175
```

Glu Ala His Tyr Lys Ala Cys Leu Tyr Ala Gly Val Gln Ile Cys Gly
            180                 185                 190

Thr Asn Ala Glu Val Met Pro Ala Gln Trp Glu Phe Gln Val Gly Pro
        195                 200                 205

Cys Glu Gly Ile Asp Met Gly Asp His Leu Trp Val Ala Arg Phe Ile
    210                 215                 220

Leu His Arg Val Cys Glu Asp Phe Gly Val Val Ala Ser Phe Asp Pro
225                 230                 235                 240

Lys Pro Ile Pro Gly Asn Trp Asn Gly Ala Gly Cys His Thr Asn Phe
                245                 250                 255

Ser Thr Lys Glu Met Arg Glu Asp Gly Gly Leu Lys Ala Ile Glu Asp
            260                 265                 270

Ser Ile Glu Lys Leu Gly Lys Arg His Ser Tyr His Ile Arg Ala Tyr
        275                 280                 285

Asp Pro Lys Gly Gly Leu Asp Asn Ala Arg Arg Leu Thr Gly Arg His
    290                 295                 300

Glu Thr Ser Asn Ile Asn Glu Phe Ser Ala Gly Val Ala Asn Arg Gly
305                 310                 315                 320

Ala Ser Ile Arg Ile Pro Arg Asn Val Gly Gln Glu Lys Lys Gly Tyr
                325                 330                 335

Phe Glu Asp Arg Arg Pro Ser Ala Asn Cys Asp Pro Tyr Ser Val Thr
            340                 345                 350

Glu Ala Leu Ile Arg Thr Cys Leu Leu Asn Glu Gly Asp Glu Pro
        355                 360                 365

Ala Asp Tyr
    370

<210> SEQ ID NO 30
<211> LENGTH: 214
<212> TYPE: PRT
<213> ORGANISM: Oncorhynchus mykiss

<400> SEQUENCE: 30

Met Glu Thr Gln Lys Arg His Glu Tyr His Ser Val Cys His Thr Cys
1               5                   10                  15

Arg Arg Thr Glu Asn Thr Arg Met Lys Val Lys Met Met Ser Ser Ser
            20                  25                  30

Asn Arg Val Leu Val Ile Ala Leu Ala Leu Thr Leu Tyr Ile Val Glu
        35                  40                  45

Val Ala Ser Ala Glu Thr Leu Cys Gly Gly Glu Leu Val Asp Ala Leu
    50                  55                  60

Gln Phe Val Cys Glu Asp Arg Gly Phe Tyr Phe Ser Arg Pro Thr Ser
65                  70                  75                  80

Arg Ser Asn Ser Arg Ser Gln Asn Arg Gly Ile Val Glu Glu Cys
                85                  90                  95

Cys Phe Arg Ser Cys Asp Leu Asn Leu Leu Glu Gln Tyr Cys Ala Lys
            100                 105                 110

Pro Ala Lys Ser Glu Arg Asp Val Ser Ala Thr Ser Leu Gln Ile Ile
        115                 120                 125

Pro Met Val Pro Thr Ile Lys Gln Asp Val Pro Arg Lys His Val Thr
    130                 135                 140

Val Lys Tyr Ser Lys Tyr Glu Ala Trp Gln Arg Lys Ala Ala Gln Arg
145                 150                 155                 160

Leu Arg Arg Gly Val Pro Ala Ile Leu Arg Ala Arg Lys Phe Arg Arg
                165                 170                 175

```
Gln Ala Val Lys Ile Lys Ala Gln Glu Gln Ala Met Phe His Arg Pro
            180                 185                 190

Leu Ile Thr Leu Pro Ser Lys Leu Pro Pro Val Leu Pro Pro Thr Asp
        195                 200                 205

Asn Tyr Val Ser His Asn
    210
```

<210> SEQ ID NO 31
<211> LENGTH: 153
<212> TYPE: PRT
<213> ORGANISM: Xenopus tropicalis

<400> SEQUENCE: 31

```
Met Glu Lys Asn Asn Ser Leu Ser Thr Gln Leu Phe Lys Cys Tyr Phe
1               5                   10                  15

Cys Asp Phe Leu Lys Leu Lys Met His Lys Met Ser Tyr Ile His Leu
            20                  25                  30

Leu Tyr Leu Ala Leu Cys Phe Leu Thr Leu Thr His Ser Ala Ala Ala
        35                  40                  45

Gly Pro Glu Thr Leu Cys Gly Ala Glu Leu Val Asp Thr Leu Gln Phe
    50                  55                  60

Val Cys Gly Asp Arg Gly Phe Tyr Phe Ser Lys Pro Thr Gly Tyr Gly
65                  70                  75                  80

Ser Ser Asn Arg Arg Ser His His Arg Gly Ile Val Asp Glu Cys Cys
                85                  90                  95

Phe Gln Ser Cys Asp Phe Arg Arg Leu Glu Met Tyr Cys Ala Pro Ala
            100                 105                 110

Lys Pro Ala Lys Ser Ala Arg Ser Val Arg Ala Gln Arg His Thr Asp
        115                 120                 125

Met Pro Lys Ala Gln Lys Glu Val His Leu Lys Asn Ala Ser Arg Gly
    130                 135                 140

Asn Thr Gly Ser Arg Gly Phe Arg Met
145                 150
```

<210> SEQ ID NO 32
<211> LENGTH: 373
<212> TYPE: PRT
<213> ORGANISM: Xenopus tropicalis

<400> SEQUENCE: 32

```
Met Ala Thr Ser Ala Ser Ala Gln Leu Ser Lys Ala Ile Lys Gln Met
1               5                   10                  15

Tyr Leu Glu Leu Pro Gln Gly Asp Lys Val Gln Ala Met Tyr Ile Trp
            20                  25                  30

Val Asp Gly Thr Gly Glu Gly Leu Arg Cys Lys Thr Arg Thr Leu Asp
        35                  40                  45

Ser Glu Pro Lys Thr Ile Glu Asp Leu Pro Glu Trp Asn Phe Asp Gly
    50                  55                  60

Ser Ser Thr Tyr Gln Ser Glu Gly Ser Asn Ser Asp Met Tyr Leu Ile
65                  70                  75                  80

Pro Val Ala Met Phe Arg Asp Pro Phe Arg Arg Asp Pro Asn Lys Leu
                85                  90                  95

Val Leu Cys Glu Val Leu Lys Tyr Asn Arg Lys Thr Ala Glu Thr Asn
            100                 105                 110

Leu Arg His Thr Cys Asn Gln Ile Met Asp Met Met Ala Asn Glu His
        115                 120                 125
```

```
Pro Trp Phe Gly Met Glu Gln Glu Tyr Thr Leu Leu Gly Met Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Ala Gly
            180                 185                 190

Thr Asn Ala Glu Val Met Pro Ala Gln Trp Glu Phe Gln Ile Gly Pro
        195                 200                 205

Cys Glu Gly Ile Glu Met Gly Asp His Leu Trp Ile Ala Arg Phe Ile
    210                 215                 220

Leu His Arg Ile Cys Glu Asp Phe Gly Ile Ile Val Ser Phe Asp Pro
225                 230                 235                 240

Lys Pro Ile Thr Gly Asn Trp Asn Gly Ala Gly Cys His Thr Asn Phe
                245                 250                 255

Ser Thr Lys Ser Met Arg Glu Gly Gly Leu Lys Asp Ile Glu Glu
            260                 265                 270

Ser Ile Glu Arg Leu Ser Lys Arg His Asp Tyr His Ile Arg Met Tyr
        275                 280                 285

Asp Pro Arg Gly Gly Lys Asp Asn Ala Arg Arg Leu Thr Gly Phe His
    290                 295                 300

Glu Thr Ser Ser Ile His Glu Phe Ser Ala Gly Val Ala Asn Arg Gly
305                 310                 315                 320

Ala Ser Ile Arg Ile Pro Arg Ser Val Gly Gln Glu Lys Lys Gly Tyr
                325                 330                 335

Phe Glu Asp Arg Arg Pro Ser Ala Asn Cys Asp Pro Tyr Ala Val Thr
            340                 345                 350

Glu Ala Met Ile Arg Thr Cys Leu Leu Asn Glu Thr Gly Asp Glu Pro
        355                 360                 365

Leu Glu Tyr Lys Asn
    370

<210> SEQ ID NO 33
<211> LENGTH: 572
<212> TYPE: PRT
<213> ORGANISM: Xenopus tropicalis

<400> SEQUENCE: 33

Met Asn Ala Leu Met Arg Arg Ala Cys Cys Gly Ala Leu Phe Pro Leu
1               5                   10                  15

Ser Phe Arg Leu Ala Ala Leu Ser Pro Met Lys Gly Ala Ser Asn Phe
            20                  25                  30

Ser Cys Gly Asn Val Cys Ala Ser Pro Ala Gly Cys Trp Ala Pro Pro
        35                  40                  45

Ser Gly His Asp Thr Gly Ile Lys Val Tyr Asn Ser Leu Thr Arg Arg
    50                  55                  60

Lys Asp Pro Leu Ile Leu Ala Asp Pro Thr Val Ala Thr Trp Tyr Ser
65                  70                  75                  80

Cys Gly Pro Thr Val Tyr Asp His Ala His Leu Gly His Ala Cys Ser
                85                  90                  95

Tyr Val Arg Phe Asp Ile Ile Arg Arg Ile Leu Leu Lys Val Phe Gly
            100                 105                 110

Ile Asp Thr Val Val Val Met Val Val Thr Asp Ile Asp Asp Lys Ile
```

```
            115                 120                 125
Ile Lys Arg Ala Lys Glu Leu Asn Ile Ser Pro Val Ala Leu Ala Arg
130                 135                 140

Thr Tyr Glu Gln Asp Phe Lys Gln Asp Met Thr Ala Leu Lys Val Leu
145                 150                 155                 160

Pro Pro Thr Val Tyr Met Arg Val Thr Glu Asn Ile Pro Gln Ile Ile
                165                 170                 175

Ser Phe Ile Glu His Ile Ile Ala Asn Gly Tyr Ala Tyr Ala Thr Ser
                180                 185                 190

Gln Gly Asn Val Tyr Phe Asp Val Gln Ser Ile Gly Glu Arg Tyr Gly
                195                 200                 205

Lys Phe Asn Asp Ser Phe Ser Asp Thr Ala Ser Glu Ser Ala Ser Gln
210                 215                 220

Asp Lys Arg His Ile Arg Asp Phe Ala Leu Trp Lys Thr Ser Lys Pro
225                 230                 235                 240

Glu Glu Pro Tyr Trp Ala Ser Pro Trp Gly Lys Gly Arg Pro Gly Trp
                245                 250                 255

His Ile Glu Cys Ser Thr Ile Ala Ser Ser Val Phe Gly Lys His Leu
                260                 265                 270

Asp Ile His Thr Gly Gly Ile Asp Leu Ala Phe Pro His His Glu Asn
                275                 280                 285

Glu Ile Ala Gln Cys Glu Ala Tyr His Gln Ser Thr Gln Trp Gly Asn
290                 295                 300

Tyr Phe Leu His Thr Gly His Leu His Leu Lys Gly Asn Glu Glu Lys
305                 310                 315                 320

Met Ser Lys Ser Leu Arg Asn Tyr Leu Thr Val Lys Glu Phe Leu Lys
                325                 330                 335

Ser Phe Ser Pro Asp Gln Phe Arg Met Phe Cys Leu Arg Ser Lys Tyr
                340                 345                 350

Lys Ser Ala Val Glu Tyr Ser Asn Gly Ser Met His Asp Ala Val Asn
                355                 360                 365

Thr Leu His Thr Ile Ser Ser Phe Val Asp Asp Ala Lys Ala Tyr Met
370                 375                 380

Lys Gly Gln Leu Ile Cys Gln Pro Val Gln Glu Ala Leu Leu Trp Gln
385                 390                 395                 400

Arg Leu Asn Glu Thr Lys Val Asn Val Lys Ala Ala Phe Ser Asp Asp
                405                 410                 415

Phe Asp Thr Pro Arg Ala Val Asp Ala Val Met Asp Leu Ile His His
                420                 425                 430

Gly Asn Arg Gln Leu Lys Ala Val Ser Lys Glu Ser Asn Ser Pro Arg
                435                 440                 445

Ser Ser Val Val Tyr Gly Ala Met Ile Ser Tyr Ile Glu Gln Phe Leu
450                 455                 460

Glu Ile Leu Gly Ile Ser Leu Ser Gln Asn Gln Val Ala Ala Glu Asp
465                 470                 475                 480

Arg His Ser Ala Val Leu Phe Asn Val Glu Glu Met Ile Ser Phe
                485                 490                 495

Arg Ser Lys Val Arg Asn Tyr Ala Leu Ala Ala Asp Glu Ser Pro Asn
                500                 505                 510

Ala Ile Gly Gln Glu Glu Lys Gln Gln Tyr Lys Glu Arg Arg Arg Gln
                515                 520                 525

Leu Leu Leu Glu Arg Glu Pro Leu Leu Gln Ala Cys Asp Ile Met Arg
530                 535                 540
```

```
Gln His Leu Ala Val Tyr Gly Ile Asn Val Lys Asp Arg Gly Asn Thr
545                 550                 555                 560

Ser Thr Trp Glu Leu Leu Asp Arg Lys Glu Glu Thr
                565                 570

<210> SEQ ID NO 34
<211> LENGTH: 182
<212> TYPE: PRT
<213> ORGANISM: Xenopus tropicalis

<400> SEQUENCE: 34

Met Arg His Leu Leu Leu Ser Ile Thr Phe Leu Val Tyr Thr Leu
1               5                   10                  15

Asp Ser Ala Lys Ala Tyr Gly Ala Thr Glu Thr Leu Cys Gly Gly Glu
                20                  25                  30

Leu Val Asp Thr Leu Gln Phe Val Cys Gly Asp Arg Gly Phe Tyr Phe
            35                  40                  45

Ser Arg Asn Asn Gly Arg Ser Asn Arg Arg Ala Asn Arg Gly Ile Val
        50                  55                  60

Glu Glu Cys Cys Phe Arg Ser Cys Asp Leu Glu Leu Leu Glu Thr Tyr
65                  70                  75                  80

Cys Ala Lys Pro Ala Lys Asn Glu Arg Asp Val Ser Thr Ala Pro Ser
                85                  90                  95

Thr Ala Ile Pro Pro Leu Asn Lys Gln Asp Leu Tyr His Lys His His
                100                 105                 110

His Thr Lys Ser Ser Lys Tyr Asp Ile Trp Gln Arg Lys Ser Ile His
            115                 120                 125

Arg Leu Arg Arg Gly Val Pro Ala Ile Val Arg Ala Arg Gln Tyr Arg
        130                 135                 140

Leu Leu Met Gln Gln Ala Glu Glu Ser Glu Gln Ala Leu Ser His Arg
145                 150                 155                 160

Pro Leu Thr Thr Leu Pro Ile Thr Arg Pro Leu His Leu Gln Gln Thr
                165                 170                 175

Ser Glu Pro Ser Leu Asn
            180

<210> SEQ ID NO 35
<211> LENGTH: 373
<212> TYPE: PRT
<213> ORGANISM: Gallus gallus

<400> SEQUENCE: 35

Met Ala Thr Ser Ala Ser Ser His Leu Ser Lys Ala Ile Lys His Met
1               5                   10                  15

Tyr Met Lys Leu Pro Gln Gly Glu Lys Val Gln Ala Met Tyr Ile Trp
                20                  25                  30

Ile Asp Gly Thr Gly Glu His Leu Arg Cys Lys Thr Arg Thr Leu Asp
            35                  40                  45

His Glu Pro Lys Ser Leu Glu Asp Leu Pro Glu Trp Asn Phe Asp Gly
        50                  55                  60

Ser Ser Thr Phe Gln Ala Glu Gly Ser Asn Ser Asp Met Tyr Leu Arg
65                  70                  75                  80

Pro Ala Ala Met Phe Arg Asp Pro Phe Arg Lys Asp Pro Asn Lys Leu
                85                  90                  95

Val Leu Cys Glu Val Phe Lys Tyr Asn Arg Gln Ser Ala Asp Thr Asn
                100                 105                 110
```

Leu Arg His Thr Cys Arg Arg Ile Met Asp Met Val Ser Asn Gln His
            115                 120                 125

Pro Trp Phe Gly Met Glu Gln Glu Tyr Thr Leu Leu Gly Thr Asp Gly
    130                 135                 140

His Pro Phe Gly Trp Pro Ser Asn Cys Phe Pro Gly Pro Gln Gly Pro
145                 150                 155                 160

Tyr Tyr Cys Gly Val Gly Ala Asp Lys Ala Tyr Gly Arg Asp Ile Val
                165                 170                 175

Glu Ala His Tyr Arg Ala Cys Leu Tyr Ala Gly Val Lys Ile Gly Gly
            180                 185                 190

Thr Asn Ala Glu Val Met Pro Ala Gln Trp Glu Phe Gln Val Gly Pro
        195                 200                 205

Cys Glu Gly Ile Glu Met Gly Asp His Leu Trp Ile Ala Arg Phe Ile
210                 215                 220

Leu His Arg Val Cys Glu Asp Phe Gly Val Ile Val Ser Phe Asp Pro
225                 230                 235                 240

Lys Pro Ile Pro Gly Asn Trp Asn Gly Ala Gly Cys His Thr Asn Phe
                245                 250                 255

Ser Thr Lys Asn Met Arg Glu Asp Gly Gly Leu Lys His Ile Glu Glu
            260                 265                 270

Ala Ile Glu Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Ser Ile His Glu Phe Ser Ala Gly Val Ala Asn Arg Gly
305                 310                 315                 320

Ala Ser Ile Arg Ile Pro Arg Asn Val Gly His Glu Lys Lys Gly Tyr
                325                 330                 335

Phe Glu Asp Arg Gly Pro Ser Ala Asn Cys Asp Pro Tyr Ala Val Thr
            340                 345                 350

Glu Ala Leu Val Arg Thr Cys Leu Leu Asn Glu Thr Gly Asp Glu Pro
        355                 360                 365

Phe Glu Tyr Lys Asn
    370

<210> SEQ ID NO 36
<211> LENGTH: 615
<212> TYPE: PRT
<213> ORGANISM: Gallus gallus

<400> SEQUENCE: 36

Met Lys Trp Val Thr Leu Ile Ser Phe Ile Phe Leu Phe Ser Ser Ala
1               5                   10                  15

Thr Ser Arg Asn Leu Gln Arg Phe Ala Arg Asp Ala Glu His Lys Ser
            20                  25                  30

Glu Ile Ala His Arg Tyr Asn Asp Leu Lys Glu Glu Thr Phe Lys Ala
        35                  40                  45

Val Ala Met Ile Thr Phe Ala Gln Tyr Leu Gln Arg Cys Ser Tyr Glu
    50                  55                  60

Gly Leu Ser Lys Leu Val Lys Asp Val Val Asp Leu Ala Gln Lys Cys
65                  70                  75                  80

Val Ala Asn Glu Asp Ala Pro Glu Cys Ser Lys Pro Leu Pro Ser Ile
                85                  90                  95

Ile Leu Asp Glu Ile Cys Gln Val Glu Lys Leu Arg Asp Ser Tyr Gly

```
            100                 105                 110
Ala Met Ala Asp Cys Cys Ser Lys Ala Asp Pro Glu Arg Asn Glu Cys
            115                 120                 125

Phe Leu Ser Phe Lys Val Ser Gln Pro Asp Phe Val Gln Pro Tyr Gln
            130                 135                 140

Arg Pro Ala Ser Asp Val Ile Cys Gln Glu Tyr Gln Asp Asn Arg Val
145                 150                 155                 160

Ser Phe Leu Gly His Phe Ile Tyr Ser Val Ala Arg Arg His Pro Phe
                    165                 170                 175

Leu Tyr Ala Pro Ala Ile Leu Ser Phe Ala Val Asp Phe Glu His Ala
                    180                 185                 190

Leu Gln Ser Cys Cys Lys Glu Ser Asp Val Gly Ala Cys Leu Asp Thr
                    195                 200                 205

Lys Glu Ile Val Met Arg Glu Lys Ala Lys Gly Val Ser Val Lys Gln
            210                 215                 220

Gln Tyr Phe Cys Gly Ile Leu Lys Gln Phe Gly Asp Arg Val Phe Gln
225                 230                 235                 240

Ala Arg Gln Leu Ile Tyr Leu Ser Gln Lys Tyr Pro Lys Ala Pro Phe
                    245                 250                 255

Ser Glu Val Ser Lys Phe Val His Asp Ser Ile Gly Val His Lys Glu
                    260                 265                 270

Cys Cys Glu Gly Asp Met Val Glu Cys Met Asp Asp Met Ala Arg Met
            275                 280                 285

Met Ser Asn Leu Cys Ser Gln Gln Asp Val Phe Ser Gly Lys Ile Lys
            290                 295                 300

Asp Cys Cys Glu Lys Pro Ile Val Glu Arg Ser Gln Cys Ile Met Glu
305                 310                 315                 320

Ala Glu Phe Asp Glu Lys Pro Ala Asp Leu Pro Ser Leu Val Glu Lys
                    325                 330                 335

Tyr Ile Glu Asp Lys Glu Val Cys Lys Ser Phe Glu Ala Gly His Asp
                    340                 345                 350

Ala Phe Met Ala Glu Phe Val Tyr Glu Tyr Ser Arg Arg His Pro Glu
                    355                 360                 365

Phe Ser Ile Gln Leu Ile Met Arg Ile Ala Lys Gly Tyr Glu Ser Leu
            370                 375                 380

Leu Glu Lys Cys Cys Lys Thr Asp Asn Pro Ala Glu Cys Tyr Ala Asn
385                 390                 395                 400

Ala Gln Glu Gln Leu Asn Gln His Ile Lys Glu Thr Gln Asp Val Val
                    405                 410                 415

Lys Thr Asn Cys Asp Leu Leu His Asp His Gly Glu Ala Asp Phe Leu
                    420                 425                 430

Lys Ser Ile Leu Ile Arg Tyr Thr Lys Lys Met Pro Gln Val Pro Thr
            435                 440                 445

Asp Leu Leu Leu Glu Thr Gly Lys Lys Met Thr Thr Ile Gly Thr Lys
            450                 455                 460

Cys Cys Gln Leu Pro Glu Asp Arg Arg Met Ala Cys Ser Glu Gly Tyr
465                 470                 475                 480

Leu Ser Ile Val Ile His Asp Thr Cys Arg Lys Gln Glu Thr Thr Pro
                    485                 490                 495

Ile Asn Asp Asn Val Ser Gln Cys Cys Ser Ser Ser Tyr Ala Asn Arg
                    500                 505                 510

Arg Pro Cys Phe Thr Ala Met Gly Val Asp Thr Lys Tyr Val Pro Pro
            515                 520                 525
```

```
Pro Phe Asn Pro Asp Met Phe Ser Phe Asp Glu Lys Leu Cys Ser Ala
    530                 535                 540

Pro Ala Glu Glu Arg Glu Val Gly Gln Met Lys Leu Leu Ile Asn Leu
545                 550                 555                 560

Ile Lys Arg Lys Pro Gln Met Thr Glu Glu Gln Ile Lys Thr Ile Ala
                565                 570                 575

Asp Gly Phe Thr Ala Met Val Asp Lys Cys Cys Lys Gln Ser Asp Ile
            580                 585                 590

Asn Thr Cys Phe Gly Glu Gly Ala Asn Leu Ile Val Gln Ser Arg
            595                 600                 605

Ala Thr Leu Gly Ile Gly Ala
    610                 615

<210> SEQ ID NO 37
<211> LENGTH: 153
<212> TYPE: PRT
<213> ORGANISM: Gallus gallus

<400> SEQUENCE: 37

Met Glu Lys Ile Asn Ser Leu Ser Thr Gln Leu Val Lys Cys Cys Phe
1               5                   10                  15

Cys Asp Phe Leu Lys Val Lys Met His Thr Val Ser Tyr Ile His Phe
                20                  25                  30

Phe Tyr Leu Gly Leu Cys Leu Leu Thr Leu Thr Ser Ser Ala Ala Ala
            35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Ser Lys Pro Thr Gly Tyr Gly
65                  70                  75                  80

Ser Ser Ser Arg Arg Leu His His Lys Gly Ile Val Asp Glu Cys Cys
                85                  90                  95

Phe Gln Ser Cys Asp Leu Arg Arg Leu Glu Met Tyr Cys Ala Pro Ile
                100                 105                 110

Lys Pro Pro Lys Ser Ala Arg Ser Val Arg Ala Gln Arg His Thr Asp
            115                 120                 125

Met Pro Lys Ala Gln Lys Glu Val His Leu Lys Asn Thr Ser Arg Gly
130                 135                 140

Asn Thr Gly Asn Arg Asn Tyr Arg Met
145                 150

<210> SEQ ID NO 38
<211> LENGTH: 187
<212> TYPE: PRT
<213> ORGANISM: Gallus gallus

<400> SEQUENCE: 38

Met Cys Ala Ala Arg Gln Ile Leu Leu Leu Leu Ala Phe Leu Ala
1               5                   10                  15

Tyr Ala Leu Asp Ser Ala Ala Ala Tyr Gly Thr Ala Glu Thr Leu Cys
                20                  25                  30

Gly Gly Glu Leu Val Asp Thr Leu Gln Phe Val Cys Gly Asp Arg Gly
            35                  40                  45

Phe Tyr Phe Ser Arg Pro Val Gly Arg Asn Asn Arg Arg Ile Asn Arg
    50                  55                  60

Gly Ile Val Glu Glu Cys Cys Phe Arg Ser Cys Asp Leu Ala Leu Leu
65                  70                  75                  80
```

```
Glu Thr Tyr Cys Ala Lys Ser Val Lys Ser Glu Arg Asp Leu Ser Ala
                85                  90                  95

Thr Ser Leu Ala Gly Leu Pro Ala Leu Asn Lys Glu Ser Phe Gln Lys
            100                 105                 110

Pro Ser His Ala Lys Tyr Ser Lys Tyr Asn Val Trp Gln Lys Lys Ser
        115                 120                 125

Ser Gln Arg Leu Gln Arg Glu Val Pro Gly Ile Leu Arg Ala Arg Arg
    130                 135                 140

Tyr Arg Trp Gln Ala Glu Gly Leu Gln Ala Ala Glu Glu Ala Arg Ala
145                 150                 155                 160

Met His Arg Pro Leu Ile Ser Leu Pro Ser Gln Arg Pro Pro Ala Pro
                165                 170                 175

Arg Ala Ser Pro Glu Ala Thr Gly Pro Gln Glu
            180                 185
```

<210> SEQ ID NO 39
<211> LENGTH: 3378
<212> TYPE: DNA
<213> ORGANISM: Bos taurus

<400> SEQUENCE: 39

| | | | | | | |
|---|---|---|---|---|---|---|
| atgccgcgcg | cgcccaggtg | ccgggccgtg | cgcgcccttc | tgcgggccag | ctaccggcag | 60 |
| gtgctgcccc | tggccgcctt | cgtacggcgc | ctgcggcccc | agggccaccg | gcttgtgcgg | 120 |
| cgcggggacc | cggcggcctt | ccgcgcgctg | gtggctcagt | gcttggtgtg | cgtgccctgg | 180 |
| gacgcgcagc | cgcccctgc | cgccccgtcc | ttccgccagg | tgtcctgcct | gaaggagctg | 240 |
| gtggccagag | tcgtgcagag | gctctgcgag | cgcggcgcga | ggaacgtgct | ggccttcggc | 300 |
| ttcacgctgc | tggccggggc | ccgcggcggg | ccgcccgtgg | ccttcacgac | cagcgtacgc | 360 |
| agctacctgc | ccaacacggt | aaccgacacg | ctgcgcggca | gcggcgcctg | ggggctgctg | 420 |
| ctgcaccgcg | tgggcgacga | cgtgctcacc | cacctgctgt | cgcgctgcgc | gctctacctg | 480 |
| ctggtgcccc | cgacctgcgc | ctaccaggtg | tgtgggccgc | cgctctatga | cctccgcgcc | 540 |
| gccgccgccg | ccgctcgtcg | gcccacgcgg | caagtgggcg | ggacccgggc | gggcttcgga | 600 |
| ctcccgcgcc | cggcctcgtc | gaacggcggc | cacggggagg | ccgaaggact | cctggaggcg | 660 |
| cgggcccagg | gcgcgaggcg | gcgtcgcagt | agcgcgcggg | gacgactgcc | tccagccaag | 720 |
| aggcccaggc | gcggcctgga | gcccgggcgg | gatctcgaag | ggcaggtggc | ccgcagcccg | 780 |
| ccccgcgtgg | tgacacctac | ccgagacgct | gcggaagcca | agtctcggaa | gggcgacgtg | 840 |
| cccgggccct | gccgcctctt | cccgggcggc | gagcggggtg | tcggctccgc | gtcctggcgg | 900 |
| ctgtcaccct | cggagggcga | gccgggtgcc | ggagcttgcg | ctgagaccaa | gaggttcctt | 960 |
| tactgctccg | gcggtggcga | acagctgcgc | cgctccttcc | tgctctgctc | cctgcctccc | 1020 |
| agcctggccg | gggcgcggac | actcgtggaa | accatctttc | tggactcgaa | gcccgggccg | 1080 |
| ccaggggctc | cccgccggcc | gcgccgcctg | ccgcgcgcgct | actggcagat | gcggcccctg | 1140 |
| ttccggaaac | tgcttgggaa | ccacgcgcgg | agccctatg | cgcgctgct | cagggcgcac | 1200 |
| tgcccgctgc | cggcctctgc | gccccgggcg | gggccagacc | atcagaagtg | ccctggtgtt | 1260 |
| ggggctgcc | cctctgagag | gccggccgct | gccccgagg | gcgaggcgaa | ctcagggcgc | 1320 |
| ctggtccagc | tgctccgcca | gcacagcagc | ccctggcagg | tgtacgggct | cctgcgggcc | 1380 |
| tgtcttcgcc | gctggtgcc | cgccggcctc | tggggctccc | ggcacaacga | gcggcgcttc | 1440 |
| ctgcggaacg | tgaagaagct | cctctccctg | gggaagcacg | gcaggctctc | gcagcaggag | 1500 |

```
ctcacgtgga agatgaaggt gcaggactgc gcctggctgc gcgcgagccc aggggctcgc      1560
tgcgtgcccg ccgcggagca ccgccagcgc gaggccgtcc tgggtcgctt cctgcactgg      1620
ctgatgggcg cctacgtggt ggagctgctc aggagcttct tctacgtcac agagaccacg      1680
ttccagaaga accggctctt cttcttccgg aagcgcatct ggagccagct gcagcgcctg      1740
ggcgtcagac aacacttaga ccgtgtgcgg cttcgagaac tgtcagaagc agaggtcagg      1800
cagcaccagg aggccaggcc ggctctgctg acatccaggc tccgtttcgt ccccaagccc      1860
ggcgggctgc ggcccatcgt gaacgtgggc tgtgttgagg gcgccccggc accgcccaga      1920
gacaagaagg tgcagcatct cagctcacgg gtcaagacgc tgttcgcggt gctgaactac      1980
gagcgagctc ggcggcctgg cctcctgggg gcctcggtgc tgggcatgga cgacatccac      2040
agggcctggc gggccttcgt gctgcccctg agggcccggg gccagccccc ccgctctac       2100 ttcgtcaagg tggacgtggt gggggcctac gatgccctcc cccaggataa gctggcagag      2160
gtgatcgcta acgtgctgca gccgcaggag aatacgtact gcgtgcgcca ctgcgccatg      2220
gtccggactg cgcgcgggcg catgcgcaag tccttcaaga gacacgtgtc caccttctcg      2280
gacttccagc cgtacctgag gcagctcgtg gagcatctgc aggcgatggg ctccctgagg      2340
gacgccgtgg tcatcgagca gagctgctcc ctgaacgagc tggcagcag cctcttcaac       2400 ctcttcctgc acctggtccg cagccacgtc atcaggatcg ggggcaggtc ctacatccag      2460
tgtcagggga tcccccaggg ctccatcctg tccaccctgc tctgcagctt ctgctatggg      2520
gacatggaga caagctcttt ccctggagtc cagcaggacg gggtgcttct gcgcctggtg      2580
gacgacttcc tgctggtcac cccacacctg acgcgggcca gagacttcct caggacgctg      2640
gtgcgcggtg tgcctgagta tggctgccag gtgaacctgc ggaagacggt ggtgaacttc      2700
cccgtggagc ccggggccct gggcggcgcg gcgccctgc agctgccggc ccactgcctg       2760 ttccctggt gcggcctgct gctggatacc cgcaccctgg aggtgcatgg cgaccactcc       2820
agttatgccc ggacgtccat cagagcgagt ctcaccttca cccagggctt caagcccggg      2880
aggaacatgc gtcgcaagct gttggcggtc ttgcagctca agtgccatgg gctcttcctg      2940
gacctgcagg tgaacagtct gcagacggtc ttcacaaacg tttacaagat attcctgctg      3000
caggcctaca ggttccacgc ctgcgtgctg cagctgccct tcagccagcc ggtcaggagc      3060
agccccgcgt tctttctcca ggtcatcgcc gacaccgcat cccgcggcta cgccctcctg      3120
aaagccagga acgcaggggc gtcactgggg gccaggggcg ccgccggcct gttcccgtct      3180 gaagctgcg agtggctgtg tctccacgcc ttcctgctca gctggctcg ccaccgtgtc        3240 acctacagcc gcctgctggg ggccctccgg acagcccgag cacggctgca ccggcagctc      3300
ccggggccca cacgggccgc cctggaggcg cggccgacc ccgccctgac cgcagacttc       3360
aagaccatct tggactga                                                    3378
```

<210> SEQ ID NO 40
<211> LENGTH: 3396
<212> TYPE: DNA
<213> ORGANISM: Sus scrofa

<400> SEQUENCE: 40

```
atgccgcgcg cgccccggtg ccgggccgtg cgctccctgc tccgggaccg ctacaggcag       60
gtgctgccgc tggccacctt cgtgcggcgc ctgggccctg agggccggcg gcttgttcgg      120
cgcggggacc cggcggccta ccgcgcgctg gtggcgcagt gcctggtgtg cgtgccctgg      180
```

```
gacgcgcagc cgcctcctgc ctccccgtcc ttccgccagg tgtcctgcct gaaggagctg     240
gtggccaggg tcgtgcagag gctctgcgag cgcggcgcga ggaacgtgct ggcctttggc     300
ttcgcgctgc tggacggggc tcgcggcggg ccgcccgtgg ccttcacgac cagcgtgcgc     360
agctacctgc ccaacaccgt gaccgacaca ctgcgcggga gcggcgcgtg ggggctgctg     420
ctgcgccgcg tgggcgacga cgtgctcacc cacctgttgg cgcgctgcgc gctgtacctg     480
ctggtgcccc cgagttgcgc ctaccaggtg tgcgggccgc cactctatga cctctacacc     540
gcagcggagg ctcggcccat gcgacacaag ggccagaccc cgactggcct cggactcacg     600
cgccccgttt gcaatgggga agccgggcga cccaggagc agaggcgca aggtgtgagg      660 cgacgtcggg gcagagcggg gggacatcca cttccagcca agaggcccag gcacgtcccg     720
gagcctgaac agggtcccga agggcaggcg tcccgggccc accagggcag ggcgcctggg     780
ccgagcgaca gcgacccccc cgtgatgaca cctaccagag ccgctgcgaa agccaagtct     840
cgggagggtg aggcgcccgg aacccggcac cttcccctc aagcaggcgg tgcgcggggt      900
acctgccccc catcctggtg gcagccacac ctccagggca agcccagtcc tcatgtgtgc     960
gctgccgaga ccaagcgctt cctctactgc tcggggagca aggaagggct gcgccgctcg    1020
ttcctgctct gctccctgcc gcccagcctg gcggggggccg ggaggctcgt ggaggtcatc   1080
tttctggcct caaagcccgg gcagccaggg gcgcgccgcg tgcccgcacg ctactggcgg    1140
atgaggcccc tgttccggga gctgcttaag aaccacgcgc ggtgccccta caaggcgctt    1200
ctcagggcgc actgcccgtt gcgggctgcg gcgaccctct cggggtccgg cggtcaggtg    1260
tgcgaccaca aagtgggccc cctcgctcca gagcggctgg cagcggccgc cgaggggac    1320 tcggcctcga ggcgcctagt ccagctgctc cgccagcaca gcagcccctg gcaggtgtac    1380
cgcctcctgc gggcctgtct tcaccggctg gtgcccccgg gcctctgggg ctccccgcac    1440
aacaagcggc gctttctgaa gaatgtgaag aagctcgtct ccctggggaa gcacgccagg    1500
ctctcgctgc aggagctgat gtggaagatg aaagtgcaag actgcatctg gctgcgccgg    1560
agcccggacg ctcgccatgt ccaggccgcc gagcaccgtc tgagagaggc cattctggcc    1620
aagttcctgc gctggttgat gggcacgtac gtggtcgagc tgctcaggtc gttttttat    1680 gtcacggaga ccacgtttca gaagaaccgg ctcttcttct tccggaagcg catctggagc    1740
cggctgcaga gcgcaggcat caggcaacac ttagatcgtg tgcggcttcg agaactgtcg    1800
gaagcagaga tcaggcgacg ccgggaggcc aggcccgctg tactgacctc caagctccgc    1860
ttcgtcccca aacccgacgg gctgcggccc atcgtgaaca tggcgaacgt cgtgcgagcc    1920
aggacaggcc ccggagacaa gaaggtccgg cgtctcacgg ggcaggtcaa gacgctgttt    1980
gctgtgctga actacgagcg ggcgcggcgc ccgcgcctcc tggggcctc cgtgctgggc     2040 gtgggtgaca tccacagggc ctggcgggcc tttgtgctgc ccctgcgggc ccaggacccg    2100
gcccccccgc tgtactttgt caaggtggac gtgacggggg cctacgacgc cctccctcag    2160
gacaggctgc tggaggtggt cgccaacgtg atccggcccc acgagagcac gtactgcgtg    2220
cgccagtgcg ccgtgctccg gaggaccgcc cgcgggcacg tgcgcaagtc cttccaaacc    2280
cacgtgtcca ccttcgcaga cctccagcct tacatgagac agtttgtggc acacctgcag    2340
gcaaccggcc cgctgaggga cgccgtggtc atcgagcaga gctgctctct gaacgaggcc    2400
ggcagccgtc tcctggagct tttcctgagc ctgctgcgaa accacgtcat ccggatcggg    2460
ggcaggtcct acgtccagtg tcaggggatc ccacagggct ccattctgtc cacgctgctc    2520
tgcagcctgt gctacgggga catggaaaac agactcttcc ccgggatcca gcgtgacggg    2580
```

```
gtgctcctgc gcttggtgga cgacttcctg ctggtgaccc ctcacctgac acgagccaaa    2640
gcctttctca ggaccctggt ccgcggcgtg cccgagtacg gctgcctggc caacttgcgg    2700
aagacggccg tgaacttccc tgtggaggac ggcgcccggg gcggcccggc cccactgcag    2760
ctgccggcac actgcctgtt ccctggtgc gggctgctgc tggacacccg cacgctggag    2820
gtgcactgcg actatgccag ttacgcccgg acctcgatca gagcgagtct caccttcaac    2880
cagggcttca agcccgggag gaacatgcgc cgcaagctct ggcggtctt gcggctaaag    2940 tgccacggga tccttctgga cctgcaggtg aacagtcttc cgacggtgct cgccaacgtt    3000
tacaagatct tcctgctgca ggcctacagg ttccacgcgt gtgtgctgca gctgcccttc    3060
cgtcagccgc ttgcgaggaa cccctcattt ttcctccggc ttgtctccga caccgcgtcc    3120
tgctgctact cgctcctgaa agccagaaac gcagggatgt ccctgggagc caggggcgcc    3180
tccggcccgt ttccctctga agccgcagag tggctctgcc tccacgcctt cctgctcaag    3240
ctggttcgtc accgcgttac ctacagctgt cttctgggc cgctccgggc agccagagag    3300
cgattgtgcc agcggctccc tggggccaca ctggccgccc tcgaggccgc cgccgaccca    3360
gccctgacta cagacttccg gaccatcctg gactga                              3396
```

<210> SEQ ID NO 41  
<211> LENGTH: 3297  
<212> TYPE: DNA  
<213> ORGANISM: Danio rerio

<400> SEQUENCE: 41

```
atgtctggac agtactcgac agatggcgga tttaggccgg ttttggagat tctgcgctcc      60
ttatatccgg tcgtgcagac tttggaggag ttcaccgacg gactgcaatt ccctgacggc     120
cgaaagccgg ttctgctgga ggaaacagac ggcgcgcgct ttaaaaagct cctcagtgga     180
cttattgtat gtgcgtacac gccgccgcag ctgcgcgtcc ccgcccagct cagcacccctg   240 ccggaggtct tggcgttcac tctgaaccac attaaacgta agaaactgag gaacgtcctg     300
ggcttcggtt atcaatgcag cgacgtgacg accagttcgg atcccttccg tttccatggc     360
gacgtttcgc agacggctgc ctccatcagc accagcgagg tctggaagcg tatcaaccag     420
cgtctgggca cggaggtaac gcggtacctg ctgcaggact gtgccgtttt caccaccgtc     480
ccgccatcgt gtgttctgca ggtgtgcgga gaacctgttt acgacttgct gatgccgcgc     540
tcatggtctg gctttttcct cagtaactca gataatgaac gaatcagcgg cgcgatgcgg     600
aaattccctg ctgtccagaa gacagtcgca atttccaaaa agagaacaag agataacgaa     660
aaatatattt cggtaaagcg gcggagggta aaggaaactg tgaataataa taacggaaat     720
tacagatctc tgtgttttgc aatttctaaa aagagagcga tagataatga agaaaatatt     780
tcgttaaagc gacggaggat ggaggaaact gaccaagtag cgaaaatacg taatgaaaat     840
cacgaatctc agagtttcgc aatttctaaa aagagagcga gagataatga agaaaatatt     900
tcgttaaagc gacaaaggat ggaggaaatt gaccaagtag cgaaaatacg taacgaaaat     960
catggatctc agagttggaa accagcagat cagcgtcctc ctcgaccctc gcaatgttca    1020
atacgcgttc tgagcatgct ctacaatggg cggggcatga gaacttcct gctcaacagg    1080 aagttgaaag gagtgggcgg ggccaggcgc atgcaagggg aggatcttgt ccgcatgatt    1140
ttcctccaat cagaatccaa cgacagcaaa ccgaaaaaac ttcccaaacg attcttcgca    1200
atggtgccgc tattcagtcg gctgttgcgg cagcacagga agtgtccgta tcggctgttc    1260
```

| | |
|---|---|
| ctgcagagga agtgtgcagg aaatccagac gtgaaggata tggagtctct gctgaagtca | 1320 |
| cactcgtctc catatagagt ttatctgttc gtcagggagt gtctgcgcca tattattccc | 1380 |
| cacgagctct ggggctgcca ggaaaaccag ctccacttcc tgtctaatgt aaagaacttc | 1440 |
| ctgcttctgg ggaagtttga gcgcctcacg ctggtccagc tgatgtggag gatgaaggtt | 1500 |
| caggcctgcc attggctggg gcccaagaaa cgtcagtgtg cgagcgagca ccgctaccgt | 1560 |
| gagtggatgt tgggtcagtg tatgggctgg atgttgagtg gttttgtggt cggtctggtc | 1620 |
| agagctcagt tctacatcac ggagagtatg ggccacaaac acacactgcg cttctacagg | 1680 |
| ggagatgtct ggagcagact gcaggaccag gccttcaggg ctcatctgtg taagggccag | 1740 |
| tggaggcccc tgtctccatc ccaggcgctg aaggtcccca atagtgcagt gacatcccgc | 1800 |
| atccgcttta ttcccaaaac cagcagcatg aggcccatca cacgcctcag cggcagcaga | 1860 |
| gacacactgc agtattttca gagctgtgtg cgtgtgctgc agaatgtgtt gagtgtgtgt | 1920 |
| gtgcgtgagg ccccggggcc catgggctcc accgtctggg gttggcagga cattcacaga | 1980 |
| cgcctgcaag acttcagccc tcagcagaag agctcgccac gaccgctcta cttcgtcaag | 2040 |
| gtggatgtga gcggagcgta tgacagtctc ccgcacctga agctggtgga ggtgctgaag | 2100 |
| gaagtgttgg gtccgtttgc agagcagagc ttcttcctgc gtcagtacag cagtgtgtgg | 2160 |
| agcgacccga cccgcggcct gcgcaaacgc ttctgcacca agctgagat gtcagagccg | 2220 |
| ctcaacatga aggggtttgt tgtggatgaa caggtcagcg ggcgcctgca tgacgctata | 2280 |
| ttagtggagc ggcactcgtc tgaggtcaga ggtggagacg tcttccagtt cttccagaag | 2340 |
| atgctctgca gttacgtcat ccattacgac cagcagatgt ccggcaggt gtgtgggatc | 2400 |
| ccgcagggct cttcagtgtc ttctctgctg tgtaatctgt gttacggaca catggagaaa | 2460 |
| gccctgctga aggacatcgc taaaggaggg tgtctgatga ggctgattga tgattttttg | 2520 |
| ctcattactc ctcatctgag taaagccaca gagttcctga ccactcttct gtctggagtt | 2580 |
| ccagattacg gttgccagat taaccctcag aaggtggcgg tgaacttccc cgtgtgtgtg | 2640 |
| tcctgggtaa actcgggcgt ctctgtgctg ccgtccagct gcctgttccc ctggtgcggc | 2700 |
| ttgatgatac acacacacac gctggacgtc tataaagact actcacggta tgacggccta | 2760 |
| tcactgcgct acagcctgac tcttggctcc gcccactctc catctacagt catgaagaag | 2820 |
| ctgctgtcgg tgctcagcat caaaagcacg gacatcttct tagacctcag gctgaactct | 2880 |
| gtggaggccg tttacaggag tctgtataag ctgattctgc tgcaggcgct caggtttcat | 2940 |
| gcgtgcgtga ggagtctgcc gttgggtcag agtgtgaaca gaaacccgtc gttcttcctg | 3000 |
| aagatgatct ggagaatgac tcgagtcacc aataaactcc tcacacacat taacaaaggt | 3060 |
| ctgcctgtgt gttctgtgga cagtggtggt gttctgcagt ctgaggcggt tcagcttta | 3120 |
| ttctgtttgg ccttcgagac gcttttcaga cggtttcgct cggtttacca ctgcctgatc | 3180 |
| cctgcactgc acaaacggaa gcgtgctctt cagcgtgagc tctgcgggat cactctggct | 3240 |
| cgggtccgtc aagcttcctc tcccagaatc cccctggatt tcagcatgcg ggtgtaa | 3297 |

<210> SEQ ID NO 42
<211> LENGTH: 3366
<212> TYPE: DNA
<213> ORGANISM: Oreochromis niloticus

<400> SEQUENCE: 42

| | |
|---|---|
| atgacgcggg cccttaaaag gtcaaacata gctaaatccc agtgtaaagt agctaacctc | 60 |
| cgtccaagtg ctccgaacac agtcggtatg tctgcgactg atatgtccgg tgtgctggat | 120 |

```
atccttcggt tactgtaccg gcacacgcag acactggagg agtttttcgga cagcatcgtg    180 ttcagagaag gacagaaagc agctctcatt gagcagacag atacaaaccg attcaaatct    240
ttcgttagga gtgtttttgt gtgctttgac aaggagctac agcaggtagc gagctgtaaa    300
cagatctgca gtctgcctga actactggcg tttgttctca acactctaaa aagaaaaaga    360
aaaaggaatg tcttggcaca tggctataac tttcagaccc tggctcagga ggatcgggat    420
gcagacttcc tcaaattcca aggcgacgta acacagagtg ctgcctacat ccacggcagt    480
gacctgtgga aaaagtcac aatgcgtctg ggcacagaca tcacgcaata tcttctggag    540
agctgctctg tgtttgtggc agttcctcct tcgtgtgttt tccaggtgtg cggccctcca    600
gtctatgaca gggtgtccat gaccatggcc tcgagtgggt ttttctcca gcctggagtc     660 aggaaacata atcgtaccaa gattgagagc tgtcgagggt cagtgagttt gaaacagaaa    720
cgcacagttg tgaatcctgc tgcaagcaag aagatgaaaa gaaggaataa aggagggaaa    780
aaagggaaaa gaaacggga aactggtgaa gaggaggagg tggcggtttg ttcaagaaag    840
aggcggcgag tagcgtctat agaacatcaa caggcgatcc aaccagttgg ctctgaaaag    900
gaaggacagg ttgtgcctgt ggaatcagca ccgcctgcag cttttcaaaca gcctgttgaa    960 atgccaacat tggagggcgg tcctagttgg agatcaggga ttttccccccc tttaccaccc   1020 tcgcaatgtt ttatccgcac cctgggattc ctgtatgggg gcaggggcat gcgtggcttt   1080
cttcttaaca ggaggaagaa gactgctcat ggatccagaa ggcttcaagg acaagatctg   1140
gtaagaatag tcttcttcga gggactagcg tatttgaatg gagtagagag gaagcctaaa   1200
aaactccccc agaggttctt tggcatggtc cccctgttta ggcagctctt acaacaacac   1260
aggagctgtt cctacaccaa aatactacag aggttatgtc catcaataga ggagagcaat   1320
gcaggacagg gagaactaaa ctcactctta cctcagcact gtgcaccgca cagggtttac   1380
ctgtttgtcc gggaatgcct ctcttctgtg atcccgcaag aactgtgggg ctctgatcaa   1440
aaccggctgc atttctttgc cagggtcagg actttcttgc gaagtggcaa gtttgagagg   1500
ctctcactgg ctgaactgat gtggaagata aggtgaatg actgtgattg gttgaagagg   1560
agtaaaacag gctgttttcc acccagcgag cttgcgtatc ggacacaggt cctgggtcag   1620
ttcttggctt ggcttctgga tggatatgtt acaggccttg tgagagcctg tttctatgca   1680
acagagagta ttgggcaaaa aaacgccatc aggttctaca ggcaggaagt ctgggccaaa   1740
ctgcaagact tggccttcag aggtcacctt tccaaaggcc agatggaaga gctgactcca   1800
gctcaggtgg catccctgcc caaaggcacc gtcatctccc gccttcgctt tattcccaag   1860
actgatggca tgaggcccat cacacgagtc ataggagcag atgccaaaac aaggctctac   1920
cgaggccgtg tcagggactt gctggatatg ctgcgggcct gtgtgcgtgc cactccatca   1980
ctgctggggt ccacagtgtg ggggatgact gacatccaca aggttttgtg ctctttggca   2040
ccagcgcaga aggaaaaacc acaaccccctc tattttgtta aggtggacgt gagtggagcc   2100
tatgagagtt tgccgcatga caactcata gaggtgattg gccaagccct gtcacctgtc    2160
cacgatgaac tctttaccat ccgccgctat gccaagatct gggcggactc ccacgaaggc   2220
ctgaaaaagg cctttgtcag acaggcagat ttcctggagg ataacatggg atccaccaac   2280
atgaagggct ttttgacgtc actgcagaga aaaggcaaag ttcatcacgc catcctggtt   2340
gagcagcact tttgctcaga tcttcatggc agagaggcat tgcagttctt tacccaaatg   2400
ctaactggca gtgttgttca gtatgggaaa aagacgtacc gtcagtgccg ggggattcct   2460
```

| | |
|---|---|
| cagggatcgg ttgtgtctag tctgctctgc tgcctttgct acggccacat ggagaatctc | 2520 |
| ctgtttaaag atattcctgg acacaaaggg tgtttgatga gactggtgga tgacttcctt | 2580 |
| ctgatcacac cagaccaaca tgaagcacaa gcttttctca agatcttgct ggccggagtg | 2640 |
| ccacagtatg gtctggcggt caacccgcag aaggtggttt tgaactttca ggtatcggga | 2700 |
| agcgtggcct cctgtcccga cattcgcatc ctgcccccctc actgcctctt ccctggtgt | 2760 |
| ggactgctgc tggacacca caagctgac gtctataaag actattccag ctatgctgga | 2820 |
| ctgtctctgc gctacagcct tactctgggt tcatcccact ctgcaggaca gcagatgaaa | 2880 |
| aggaaactaa tggctatcct caggctcaag tgtcatgccc tgttcttcga cttgaagact | 2940 |
| aattctcttg aagcggtcta caagaacatc tacaagctgg tgctgctgca tgcgtgcagg | 3000 |
| tttcatgtct gtgcccaaag cttgcccttt ggtcagaccg tttccaagaa ccccgtcttc | 3060 |
| tttctgcagt tgatatggga gatggcccag tactgcaaca agctcatcag acgcagcaac | 3120 |
| aaaggactga ttttaggtga taggcccag acggggatcg tgcagtacga agcagtggag | 3180 |
| ctgcttttct gtctgtgctt cttgctggtg ctgtcacaac atcgtcttct ctataaagat | 3240 |
| ctgctcgcac acttgcacaa gcgaaagcgc agtctggagc ggcgtctggg ggacctgagg | 3300 |
| ctggccaggg tgcggcaggc tgctagcccc aggactccag tcgacttctt ggccattcag | 3360 |
| acataa | 3366 |

<210> SEQ ID NO 43
<211> LENGTH: 3549
<212> TYPE: DNA
<213> ORGANISM: Oncorhynchus mykiss

<400> SEQUENCE: 43

| | |
|---|---|
| atgcccagtg gcgatatgac acgtgtgctc ggcatactcg gctctctgta tcggcacgtc | 60 |
| gagaccctgg aggagtttgc agaccatatt gtattcagag agggacagag agcggtgctc | 120 |
| atcgaaccga cagatacaac gcgcttcata tcgtttgtcc ggggagtgtt ggtctgcacg | 180 |
| gataaaaccc tacaggacgt ccccagctgc aatcagatca gcaccgtgcc tgagctgttg | 240 |
| gcgttcgtgt tgaacaacat caagaggaaa aagaaaagga atgtcctggc gcacggttac | 300 |
| ggttacacgt tccaggaccg cgacgcagac cagtttaagt ttcatggcga gatcactcag | 360 |
| agtgccatgt acatccactg cagcgactta tggaagaggg cctgccagcg cctcggcacg | 420 |
| gacatctcca gtacctcct ggagagctgt tctttgttcg tgacggtgcc gccgtcgtcc | 480 |
| gcgttccagg tgtgcggcgt gcctgtgtac gaccgcgttt ccatgtcaac gggtatctct | 540 |
| aggttccacc tgggatacaa acggaatggt actactagga acagcagagg gagaagtaag | 600 |
| gaggtcagaa atgggggatg ggaatttcag ggttctgctg ggagaaatag gagaaaggat | 660 |
| ggaggtagag acactgggaa aaggaaggga gacgaggtca gtttgggagg gaagaggaag | 720 |
| agggagaggg aggaggtgga aggagatgtg tgtttgcctg gaaaaaggag atgcactcaa | 780 |
| agagaagctc ccacagtctc cagtgggact agcgatcgta agcacagaac actggaaaca | 840 |
| aatggggtca agagaccagt ggaggtcatt tctctcacca agggacccac acagagccta | 900 |
| caggttttca atggttctag caatgtgaa caggtgtcag cagaaatgga acgtctcagg | 960 |
| aagccagtgg agaaactggc tggacccgga agaccattgg aggctgtgat ggtcaccata | 1020 |
| gcacccgctg agagctctaa acaggtctcc aacggcacag gtaatatcga gcagatgtca | 1080 |
| atgaaaacag acatagaag gccagcggct gtagtcccaa gaccagtaga agaacagtct | 1140 |
| ggacctgtat cggccaccgt ccatgtagag gggggcccta gttggagaac agggtcgttc | 1200 |

```
ccaccgcttc cccactccca gtgtttcatc cgcaccctgg gcatgctcta cggagggcgg      1260
ggcatgcgcc gcttcctact aaacaggaag aggaaaagta gggacgaggg gcccaggcgt      1320 ctgcagggc gagacttagt gagactggtc ttctttgaag gcgtggccta tctgaacgga       1380
acagaaagga agcctgagag acttcccaga agattttca ccttggtgcc tctgttttgt       1440
cagttgttac gtcgacacag gaggtgtccc tattctaaga tactgcagag ggtttgtcca      1500
gcagtgggac aggggatat ggcctccctc ctgccccagc acagtgcacc tcaccgggtg       1560
tacctctttg tcagagagtg cctcaacgcg gtggtcccct cggagttctg ggggtcggac      1620
cataaccgat tcaaattcct gtccgcagtc aggaacttcc tgtccatggg caagtttgag     1680
aggatgtcat ggctgagct gatgtggaag atgaaggtga atgactgtga ttggctgaag      1740
atcagcaaga caggccgctg cccgcccagt gagctgtcgt atcggacgcg ggtgctaggc     1800
cagctcctgg cttggctgct ggatggctat gtgctaggcc tggtgagagc tatgttctac     1860
gtcacagaga gcatgggaca gaagaacgca ctgcgcttct acagatacca ggtctgggcc      1920
aagctgcagg agctggcttt cagtggtcac ctctctaaag gtcagatgtc agagttgacc    1980
ctggcccagg tgacgtcgct ccccaaaacc actgtcccct cccgcctccg cttcatcccc      2040
aagaccgaag ggatgagacc catcacacgg gtcatagggg ctgacgccaa acaaggttg      2100 ttccagaccc gtgtgaagga gctgttagat gtgctaggtg tctgtgtacg gtcctctccc     2160
tctctcctgg gctctacagt gtgggggttg accgacatcc acagagtcct ctcttccatc     2220
acccctgctc agaaagacaa accacagcgg ctctactttg tcaaggtgga tgtgagtggg     2280
gcctatgaca gtctaccca cactcagctc ttggaggtga ttggtcaggt cctgtcacat      2340
gtgcagcaag agcttttctc ggtgcgacgc tatgccaagg tgtgggccga cacccacgag     2400
ggcctcaaga agacctttgt cagacaggca gacttcacgg aagacactgt gtcgtccacc    2460
aacatgaaag gctttgtgat gtcactgcag agagagggca agttcacgca tgccatactg     2520
gtggagcagc atttctccac agatattcat ggcaaagacg tcttggagtt cttcacccag     2580
atgctctcta gctgtgttgt ccagtttggg aagaaatcgt tccgtcagtg tcaggggatt      2640
cctcagggtt ccgcggtgtc gtctctgctg tgctgcctct gttacggcca catggagaac     2700
cttctgtttc ctaacgtcag tcggcgagga gggtgtctga tgagactggt tgacgatttc     2760
ctcctcatca ctcctgacct gagccaggca cagaccttcc tcaagaccct gatggcgggg     2820
gtaccacggt acgggtgtgt ggtgaacccc cagaaggtgg ctgttaactt ccctttgggt     2880
gagtgggggt cctgtcctgc tggggtacgc ctgctgcctt tacactgtct gttccctgg     2940 tgtggactat tgctgaatac acacaccctg gacgtccaca caactacgc cagctacgct      3000 ggcctatccc tgcgctacag cctgacgcta ggctccgccc actgcgcggg gcagcaaatg    3060
aagaggaagc tcatgtccat ccttagattc aagtgccacg ccctcttcct ggacctcaaa     3120
accaactccc tggaggctgt ctatagcaac gtctacaagt tagtgttgct gcaggcgttc    3180
aggttccatg cctgtgcaca gagtttgccg tttggtcaga aagtgggcgg aaaccactcg     3240
tacttcctca atctgatctg ggacttggcg gagtacacca accatctagt cagactctgc      3300
aacaaaggtg tgtctctagg ctgtaaggct ttaacaggta gccttcagta tgaggcagta      3360
gaactgatat actgtctggc cttcctgttg gttctgtccc gtcatcgccc cctctactac     3420
catctcctcg ctccgctacg cacacgtaag aggaagctgg aggggaagct ggagggtttg     3480
agattggccc gaatcagaca ggctgccaca cccaaaatgc ctgaagactt caaggccatc     3540
```

```
caggcctag                                                         3549

<210> SEQ ID NO 44
<211> LENGTH: 3645
<212> TYPE: DNA
<213> ORGANISM: Xenopus tropicalis

<400> SEQUENCE: 44
atgactctgt gtaccggagg agctgaacta ctgagcattt tgcacagcct ttatggccag     60
gtccttggga ttgtggaata tatcgactca ctgcatgttc ccggcggcat taaggtgcct    120
gtgctgcgag agggagaccc ggagaagttc aagtcatttg ttgcggaact gatgctgtgc    180
attccaagag gaacaaagtc gcttccgtcc cctgtctcct ttcttcagct atcaactcag    240
agagaagtag tggcgcgagt aattcagcgg atttgtgaaa agaaaagaaa aaatgttctt    300
gcttttggtt atggcttagt tgatgaaaaa agctctctga atattcgatt gactccaaat    360
atttgcagtt attttcctaa ttccacaaca acaacaatca gcacaagtat tctttgggaa    420
actctgctta ctagagtagg tgatgatgtt atgatgtatt ggctggaaca atgctcagtt    480
tttgtatttg tgccacctag ttgttgttat caaatcagtg ggcagccaat ctacacttta    540
ccctatgata gtatgtgttc atttcgatct cagtcatttt tgcatagcaa tgttttgttg    600
cagtacatta aaagaaatgc cttttcttg cggaaaaaat atctgaagcc aaaaagtgg     660
tggaaaacgg tgttaaacag caaagtagaa aaacattcaa agacttctca aatgctaaca    720
tggcaaaata aaagtccac atcagcattg cctatttgta gtgagtcatc tatgaaagtt    780
accacaaaaa tacattccaa aaggaagatg tgtactacag atatttgtga cattccaact    840
aagaaacgca gagtcaactt ggacaaagat gataaaatgg accacgtttc ctttacgtct    900
gcatgtcttt cttccttctc aaatgtgtgc cctgaagcta aagtacaagc aacggaattt    960
attacctcaa gatatggaaa aaaaacaaaa attcaatgtc caaaatcgac ttcatactca   1020
gttgatggtg aatttaatgt aactcttcaa aataatgcta atacgtttat taccaatgct   1080
tctgtcccta caatacaaag caaaacttca ttttcaaata ttttttattga aattggaaga   1140
acattgtatt caagtattag tttcaagaag ggcttctctg aaagttttat acttaacagt   1200
ttagactgta ccccttctgg gagccaaaaa ttagtggaaa ccatatttct aaacaacttt   1260
ttaactgagc aaaattttga ccagccaaaa cgggatgaaa actttagatc taaacttccc   1320
aaacgttatt ggagaatgag aaaatatttc caagaattaa tacagaacca taagaatttc   1380
ccttatctgg tatatttgaa taaacactgc cctgttaggc cttcaatggc ttgttcacac   1440
aaactggcgt tgcagaaaaa gaataaatgt aaatggata aatcaatttg tgacttaagt   1500
aatacctcag ttatgaaaaa caaaattgta aatgatgaaa agccgctaaa acatgttaca   1560
gccgaagcaa cttttttacc tcttcttaaa caacacagca gcagttggca agtgtacatg   1620
tttgttagag aatgttttaaa tagtttagtg cctgatttca tatggggctc cagtcacaac   1680
aagtgccgtt tccttagaaa tgtaaaatct tttctttttt tttctggcaa atttggcaag   1740
gtctctttat tagagcttat gtggaagatg aaagtagaag actgctcttg gattcgtcta   1800
cgaaaaagtg atcactttgt tcctgcttca gaacacttgc tacagagagag aatccttgcc   1860
aaatttatct tttggctaat ggacacctat gtcatacagt tgctgaaatc attttttttt   1920
gtcacggaaa ccatgtttca gaagaataga cttttgttct acagaaaaag aatttggaag   1980
aaacttcaaa atttaggtct aagaaaacat ctagagaagg tgaaattgcg tccattgtcc   2040
tgcgatgaac tagaaaagat gcaacaatgg aaaaacattc cactggtttc caggctcaga   2100
```

| | |
|---|---|
| ttcataccaa aaacaaatgg actacgtcca atatctagag tatccagtac tttgggtagc | 2160 |
| caacaaagca aagaaaacca agagaagaag attcaacatt ttacctctcg ggttcgaaac | 2220 |
| cttttagtg ttcttaacta tgaatggaat agaaattgca gcctaattgg ctcatctgtt | 2280 |
| tttggcatgg atgatatata caaacagtgg aaaaaatttg tgctagattt tgaaaaatcg | 2340 |
| agagctgaaa aaggcaaatt ttactttgtg aagacagatg ttaagggagc atatgatacc | 2400 |
| attccacatt caaagctcga tgaagtgatc ttaaaagtaa ttaatccaaa tgcaaatgaa | 2460 |
| gtatattgca tacgacgtta tgcctcagtt tcagtggatt caactggacg cattataaaa | 2520 |
| tctttcaaaa gacatgtatc tgcattagca gatgttcttc caaatatgaa acagtttgtt | 2580 |
| tcaaatcaac aagaaaaaaa cttgacacgt aacacaattc tagtggaaca gagccttta | 2640 |
| ttgaatgaga gctctgtcaa acttcttgct gtttttcaac aaatgatcag atcccatatt | 2700 |
| ttaagaatag aagatcgata ttacatgcag tgctgtggaa taccacaggg ttcaatgtta | 2760 |
| tctacaatcc tatgcagttt atgctatgga gacatgaaa ataaactgtt tggcggaata | 2820 |
| cagcaaaatg gggtactaat gcgattgatt gatgattttt tgtttgtaac acctcatctt | 2880 |
| aaccaggcaa aaacatttttt aaggactctg cagaaggaa ttccccaata tgggtgctcc | 2940 |
| atcagccctc aaaaaacagt ggtaaacttt cctgttgatg acatcccagc atgctctgag | 3000 |
| gtggaacaat taccagttca ctgcttgttc cggtggtgtg gtcttttgct ggacactcag | 3060 |
| actttggatg tttactatga ttattcaagc tatgcctgta cctcaatccg atcaagtatg | 3120 |
| acattttgtc acagttctgc agcaggaaaa aacatgaaac aaaaacttct aagagtcctt | 3180 |
| aaattgaagt gccacagtct ctttcttgat ttacaggtaa acagtttaag gacagtttc | 3240 |
| atcaatactt ataagatatt cttacttcaa gcttacagat tccatgcttg tgttgttcag | 3300 |
| cttccatttg gccagcgtgt aatgaataat ccacctttt ttcttactgt gatttctgat | 3360 |
| atggcaccctt gcttttacac tactttaag tccaaaaaca aagatgtcac acgtgggtac | 3420 |
| aaggatgtga gctgccagtt taactttgaa gcagtccagt ggctcagtta tcaagctttt | 3480 |
| cttactaagc ttcgcaatca caaaatatta tacaaatgtc ttattgggcc actgcagaac | 3540 |
| tgtaaaatgc agttatctag aagactttcg cagtatacta ttgatcttct aaaagctgtc | 3600 |
| acagattctt cccttcacaa agacttttca tgtataatgg attag | 3645 |

<210> SEQ ID NO 45
<211> LENGTH: 4041
<212> TYPE: DNA
<213> ORGANISM: Gallus gallus

<400> SEQUENCE: 45

| | |
|---|---|
| atggagcgcg gggctcagcc gggagtcggc gtgcggcggc tccgcaatgt agcgcgggag | 60 |
| gagcccttcg ccgcggtcct gggcgcgctg cggggctgct acgccgaggc cacgccgctg | 120 |
| gaggccttcg tccggcggct gcaggagggt ggcaccgggg aggtcgaggt gctgcgaggc | 180 |
| gacgacgctc agtgctaccg gaccttcgtg tcgcagtgcg tggtgtgcgt ccccgcggt | 240 |
| gctcgcgcca tccccggcc catctgcttc cagcagttat ccagtcagag cgaagtcatc | 300 |
| acaagaatcg ttcagaggct gtgtgaaaag aaaaagaaga catccttgc gtatggatac | 360 |
| tccttgctgg atgagaacag ttgtcacttc agagttttgc catcttcgtg tatatacagc | 420 |
| tatctgtcca atactgtaac agaaacgatt cgcatcagtg gcctctggga gatactgctg | 480 |
| agtaggatag gggacgacgt gatgatgtac ctgctggagc actgtgcact cttcatgctg | 540 |

```
gttcccccaa gtaactgtta ccaggtctgc gggcaaccaa tttatgaact tatttcgcgt    600
aacgtagggc catccccagg gtttgttaga cgacggtact caaggtttaa acataatagc    660
ttgcttgact atgtgcgaaa aaggcttgtg tttcacaggc actatctttc caagtcacag    720
tggtggaagt gcaggccgag acgtcgaggt cgtgtctcca gcaggagaaa agaaggagc     780 cataggatac aaagcctaag gtctggttat cagccttctg caaaagtgaa ctttcaagca    840
ggtaggcaga tcagcactgt tactgcacgt ctggaaaaac agagctgctc cagtttatgt    900
ttgccagcta gagcaccatc tttaaaaagg aagcgtgatg gagaacaggt tgaaatcaca    960
gctaagagag tgaaagtaat ggagaaagag atagaggaac aggcttgtag tatcgttcct   1020
gatgtaaacc aaagtagctc ccagaggcat ggaacctcct ggcatgtagc accacgtgct   1080
gtaggtctta ttaaagaaca ttacatttct gaaagaagta acagtgagat gtctggtcct   1140
tctgtagttc gcagatctca ccctgggaag aggcctgtgg cagacaaaag ctcttttcca   1200
caaggagttc agggtaacaa acgcataaag accggtgcag aaaaacgagc agaatccaat   1260 agaagggca tagagatgta tataaaccca atccataaac ccaatagaag ggcatagag    1320 aggcgtataa atccaaccca caaacctgag ttgaattctg tacaaactga accaatggaa   1380
ggtgcttctt caggggacag aaagcaggaa atccccccag ctcatttggc aaagcagtta   1440
ccaaatacat tgtcgcgctc tacagtgtac tttgagaaga aatttcttct gtattcccgc   1500
agttaccaag aatattttcc taaatcgttc atactgagcc gcctgcaggg ttgtcaggca   1560
ggtggaaggc ggcttataga aactatattc ttaagccaaa acccattaaa ggaacagcag   1620
aaccaaagcc taccacagca aaagtggcga agaagaggt tgcccaaacg ctactggcaa    1680
atgagagaga tatttcagaa gctggtaaag aaccatgaga agtgcccta tttagttttc    1740 ttgaggaaaa attgccctgt tttgctttct gaagcatgtt tgaaaaagac ggagctgacc   1800
ttgcaggcgg ctctgcctgg ggaagcaaag gttcacaagc acacagaaca tgggaaagag   1860
tccactgagg gtactgcacc gaacagcttc ctcgctcctc cctcagtgct agcgtgtggg   1920
cagccagaga gaggggaaca gcaccctgca gaggggagtg atccgctcct cagggagctg   1980
ctcaggcagc acagcagcca ctggcaggtg tatggctttg tgagggagtg cctggagcgg   2040
gtgatccctg ctgagctgtg gggttcaagc cataacaaat gccggttctt taaaaacgtg   2100
aaagcattca tttccatggg gaagtatgct aagctttcat tgcagcagct gatgtggaag   2160
atgagagtga atgactgcgt atggcttcgt ctggccaaag gtaatcactc tgttcctgcc   2220
tatgaacatt gttaccgtga agaaattctg gcaaaattcc tatactggct gatggattcc   2280
tatgttatcg agttgctcaa atcatttttc tatatcaccg agaccatgtt ccagaaaaac   2340 atgctttct actaccgaaa gtttatctgg ggcaagttac agaacattgg aattagagac   2400
cattttgcca agtacatct acgtgccttg tcttcagagg agatggaagt gatccgtcaa   2460
aaaaagtatt ttcctattgc atcaaggctc cggttcattc ctaaaatgaa tggtttaaga   2520
cccgtagtaa gactaagccg tgttgttgaa ggacagaaac tcagcaagga aagcagagaa   2580
aagaagatac agcgctataa cactcagcta aaaaatctat ttagtgtttt aaactatgaa   2640
cgaactgtaa acaccagtat cattggctct tcagtattcg ggagagatga tatctacagg   2700
aagtggaagg agtttgttac aaaggttttt gaatcaggtg gtgaaatgcc tcatttctac   2760
tttgtaaagg gtgatgtatc cagagctttt gataccattc ctcacaagaa acttgtggaa   2820
gtgatatcac aggtcttgaa acctgagagc caaactgtct atggaataag gtggtatgca   2880
gtgattatga ttaccccaac tggaaaagcc aggaaactct ataagagaca tgtttctact   2940
```

```
ttcgaggatt ttattccaga catgaagcag tttgtgtcca agcttcaaga gagaacttca    3000
ttacgaaatg caatagtagt tgaacagtgc ttaacttta atgagaacag ttccaccctg    3060
tttactttct ttcttcaaat gttacataat aacatcctgg agattgggca caggtactat    3120
atacagtgct ctggaatccc acagggctcc attttgtcaa ccttactttg cagcttatgc    3180
tacggagaca tggaaaacaa attactctgt gggatccaga aggatggagt cctaatacgt    3240
cttattgatg actttttgct ggttacgcca catttaatgc aggcaagaac ttttctaagg    3300
actatagcag caggtattcc tgagtatggc ttttttaataa atgccaagaa gactgtggtg    3360
aattttcctg ttgatgatat cccgggatgt tccaagttca acatctgcc agattgtcgt    3420 ttgatctcat ggtgtggttt attattggat gtgcagacac ttgaggttta ttgtgattac    3480
tccagttatg cctttacttc tatcagatca agtctttcct tcaattcaag tagaatagct    3540
ggaaaaaaca tgaaatgcaa attgactgca gtcctcaaac tgaaatgcca tcctttactt    3600
cttgacttaa agatcaacag ccttcagaca gttctaatta acatctacaa gatatttta    3660 cttcaggctt acaggttcca tgcctgtgtt cttcagcttc cattcaacca gaaagttagg    3720
aataatcctg atttcttcct aaggatcatc tctgatactg cttcatgctg ctattttatc    3780
ctgaaagcta aaaatccagg agtttcttta ggtagcaaag atgcatctgg catgttccct    3840
tttgaggcag cagaatggct gtgctaccat gccttcattg tcaaactgtc caaccacaaa    3900
gttatttaca aatgcttact taagccccctt aaagtctata agatgcatct gtttgggaag    3960
atcccaaggg atactatgga actgctgaag acggtgacgg aaccatcgct ttgtcaagat    4020
ttcaaaacta tactggacta a                                              4041

<210> SEQ ID NO 46
<211> LENGTH: 3804
<212> TYPE: DNA
<213> ORGANISM: Meleagris gallopavo

<400> SEQUENCE: 46
atgtctgggg ctcggggggct cgtctggtgc gacgagcgag cgtggctgtt atccagtcag      60
agcgaagtca tcacaagaat cgttcagaga ctatgtgaaa agaaaaagaa gaacatcctt     120
gcgtatggat actccttgct ggatgaaaac agttgtcact tcaggatttt gccatcttcg     180
tgcatataca gctatctgcc caatactgta acagaacga ttcgcatcag tggcctctgg      240
gagatactgc tgagcaggat aggggacgat gtgatgatgt acctgctgga gcactgtgca     300
ctcttcatgc tggttccccc aagtaactgt taccaggtct gcgggcaacc aatttatgaa     360
cttatttcgc gtaacatagg gccgtcccca gggttcgtta gacgacgata ttcaaggttt     420
aaacataata acttgcttaa ctatgtgcga aaaagacttg tgtttcatag cactatctt      480 tccagtcac agtggtggaa gtgcgggccg agacgtcaag gtcgtgtctc cagcagaaga    540 aaagaagga cccataggat acaaagccca aggtctggtt accagtcttc tgcaaaagtg     600
aactttcaag caggcatgcg gatcagcaca gttactgcac atctggaaaa acagaactgc     660
tccagtttat gtttgccagc tagaacacca tcttaaaaaa ggaagcgtga tggagaacag    720
gttgaaacca cagctaagag agtgaaagta atggagagag ggaacaggc ttgtagtatc      780 gttcctgatg taaatcgaag tagctcccgg aggcatggag tttggcatgt agcaccacgt    840
gctgtaggtc ttattaaaga acgttacgtt tctgaaagaa gttacagtga gatgtctggt     900
ccttctgtag ttcacagatc tcaccctggg aagaggcctg tagcagacaa aagctctttt    960
```

-continued

```
ccaagaggag ttcagggtaa caaacacata aagaccggtg cagaaaaacg agcagaatcc    1020
aataaaaggg gcatagagat gtatataaac ccaatctgta aacccaatag aagggggtata    1080 gagaggcata taaatccaac ccataaacct gggttgaatt ctgtacaaac tgaaccaatg    1140
gaaagtgctt cttcgggga cagaaagcag gaaaatcccc cagctcattt ggcaaagcag    1200
ttaccaaata cattcttgcg ctctgcagtg tactttgaga agaaatttct tctgtattcc    1260
cgtagttacc aagaatattt tcctaaatcg ttcatactga gccgcctgca gggttgtcag    1320
gcaggtggaa ggcagcttat agaaactata tttttaagcc aaaacccatt aaaggaaaag    1380
cagaaccaaa gcctaaaaca gcaaagtgg agaaagaaga ggttgcccaa acgctactgg    1440
caaatgagag agatatttca gaagctgtta aaaaaccacg agaagtgccc ttatttagtt    1500
ttcttgagaa aaaattgccc tgttttgctt tctgaagcat gtttgaaaaa aacgagctg    1560 accttgcagg cagctctgcc tggggaagca aaggttcaca agcacacaga acatgggaa    1620 gagaccactg agggtactgc accgaacagc ttctacactc ctccctcaat gccattgtgt    1680
gggcagacag agagagagga gcagcacctt gcagagggga gtgatccgct cctcaggag    1740 ctgctcaggc agcacagcag ccactggcag gtgtatggct ttgtgaggga gtgcctggag    1800
cgggtgattc ctgccgagct gtggggttca agccataaca aatgccggtt ctttaaaaac    1860
gtgaaagcat tcatttccat ggggaagtat gctaagcttt cattgcagca gctgatgtgg    1920
aagatgagag tgaatgactg cgtatggctt cgtctggcca aagtaatca ttctgttcct    1980 gcctatgaac attgttaccg tgaagaaatt ttggcaaaat tcctatactg gctgatggat    2040
tcctatgtta tcgagttgct caaatcattt ttctatatca ccgagaccat gttccagaaa    2100
aacatgcttt tctactaccg aaagtttatc tggggcaagt tacagaacat tggaattaga    2160
aaccattttg ccaaagtaca tctacgtgct ttatcttcag aggagatgga agtgatccat    2220 caaaaaagt attttcctat tgcatcaagg ctccggttca ttcctaaaat caatggttta    2280
agacccgtag taagactaag ccgtgttgtt aaggacaga aactcagcaa ggaaagcaga    2340
gaaaagaaga tacagcgcta taacactcag ctaaaaaatc tatttagtgt gttaaattat    2400
gaacgaactg taaacaccag tatcattggc tcttcagtat tcgggagaga tgatatctac    2460
aggaagtgga aggagtttgt tacaaaggtt tttgaatcag gtggtgaaat gcctcatttc    2520
tactttgtga agggtgatgt gtccagagct tttgatacta ttcctcacaa gaaacttgtg    2580
gaagtgatct cacaggtctt gaaacctgag agccaaactg tatatggaat aaggtggtat    2640
gctgtgatta tgattacccc aactggaaaa gccaggaagc tctataagag acacgtttct    2700
acttttgagg attttattcc agacatgaag cagtttgtgt ccaagcttca agagagaact    2760
tcattacgaa atgcaatagt agttgaacag tgcttaactt ttaatgagaa cagttccacc    2820
ctgtttactt tctttcttca aatgttacat aataacatcc tggagattgg gcacaggtac    2880
tatatacagt gctctggaat cccacagggc tccattttgt caaccttact ttgcagctta    2940
tgctatggag acatggaaaa caaattactt tgtggaatcc agaaggatgg aatcctaata    3000
cgtcttattg atgactttt gctggttaca ccacatttaa tgcaggcaaa aactttttcta    3060 aggactatag cagcaggtat tcctgagtat ggcttttttaa taaatgccaa gaagacagtg    3120
gtgaattttc ctgttgatga tattccggga tgttctaagt tcaaacagct gccagattgt    3180
cgtttgatct catggtgcgg tttattactg gatatgcaga cacttgaggt ttattgtgat    3240
tactccagtt atgcctttac ttctatcaga tcaagtcttt ccttcaattc aagtagaata    3300
gctggaaaaa acatgaaatg caaattgact gcagtcctca aactgaaatg ccatccttta    3360
```

| | |
|---|---|
| tttcttgact taaagatcaa cagccttaaa acagttttaa ttaacatcta caagatattt | 3420 |
| ttacttcagg cttacagatt ccatgcctgt gttcttcagc ttccattcaa ccagaaagtt | 3480 |
| aggaataatc cttatttctt tgtaaggatc atctctgata ctgcttcatg ctgctatttt | 3540 |
| atcctgaaag ctaaaaatcc aggggtttgt ttaggttgca aagatgcatc tggcatgttc | 3600 |
| ccttttgagg cagcagaatg gctctgctac catgctttca ttgtcaaact gtccaaccac | 3660 |
| aaagttattt acaaatgctt acttaagccc cttaaagtct ataagatgca tctgtttggg | 3720 |
| aagataccaa gggatactat ggtactgctg aagacagtga cggaaccatc tctttgtcaa | 3780 |
| gatttcaaaa ctatactgga ctaa | 3804 |

<210> SEQ ID NO 47
<211> LENGTH: 3468
<212> TYPE: DNA
<213> ORGANISM: Anas platyrhynchos

<400> SEQUENCE: 47

| | |
|---|---|
| atgcagaggc tgtgtgggaa aaagaagaag aacatcctca cgtatggata ctccttgctg | 60 |
| gatgaaaaca gttctcactt ccaaatcatg ccgctctcaa acgtgtacag ctacctgccc | 120 |
| aacaccgcaa cagaaaccat gcgtatcagt ggcctctggg aaacgctgct gagcaggata | 180 |
| ggggatgacg tgatgatgta tttattggaa cactgtgcga tctttatgct ggttcccccct | 240 |
| agtaactgtt accaagtctg tgggcaacca atttatgaac ttatttcgca aaatgtagaa | 300 |
| tcagccccag cgtttgttaa acaacggctt caaagcaca aacgtagtag cttgcttaag | 360 |
| tatacccaga aaaggctaac gtttcacaga cagtatcttt caaagtcacg tcagtcgaaa | 420 |
| cgcaggcaaa gacttgaagc taatgtctcc agcgtgagaa ataaaaccag caataatata | 480 |
| caaagcctag ggtccgctgc tctggaaaaa cagagtagct ccaatgcagg tttgtcagct | 540 |
| acagcaccgt ccttaaaaag gaagcttgct agggagcaac tggaagtcac ggctaagaga | 600 |
| gcaagattag aagagaaaga gagggaggaa caggcatgta atactgctcc taatgtaaac | 660 |
| cagagcattc ccaagaggta tggaaccggc tgtgtagcat cacgttctgt aagtctgact | 720 |
| aaagaaaaaa acatttctca aagaagtaac agtgatatgc ctcgtccttc tttagttcac | 780 |
| aattctcatc gcgggaagaa gtctgtggca gacaaaagct ctttcctgca aggagctgag | 840 |
| agtaacagac atttaaagcc cagcattgaa atgcaagcag atccagcag gaagggagtg | 900 |
| gagacacgca ggcctatacc tcggttggat tgggtaccaa tcgaaccggc ggaaagtagt | 960 |
| tcttcaggac acaaaaagca ggaaggtccc ctagctcatc tggcagagga ggtaccaaat | 1020 |
| agggttttgc catctacaat atacattgac aggaagtttc tgtattctcg cagatactgg | 1080 |
| ggggagcgtt tcccgaaatc cttcctattg aatcgcctga agggtagcca ggcaggtgta | 1140 |
| aagcggctaa tagaaacgat attcttaagc caaaatccgt ttgggcaaaa gtgcaaccaa | 1200 |
| ggtctgccac agaaaaaacg gagaaagaag aagcttccca aacgcttctg gagaatgaga | 1260 |
| agtatatttc aacaactctt aaagaatcat ggaaagttcc cttacgtagc tttcttgaga | 1320 |
| caaaattgcc ctcttcggat atctgacacc attttgggaa aagccaagct gctcagtcgg | 1380 |
| gcacctttgc ctgggcaagc agaggctcgc aagcaagcag aacagcttgg gaaggagcct | 1440 |
| gctgagcgtg tggcaagcag cagatgtgaa tctggtcaca ccaacgtgcc cagcagcgta | 1500 |
| cgcgctcctc tcgcagcatc tgcgtgtggg gagccggggg gtgaggagca gatccctgca | 1560 |
| gaggcgtctg attcagtcct cagggagctt ctcaaggagc actgcagcca cttccaggtg | 1620 |

```
tacctctttg tgagggagtg cgtggagagg gtgatcccca ccgagctctg gggttcaaac    1680
cataacaagc gccggttctt caagaacgtg aaagcgttca tttccatggg gaagtacgct    1740
aagctttcct tgcaggtgtt gatgtggaag atgagagtaa atgactgcat gtggcttcgt    1800
ctggccaaag gtaatcactt tgttcctgcc tctgaacacc tttaccgtga agaaattttg    1860
gctaaattcc tatactggct gatggatacg tatgttgttc agttgctcag atcatttttc    1920
tatgtcaccg agaccatgtt ccagaaaaac atgctcttct actaccgaaa gtgtatttgg    1980
ggcaagttac aggacattgg aattagaaag cattttttcca aagtgaagct acgtccttta   2040
actgcagagg agatggaagc gatccatcaa aaaaaatacc ttcctatggc gtcaaagctc    2100
cgtttcattc ccaaagtcac tggactaaga cccatcgtca gaatgagcgg tgttgttgaa    2160
gcacaaacgt tgagcaagga aagcagagca agaaggccg atgtgtccag ggcttttgat     2220
agcattcctc acaataaact tgtggaagtg atttcacagg tcttaaaacc cgagaaaaaa    2280
actgtctact gcatacggcg ctatgcagtg gttatgatca ctggaagtgg aaaaaccagg    2340
aagttatata agagacatgt ttctactttc aaggatttta tgccagacat gaagcagttt    2400
gtgtcccggc ttcatgagag tacctcattg cgagatgcaa taatagttga acagagccta    2460
actttcaatg agacaagtgc cagtctattt aattttttc ttcaaatgct aaataataac     2520
atcctggaaa ttgagcgcag ttactactta cagtgctctg gaattccaca gggctcccctt   2580
ttgtcaacct tgctttgcag cttgtgctat ggagacatga aaaacaaatt attcagtggg    2640
gtacagaagg atggagtcct gatccgtctc attgatgact ttttgctggt tacaccacat    2700
ttaatgcatg caagaacttt tctaaggact ctagcaatgg gcattcctga gtatggctttt   2760
ttgataaacc ccaaaagac agtggtgaat ttttctgctg acgatatccc agaatgttct     2820
gaatttaaac agctgccaaa ctgtcgtttg atcccatggt gtggcttatt attggatcaa    2880
cagacacttg aggtttactg cgattactcc agctattcct gtacttctat cagatcaagt    2940
cttttccttca attcaaacag aacagctggg aaaaacatga acacaaatt gcttgcagtc    3000
cttaaactga aatgccatgg cttgtttctc gatttacaga tcaatagcct taaaacagtt    3060
ttcattaacg tctacaagat atttttactt caggcttaca ggttccatgc ctgtgttatt    3120
caacttccat tcaaccagaa agttaggaac aatcctgatt tcttcctcag agtcatcgct    3180
gagaatgcat cgtgctgcta ttctatgcta aaagctaaaa atccagggtt tactttaggt    3240
aacagaggtg catctggcat gtttccttct gaggcagcag agtggctctg ctatcatgcc    3300
ttcactgtca aactgtcaaa ccacaaagtt gtttacaaat gcttgctgaa gcccctgaag    3360
ttctgtatga tgcagctatt ccggaagatc ccaaaggata ctaaggcact actgaagaca    3420
gtgacagaac catctatttg taaagatttc aaatctatcc tggactga                 3468
```

<210> SEQ ID NO 48
<211> LENGTH: 1125
<212> TYPE: PRT
<213> ORGANISM: Bos taurus

<400> SEQUENCE: 48

```
Met Pro Arg Ala Pro Arg Cys Arg Ala Val Arg Ala Leu Leu Arg Ala
1               5                   10                  15

Ser Tyr Arg Gln Val Leu Pro Leu Ala Ala Phe Val Arg Arg Leu Arg
                20                  25                  30

Pro Gln Gly His Arg Leu Val Arg Arg Gly Asp Pro Ala Ala Phe Arg
            35                  40                  45
```

```
Ala Leu Val Ala Gln Cys Leu Val Cys Val Pro Trp Asp Ala Gln Pro
 50                  55                  60

Pro Pro Ala Ala Pro Ser Phe Arg Gln Val Ser Cys Leu Lys Glu Leu
 65                  70                  75                  80

Val Ala Arg Val Val Gln Arg Leu Cys Glu Arg Gly Ala Arg Asn Val
                 85                  90                  95

Leu Ala Phe Gly Phe Thr Leu Leu Ala Gly Ala Arg Gly Gly Pro Pro
            100                 105                 110

Val Ala Phe Thr Thr Ser Val Arg Ser Tyr Leu Pro Asn Thr Val Thr
            115                 120                 125

Asp Thr Leu Arg Gly Ser Gly Ala Trp Gly Leu Leu Leu His Arg Val
130                 135                 140

Gly Asp Asp Val Leu Thr His Leu Leu Ser Arg Cys Ala Leu Tyr Leu
145                 150                 155                 160

Leu Val Pro Pro Thr Cys Ala Tyr Gln Val Cys Gly Pro Pro Leu Tyr
                165                 170                 175

Asp Leu Arg Ala Ala Ala Ala Ala Arg Arg Pro Thr Arg Gln Val
            180                 185                 190

Gly Gly Thr Arg Ala Gly Phe Gly Leu Pro Arg Pro Ala Ser Ser Asn
            195                 200                 205

Gly Gly His Gly Glu Ala Glu Gly Leu Leu Glu Ala Arg Ala Gln Gly
            210                 215                 220

Ala Arg Arg Arg Arg Ser Ser Ala Arg Gly Arg Leu Pro Pro Ala Lys
225                 230                 235                 240

Arg Pro Arg Arg Gly Leu Glu Pro Gly Arg Asp Leu Glu Gly Gln Val
                245                 250                 255

Ala Arg Ser Pro Pro Arg Val Val Thr Pro Thr Arg Asp Ala Ala Glu
            260                 265                 270

Ala Lys Ser Arg Lys Gly Asp Val Pro Gly Pro Cys Arg Leu Phe Pro
            275                 280                 285

Gly Gly Glu Arg Gly Val Gly Ser Ala Ser Trp Arg Leu Ser Pro Ser
290                 295                 300

Glu Gly Glu Pro Gly Ala Gly Ala Cys Ala Glu Thr Lys Arg Phe Leu
305                 310                 315                 320

Tyr Cys Ser Gly Gly Gly Glu Gln Leu Arg Arg Ser Phe Leu Leu Cys
                325                 330                 335

Ser Leu Pro Pro Ser Leu Ala Gly Ala Arg Thr Leu Val Glu Thr Ile
            340                 345                 350

Phe Leu Asp Ser Lys Pro Gly Pro Gly Ala Pro Arg Arg Pro Arg
            355                 360                 365

Arg Leu Pro Ala Arg Tyr Trp Gln Met Arg Pro Leu Phe Arg Lys Leu
370                 375                 380

Leu Gly Asn His Ala Arg Ser Pro Tyr Gly Ala Leu Leu Arg Ala His
385                 390                 395                 400

Cys Pro Leu Pro Ala Ser Ala Pro Arg Ala Gly Pro Asp His Gln Lys
                405                 410                 415

Cys Pro Gly Val Gly Gly Cys Pro Ser Glu Arg Pro Ala Ala Pro
            420                 425                 430

Glu Gly Glu Ala Asn Ser Gly Arg Leu Val Gln Leu Leu Arg Gln His
            435                 440                 445

Ser Ser Pro Trp Gln Val Tyr Gly Leu Leu Arg Ala Cys Leu Arg Arg
450                 455                 460

Leu Val Pro Ala Gly Leu Trp Gly Ser Arg His Asn Glu Arg Arg Phe
```

```
                465                 470                 475                 480
        Leu Arg Asn Val Lys Lys Leu Leu Ser Leu Gly Lys His Gly Arg Leu
                            485                 490                 495

Ser Gln Gln Glu Leu Thr Trp Lys Met Lys Val Gln Asp Cys Ala Trp
                    500                 505                 510

Leu Arg Ala Ser Pro Gly Ala Arg Cys Val Pro Ala Glu His Arg
                    515                 520                 525

Gln Arg Glu Ala Val Leu Gly Arg Phe Leu His Trp Leu Met Gly Ala
                    530                 535                 540

Tyr Val Val Glu Leu Leu Arg Ser Phe Phe Tyr Val Thr Glu Thr Thr
        545                 550                 555                 560

Phe Gln Lys Asn Arg Leu Phe Phe Phe Arg Lys Arg Ile Trp Ser Gln
                            565                 570                 575

Leu Gln Arg Leu Gly Val Arg Gln His Leu Asp Arg Val Arg Leu Arg
                    580                 585                 590

Glu Leu Ser Glu Ala Glu Val Arg Gln His Gln Glu Ala Arg Pro Ala
                    595                 600                 605

Leu Leu Thr Ser Arg Leu Arg Phe Val Pro Lys Pro Gly Gly Leu Arg
                    610                 615                 620

Pro Ile Val Asn Val Gly Cys Val Glu Gly Ala Pro Ala Pro Pro Arg
        625                 630                 635                 640

Asp Lys Lys Val Gln His Leu Ser Ser Arg Val Lys Thr Leu Phe Ala
                            645                 650                 655

Val Leu Asn Tyr Glu Arg Ala Arg Arg Pro Gly Leu Leu Gly Ala Ser
                    660                 665                 670

Val Leu Gly Met Asp Asp Ile His Arg Ala Trp Arg Ala Phe Val Leu
                    675                 680                 685

Pro Leu Arg Ala Arg Gly Pro Ala Pro Leu Tyr Phe Val Lys Val
                    690                 695                 700

Asp Val Val Gly Ala Tyr Asp Ala Leu Pro Gln Asp Lys Leu Ala Glu
        705                 710                 715                 720

Val Ile Ala Asn Val Leu Gln Pro Gln Glu Asn Thr Tyr Cys Val Arg
                            725                 730                 735

His Cys Ala Met Val Arg Thr Ala Arg Gly Arg Met Arg Lys Ser Phe
                    740                 745                 750

Lys Arg His Val Ser Thr Phe Ser Asp Phe Gln Pro Tyr Leu Arg Gln
                    755                 760                 765

Leu Val Glu His Leu Gln Ala Met Gly Ser Leu Arg Asp Ala Val Val
                    770                 775                 780

Ile Glu Gln Ser Cys Ser Leu Asn Glu Pro Gly Ser Ser Leu Phe Asn
        785                 790                 795                 800

Leu Phe Leu His Leu Val Arg Ser His Val Ile Arg Ile Gly Gly Arg
                            805                 810                 815

Ser Tyr Ile Gln Cys Gln Gly Ile Pro Gln Gly Ser Ile Leu Ser Thr
                    820                 825                 830

Leu Leu Cys Ser Phe Cys Tyr Gly Asp Met Glu Asn Lys Leu Phe Pro
                    835                 840                 845

Gly Val Gln Gln Asp Gly Val Leu Leu Arg Leu Val Asp Asp Phe Leu
                    850                 855                 860

Leu Val Thr Pro His Leu Thr Arg Ala Arg Asp Phe Leu Arg Thr Leu
        865                 870                 875                 880

Val Arg Gly Val Pro Glu Tyr Gly Cys Gln Val Asn Leu Arg Lys Thr
                            885                 890                 895
```

-continued

```
Val Val Asn Phe Pro Val Glu Pro Gly Ala Leu Gly Ala Ala Pro
            900                 905                 910

Leu Gln Leu Pro Ala His Cys Leu Phe Pro Trp Cys Gly Leu Leu Leu
            915                 920                 925

Asp Thr Arg Thr Leu Glu Val His Gly Asp His Ser Ser Tyr Ala Arg
            930                 935                 940

Thr Ser Ile Arg Ala Ser Leu Thr Phe Thr Gln Gly Phe Lys Pro Gly
945                 950                 955                 960

Arg Asn Met Arg Arg Lys Leu Ala Val Leu Gln Leu Lys Cys His
                965                 970                 975

Gly Leu Phe Leu Asp Leu Gln Val Asn Ser Leu Gln Thr Val Phe Thr
            980                 985                 990

Asn Val Tyr Lys Ile Phe Leu Leu Gln Ala Tyr Arg Phe His Ala Cys
            995                 1000                1005

Val Leu Gln Leu Pro Phe Ser Gln Pro Val Arg Ser Ser Pro Ala
        1010                1015                1020

Phe Phe Leu Gln Val Ile Ala Asp Thr Ala Ser Arg Gly Tyr Ala
        1025                1030                1035

Leu Leu Lys Ala Arg Asn Ala Gly Ala Ser Leu Gly Ala Arg Gly
        1040                1045                1050

Ala Ala Gly Leu Phe Pro Ser Glu Ala Ala Gln Trp Leu Cys Leu
        1055                1060                1065

His Ala Phe Leu Leu Lys Leu Ala Arg His Arg Val Thr Tyr Ser
        1070                1075                1080

Arg Leu Leu Gly Ala Leu Arg Thr Ala Arg Ala Arg Leu His Arg
        1085                1090                1095

Gln Leu Pro Gly Pro Thr Arg Ala Ala Leu Glu Ala Ala Ala Asp
        1100                1105                1110

Pro Ala Leu Thr Ala Asp Phe Lys Thr Ile Leu Asp
        1115                1120                1125

<210> SEQ ID NO 49
<211> LENGTH: 1131
<212> TYPE: PRT
<213> ORGANISM: Sus scrofa

<400> SEQUENCE: 49

Met Pro Arg Ala Pro Arg Cys Arg Ala Val Arg Ser Leu Leu Arg Asp
1               5                   10                  15

Arg Tyr Arg Gln Val Leu Pro Leu Ala Thr Phe Val Arg Arg Leu Gly
            20                  25                  30

Pro Glu Gly Arg Arg Leu Val Arg Arg Gly Asp Pro Ala Ala Tyr Arg
        35                  40                  45

Ala Leu Val Ala Gln Cys Leu Val Cys Val Pro Trp Asp Ala Gln Pro
    50                  55                  60

Pro Pro Ala Ser Pro Ser Phe Arg Gln Val Ser Cys Leu Lys Glu Leu
65                  70                  75                  80

Val Ala Arg Val Val Gln Arg Leu Cys Glu Arg Gly Ala Arg Asn Val
                85                  90                  95

Leu Ala Phe Gly Phe Ala Leu Leu Asp Gly Ala Arg Gly Gly Pro Pro
            100                 105                 110

Val Ala Phe Thr Thr Ser Val Arg Ser Tyr Leu Pro Asn Thr Val Thr
        115                 120                 125

Asp Thr Leu Arg Gly Ser Gly Ala Trp Gly Leu Leu Leu Arg Arg Val
```

```
            130                 135                 140
Gly Asp Asp Val Leu Thr His Leu Leu Ala Arg Cys Ala Leu Tyr Leu
145                 150                 155                 160

Leu Val Pro Pro Ser Cys Ala Tyr Gln Val Cys Gly Pro Pro Leu Tyr
                165                 170                 175

Asp Leu Tyr Thr Ala Ala Glu Ala Arg Pro Met Arg His Lys Gly Gln
            180                 185                 190

Thr Pro Thr Gly Leu Gly Leu Thr Arg Pro Val Cys Asn Gly Glu Ala
            195                 200                 205

Gly Arg Pro Gln Glu Gln Arg Ala Gln Gly Val Arg Arg Arg Gly
210                 215                 220

Arg Ala Gly Gly His Pro Leu Pro Ala Lys Arg Pro Arg His Val Pro
225                 230                 235                 240

Glu Pro Glu Gln Gly Pro Glu Gly Gln Ala Ser Arg Ala His Gln Gly
                245                 250                 255

Arg Ala Pro Gly Pro Ser Asp Ser Asp Pro Val Met Thr Pro Thr
            260                 265                 270

Arg Ala Ala Lys Ala Lys Ser Arg Glu Gly Glu Ala Pro Gly Thr
            275                 280                 285

Arg His Leu Ser Pro Gln Ala Gly Gly Ala Arg Gly Thr Cys Pro Pro
            290                 295                 300

Ser Trp Trp Gln Pro His Leu Gln Gly Lys Pro Ser Pro His Val Cys
305                 310                 315                 320

Ala Ala Glu Thr Lys Arg Phe Leu Tyr Cys Ser Gly Ser Lys Glu Gly
                325                 330                 335

Leu Arg Arg Ser Phe Leu Leu Cys Ser Leu Pro Pro Ser Leu Ala Gly
            340                 345                 350

Ala Gly Arg Leu Val Glu Val Ile Phe Leu Ala Ser Lys Pro Gly Gln
            355                 360                 365

Pro Gly Ala Arg Arg Val Pro Ala Arg Tyr Trp Arg Met Arg Pro Leu
            370                 375                 380

Phe Arg Glu Leu Leu Lys Asn His Ala Arg Cys Pro Tyr Lys Ala Leu
385                 390                 395                 400

Leu Arg Ala His Cys Pro Leu Arg Ala Ala Thr Leu Ser Gly Ser
                405                 410                 415

Gly Gly Gln Val Cys Asp His Lys Val Gly Pro Leu Ala Pro Glu Arg
                420                 425                 430

Leu Ala Ala Ala Ala Glu Gly Asp Ser Ala Ser Arg Arg Leu Val Gln
            435                 440                 445

Leu Leu Arg Gln His Ser Ser Pro Trp Gln Val Tyr Arg Leu Leu Arg
450                 455                 460

Ala Cys Leu His Arg Leu Val Pro Pro Gly Leu Trp Gly Ser Pro His
465                 470                 475                 480

Asn Lys Arg Arg Phe Leu Lys Asn Val Lys Lys Leu Val Ser Leu Gly
                485                 490                 495

Lys His Ala Arg Leu Ser Leu Gln Glu Leu Met Trp Lys Met Lys Val
            500                 505                 510

Gln Asp Cys Ile Trp Leu Arg Arg Ser Pro Asp Ala Arg His Val Gln
            515                 520                 525

Ala Ala Glu His Arg Leu Arg Glu Ala Ile Leu Ala Lys Phe Leu Arg
            530                 535                 540

Trp Leu Met Gly Thr Tyr Val Val Glu Leu Leu Arg Ser Phe Phe Tyr
545                 550                 555                 560
```

-continued

```
Val Thr Glu Thr Thr Phe Gln Lys Asn Arg Leu Phe Phe Arg Lys
                565                 570                 575

Arg Ile Trp Ser Arg Leu Gln Ser Ala Gly Ile Arg Gln His Leu Asp
            580                 585                 590

Arg Val Arg Leu Arg Glu Leu Ser Glu Ala Glu Ile Arg Arg Arg Arg
        595                 600                 605

Glu Ala Arg Pro Ala Val Leu Thr Ser Lys Leu Arg Phe Val Pro Lys
    610                 615                 620

Pro Asp Gly Leu Arg Pro Ile Val Asn Met Ala Asn Val Val Arg Ala
625                 630                 635                 640

Arg Thr Gly Pro Gly Asp Lys Lys Val Arg Arg Leu Thr Gly Gln Val
                645                 650                 655

Lys Thr Leu Phe Ala Val Leu Asn Tyr Glu Arg Ala Arg Arg Pro Arg
            660                 665                 670

Leu Leu Gly Ala Ser Val Leu Gly Val Gly Asp Ile His Arg Ala Trp
        675                 680                 685

Arg Ala Phe Val Leu Pro Leu Arg Ala Gln Asp Pro Ala Pro Pro Leu
    690                 695                 700

Tyr Phe Val Lys Val Asp Val Thr Gly Ala Tyr Asp Ala Leu Pro Gln
705                 710                 715                 720

Asp Arg Leu Leu Glu Val Val Ala Asn Val Ile Arg Pro His Glu Ser
                725                 730                 735

Thr Tyr Cys Val Arg Gln Cys Ala Val Leu Arg Arg Thr Ala Arg Gly
            740                 745                 750

His Val Arg Lys Ser Phe Gln Thr His Val Ser Thr Phe Ala Asp Leu
        755                 760                 765

Gln Pro Tyr Met Arg Gln Phe Val Ala His Leu Gln Ala Thr Gly Pro
    770                 775                 780

Leu Arg Asp Ala Val Val Ile Glu Gln Ser Cys Ser Leu Asn Glu Ala
785                 790                 795                 800

Gly Ser Arg Leu Leu Glu Leu Phe Leu Ser Leu Leu Arg Asn His Val
                805                 810                 815

Ile Arg Ile Gly Gly Arg Ser Tyr Val Gln Cys Gln Gly Ile Pro Gln
            820                 825                 830

Gly Ser Ile Leu Ser Thr Leu Leu Cys Ser Leu Cys Tyr Gly Asp Met
        835                 840                 845

Glu Asn Arg Leu Phe Pro Gly Ile Gln Arg Asp Gly Val Leu Leu Arg
    850                 855                 860

Leu Val Asp Asp Phe Leu Leu Val Thr Pro His Leu Thr Arg Ala Lys
865                 870                 875                 880

Ala Phe Leu Arg Thr Leu Val Arg Gly Val Pro Glu Tyr Gly Cys Leu
                885                 890                 895

Ala Asn Leu Arg Lys Thr Ala Val Asn Phe Pro Val Glu Asp Gly Ala
            900                 905                 910

Arg Gly Gly Pro Ala Pro Leu Gln Leu Pro Ala His Cys Leu Phe Pro
        915                 920                 925

Trp Cys Gly Leu Leu Leu Asp Thr Arg Thr Leu Glu Val His Cys Asp
    930                 935                 940

Tyr Ala Ser Tyr Ala Arg Thr Ser Ile Arg Ala Ser Leu Thr Phe Asn
945                 950                 955                 960

Gln Gly Phe Lys Pro Gly Arg Asn Met Arg Arg Lys Leu Leu Ala Val
                965                 970                 975
```

-continued

```
Leu Arg Leu Lys Cys His Gly Ile Leu Leu Asp Leu Gln Val Asn Ser
                980                 985                 990

Leu Pro Thr Val Leu Ala Asn Val Tyr Lys Ile Phe Leu Leu Gln Ala
        995                1000                1005

Tyr Arg Phe His Ala Cys Val Leu Gln Leu Pro Phe Arg Gln Pro
1010                1015                1020

Leu Ala Arg Asn Pro Ser Phe Phe Leu Arg Leu Val Ser Asp Thr
    1025                1030                1035

Ala Ser Cys Cys Tyr Ser Leu Leu Lys Ala Arg Asn Ala Gly Met
    1040                1045                1050

Ser Leu Gly Ala Arg Gly Ala Ser Gly Pro Phe Pro Ser Glu Ala
    1055                1060                1065

Ala Glu Trp Leu Cys Leu His Ala Phe Leu Leu Lys Leu Val Arg
    1070                1075                1080

His Arg Val Thr Tyr Ser Cys Leu Leu Gly Pro Leu Arg Ala Ala
    1085                1090                1095

Arg Glu Arg Leu Cys Gln Arg Leu Pro Gly Ala Thr Leu Ala Ala
    1100                1105                1110

Leu Glu Ala Ala Ala Asp Pro Ala Leu Thr Thr Asp Phe Arg Thr
    1115                1120                1125

Ile Leu Asp
    1130

<210> SEQ ID NO 50
<211> LENGTH: 1098
<212> TYPE: PRT
<213> ORGANISM: Danio rerio

<400> SEQUENCE: 50

Met Ser Gly Gln Tyr Ser Thr Asp Gly Gly Phe Arg Pro Val Leu Glu
1               5                   10                  15

Ile Leu Arg Ser Leu Tyr Pro Val Val Gln Thr Leu Glu Glu Phe Thr
            20                  25                  30

Asp Gly Leu Gln Phe Pro Asp Gly Arg Lys Pro Val Leu Leu Glu Glu
        35                  40                  45

Thr Asp Gly Ala Arg Phe Lys Lys Leu Leu Ser Gly Leu Ile Val Cys
    50                  55                  60

Ala Tyr Thr Pro Pro Gln Leu Arg Val Pro Ala Gln Leu Ser Thr Leu
65                  70                  75                  80

Pro Glu Val Leu Ala Phe Thr Leu Asn His Ile Lys Arg Lys Lys Leu
                85                  90                  95

Arg Asn Val Leu Gly Phe Gly Tyr Gln Cys Ser Asp Val Thr Thr Ser
            100                 105                 110

Ser Asp Pro Phe Arg Phe His Gly Asp Val Ser Gln Thr Ala Ala Ser
        115                 120                 125

Ile Ser Thr Ser Glu Val Trp Lys Arg Ile Asn Gln Arg Leu Gly Thr
    130                 135                 140

Glu Val Thr Arg Tyr Leu Leu Gln Asp Cys Ala Val Phe Thr Thr Val
145                 150                 155                 160

Pro Pro Ser Cys Val Leu Gln Val Cys Gly Glu Pro Val Tyr Asp Leu
                165                 170                 175

Leu Met Pro Arg Ser Trp Ser Gly Phe Phe Leu Ser Asn Ser Asp Asn
            180                 185                 190

Glu Arg Ile Ser Gly Ala Met Arg Lys Phe Pro Ala Val Gln Lys Thr
        195                 200                 205
```

-continued

```
Val Ala Ile Ser Lys Lys Arg Thr Arg Asp Asn Glu Lys Tyr Ile Ser
    210                 215                 220
Val Lys Arg Arg Arg Val Lys Glu Thr Val Asn Asn Asn Asn Gly Asn
225                 230                 235                 240
Tyr Arg Ser Leu Cys Phe Ala Ile Ser Lys Lys Arg Ala Ile Asp Asn
                245                 250                 255
Glu Glu Asn Ile Ser Leu Lys Arg Arg Met Glu Glu Thr Asp Gln
            260                 265                 270
Val Ala Lys Ile Arg Asn Glu Asn His Glu Ser Gln Ser Phe Ala Ile
        275                 280                 285
Ser Lys Lys Arg Ala Arg Asp Asn Glu Glu Asn Ile Ser Leu Lys Arg
    290                 295                 300
Gln Arg Met Glu Glu Ile Asp Gln Val Ala Lys Ile Arg Asn Glu Asn
305                 310                 315                 320
His Gly Ser Gln Ser Trp Lys Pro Ala Asp Gln Arg Pro Pro Arg Pro
                325                 330                 335
Ser Gln Cys Ser Ile Arg Val Leu Ser Met Leu Tyr Asn Gly Arg Gly
            340                 345                 350
Met Lys Asn Phe Leu Leu Asn Arg Lys Leu Lys Gly Val Gly Gly Ala
        355                 360                 365
Arg Arg Met Gln Gly Glu Asp Leu Val Arg Met Ile Phe Leu Gln Ser
    370                 375                 380
Glu Ser Asn Asp Ser Lys Pro Lys Lys Leu Pro Lys Arg Phe Phe Ala
385                 390                 395                 400
Met Val Pro Leu Phe Ser Arg Leu Leu Arg Gln His Arg Lys Cys Pro
                405                 410                 415
Tyr Arg Leu Phe Leu Gln Arg Lys Cys Ala Gly Asn Pro Asp Val Lys
            420                 425                 430
Asp Met Glu Ser Leu Leu Lys Ser His Ser Ser Pro Tyr Arg Val Tyr
        435                 440                 445
Leu Phe Val Arg Glu Cys Leu Arg His Ile Ile Pro His Glu Leu Trp
    450                 455                 460
Gly Cys Gln Glu Asn Gln Leu His Phe Leu Ser Asn Val Lys Asn Phe
465                 470                 475                 480
Leu Leu Leu Gly Lys Phe Glu Arg Leu Thr Leu Val Gln Leu Met Trp
                485                 490                 495
Arg Met Lys Val Gln Ala Cys His Trp Leu Gly Pro Lys Lys Arg Gln
            500                 505                 510
Cys Ala Ser Glu His Arg Tyr Arg Glu Trp Met Leu Gly Gln Cys Met
        515                 520                 525
Gly Trp Met Leu Ser Gly Phe Val Val Gly Leu Val Arg Ala Gln Phe
    530                 535                 540
Tyr Ile Thr Glu Ser Met Gly His Lys His Thr Leu Arg Phe Tyr Arg
545                 550                 555                 560
Gly Asp Val Trp Ser Arg Leu Gln Asp Gln Ala Phe Arg Ala His Leu
                565                 570                 575
Cys Lys Gly Gln Trp Arg Pro Leu Ser Pro Ser Gln Ala Leu Lys Val
            580                 585                 590
Pro Asn Ser Ala Val Thr Ser Arg Ile Arg Phe Ile Pro Lys Thr Ser
        595                 600                 605
Ser Met Arg Pro Ile Thr Arg Leu Ser Gly Ser Arg Asp Thr Leu Gln
    610                 615                 620
```

```
Tyr Phe Gln Ser Cys Val Arg Val Leu Gln Asn Val Leu Ser Val Cys
625                 630                 635                 640

Val Arg Glu Ala Pro Gly Pro Met Gly Ser Thr Val Trp Gly Trp Gln
            645                 650                 655

Asp Ile His Arg Arg Leu Gln Asp Phe Ser Pro Gln Gln Lys Ser Ser
            660                 665                 670

Pro Arg Pro Leu Tyr Phe Val Lys Val Asp Val Ser Gly Ala Tyr Asp
            675                 680                 685

Ser Leu Pro His Leu Lys Leu Val Glu Val Leu Lys Glu Val Leu Gly
            690                 695                 700

Pro Phe Ala Glu Gln Ser Phe Phe Leu Arg Gln Tyr Ser Ser Val Trp
705                 710                 715                 720

Ser Asp Pro Thr Arg Gly Leu Arg Lys Arg Phe Cys Thr Lys Ala Glu
            725                 730                 735

Met Ser Glu Pro Leu Asn Met Lys Gly Phe Val Val Asp Glu Gln Val
            740                 745                 750

Ser Gly Arg Leu His Asp Ala Ile Leu Val Glu Arg His Ser Ser Glu
            755                 760                 765

Val Arg Gly Gly Asp Val Phe Gln Phe Gln Lys Met Leu Cys Ser
770                 775                 780

Tyr Val Ile His Tyr Asp Gln Gln Met Phe Arg Gln Val Cys Gly Ile
785                 790                 795                 800

Pro Gln Gly Ser Ser Val Ser Ser Leu Leu Cys Asn Leu Cys Tyr Gly
            805                 810                 815

His Met Glu Lys Ala Leu Leu Lys Asp Ile Ala Lys Gly Gly Cys Leu
            820                 825                 830

Met Arg Leu Ile Asp Asp Phe Leu Leu Ile Thr Pro His Leu Ser Lys
            835                 840                 845

Ala Thr Glu Phe Leu Thr Thr Leu Leu Ser Gly Val Pro Asp Tyr Gly
850                 855                 860

Cys Gln Ile Asn Pro Gln Lys Val Ala Val Asn Phe Pro Val Cys Val
865                 870                 875                 880

Ser Trp Val Asn Ser Gly Val Ser Val Leu Pro Ser Ser Cys Leu Phe
            885                 890                 895

Pro Trp Cys Gly Leu Met Ile His Thr His Thr Leu Asp Val Tyr Lys
            900                 905                 910

Asp Tyr Ser Arg Tyr Asp Gly Leu Ser Leu Arg Tyr Ser Leu Thr Leu
            915                 920                 925

Gly Ser Ala His Ser Pro Ser Thr Val Met Lys Lys Leu Leu Ser Val
930                 935                 940

Leu Ser Ile Lys Ser Thr Asp Ile Phe Leu Asp Leu Arg Leu Asn Ser
945                 950                 955                 960

Val Glu Ala Val Tyr Arg Ser Leu Tyr Lys Leu Ile Leu Leu Gln Ala
            965                 970                 975

Leu Arg Phe His Ala Cys Val Arg Ser Leu Pro Leu Gly Gln Ser Val
            980                 985                 990

Asn Arg Asn Pro Ser Phe Phe Leu Lys Met Ile Trp Arg Met Thr Arg
            995                 1000                1005

Val Thr Asn Lys Leu Leu Thr His Ile Asn Lys Gly Leu Pro Val
            1010                1015                1020

Cys Ser Val Asp Ser Gly Gly Val Leu Gln Ser Glu Ala Val Gln
            1025                1030                1035

Leu Leu Phe Cys Leu Ala Phe Glu Thr Leu Phe Arg Arg Phe Arg
```

```
                    1040                1045                1050

Ser Val Tyr His Cys Leu Ile Pro Ala Leu His Lys Arg Lys Arg
        1055                1060                1065

Ala Leu Gln Arg Glu Leu Cys Gly Ile Thr Leu Ala Arg Val Arg
        1070                1075                1080

Gln Ala Ser Ser Pro Arg Ile Pro Leu Asp Phe Ser Met Arg Val
        1085                1090                1095

<210> SEQ ID NO 51
<211> LENGTH: 1121
<212> TYPE: PRT
<213> ORGANISM: Oreochromis niloticus

<400> SEQUENCE: 51

Met Thr Arg Ala Leu Lys Arg Ser Asn Ile Ala Lys Ser Gln Cys Lys
1               5                   10                  15

Val Ala Asn Leu Arg Pro Ser Ala Pro Asn Thr Val Gly Met Ser Ala
            20                  25                  30

Thr Asp Met Ser Gly Val Leu Asp Ile Leu Arg Leu Leu Tyr Arg His
        35                  40                  45

Thr Gln Thr Leu Glu Glu Phe Ser Asp Ser Ile Val Phe Arg Glu Gly
    50                  55                  60

Gln Lys Ala Ala Leu Ile Glu Gln Thr Asp Thr Asn Arg Phe Lys Ser
65                  70                  75                  80

Phe Val Arg Ser Val Phe Val Cys Phe Asp Lys Glu Leu Gln Gln Val
                85                  90                  95

Ala Ser Cys Lys Gln Ile Cys Ser Leu Pro Glu Leu Leu Ala Phe Val
            100                 105                 110

Leu Asn Thr Leu Lys Arg Lys Arg Lys Arg Asn Val Leu Ala His Gly
        115                 120                 125

Tyr Asn Phe Gln Thr Leu Ala Gln Glu Asp Arg Asp Ala Asp Phe Leu
    130                 135                 140

Lys Phe Gln Gly Asp Val Thr Gln Ser Ala Ala Tyr Ile His Gly Ser
145                 150                 155                 160

Asp Leu Trp Lys Lys Val Thr Met Arg Leu Gly Thr Asp Ile Thr Gln
                165                 170                 175

Tyr Leu Leu Glu Ser Cys Ser Val Phe Val Ala Val Pro Ser Cys
            180                 185                 190

Val Phe Gln Val Cys Gly Pro Pro Val Tyr Asp Arg Val Ser Met Thr
        195                 200                 205

Met Ala Ser Ser Gly Phe Phe Leu Gln Pro Gly Val Arg Lys His Asn
    210                 215                 220

Arg Thr Lys Ile Glu Ser Cys Arg Gly Ser Val Ser Leu Lys Gln Lys
225                 230                 235                 240

Arg Thr Val Val Asn Pro Ala Ala Ser Lys Lys Met Lys Arg Arg Asn
                245                 250                 255

Lys Gly Gly Lys Lys Gly Lys Arg Lys Arg Glu Thr Gly Glu Glu Glu
            260                 265                 270

Glu Val Ala Val Cys Ser Arg Lys Arg Arg Val Ala Ser Ile Glu
        275                 280                 285

His Gln Gln Ala Ile Gln Pro Val Gly Ser Glu Lys Glu Gly Gln Val
    290                 295                 300

Val Pro Val Glu Ser Ala Pro Ala Ala Phe Lys Gln Pro Val Glu
305                 310                 315                 320
```

```
Met Pro Thr Leu Glu Gly Gly Pro Ser Trp Arg Ser Gly Ile Phe Pro
                325                 330                 335
Pro Leu Pro Pro Ser Gln Cys Phe Ile Arg Thr Leu Gly Phe Leu Tyr
            340                 345                 350
Gly Gly Arg Gly Met Arg Gly Phe Leu Leu Asn Arg Arg Lys Lys Thr
        355                 360                 365
Ala His Gly Ser Arg Arg Leu Gln Gly Gln Asp Leu Val Arg Ile Val
370                 375                 380
Phe Phe Glu Gly Leu Ala Tyr Leu Asn Gly Val Glu Arg Lys Pro Lys
385                 390                 395                 400
Lys Leu Pro Gln Arg Phe Phe Gly Met Val Pro Leu Phe Arg Gln Leu
            405                 410                 415
Leu Gln Gln His Arg Ser Cys Ser Tyr Thr Lys Ile Leu Gln Arg Leu
        420                 425                 430
Cys Pro Ser Ile Glu Glu Ser Asn Ala Gly Gln Gly Glu Leu Asn Ser
    435                 440                 445
Leu Leu Pro Gln His Cys Ala Pro His Arg Val Tyr Leu Phe Val Arg
450                 455                 460
Glu Cys Leu Ser Ser Val Ile Pro Gln Glu Leu Trp Gly Ser Asp Gln
465                 470                 475                 480
Asn Arg Leu His Phe Phe Ala Arg Val Arg Thr Phe Leu Arg Ser Gly
            485                 490                 495
Lys Phe Glu Arg Leu Ser Leu Ala Glu Leu Met Trp Lys Ile Lys Val
        500                 505                 510
Asn Asp Cys Asp Trp Leu Lys Arg Ser Lys Thr Gly Cys Phe Pro Pro
    515                 520                 525
Ser Glu Leu Ala Tyr Arg Thr Gln Val Leu Gly Gln Phe Leu Ala Trp
530                 535                 540
Leu Leu Asp Gly Tyr Val Thr Gly Leu Val Arg Ala Cys Phe Tyr Ala
545                 550                 555                 560
Thr Glu Ser Ile Gly Gln Lys Asn Ala Ile Arg Phe Tyr Arg Gln Glu
            565                 570                 575
Val Trp Ala Lys Leu Gln Asp Leu Ala Phe Arg Gly His Leu Ser Lys
        580                 585                 590
Gly Gln Met Glu Glu Leu Thr Pro Ala Gln Val Ala Ser Leu Pro Lys
    595                 600                 605
Gly Thr Val Ile Ser Arg Leu Arg Phe Ile Pro Lys Thr Asp Gly Met
610                 615                 620
Arg Pro Ile Thr Arg Val Ile Gly Ala Asp Ala Lys Thr Arg Leu Tyr
625                 630                 635                 640
Arg Gly Arg Val Arg Asp Leu Leu Asp Met Leu Arg Ala Cys Val Arg
            645                 650                 655
Ala Thr Pro Ser Leu Leu Gly Ser Thr Val Trp Gly Met Thr Asp Ile
        660                 665                 670
His Lys Val Leu Cys Ser Leu Ala Pro Ala Gln Lys Glu Lys Pro Gln
    675                 680                 685
Pro Leu Tyr Phe Val Lys Val Asp Val Ser Gly Ala Tyr Glu Ser Leu
690                 695                 700
Pro His Asp Lys Leu Ile Glu Val Ile Gly Gln Ala Leu Ser Pro Val
705                 710                 715                 720
His Asp Glu Leu Phe Thr Ile Arg Arg Tyr Ala Lys Ile Trp Ala Asp
            725                 730                 735
Ser His Glu Gly Leu Lys Lys Ala Phe Val Arg Gln Ala Asp Phe Leu
```

```
                        740                 745                 750
Glu Asp Asn Met Gly Ser Thr Asn Met Lys Gly Phe Leu Thr Ser Leu
            755                 760                 765

Gln Arg Lys Gly Lys Val His His Ala Ile Leu Val Glu Gln His Phe
        770                 775                 780

Cys Ser Asp Leu His Gly Arg Glu Ala Leu Gln Phe Phe Thr Gln Met
785                 790                 795                 800

Leu Thr Gly Ser Val Val Gln Tyr Gly Lys Lys Thr Tyr Arg Gln Cys
                805                 810                 815

Arg Gly Ile Pro Gln Gly Ser Val Val Ser Leu Leu Cys Cys Leu
            820                 825                 830

Cys Tyr Gly His Met Glu Asn Leu Leu Phe Lys Asp Ile Pro Gly His
        835                 840                 845

Lys Gly Cys Leu Met Arg Leu Val Asp Asp Phe Leu Leu Ile Thr Pro
    850                 855                 860

Asp Gln His Glu Ala Gln Ala Phe Leu Lys Ile Leu Leu Ala Gly Val
865                 870                 875                 880

Pro Gln Tyr Gly Leu Ala Val Asn Pro Gln Lys Val Val Leu Asn Phe
                885                 890                 895

Gln Val Ser Gly Ser Val Ala Ser Cys Pro Asp Ile Arg Ile Leu Pro
            900                 905                 910

Pro His Cys Leu Phe Pro Trp Cys Gly Leu Leu Leu Asp Thr His Lys
        915                 920                 925

Leu Asp Val Tyr Lys Asp Tyr Ser Ser Tyr Ala Gly Leu Ser Leu Arg
    930                 935                 940

Tyr Ser Leu Thr Leu Gly Ser Ser His Ser Ala Gly Gln Gln Met Lys
945                 950                 955                 960

Arg Lys Leu Met Ala Ile Leu Arg Leu Lys Cys His Ala Leu Phe Phe
                965                 970                 975

Asp Leu Lys Thr Asn Ser Leu Glu Ala Val Tyr Lys Asn Ile Tyr Lys
            980                 985                 990

Leu Val Leu Leu His Ala Cys Arg Phe His Val Cys Ala Gln Ser Leu
        995                 1000                1005

Pro Phe Gly Gln Thr Val Ser Lys Asn Pro Val Phe Phe Leu Gln
    1010                1015                1020

Leu Ile Trp Glu Met Ala Gln Tyr Cys Asn Lys Leu Ile Arg Arg
    1025                1030                1035

Ser Asn Lys Gly Leu Ile Leu Gly Asp Lys Ala Gln Thr Gly Ile
    1040                1045                1050

Val Gln Tyr Glu Ala Val Glu Leu Leu Phe Cys Leu Cys Phe Leu
    1055                1060                1065

Leu Val Leu Ser Gln His Arg Leu Leu Tyr Lys Asp Leu Leu Ala
    1070                1075                1080

His Leu His Lys Arg Lys Arg Ser Leu Glu Arg Arg Leu Gly Asp
    1085                1090                1095

Leu Arg Leu Ala Arg Val Arg Gln Ala Ala Ser Pro Arg Thr Pro
    1100                1105                1110

Val Asp Phe Leu Ala Ile Gln Thr
    1115                1120

<210> SEQ ID NO 52
<211> LENGTH: 1182
<212> TYPE: PRT
<213> ORGANISM: Oncorhynchus mykiss
```

<400> SEQUENCE: 52

```
Met Pro Ser Gly Asp Met Thr Arg Val Leu Gly Ile Leu Gly Ser Leu
1               5                   10                  15

Tyr Arg His Val Glu Thr Leu Glu Glu Phe Ala Asp His Ile Val Phe
            20                  25                  30

Arg Glu Gly Gln Arg Ala Val Leu Ile Glu Pro Thr Asp Thr Thr Arg
        35                  40                  45

Phe Ile Ser Phe Val Arg Gly Val Leu Val Cys Thr Asp Lys Thr Leu
    50                  55                  60

Gln Asp Val Pro Ser Cys Asn Gln Ile Ser Thr Val Pro Glu Leu Leu
65                  70                  75                  80

Ala Phe Val Leu Asn Asn Ile Lys Arg Lys Lys Arg Asn Val Leu
                85                  90                  95

Ala His Gly Tyr Gly Tyr Thr Phe Gln Asp Arg Asp Ala Asp Gln Phe
                100                 105                 110

Lys Phe His Gly Glu Ile Thr Gln Ser Ala Met Tyr Ile His Cys Ser
            115                 120                 125

Asp Leu Trp Lys Arg Ala Cys Gln Arg Leu Gly Thr Asp Ile Ser Lys
        130                 135                 140

Tyr Leu Leu Glu Ser Cys Ser Leu Phe Val Thr Val Pro Ser Ser
145                 150                 155                 160

Ala Phe Gln Val Cys Gly Val Pro Val Tyr Asp Arg Val Ser Met Ser
                165                 170                 175

Thr Gly Ile Ser Arg Phe His Leu Gly Tyr Lys Arg Asn Gly Thr Thr
            180                 185                 190

Arg Asn Ser Arg Gly Arg Ser Lys Glu Val Arg Asn Gly Gly Trp Glu
        195                 200                 205

Phe Gln Gly Ser Ala Gly Arg Asn Arg Arg Lys Asp Gly Gly Arg Asp
210                 215                 220

Thr Gly Lys Arg Lys Gly Asp Glu Val Ser Leu Gly Gly Lys Arg Lys
225                 230                 235                 240

Arg Glu Arg Glu Glu Val Glu Gly Asp Val Cys Leu Pro Gly Lys Arg
                245                 250                 255

Arg Cys Thr Gln Arg Glu Ala Pro Thr Val Ser Ser Gly Thr Ser Asp
            260                 265                 270

Arg Lys His Arg Thr Leu Glu Thr Asn Gly Val Lys Arg Pro Val Glu
        275                 280                 285

Val Ile Ser Leu Thr Lys Gly Pro Thr Gln Ser Leu Gln Val Phe Asn
    290                 295                 300

Gly Ser Ser Asn Val Glu Gln Val Ser Ala Glu Met Glu Arg Leu Arg
305                 310                 315                 320

Lys Pro Val Glu Lys Leu Ala Gly Pro Gly Arg Pro Leu Glu Ala Val
                325                 330                 335

Met Val Thr Ile Ala Pro Ala Glu Ser Ser Lys Gln Val Ser Asn Gly
            340                 345                 350

Thr Gly Asn Ile Glu Gln Met Ser Met Lys Thr Gly His Arg Arg Pro
        355                 360                 365

Ala Ala Val Val Pro Arg Pro Val Glu Glu Gln Ser Gly Pro Val Ser
    370                 375                 380

Ala Thr Val His Val Glu Gly Gly Pro Ser Trp Arg Thr Gly Ser Phe
385                 390                 395                 400

Pro Pro Leu Pro His Ser Gln Cys Phe Ile Arg Thr Leu Gly Met Leu
```

```
            405                 410                 415
Tyr Gly Gly Arg Gly Met Arg Arg Phe Leu Asn Arg Lys Arg Lys
                420                 425                 430

Ser Arg Asp Glu Gly Pro Arg Leu Gln Gly Arg Asp Leu Val Arg
            435                 440                 445

Leu Val Phe Phe Glu Gly Val Ala Tyr Leu Asn Gly Thr Glu Arg Lys
        450                 455                 460

Pro Glu Arg Leu Pro Arg Arg Phe Phe Thr Leu Val Pro Leu Phe Cys
465                 470                 475                 480

Gln Leu Leu Arg Arg His Arg Arg Cys Pro Tyr Ser Lys Ile Leu Gln
                485                 490                 495

Arg Val Cys Pro Ala Val Gly Gln Gly Asp Met Ala Ser Leu Leu Pro
            500                 505                 510

Gln His Ser Ala Pro His Arg Val Tyr Leu Phe Val Arg Glu Cys Leu
        515                 520                 525

Asn Ala Val Val Pro Ser Glu Phe Trp Gly Ser Asp His Asn Arg Phe
530                 535                 540

Lys Phe Leu Ser Ala Val Arg Asn Phe Leu Ser Met Gly Lys Phe Glu
545                 550                 555                 560

Arg Met Ser Leu Ala Glu Leu Met Trp Lys Met Lys Val Asn Asp Cys
                565                 570                 575

Asp Trp Leu Lys Ile Ser Lys Thr Gly Arg Cys Pro Pro Ser Glu Leu
            580                 585                 590

Ser Tyr Arg Thr Arg Val Leu Gly Gln Leu Leu Ala Trp Leu Leu Asp
        595                 600                 605

Gly Tyr Val Leu Gly Leu Val Arg Ala Met Phe Tyr Val Thr Glu Ser
    610                 615                 620

Met Gly Gln Lys Asn Ala Leu Arg Phe Tyr Arg Tyr Gln Val Trp Ala
625                 630                 635                 640

Lys Leu Gln Glu Leu Ala Phe Ser Gly His Leu Ser Lys Gly Gln Met
                645                 650                 655

Ser Glu Leu Thr Leu Ala Gln Val Thr Ser Leu Pro Lys Thr Thr Val
            660                 665                 670

Pro Ser Arg Leu Arg Phe Ile Pro Lys Thr Glu Gly Met Arg Pro Ile
        675                 680                 685

Thr Arg Val Ile Gly Ala Asp Ala Lys Thr Arg Leu Phe Gln Thr Arg
    690                 695                 700

Val Lys Glu Leu Leu Asp Val Leu Gly Val Cys Val Arg Ser Ser Pro
705                 710                 715                 720

Ser Leu Leu Gly Ser Thr Val Trp Gly Leu Thr Asp Ile His Arg Val
                725                 730                 735

Leu Ser Ser Ile Thr Pro Ala Gln Lys Asp Lys Pro Gln Arg Leu Tyr
            740                 745                 750

Phe Val Lys Val Asp Val Ser Gly Ala Tyr Asp Ser Leu Pro His Thr
        755                 760                 765

Gln Leu Leu Glu Val Ile Gly Gln Val Leu Ser His Val Gln Gln Glu
    770                 775                 780

Leu Phe Ser Val Arg Arg Tyr Ala Lys Val Trp Ala Asp Thr His Glu
785                 790                 795                 800

Gly Leu Lys Lys Thr Phe Val Arg Gln Ala Asp Phe Thr Glu Asp Thr
                805                 810                 815

Val Ser Ser Thr Asn Met Lys Gly Phe Val Met Ser Leu Gln Arg Glu
            820                 825                 830
```

Gly Lys Val His Asp Ala Ile Leu Val Glu Gln His Phe Ser Thr Asp
            835                 840                 845

Ile His Gly Lys Asp Val Leu Glu Phe Phe Thr Gln Met Leu Ser Ser
        850                 855                 860

Cys Val Gln Phe Gly Lys Lys Ser Phe Arg Gln Cys Gln Gly Ile
865                 870                 875                 880

Pro Gln Gly Ser Ala Val Ser Ser Leu Leu Cys Cys Leu Cys Tyr Gly
            885                 890                 895

His Met Glu Asn Leu Leu Phe Pro Asn Val Ser Arg Arg Gly Gly Cys
            900                 905                 910

Leu Met Arg Leu Val Asp Asp Phe Leu Leu Ile Thr Pro Asp Leu Ser
            915                 920                 925

Gln Ala Gln Thr Phe Leu Lys Thr Leu Met Ala Gly Val Pro Arg Tyr
            930                 935                 940

Gly Cys Val Val Asn Pro Gln Lys Val Ala Val Asn Phe Pro Leu Gly
945                 950                 955                 960

Glu Trp Gly Ser Cys Pro Ala Gly Val Arg Leu Pro Leu His Cys
            965                 970                 975

Leu Phe Pro Trp Cys Gly Leu Leu Asn Thr His Thr Leu Asp Val
        980                 985                 990

His Asn Asn Tyr Ala Ser Tyr Ala Gly Leu Ser Leu Arg Tyr Ser Leu
            995                 1000                1005

Thr Leu Gly Ser Ala His Cys Ala Gly Gln Gln Met Lys Arg Lys
    1010                1015                1020

Leu Met Ser Ile Leu Arg Phe Lys Cys His Ala Leu Phe Leu Asp
    1025                1030                1035

Leu Lys Thr Asn Ser Leu Glu Ala Val Tyr Ser Asn Val Tyr Lys
    1040                1045                1050

Leu Val Leu Leu Gln Ala Phe Arg Phe His Ala Cys Ala Gln Ser
    1055                1060                1065

Leu Pro Phe Gly Gln Lys Val Gly Gly Asn His Ser Tyr Phe Leu
    1070                1075                1080

Asn Leu Ile Trp Asp Leu Ala Glu Tyr Thr Asn His Leu Val Arg
    1085                1090                1095

Leu Cys Asn Lys Gly Val Ser Leu Gly Cys Lys Ala Leu Thr Gly
    1100                1105                1110

Ser Leu Gln Tyr Glu Ala Val Glu Leu Ile Tyr Cys Leu Ala Phe
    1115                1120                1125

Leu Leu Val Leu Ser Arg His Arg Pro Leu Tyr Tyr His Leu Leu
    1130                1135                1140

Ala Pro Leu Arg Thr Arg Lys Arg Lys Leu Glu Gly Lys Leu Glu
    1145                1150                1155

Gly Leu Arg Leu Ala Arg Ile Arg Gln Ala Ala Thr Pro Lys Met
    1160                1165                1170

Pro Glu Asp Phe Lys Ala Ile Gln Ala
    1175                1180

<210> SEQ ID NO 53
<211> LENGTH: 1214
<212> TYPE: PRT
<213> ORGANISM: Xenopus tropicalis

<400> SEQUENCE: 53

Met Thr Leu Cys Thr Gly Gly Ala Glu Leu Leu Ser Ile Leu His Ser

```
1               5                    10                   15
Leu Tyr Gly Gln Val Leu Gly Ile Val Glu Tyr Ile Asp Ser Leu His
            20                  25                  30
Val Pro Gly Gly Ile Lys Val Pro Val Leu Arg Glu Gly Asp Pro Glu
            35                  40                  45
Lys Phe Lys Ser Phe Val Ala Glu Leu Met Leu Cys Ile Pro Arg Gly
 50                      55                  60
Thr Lys Ser Leu Pro Ser Pro Val Ser Phe Leu Gln Leu Ser Thr Gln
 65                  70                  75                  80
Arg Glu Val Val Ala Arg Val Ile Gln Arg Ile Cys Glu Lys Lys Arg
                    85                  90                  95
Lys Asn Val Leu Ala Phe Gly Tyr Gly Leu Val Asp Glu Lys Ser Ser
                100                 105                 110
Leu Asn Ile Arg Leu Thr Pro Asn Ile Cys Ser Tyr Phe Pro Asn Ser
                115                 120                 125
Thr Thr Thr Thr Ile Ser Thr Ser Ile Leu Trp Glu Thr Leu Leu Thr
 130                 135                 140
Arg Val Gly Asp Asp Val Met Met Tyr Trp Leu Glu Gln Cys Ser Val
 145                     150                 155                 160
Phe Val Phe Val Pro Pro Ser Cys Cys Tyr Gln Ile Ser Gly Gln Pro
                165                 170                 175
Ile Tyr Thr Leu Pro Tyr Asp Ser Met Cys Ser Phe Arg Ser Gln Ser
                180                 185                 190
Phe Met His Ser Asn Val Leu Leu Gln Tyr Ile Lys Arg Asn Ala Phe
                195                 200                 205
Phe Leu Arg Lys Lys Tyr Leu Lys Pro Lys Lys Trp Trp Lys Thr Val
 210                     215                 220
Leu Asn Ser Lys Val Glu Lys His Ser Lys Thr Ser Gln Met Leu Thr
 225                     230                 235                 240
Trp Gln Asn Lys Lys Ser Thr Ser Ala Leu Pro Ile Cys Ser Glu Ser
                245                 250                 255
Ser Met Lys Val Thr Thr Lys Ile His Ser Lys Arg Lys Met Cys Thr
                260                 265                 270
Thr Asp Ile Cys Asp Ile Pro Thr Lys Lys Arg Arg Val Asn Leu Asp
                275                 280                 285
Lys Asp Asp Lys Met Asp His Val Ser Phe Thr Ser Ala Cys Leu Ser
                290                 295                 300
Ser Phe Ser Asn Val Cys Pro Glu Ala Lys Val Gln Ala Thr Glu Phe
 305                     310                 315                 320
Ile Thr Ser Arg Tyr Gly Lys Lys Thr Lys Ile Gln Cys Pro Lys Ser
                325                 330                 335
Thr Ser Tyr Ser Val Asp Gly Glu Phe Asn Val Thr Leu Gln Asn Asn
                340                 345                 350
Ala Asn Thr Phe Ile Thr Asn Ala Ser Val Pro Thr Ile Gln Ser Lys
                355                 360                 365
Thr Ser Phe Ser Asn Ile Phe Ile Glu Ile Gly Arg Thr Leu Tyr Ser
                370                 375                 380
Ser Ile Ser Phe Lys Lys Gly Phe Ser Glu Ser Phe Ile Leu Asn Ser
 385                     390                 395                 400
Leu Asp Cys Thr Pro Ser Gly Ser Gln Lys Leu Val Glu Thr Ile Phe
                405                 410                 415
Leu Asn Asn Phe Leu Thr Glu Gln Asn Phe Asp Gln Pro Lys Arg Asp
                420                 425                 430
```

```
Glu Asn Phe Arg Ser Lys Leu Pro Lys Arg Tyr Trp Arg Met Arg Lys
        435                 440                 445

Tyr Phe Gln Glu Leu Ile Gln Asn His Lys Asn Phe Pro Tyr Leu Val
450                 455                 460

Tyr Leu Asn Lys His Cys Pro Val Arg Pro Ser Met Ala Cys Ser His
465                 470                 475                 480

Lys Leu Ala Leu Gln Lys Lys Asn Lys Cys Lys Met Asp Lys Ser Ile
                485                 490                 495

Cys Asp Leu Ser Asn Thr Ser Val Met Lys Asn Lys Ile Val Asn Asp
                500                 505                 510

Glu Lys Pro Leu Lys His Val Thr Ala Glu Ala Thr Phe Leu Pro Leu
        515                 520                 525

Leu Lys Gln His Ser Ser Ser Trp Gln Val Tyr Met Phe Val Arg Glu
        530                 535                 540

Cys Leu Asn Ser Leu Val Pro Asp Phe Ile Trp Gly Ser Ser His Asn
545                 550                 555                 560

Lys Cys Arg Phe Leu Arg Asn Val Lys Ser Phe Leu Phe Ser Gly
                565                 570                 575

Lys Phe Gly Lys Val Ser Leu Leu Glu Leu Met Trp Lys Met Lys Val
                580                 585                 590

Glu Asp Cys Ser Trp Ile Arg Leu Arg Lys Ser Asp His Phe Val Pro
                595                 600                 605

Ala Ser Glu His Leu Leu Arg Glu Arg Ile Leu Ala Lys Phe Ile Phe
        610                 615                 620

Trp Leu Met Asp Thr Tyr Val Ile Gln Leu Leu Lys Ser Phe Phe Phe
625                 630                 635                 640

Val Thr Glu Thr Met Phe Gln Lys Asn Arg Leu Leu Phe Tyr Arg Lys
                645                 650                 655

Arg Ile Trp Lys Lys Leu Gln Asn Leu Gly Leu Arg Lys His Leu Glu
                660                 665                 670

Lys Val Lys Leu Arg Pro Leu Ser Cys Asp Glu Leu Glu Lys Met Gln
                675                 680                 685

Gln Trp Lys Asn Ile Pro Leu Val Ser Arg Leu Arg Phe Ile Pro Lys
        690                 695                 700

Thr Asn Gly Leu Arg Pro Ile Ser Arg Val Ser Ser Thr Leu Gly Ser
705                 710                 715                 720

Gln Gln Ser Lys Glu Asn Gln Glu Lys Lys Ile Gln His Phe Thr Ser
                725                 730                 735

Arg Val Arg Asn Leu Phe Ser Val Leu Asn Tyr Glu Trp Asn Arg Asn
                740                 745                 750

Cys Ser Leu Ile Gly Ser Ser Val Phe Gly Met Asp Asp Ile Tyr Lys
        755                 760                 765

Gln Trp Lys Lys Phe Val Leu Asp Phe Glu Lys Ser Arg Ala Glu Lys
        770                 775                 780

Gly Lys Phe Tyr Phe Val Lys Thr Asp Val Lys Gly Ala Tyr Asp Thr
785                 790                 795                 800

Ile Pro His Ser Lys Leu Asp Glu Val Ile Leu Lys Val Ile Asn Pro
                805                 810                 815

Asn Ala Asn Glu Val Tyr Cys Ile Arg Arg Tyr Ala Ser Val Ser Val
                820                 825                 830

Asp Ser Thr Gly Arg Ile Ile Lys Ser Phe Lys Arg His Val Ser Ala
        835                 840                 845
```

```
Leu Ala Asp Val Leu Pro Asn Met Lys Gln Phe Val Ser Asn Gln Gln
            850                 855                 860

Glu Lys Asn Leu Thr Arg Asn Thr Ile Leu Val Glu Gln Ser Leu Leu
865                 870                 875                 880

Leu Asn Glu Ser Ser Val Lys Leu Leu Ala Val Phe Gln Gln Met Ile
                885                 890                 895

Arg Ser His Ile Leu Arg Ile Glu Asp Arg Tyr Tyr Met Gln Cys Cys
            900                 905                 910

Gly Ile Pro Gln Gly Ser Met Leu Ser Thr Ile Leu Cys Ser Leu Cys
            915                 920                 925

Tyr Gly Asp Met Glu Asn Lys Leu Phe Gly Ile Gln Gln Asn Gly
            930                 935                 940

Val Leu Met Arg Leu Ile Asp Asp Phe Leu Phe Val Thr Pro His Leu
945                 950                 955                 960

Asn Gln Ala Lys Thr Phe Leu Arg Thr Leu Ala Glu Gly Ile Pro Gln
                965                 970                 975

Tyr Gly Cys Ser Ile Ser Pro Gln Lys Thr Val Val Asn Phe Pro Val
            980                 985                 990

Asp Asp Ile Pro Ala Cys Ser Glu  Val Glu Gln Leu Pro  Val His Cys
            995                 1000                1005

Leu Phe  Arg Trp Cys Gly  Leu  Leu Leu Asp Thr Gln  Thr Leu Asp
1010                1015                1020

Val Tyr  Tyr Asp Tyr Ser  Ser  Tyr Ala Cys Thr Ser  Ile Arg Ser
1025                1030                1035

Ser Met  Thr Phe Cys His  Ser  Ala Ala Gly Lys  Asn Met Lys
1040                1045                1050

Gln Lys  Leu Leu Arg Val  Leu  Lys Leu Lys Cys His  Ser Leu Phe
1055                1060                1065

Leu Asp  Leu Gln Val Asn  Ser  Leu Arg Thr Val Phe  Ile Asn Thr
1070                1075                1080

Tyr Lys  Ile Phe Leu Leu  Gln  Ala Tyr Arg Phe His  Ala Cys Val
1085                1090                1095

Val Gln  Leu Pro Phe Gly  Gln  Arg Val Met Asn Asn  Pro Pro Phe
1100                1105                1110

Phe Leu  Thr Val Ile Ser  Asp  Met Ala Pro Cys Phe  Tyr Thr Thr
1115                1120                1125

Phe Lys  Ser Lys Asn Lys  Asp  Val Thr Arg Gly Tyr  Lys Asp Val
1130                1135                1140

Ser Cys  Gln Phe Asn Phe  Glu  Ala Val Gln Trp Leu  Ser Tyr Gln
1145                1150                1155

Ala Phe  Leu Thr Lys Leu  Arg  Asn His Lys Ile Leu  Tyr Lys Cys
1160                1165                1170

Leu Ile  Gly Pro Leu Gln  Asn  Cys Lys Met Gln Leu  Ser Arg Arg
1175                1180                1185

Leu Ser  Gln Tyr Thr Ile  Asp  Leu Leu Lys Ala Val  Thr Asp Ser
1190                1195                1200

Ser Leu  His Lys Asp Phe  Ser  Cys Ile Met Asp
1205                1210

<210> SEQ ID NO 54
<211> LENGTH: 1346
<212> TYPE: PRT
<213> ORGANISM: Gallus gallus

<400> SEQUENCE: 54
```

```
Met Glu Arg Gly Ala Gln Pro Gly Val Gly Val Arg Leu Arg Asn
1               5                   10                  15

Val Ala Arg Glu Glu Pro Phe Ala Ala Val Leu Gly Ala Leu Arg Gly
            20                  25                  30

Cys Tyr Ala Glu Ala Thr Pro Leu Glu Ala Phe Val Arg Arg Leu Gln
            35                  40                  45

Glu Gly Gly Thr Gly Glu Val Glu Val Leu Arg Gly Asp Asp Ala Gln
            50                  55                  60

Cys Tyr Arg Thr Phe Val Ser Gln Cys Val Val Cys Val Pro Arg Gly
65                  70                  75                  80

Ala Arg Ala Ile Pro Arg Pro Ile Cys Phe Gln Gln Leu Ser Ser Gln
                85                  90                  95

Ser Glu Val Ile Thr Arg Ile Val Gln Arg Leu Cys Glu Lys Lys Lys
                100                 105                 110

Lys Asn Ile Leu Ala Tyr Gly Tyr Ser Leu Leu Asp Glu Asn Ser Cys
            115                 120                 125

His Phe Arg Val Leu Pro Ser Ser Cys Ile Tyr Ser Tyr Leu Ser Asn
            130                 135                 140

Thr Val Thr Glu Thr Ile Arg Ile Ser Gly Leu Trp Glu Ile Leu Leu
145                 150                 155                 160

Ser Arg Ile Gly Asp Asp Val Met Met Tyr Leu Leu Glu His Cys Ala
                165                 170                 175

Leu Phe Met Leu Val Pro Pro Ser Asn Cys Tyr Gln Val Cys Gly Gln
            180                 185                 190

Pro Ile Tyr Glu Leu Ile Ser Arg Asn Val Gly Pro Ser Pro Gly Phe
            195                 200                 205

Val Arg Arg Arg Tyr Ser Arg Phe Lys His Asn Ser Leu Leu Asp Tyr
210                 215                 220

Val Arg Lys Arg Leu Val Phe His Arg His Tyr Leu Ser Lys Ser Gln
225                 230                 235                 240

Trp Trp Lys Cys Arg Pro Arg Arg Gly Arg Val Ser Ser Arg Arg
                245                 250                 255

Lys Arg Arg Ser His Arg Ile Gln Ser Leu Arg Ser Gly Tyr Gln Pro
            260                 265                 270

Ser Ala Lys Val Asn Phe Gln Ala Gly Arg Gln Ile Ser Thr Val Thr
            275                 280                 285

Ala Arg Leu Glu Lys Gln Ser Cys Ser Ser Leu Cys Leu Pro Ala Arg
            290                 295                 300

Ala Pro Ser Leu Lys Arg Lys Arg Asp Gly Glu Gln Val Glu Ile Thr
305                 310                 315                 320

Ala Lys Arg Val Lys Val Met Glu Lys Glu Ile Glu Glu Gln Ala Cys
                325                 330                 335

Ser Ile Val Pro Asp Val Asn Gln Ser Ser Gln Arg His Gly Thr
            340                 345                 350

Ser Trp His Val Ala Pro Arg Ala Val Gly Leu Ile Lys Glu His Tyr
            355                 360                 365

Ile Ser Glu Arg Ser Asn Ser Glu Met Ser Gly Pro Ser Val Val Arg
            370                 375                 380

Arg Ser His Pro Gly Lys Arg Pro Val Ala Asp Lys Ser Ser Phe Pro
385                 390                 395                 400

Gln Gly Val Gln Gly Asn Lys Arg Ile Lys Thr Gly Ala Glu Lys Arg
                405                 410                 415
```

```
Ala Glu Ser Asn Arg Arg Gly Ile Glu Met Tyr Ile Asn Pro Ile His
            420                 425                 430

Lys Pro Asn Arg Arg Gly Ile Glu Arg Arg Ile Asn Pro Thr His Lys
        435                 440                 445

Pro Glu Leu Asn Ser Val Gln Thr Glu Pro Met Glu Gly Ala Ser Ser
    450                 455                 460

Gly Asp Arg Lys Gln Glu Asn Pro Pro Ala His Leu Ala Lys Gln Leu
465                 470                 475                 480

Pro Asn Thr Leu Ser Arg Ser Thr Val Tyr Phe Glu Lys Lys Phe Leu
                485                 490                 495

Leu Tyr Ser Arg Ser Tyr Gln Glu Tyr Phe Pro Lys Ser Phe Ile Leu
            500                 505                 510

Ser Arg Leu Gln Gly Cys Gln Ala Gly Gly Arg Arg Leu Ile Glu Thr
        515                 520                 525

Ile Phe Leu Ser Gln Asn Pro Leu Lys Glu Gln Gln Asn Gln Ser Leu
            530                 535                 540

Pro Gln Gln Lys Trp Arg Lys Arg Leu Pro Lys Arg Tyr Trp Gln
545                 550                 555                 560

Met Arg Glu Ile Phe Gln Lys Leu Val Lys Asn His Glu Lys Cys Pro
                565                 570                 575

Tyr Leu Val Phe Leu Arg Lys Asn Cys Pro Val Leu Leu Ser Glu Ala
            580                 585                 590

Cys Leu Lys Lys Thr Glu Leu Thr Leu Gln Ala Ala Leu Pro Gly Glu
        595                 600                 605

Ala Lys Val His Lys His Thr Glu His Gly Lys Glu Ser Thr Glu Gly
610                 615                 620

Thr Ala Pro Asn Ser Phe Leu Ala Pro Pro Ser Val Leu Ala Cys Gly
625                 630                 635                 640

Gln Pro Glu Arg Gly Glu Gln His Pro Ala Glu Gly Ser Asp Pro Leu
                645                 650                 655

Leu Arg Glu Leu Leu Arg Gln His Ser Ser His Trp Gln Val Tyr Gly
            660                 665                 670

Phe Val Arg Glu Cys Leu Glu Arg Val Ile Pro Ala Glu Leu Trp Gly
        675                 680                 685

Ser Ser His Asn Lys Cys Arg Phe Lys Asn Val Lys Ala Phe Ile
690                 695                 700

Ser Met Gly Lys Tyr Ala Lys Leu Ser Leu Gln Gln Leu Met Trp Lys
705                 710                 715                 720

Met Arg Val Asn Asp Cys Val Trp Leu Arg Leu Ala Lys Gly Asn His
                725                 730                 735

Ser Val Pro Ala Tyr Glu His Cys Tyr Arg Glu Glu Ile Leu Ala Lys
            740                 745                 750

Phe Leu Tyr Trp Leu Met Asp Ser Tyr Val Ile Glu Leu Leu Lys Ser
        755                 760                 765

Phe Phe Tyr Ile Thr Glu Thr Met Phe Gln Lys Asn Met Leu Phe Tyr
            770                 775                 780

Tyr Arg Lys Phe Ile Trp Gly Lys Leu Gln Asn Ile Gly Ile Arg Asp
785                 790                 795                 800

His Phe Ala Lys Val His Leu Arg Ala Leu Ser Ser Glu Glu Met Glu
                805                 810                 815

Val Ile Arg Gln Lys Lys Tyr Phe Pro Ile Ala Ser Arg Leu Arg Phe
            820                 825                 830

Ile Pro Lys Met Asn Gly Leu Arg Pro Val Val Arg Leu Ser Arg Val
```

```
                835                 840                 845
Val Glu Gly Gln Lys Leu Ser Lys Glu Ser Arg Glu Lys Lys Ile Gln
    850                 855                 860
Arg Tyr Asn Thr Gln Leu Lys Asn Leu Phe Ser Val Leu Asn Tyr Glu
865                 870                 875                 880
Arg Thr Val Asn Thr Ser Ile Ile Gly Ser Ser Val Phe Gly Arg Asp
                885                 890                 895
Asp Ile Tyr Arg Lys Trp Lys Glu Phe Val Thr Lys Val Phe Glu Ser
                900                 905                 910
Gly Gly Glu Met Pro His Phe Tyr Phe Val Lys Gly Asp Val Ser Arg
            915                 920                 925
Ala Phe Asp Thr Ile Pro His Lys Lys Leu Val Glu Val Ile Ser Gln
        930                 935                 940
Val Leu Lys Pro Glu Ser Gln Thr Val Tyr Gly Ile Arg Trp Tyr Ala
945                 950                 955                 960
Val Ile Met Ile Thr Pro Thr Gly Lys Ala Arg Lys Leu Tyr Lys Arg
                965                 970                 975
His Val Ser Thr Phe Glu Asp Phe Ile Pro Asp Met Lys Gln Phe Val
                980                 985                 990
Ser Lys Leu Gln Glu Arg Thr Ser  Leu Arg Asn Ala Ile  Val Val Glu
            995                 1000                 1005
Gln Cys  Leu Thr Phe Asn Glu  Asn Ser Ser Thr Leu  Phe Thr Phe
    1010                 1015                 1020
Phe Leu  Gln Met Leu His Asn  Asn Ile Leu Glu Ile  Gly His Arg
    1025                 1030                 1035
Tyr Tyr  Ile Gln Cys Ser Gly  Ile Pro Gln Gly Ser  Ile Leu Ser
    1040                 1045                 1050
Thr Leu  Leu Cys Ser Leu Cys  Tyr Gly Asp Met Glu  Asn Lys Leu
    1055                 1060                 1065
Leu Cys  Gly Ile Gln Lys Asp  Gly Val Leu Ile Arg  Leu Ile Asp
    1070                 1075                 1080
Asp Phe  Leu Leu Val Thr Pro  His Leu Met Gln Ala  Arg Thr Phe
    1085                 1090                 1095
Leu Arg  Thr Ile Ala Ala Gly  Ile Pro Glu Tyr Gly  Phe Leu Ile
    1100                 1105                 1110
Asn Ala  Lys Lys Thr Val Val  Asn Phe Pro Val Asp  Asp Ile Pro
    1115                 1120                 1125
Gly Cys  Ser Lys Phe Lys His  Leu Pro Asp Cys Arg  Leu Ile Ser
    1130                 1135                 1140
Trp Cys  Gly Leu Leu Leu Asp  Val Gln Thr Leu Glu  Val Tyr Cys
    1145                 1150                 1155
Asp Tyr  Ser Ser Tyr Ala Phe  Thr Ser Ile Arg Ser  Ser Leu Ser
    1160                 1165                 1170
Phe Asn  Ser Ser Arg Ile Ala  Gly Lys Asn Met Lys  Cys Lys Leu
    1175                 1180                 1185
Thr Ala  Val Leu Lys Leu Lys  Cys His Pro Leu Leu  Leu Asp Leu
    1190                 1195                 1200
Lys Ile  Asn Ser Leu Gln Thr  Val Leu Ile Asn Ile  Tyr Lys Ile
    1205                 1210                 1215
Phe Leu  Leu Gln Ala Tyr Arg  Phe His Ala Cys Val  Leu Gln Leu
    1220                 1225                 1230
Pro Phe  Asn Gln Lys Val Arg  Asn Asn Pro Asp Phe  Phe Leu Arg
    1235                 1240                 1245
```

```
Ile Ile Ser Asp Thr Ala Ser   Cys Cys Tyr Phe Ile   Leu Lys Ala
    1250                1255                1260

Lys Asn Pro Gly Val Ser Leu   Gly Ser Lys Asp Ala   Ser Gly Met
    1265                1270                1275

Phe Pro Phe Glu Ala Ala Glu   Trp Leu Cys Tyr His   Ala Phe Ile
    1280                1285                1290

Val Lys Leu Ser Asn His Lys   Val Ile Tyr Lys Cys   Leu Leu Lys
    1295                1300                1305

Pro Leu Lys Val Tyr Lys Met   His Leu Phe Gly Lys   Ile Pro Arg
    1310                1315                1320

Asp Thr Met Glu Leu Leu Lys   Thr Val Thr Glu Pro   Ser Leu Cys
    1325                1330                1335

Gln Asp Phe Lys Thr Ile Leu   Asp
    1340                1345

<210> SEQ ID NO 55
<211> LENGTH: 1267
<212> TYPE: PRT
<213> ORGANISM: Meleagris gallopavo

<400> SEQUENCE: 55

Met Ser Gly Ala Arg Gly Leu Val Trp Cys Asp Glu Arg Ala Trp Leu
1               5                   10                  15

Leu Ser Ser Gln Ser Glu Val Ile Thr Arg Ile Val Gln Arg Leu Cys
            20                  25                  30

Glu Lys Lys Lys Lys Asn Ile Leu Ala Tyr Gly Tyr Ser Leu Leu Asp
        35                  40                  45

Glu Asn Ser Cys His Phe Arg Ile Leu Pro Ser Ser Cys Ile Tyr Ser
    50                  55                  60

Tyr Leu Pro Asn Thr Val Thr Glu Thr Ile Arg Ile Ser Gly Leu Trp
65                  70                  75                  80

Glu Ile Leu Leu Ser Arg Ile Gly Asp Asp Val Met Met Tyr Leu Leu
                85                  90                  95

Glu His Cys Ala Leu Phe Met Leu Val Pro Pro Ser Asn Cys Tyr Gln
            100                 105                 110

Val Cys Gly Gln Pro Ile Tyr Glu Leu Ile Ser Arg Asn Ile Gly Pro
        115                 120                 125

Ser Pro Gly Phe Val Arg Arg Arg Tyr Ser Arg Phe Lys His Asn Asn
    130                 135                 140

Leu Leu Asn Tyr Val Arg Lys Arg Leu Val Phe His Arg His Tyr Leu
145                 150                 155                 160

Ser Lys Ser Gln Trp Trp Lys Cys Gly Pro Arg Arg Gln Gly Arg Val
                165                 170                 175

Ser Ser Arg Arg Lys Arg Arg Thr His Arg Ile Gln Ser Pro Arg Ser
            180                 185                 190

Gly Tyr Gln Ser Ser Ala Lys Val Asn Phe Gly Ala Gly Met Arg Ile
        195                 200                 205

Ser Thr Val Thr Ala His Leu Glu Lys Gln Asn Cys Ser Ser Leu Cys
    210                 215                 220

Leu Pro Ala Arg Thr Pro Ser Leu Lys Arg Lys Arg Asp Gly Glu Gln
225                 230                 235                 240

Val Glu Thr Thr Ala Lys Arg Val Lys Val Met Glu Arg Glu Glu Gln
                245                 250                 255

Ala Cys Ser Ile Val Pro Asp Val Asn Arg Ser Ser Ser Arg Arg His
```

```
              260           265           270
Gly Val Trp His Val Ala Pro Arg Ala Val Gly Leu Ile Lys Glu Arg
            275               280               285
Tyr Val Ser Glu Arg Ser Tyr Ser Glu Met Ser Gly Pro Ser Val Val
290               295               300
His Arg Ser His Pro Gly Lys Arg Pro Val Ala Asp Lys Ser Ser Phe
305               310               315               320
Pro Arg Gly Val Gln Gly Asn Lys His Ile Lys Thr Gly Ala Glu Lys
                325               330               335
Arg Ala Glu Ser Asn Lys Arg Gly Ile Glu Met Tyr Ile Asn Pro Ile
            340               345               350
Cys Lys Pro Asn Arg Arg Gly Ile Glu Arg His Ile Asn Pro Thr His
            355               360               365
Lys Pro Gly Leu Asn Ser Val Gln Thr Glu Pro Met Glu Ser Ala Ser
        370               375               380
Ser Gly Asp Arg Lys Gln Glu Asn Pro Pro Ala His Leu Ala Lys Gln
385               390               395               400
Leu Pro Asn Thr Phe Leu Arg Ser Ala Val Tyr Phe Glu Lys Lys Phe
                405               410               415
Leu Leu Tyr Ser Arg Ser Tyr Gln Glu Tyr Phe Pro Lys Ser Phe Ile
            420               425               430
Leu Ser Arg Leu Gln Gly Cys Gln Ala Gly Arg Gln Leu Ile Glu
            435               440               445
Thr Ile Phe Leu Ser Gln Asn Pro Leu Lys Glu Lys Gln Asn Gln Ser
        450               455               460
Leu Lys Gln Gln Lys Trp Arg Lys Arg Leu Pro Lys Arg Tyr Trp
465               470               475               480
Gln Met Arg Glu Ile Phe Gln Lys Leu Leu Lys Asn His Glu Lys Cys
                485               490               495
Pro Tyr Leu Val Phe Leu Arg Lys Asn Cys Pro Val Leu Leu Ser Glu
            500               505               510
Ala Cys Leu Lys Lys Thr Glu Leu Thr Leu Gln Ala Ala Leu Pro Gly
        515               520               525
Glu Ala Lys Val His Lys His Thr Glu His Gly Glu Glu Thr Thr Glu
        530               535               540
Gly Thr Ala Pro Asn Ser Phe Tyr Thr Pro Pro Ser Met Pro Leu Cys
545               550               555               560
Gly Gln Thr Glu Arg Glu Glu Gln His Leu Ala Glu Gly Ser Asp Pro
            565               570               575
Leu Leu Arg Glu Leu Leu Arg Gln His Ser Ser His Trp Gln Val Tyr
            580               585               590
Gly Phe Val Arg Glu Cys Leu Glu Arg Val Ile Pro Ala Glu Leu Trp
            595               600               605
Gly Ser Ser His Asn Lys Cys Arg Phe Lys Asn Val Lys Ala Phe
        610               615               620
Ile Ser Met Gly Lys Tyr Ala Lys Leu Ser Leu Gln Gln Leu Met Trp
625               630               635               640
Lys Met Arg Val Asn Asp Cys Val Trp Leu Arg Leu Ala Lys Gly Asn
                645               650               655
His Ser Val Pro Ala Tyr Glu His Cys Tyr Arg Glu Glu Ile Leu Ala
            660               665               670
Lys Phe Leu Tyr Trp Leu Met Asp Ser Tyr Val Ile Glu Leu Leu Lys
        675               680               685
```

Ser Phe Phe Tyr Ile Thr Glu Thr Met Phe Gln Lys Asn Met Leu Phe
    690                 695                 700

Tyr Tyr Arg Lys Phe Ile Trp Gly Lys Leu Gln Asn Ile Gly Ile Arg
705                 710                 715                 720

Asn His Phe Ala Lys Val His Leu Arg Ala Leu Ser Ser Glu Glu Met
                725                 730                 735

Glu Val Ile His Gln Lys Lys Tyr Phe Pro Ile Ala Ser Arg Leu Arg
            740                 745                 750

Phe Ile Pro Lys Ile Asn Gly Leu Arg Pro Val Val Arg Leu Ser Arg
        755                 760                 765

Val Val Glu Gly Gln Lys Leu Ser Lys Glu Ser Arg Glu Lys Lys Ile
    770                 775                 780

Gln Arg Tyr Asn Thr Gln Leu Lys Asn Leu Phe Ser Val Leu Asn Tyr
785                 790                 795                 800

Glu Arg Thr Val Asn Thr Ser Ile Ile Gly Ser Ser Val Phe Gly Arg
                805                 810                 815

Asp Asp Ile Tyr Arg Lys Trp Lys Glu Phe Val Thr Lys Val Phe Glu
            820                 825                 830

Ser Gly Gly Glu Met Pro His Phe Tyr Phe Val Lys Gly Asp Val Ser
        835                 840                 845

Arg Ala Phe Asp Thr Ile Pro His Lys Lys Leu Val Glu Val Ile Ser
    850                 855                 860

Gln Val Leu Lys Pro Glu Ser Gln Thr Val Tyr Gly Ile Arg Trp Tyr
865                 870                 875                 880

Ala Val Ile Met Ile Thr Pro Thr Gly Lys Ala Arg Lys Leu Tyr Lys
                885                 890                 895

Arg His Val Ser Thr Phe Glu Asp Phe Ile Pro Asp Met Lys Gln Phe
            900                 905                 910

Val Ser Lys Leu Gln Glu Arg Thr Ser Leu Arg Asn Ala Ile Val Val
        915                 920                 925

Glu Gln Cys Leu Thr Phe Asn Glu Asn Ser Ser Thr Leu Phe Thr Phe
    930                 935                 940

Phe Leu Gln Met Leu His Asn Asn Ile Leu Glu Ile Gly His Arg Tyr
945                 950                 955                 960

Tyr Ile Gln Cys Ser Gly Ile Pro Gln Gly Ser Ile Leu Ser Thr Leu
                965                 970                 975

Leu Cys Ser Leu Cys Tyr Gly Asp Met Glu Asn Lys Leu Leu Cys Gly
            980                 985                 990

Ile Gln Lys Asp Gly Ile Leu Ile Arg Leu Ile Asp Asp Phe Leu Leu
        995                 1000                1005

Val Thr Pro His Leu Met Gln Ala Lys Thr Phe Leu Arg Thr Ile
    1010                1015                1020

Ala Ala Gly Ile Pro Glu Tyr Gly Phe Leu Ile Asn Ala Lys Lys
    1025                1030                1035

Thr Val Val Asn Phe Pro Val Asp Asp Ile Pro Gly Cys Ser Lys
    1040                1045                1050

Phe Lys Gln Leu Pro Asp Cys Arg Leu Ile Ser Trp Cys Gly Leu
    1055                1060                1065

Leu Leu Asp Met Gln Thr Leu Glu Val Tyr Cys Asp Tyr Ser Ser
    1070                1075                1080

Tyr Ala Phe Thr Ser Ile Arg Ser Ser Leu Ser Phe Asn Ser Ser
    1085                1090                1095

```
Arg Ile Ala Gly Lys Asn Met Lys Cys Lys Leu Thr Ala Val Leu
    1100            1105            1110

Lys Leu Lys Cys His Pro Leu Phe Leu Asp Leu Lys Ile Asn Ser
    1115            1120            1125

Leu Lys Thr Val Leu Ile Asn Ile Tyr Lys Ile Phe Leu Leu Gln
    1130            1135            1140

Ala Tyr Arg Phe His Ala Cys Val Leu Gln Leu Pro Phe Asn Gln
    1145            1150            1155

Lys Val Arg Asn Asn Pro Tyr Phe Phe Val Arg Ile Ile Ser Asp
    1160            1165            1170

Thr Ala Ser Cys Cys Tyr Phe Ile Leu Lys Ala Lys Asn Pro Gly
    1175            1180            1185

Val Cys Leu Gly Cys Lys Asp Ala Ser Gly Met Phe Pro Phe Glu
    1190            1195            1200

Ala Ala Glu Trp Leu Cys Tyr His Ala Phe Ile Val Lys Leu Ser
    1205            1210            1215

Asn His Lys Val Ile Tyr Lys Cys Leu Leu Lys Pro Leu Lys Val
    1220            1225            1230

Tyr Lys Met His Leu Phe Gly Lys Ile Pro Arg Asp Thr Met Val
    1235            1240            1245

Leu Leu Lys Thr Val Thr Glu Pro Ser Leu Cys Gln Asp Phe Lys
    1250            1255            1260

Thr Ile Leu Asp
    1265

<210> SEQ ID NO 56
<211> LENGTH: 1155
<212> TYPE: PRT
<213> ORGANISM: Anas platyrhynchos

<400> SEQUENCE: 56

Met Gln Arg Leu Cys Gly Lys Lys Lys Asn Ile Leu Thr Tyr Gly
1               5               10              15

Tyr Ser Leu Leu Asp Glu Asn Ser Ser His Phe Gln Ile Met Pro Leu
                20              25              30

Ser Asn Val Tyr Ser Tyr Leu Pro Asn Thr Ala Thr Glu Thr Met Arg
            35              40              45

Ile Ser Gly Leu Trp Glu Thr Leu Leu Ser Arg Ile Gly Asp Asp Val
        50              55              60

Met Met Tyr Leu Leu Glu His Cys Ala Ile Phe Met Leu Val Pro Pro
65              70              75              80

Ser Asn Cys Tyr Gln Val Cys Gly Gln Pro Ile Tyr Glu Leu Ile Ser
                85              90              95

Gln Asn Val Glu Ser Ala Pro Ala Phe Val Lys Gln Arg Leu Ser Lys
            100             105             110

His Lys Arg Ser Ser Leu Leu Lys Tyr Thr Gln Lys Arg Leu Thr Phe
        115             120             125

His Arg Gln Tyr Leu Ser Lys Ser Arg Gln Ser Lys Arg Arg Gln Arg
    130             135             140

Leu Glu Ala Asn Val Ser Ser Val Arg Asn Lys Thr Ser Asn Asn Ile
145             150             155             160

Gln Ser Leu Gly Ser Ala Ala Leu Glu Lys Gln Ser Ser Ser Asn Ala
                165             170             175

Gly Leu Ser Ala Thr Ala Pro Ser Leu Lys Arg Lys Leu Ala Arg Glu
            180             185             190
```

```
Gln Leu Glu Val Thr Ala Lys Arg Ala Arg Leu Glu Lys Glu Arg
            195                 200                 205

Glu Glu Gln Ala Cys Asn Thr Ala Pro Asn Val Asn Gln Ser Ile Pro
        210                 215                 220

Lys Arg Tyr Gly Thr Gly Cys Val Ala Ser Arg Ser Val Ser Leu Thr
225                 230                 235                 240

Lys Glu Lys Asn Ile Ser Gln Arg Ser Asn Ser Asp Met Pro Arg Pro
            245                 250                 255

Ser Leu Val His Asn Ser His Arg Gly Lys Lys Ser Val Ala Asp Lys
            260                 265                 270

Ser Ser Phe Leu Gln Gly Ala Glu Ser Asn Arg His Leu Lys Pro Ser
        275                 280                 285

Ile Glu Met Gln Ala Gly Ser Ser Arg Lys Gly Val Glu Thr Arg Arg
        290                 295                 300

Pro Ile Pro Arg Leu Asp Trp Val Pro Ile Glu Pro Ala Glu Ser Ser
305                 310                 315                 320

Ser Ser Gly His Lys Lys Gln Glu Gly Pro Leu Ala His Leu Ala Glu
            325                 330                 335

Glu Val Pro Asn Arg Val Leu Pro Ser Thr Ile Tyr Ile Asp Arg Lys
            340                 345                 350

Phe Leu Tyr Ser Arg Arg Tyr Trp Gly Glu Arg Phe Pro Lys Ser Phe
        355                 360                 365

Leu Leu Asn Arg Leu Lys Gly Ser Gln Ala Gly Val Lys Arg Leu Ile
        370                 375                 380

Glu Thr Ile Phe Leu Ser Gln Asn Pro Phe Gly Gln Lys Cys Asn Gln
385                 390                 395                 400

Gly Leu Pro Gln Lys Lys Arg Lys Lys Leu Pro Lys Arg Phe
            405                 410                 415

Trp Arg Met Arg Ser Ile Phe Gln Gln Leu Leu Lys Asn His Gly Lys
            420                 425                 430

Phe Pro Tyr Val Ala Phe Leu Arg Gln Asn Cys Pro Leu Arg Ile Ser
        435                 440                 445

Asp Thr Ile Leu Gly Lys Ala Lys Leu Leu Ser Arg Ala Pro Leu Pro
        450                 455                 460

Gly Gln Ala Glu Ala Arg Lys Gln Ala Glu Gln Leu Gly Lys Glu Pro
465                 470                 475                 480

Ala Glu Arg Val Ala Ser Ser Arg Cys Glu Ser Gly His Thr Asn Val
                485                 490                 495

Pro Ser Ser Val Arg Ala Pro Leu Ala Ala Ser Ala Cys Gly Glu Pro
            500                 505                 510

Gly Gly Glu Glu Gln Ile Pro Ala Glu Ala Ser Asp Ser Val Leu Arg
        515                 520                 525

Glu Leu Leu Lys Glu His Cys Ser His Phe Gln Val Tyr Leu Phe Val
        530                 535                 540

Arg Glu Cys Val Glu Arg Val Ile Pro Thr Glu Leu Trp Gly Ser Asn
545                 550                 555                 560

His Asn Lys Arg Arg Phe Phe Lys Asn Val Lys Ala Phe Ile Ser Met
            565                 570                 575

Gly Lys Tyr Ala Lys Leu Ser Leu Gln Val Leu Met Trp Lys Met Arg
            580                 585                 590

Val Asn Asp Cys Met Trp Leu Arg Leu Ala Lys Gly Asn His Phe Val
            595                 600                 605
```

-continued

```
Pro Ala Ser Glu His Leu Tyr Arg Glu Glu Ile Leu Ala Lys Phe Leu
    610                 615                 620
Tyr Trp Leu Met Asp Thr Tyr Val Val Gln Leu Leu Arg Ser Phe Phe
625                 630                 635                 640
Tyr Val Thr Glu Thr Met Phe Gln Lys Asn Met Leu Phe Tyr Tyr Arg
                645                 650                 655
Lys Cys Ile Trp Gly Lys Leu Gln Asp Ile Gly Ile Arg Lys His Phe
                660                 665                 670
Ser Lys Val Lys Leu Arg Pro Leu Thr Ala Glu Met Glu Ala Ile
                675                 680                 685
His Gln Lys Lys Tyr Leu Pro Met Ala Ser Lys Leu Arg Phe Ile Pro
    690                 695                 700
Lys Val Thr Gly Leu Arg Pro Ile Val Arg Met Ser Gly Val Val Glu
705                 710                 715                 720
Ala Gln Thr Leu Ser Lys Glu Ser Arg Ala Lys Lys Ala Asp Val Ser
                725                 730                 735
Arg Ala Phe Asp Ser Ile Pro His Asn Lys Leu Val Glu Val Ile Ser
                740                 745                 750
Gln Val Leu Lys Pro Glu Lys Lys Thr Val Tyr Cys Ile Arg Arg Tyr
    755                 760                 765
Ala Val Val Met Ile Thr Gly Ser Gly Lys Thr Arg Lys Leu Tyr Lys
770                 775                 780
Arg His Val Ser Thr Phe Lys Asp Phe Met Pro Asp Met Lys Gln Phe
785                 790                 795                 800
Val Ser Arg Leu His Glu Ser Thr Ser Leu Arg Asp Ala Ile Ile Val
                805                 810                 815
Glu Gln Ser Leu Thr Phe Asn Glu Thr Ser Ala Ser Leu Phe Asn Phe
                820                 825                 830
Phe Leu Gln Met Leu Asn Asn Asn Ile Leu Glu Ile Glu Arg Ser Tyr
    835                 840                 845
Tyr Leu Gln Cys Ser Gly Ile Pro Gln Gly Ser Leu Leu Ser Thr Leu
850                 855                 860
Leu Cys Ser Leu Cys Tyr Gly Asp Met Glu Asn Lys Leu Phe Ser Gly
865                 870                 875                 880
Val Gln Lys Asp Gly Val Leu Ile Arg Leu Ile Asp Asp Phe Leu Leu
                885                 890                 895
Val Thr Pro His Leu Met His Ala Arg Thr Phe Leu Arg Thr Leu Ala
                900                 905                 910
Met Gly Ile Pro Glu Tyr Gly Phe Leu Ile Asn Pro Lys Lys Thr Val
    915                 920                 925
Val Asn Phe Ser Ala Asp Ile Pro Glu Cys Ser Glu Phe Lys Gln
930                 935                 940
Leu Pro Asn Cys Arg Leu Ile Pro Trp Cys Gly Leu Leu Leu Asp Thr
945                 950                 955                 960
Gln Thr Leu Glu Val Tyr Cys Asp Tyr Ser Ser Tyr Ser Cys Thr Ser
                965                 970                 975
Ile Arg Ser Ser Leu Ser Phe Asn Ser Asn Arg Thr Ala Gly Lys Asn
                980                 985                 990
Met Lys His Lys Leu Leu Ala Val Leu Lys Leu Lys Cys His Gly Leu
    995                 1000                1005
Phe Leu Asp Leu Gln Ile Asn Ser Leu Lys Thr Val Phe Ile Asn
    1010                1015                1020
Val Tyr Lys Ile Phe Leu Leu Gln Ala Tyr Arg Phe His Ala Cys
```

```
                1025                1030                1035
Val Ile Gln Leu Pro Phe Asn Gln Lys Val Arg Asn Asn Pro Asp
                1040                1045                1050

Phe Phe Leu Arg Val Ile Ala Glu Asn Ala Ser Cys Cys Tyr Ser
                1055                1060                1065

Met Leu Lys Ala Lys Asn Pro Gly Phe Thr Leu Gly Asn Arg Gly
                1070                1075                1080

Ala Ser Gly Met Phe Pro Ser Glu Ala Ala Glu Trp Leu Cys Tyr
                1085                1090                1095

His Ala Phe Thr Val Lys Leu Ser Asn His Lys Val Val Tyr Lys
                1100                1105                1110

Cys Leu Leu Lys Pro Leu Lys Phe Cys Met Met Gln Leu Phe Arg
                1115                1120                1125

Lys Ile Pro Lys Asp Thr Lys Ala Leu Leu Lys Thr Val Thr Glu
                1130                1135                1140

Pro Ser Ile Cys Lys Asp Phe Lys Ser Ile Leu Asp
                1145                1150                1155

<210> SEQ ID NO 57
<211> LENGTH: 8
<212> TYPE: PRT
<213> ORGANISM: Artificial Sequence
<220> FEATURE:
<223> OTHER INFORMATION: synthetic sequence

<400> SEQUENCE: 57

Asp Tyr Lys Asp Asp Asp Asp Lys
1               5

<210> SEQ ID NO 58
<211> LENGTH: 4
<212> TYPE: PRT
<213> ORGANISM: Artificial Sequence
<220> FEATURE:
<223> OTHER INFORMATION: Synthetic sequence

<400> SEQUENCE: 58

Lys Asp Tyr Lys
1
```

COMPOSITIONS AND METHODS FOR INCREASING THE EFFICIENCY OF CELL CULTURES USED FOR FOOD PRODUCTION

CROSS-REFERENCE TO RELATED APPLICATIONS

The present application is a 371 National Stage application of PCT Application No. PCT/US2018/042187, filed on Jul. 13, 2018, which claims the benefit of priority to U.S. Provisional Application No. 62/532,345, filed Jul. 13, 2017, all of which are hereby incorporated by reference in their entireties for all purposes.

REFERENCE TO SEQUENCE LISTING

The instant application contains a Sequence Listing with 58 sequences, which has been submitted via EFS-Web and is hereby incorporated herein by reference in its entirety. Said ASCII copy, created on Jun. 29, 2022, is named 39028-50238-Seqeunce-listing.txt, and is 199 kilobytes (KB) in size.

BACKGROUND OF THE INVENTION

The mass production of cells for biomass production remains limited by several factors, thus limiting final yields. Examples of such factors include (1) accumulation of extracellular metabolic waste products such as ammonia/ammonium hydroxide, in the cell culture medium to toxic levels, (2) depletion of necessary nutrients, such as glutamine, in the cell culture medium, requiring a constant supply and supplementation of such nutrients, incurring both expense and additional manipulation of the cells, and the (3) requirement for supplemented proteins, such as growth factors, which support the productivity of a cultivation process.

Provided herein are compositions and methods that address this need.

BRIEF SUMMARY OF THE INVENTION

Provided herein are compositions and methods to make and use modified cells, for the purpose of increasing the efficiency of cell cultures, increasing the cell density of metazoan cell cultures, and for making a cultured edible product for human or non-human consumption.

In one aspect, provided herein is a method for increasing the cell density of a culture comprising metazoan cells, the method comprising: (a) introducing into the cells one or more polynucleotide sequences encoding glutamine synthetase (GS), insulin-like growth factor (IGF), and albumin; and (b) culturing the cells in a cultivation infrastructure.

In another aspect, provided herein is a method for increasing the cell density of a culture comprising metazoan cells, the method comprising: (a) introducing into the cells one or more polynucleotide sequences encoding glutamine synthetase (GS), insulin-like growth factor (IGF), albumin or a combination thereof; and (b) culturing the cells in a cultivation infrastructure.

In yet another aspect, provided herein is a method for increasing the cell density of a culture comprising metazoan cells, the method comprising: (a) introducing into the cells one or more polynucleotide sequences encoding glutamine synthetase (GS), insulin-like growth factor (IGF), albumin or a combination thereof; (b) introducing into the cells a polynucleotide sequence encoding a telomerase reverse transcriptase (TERT); and (c) culturing the cells in a cultivation infrastructure.

In one aspect provided herein is a method of decreasing the concentration of ammonia and/or ammonium hydroxide in the medium of cells in culture comprising increasing the expression of glutamine synthetase (GS) protein in the cells, wherein the cells are of livestock, poultry, game or aquatic animal species, and wherein the concentration of ammonia (i.e. ammonium hydroxide) in the medium is decreased by at least 2.5%.

In another aspect, provided herein is a method of increasing the production of glutamine in cells comprising increasing the expression of glutamine synthetase (GS) protein in the cells, wherein the cells are of livestock, poultry, game or aquatic animal species, and wherein the concentration of glutamine in the cells is increased by at least 2.5%.

In another aspect, provided herein, is a method of increasing the concentration of Insulin-like growth factor (IGF) in the medium of cells in culture comprising increasing the expression of IGF protein in the cells, wherein the cells are of livestock, poultry, game or aquatic animal species, and wherein the concentration of IGF in the medium is increased by at least 2.5% or is increased to at least 0.001 ng/mL.

In another aspect, provided herein is a method of increasing the concentration of albumin in the medium of cells in culture comprising increasing the expression of albumin in the cells, wherein the cells are of livestock, poultry, game or aquatic animal species, and wherein the concentration of albumin in the medium is increased at least 2.5% or is increased to at least 0.1 µg/mL.

In one aspect, provided herein is an in vitro method for producing a cultured edible product, the method comprising: (a) introducing one or more polynucleotide sequences encoding glutamine synthetase (GS), insulin-like growth factor (IGF), albumin or a combination thereof into myogenic cells; (b) optionally introducing a polynucleotide sequence encoding a telomerase reverse transcriptase (TERT) into the cells; (c) inducing myogenic differentiation of the cells expressing GS, IGF, albumin or combinations thereof and optionally TERT, wherein the differentiated cells form myocytes and multinucleated myotubes; and (d) culturing the myocytes and myotubes to generate skeletal muscle fibers, thereby producing a cultured edible product.

In another aspect, provided herein is an in vitro method for producing a cultured edible product, the method comprising: (a) overexpressing GS, IGF, albumin, or a combination thereof in a self-renewing cell line, wherein the cell line is a myogenic transcription factor-modified cell line, and wherein the cell line is of a livestock, poultry, game or aquatic animal species; (b) inducing myogenic differentiation of the cell line, wherein the differentiated cell line forms myocytes and multinucleated myotubes; and (c) culturing the myocytes and myotubes to generate skeletal muscle fibers, thereby producing a cultured edible product. In another aspect provided herein is a cultured edible product produced by the in vitro method.

In one aspect, provided herein is a method for increasing the secretion of glutamine by cells into a culture medium, the method comprising increasing the expression of a glutamine synthetase (GS) protein in the cells, wherein the cells are from livestock, poultry, game or aquatic animal species, and wherein the concentration of glutamine secreted into the culture medium is increased by at least 2.5%.

In one aspect, provided herein is a method for increasing the rate of proliferation of cells in a cultivation infrastructure, comprising: (a) introducing into the cells one or more polynucleotide sequences encoding glutamine synthetase (GS), insulin-like growth factor (IGF), albumin or a combination thereof; and (b) culturing the cells in a cultivation infrastructure, wherein the cells are from livestock, poultry, game or aquatic animal species.

In another aspect, provided herein is a method for decreasing death of cells in a cultivation infrastructure, comprising: (a) introducing into the cells one or more polynucleotide sequences encoding glutamine synthetase (GS), insulin-like growth factor (IGF), albumin or a combination thereof; and (b) culturing the cells in a cultivation infrastructure, wherein the cells are from livestock, poultry, game or aquatic animal species.

In another aspect, provided herein is a method for increasing protein production in cells in a cultivation infrastructure, comprising: (a) introducing into the cells a polynucleotide sequence encoding insulin-like growth factor (IGF); and (b) culturing the cells in a cultivation infrastructure, wherein the cells are from livestock, poultry, game or aquatic animal species.

In another aspect provided herein is a cultured edible product comprising cells having increased expression of GS, increased expression of IGF, increased expression of albumin, increased expression of telomerase reverse transcriptase (TERT), loss-of-function mutations in cyclin-dependent kinase inhibitor (CM) proteins, increased expression of YAP, increased expression of TAZ, and/or increased expression of myogenic transcription factors.

In another aspect provided herein is a construct comprising any one of the sequences selected from Tables 1A and 1B.

In another aspect provided herein is an expression vector comprising any one of the sequences selected from Tables 1A and 1B.

In another aspect provided herein is a cell comprising an expression vector comprising any one of the sequences selected from Tables 1A and 1B. In some embodiments, the cell is from a livestock, poultry, game, or aquatic species.

BRIEF DESCRIPTION OF THE DRAWINGS

FIG. 2A shows fibroblasts transfected with vehicle-only and grown in media with supplemented glutamine. FIG. 2B shows fibroblasts transfected with mouse GS and grown in media with supplemented glutamine. FIG. 2C shows fibroblasts transfected with vehicle-only and grown in media without supplemented glutamine.

FIG. 2D shows fibroblasts transfected with a mouse GS gene and grown in media without supplemented glutamine.

FIG. 5A shows myoblasts transfected with vehicle-only and grown in medium with supplemented glutamine. FIG. 5B shows myoblasts transfected with mouse GS and grown in media with supplemented glutamine. FIG. 5C shows myoblasts transfected with vehicle-only and grown in media without supplemented glutamine. FIG. 5D shows myoblasts transfected with a mouse GS gene and grown in media without supplemented glutamine.

FIG. 10A shows fibroblasts transfected with vehicle-only. FIG. 10B shows fibroblasts transfected with a human IGF-1 gene.

FIG. 10C Fibroblasts transfected with a mouse albumin gene. FIG. 10D shows fibroblasts transfected with a human albumin gene.

FIG. 11A shows myoblasts transfected with vehicle-only. FIG. 11B shows myoblasts transfected with a human IGF-1 gene. FIG. 11C shows myoblasts transfected with a mouse albumin gene. FIG. 11D shows myoblasts transfected with human albumin gene.

DETAILED DESCRIPTION OF THE INVENTION

Figure 1:
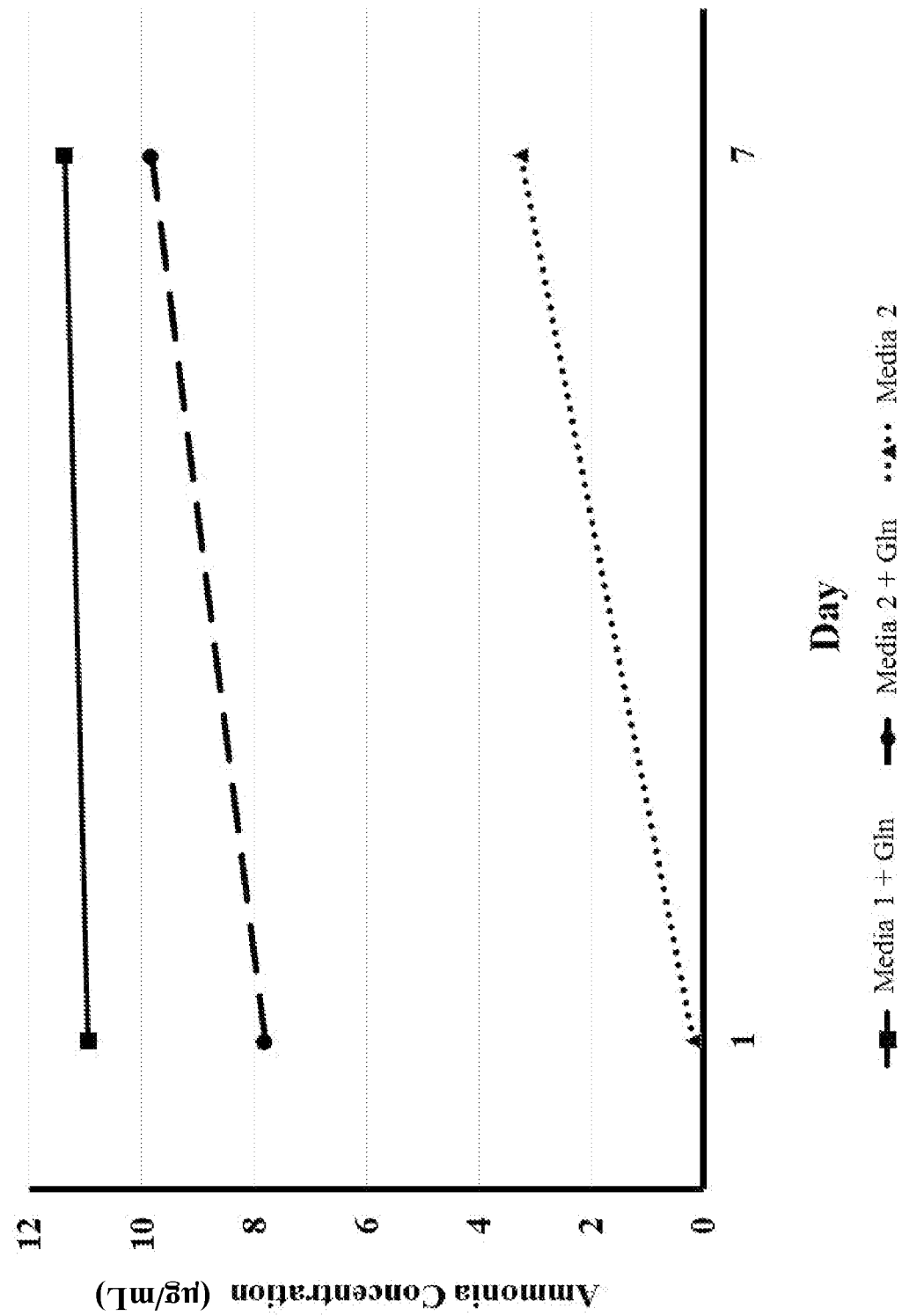
FIG. 1 shows a spontaneous increase in ammonia concentration in various cell culture media.

Provided herein are compositions and methods to make and use engineered cells, for the purpose of increasing the efficiency of cell cultures. Specifically, provided herein are exemplary methods of increasing culture density (e.g. cell density of metazoan cells in culture) and methods for producing cultured edible product. Also provided are methods of making and using cells with reduced requirements for glutamine supplementation, and reduced supplementation with certain animal-cell secreted components such as insulin-like growth factor (IGF) and albumin.

Before describing certain embodiments in detail, it is to be understood that this invention is not limited to particular compositions or biological systems, which can vary. It is also to be understood that the terminology used herein is for the purpose of describing particular illustrative embodiments only, and is not intended to be limiting. The terms used in this specification generally have their ordinary meaning in the art, within the context of this invention and in the specific context where each term is used. Certain terms are discussed below or elsewhere in the specification, to provide additional guidance to the practitioner in describing the compositions and methods of the invention and how to make and use them. The scope and meaning of any use of a term will be apparent from the specific context in which the term is used. As such, the definitions set forth herein are intended to provide illustrative guidance in ascertaining particular embodiments of the invention, without limitation to particular compositions or biological systems.

As used in the present disclosure and the appended claims, the singular forms "a," "an" and "the" include plural references unless the content clearly dictates otherwise.

Throughout the present disclosure and the appended claims, unless the context requires otherwise, the word "comprise", or variations such as "comprises" or "comprising", will be understood to imply the inclusion of a stated element or group of elements but not the exclusion of any other element or group of elements.

Standard techniques may be used for recombinant DNA, oligonucleotide synthesis, and tissue culture and transduction (e.g., electroporation, transfection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, production, and delivery.

Cells

Provided herein are methods for modifying cells to overexpress and/or inhibit certain gene products, for the purpose of achieving increased cell density and in some embodiments, for the purpose of providing a cultured edible product. For example, in certain aspects, cells modified as described herein may be cultivated for food production, e.g. production of cultured chicken, cultured beef, and cultured fish.

The cells used in the methods of the present disclosure can be primary cells, or cell lines. The methods provided herein are applicable to any metazoan cell in culture. In various embodiments, methods of the present disclosure may use any one of the cell populations described herein.

In some embodiments, the cells are harvested for the production of cell-based food products, such as cultured edible product from an animal (e.g. cultured poultry, cultured livestock, cultured game, cultured fish). Thus in some embodiments, the methods utilize cells with the potential to differentiate into skeletal muscle. In certain embodiments, the cells are from livestock such as domestic cattle, pigs, sheep, goats, camels, water buffalo, rabbits and the like. In certain embodiments, the cells are from poultry such as domestic chicken, turkeys, ducks, geese, pigeons and the like. In certain embodiments, the cells are from game species such as wild deer, gallinaceous fowl, waterfowl, hare and the like. In certain embodiments, the cells are from aquatic species or semi-aquatic species harvested commercially from wild fisheries or aquaculture operations, or for sport, including certain fish, crustaceans, mollusks, cephalopods, cetaceans, crocodilians, turtles, frogs and the like. In certain embodiments, the cells are from exotic, conserved or extinct animal species. In certain embodiments, the cells are from any metazoan species demonstrating the capacity for skeletal muscle tissue specification. In certain embodiments, the cells are modifiable by a genetic switch to induce rapid and efficient conversion of the cells to skeletal muscle for cultured food production (e.g. cultured poultry, cultured livestock, cultured game, and cultured fish).

In some embodiments, the cells are from *Gallus gallus, Bos taurus, Sous scrofa, Meleagris gallopavo, Anas platyrynchos, Salmo salar, Thunnus thynnus, Ovis aries, Coturnix coturnix, Capra aegagrus hircus,* or *Homarus americanus.*

In some embodiments, the cells are from any animal species intended for human or non-human dietary consumption.

In some embodiments, the cells are from livestock, poultry, game, or aquatic species. In other embodiments, the cells are from humans, primates (e.g. monkeys), rodents, including rats and mice, and companion animals such as dogs, cats, horses, and the like.

In some embodiments, the cells are self-renewing stem cell lines.

In some embodiments, the cells are satellite cells, myoblasts, myocytes, fibroblasts, induced pluripotent stem cells, hepatocytes, vascular endothelial cells, pericytes, embryonic stem cells, mesenchymal stem cells, extraembryonic cell lines, somatic cell lines, adipocytes, embryonic stem cells or chondrocytes.

In some embodiments, the cells are myogenic cells. In some embodiments, the myogenic cells are natively myogenic (e.g. are myogenic cells that are cultured in the cultivation infrastructure). Natively myogenic cells include, but are not limited to, myoblasts, myocytes, satellite cells, side population cells, muscle derived stem cells, mesenchymal stem cells, myogenic pericytes, or mesoangioblasts. In other embodiments, the myogenic cells are not natively myogenic (e.g. are non-myogenic cells that are specified to become myogenic cells in the cultivation infrastructure). In some embodiments, non-myogenic cells include embryonic stem cells, induced pluripotent stem cells, extraembryonic cell lines, and somatic cells other than muscle cells.

In some embodiments, non-myogenic cells are modified to become myogenic cells through the expression of one or more myogenic transcription factors. In exemplary embodiments, the myogenic transcription factor is MYOD1, MYOG, MYF5, MYF6, PAX3, PAX7, paralogs, orthologs, or genetic variants thereof.

In some embodiments, cells are modified to extend their renewal capacity through inactivation of cyclin-dependent kinase inhibitor (CM) proteins and/or activation of Telomerase reverse transcriptase (TERT). Accordingly, in some embodiments, cells used in the methods of the present disclosure comprise a polynucleotide sequence expressing TERT. In some embodiments, cells used in the methods of the present disclosure comprise one or more loss-of-function mutations in the endogenous genes encoding CM proteins. In some embodiments, cells comprise loss-of-function mutations in CM proteins p15, p16, paralogs, orthologs, or genetic variants thereof. In some embodiments, cells used in the methods of the present disclosure comprise a polynucleotide sequence expressing TERT and one or more loss-of-function mutations in the endogenous genes encoding CM proteins. The loss-of-function mutation may partially or completely inhibit the activity of CM proteins.

In some embodiments, the process of extending the renewal capacity of the cells comprises activating Telomerase reverse transcriptase (TERT) activity in the cells and/or inactivating CM proteins.

In some embodiments, the process of extending the renewal capacity of the cells comprises ectopic expression of TERT. In some embodiments, the process of extending the renewal capacity of the cells comprises introducing targeted mutations in the TERT promoter. In some embodiments, the process of extending the renewal capacity of the cells comprises activating endogenous TERT expression by an engineered transcriptional activator. In some embodiments, the process of extending the renewal capacity of the cells comprises transient transfection of TERT mRNA. In some embodiments, induction of endogenous pluripotency-associated telomerase activity in stem cells such as ESC and iPSC supports extended and indefinite cell renewal. In some embodiments, maintenance endogenous pluripotency-associated telomerase activity in stem cells such as ESC and iPSC supports extended and indefinite cell renewal.

In some embodiments, the process of extending the renewal capacity of the cells comprises inactivating one or more CM proteins. In some embodiments, inactivating CM proteins comprises introducing loss-of-function mutations in one or more genes encoding CM proteins. In some embodiments, the loss-of-function mutation partially inhibits the activity of one or more CM proteins. In some embodiments, the loss-of-function mutation completely inhibits the activity of one or more CM proteins.

In some embodiments, the inactivation of CM proteins and/or activation of TERT in the cells extend their renewal capacity for at least 25 population-doublings, at least 50 population-doublings, at least 60 population-doublings, at least 70 population-doublings, at least 80 population-doublings, at least 90 population-doublings, at least 100 population-doublings, at least 110 population-doublings, at least 120 population-doublings, at least 130 population-doublings, at least 140 population-doublings, at least 150 population-doublings, at least 160 population-doublings, at least 170 population-doublings, at least 180 population-doublings, at least 190 population-doublings, or at least 200 population-doublings. In some exemplary embodiments, the cells are primary myoblasts of a livestock, game, aquatic, or poultry species, whose renewal capacity is further extended.

In some embodiments, the cells are modified to inhibit HIPPO signaling, for example, by activating Yes-Associated Protein 1 (YAP1), Transcriptional co-Activator with PDZ-binding motif (TAZ), or a combination thereof in the cells.

In some embodiments, the cells are somatic cells. In some embodiments, the cells are not somatic cells.

In some embodiments, the cells are anchorage-dependent cells and are cultivated in on a substrate. In some embodiments, the cells are anchorage independent cells and are cultivated in a suspension culture. In some embodiments, the cells are cultivated in a suspension culture and form a self-adherent aggregate.

It is noted that the cells can be cultivated for any downstream application, not just limited to food production.

Cellular Modifications

Provided herein are compositions and methods to modify any one of the cells provided herein with a gene of interest in order to increase cell density of metazoan cells in a culture medium, decrease waste products, such as ammonia or ammonium hydroxide, decrease dependency on exogenous addition of factors such as glutamine, albumin, and IGF to the media and to provide a cultured edible product.

Glutamine Synthetase (GS)

Provided herein are cells that overexpress a GS protein.

Provided herein is a method of increasing the production of glutamine in cells or by cells, increasing glutamine secretion into culture medium, and/or decreasing the concentration of extracellular ammonia (to be used interchangeably with ammonium hydroxide where ammonium hydroxide is the form of ammonia present in an aqueous solution) in the medium of cells in culture, comprising increasing the expression of a glutamine synthetase (GS) protein in cells. Also provided herein is a method of increasing the cell density of metazoan cell in culture, comprising increasing the expression of GS in the cells in combination with other modifications described herein and culturing the cells in a cultivation infrastructure. Also provided is an in vitro method for producing a cultured edible product comprising increasing the expression of GS in the cells in combination with other modifications described herein.

In some embodiments, the cells are modified to overexpress a gene encoding a GS protein. In some embodiments, cells ectopically express a GS gene. In some embodiments, the cells are genetically modified and carry stable integrations of one or more copies of a GS gene. In some embodiments, the cells overexpress the gene encoding the GS protein at levels sufficient to decrease the ammonia production, increase the production of glutamine, or any combination thereof. In some embodiments, methods described herein to overexpress GS comprise introducing into the cells a polynucleotide sequence from Table 1B comprising a GS gene.

Increase of GS expression may be achieved using different approaches. In some embodiments, the expression is inducible. In some embodiments, the method comprises expressing nucleotides that encode the GS gene. In some embodiments, the nucleotides are ectopically expressed from constructs that are introduced into the cells, for example expressed from a plasmid, or other expression vector. In some embodiments, the constructs are integrated into the cell's genome, and the expression is driven in that manner (e.g. homologous recombination, introduction mediated by CRISPR-based technology). In some embodiments, expression of the GS gene involves electroporating a DNA, delivering a DNA complexed with a transfection vehicle, using a viral vector (e.g. retrovirus, lentivirus, adenovirus, adeno-associated virus, herpes simplex virus), and the like, or combinations thereof. In some embodiments, the expression is constitutive. In some embodiments, the expression is conditional, e.g. inducible, e.g. under the control of an inducible promoter, e.g. an inducible Tet construct. In some embodiments, the expression of GS is constitutive, but the expression of additional genes of interest is inducible. In some embodiments, the expression of GS is inducible, but the expression of additional genes of interest is constitutive.

In the methods described herein, a polynucleotide sequence encoding the GS gene may encode any homolog of GS, including GS paralogs, or a GS protein translated from any splice variants of a GS gene, or may comprise any mutations in the GS gene sequence including, but not limited to nucleotide deletions, truncations, fusions, or substitutions. Mutations may be synthetic or naturally occurring.

The GS gene can be from of any organism. The GS gene can be from bacteria, plants, fungi, and archaea. The GS gene can be from any animal, such as vertebrate and invertebrate animal species. The GS gene can be from any vertebrate animal species such as mammals, reptiles, birds, amphibians, and the like. The GS gene can be from any mammalian species such as a human, murine, bovine, porcine, and the like.

In some embodiments, the cells are of a livestock, poultry, game or aquatic animal species. In an exemplary embodiment, the renewal capacity of the primary duck myoblasts are extended, and the myoblasts are engineered to stably overexpress GS. In another exemplary embodiment, the renewal capacity of the primary duck myoblasts are extended, and the myoblasts are engineered to transiently overexpress GS. In another exemplary embodiment, the renewal capacity of the primary duck myoblasts are extended and are engineered to ectopically overexpress GS.

In some embodiments, the synthesis of glutamine by the cells is increased by at least 2.5%, by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 225%, at least 250%, at least 275%, at least 300%, at least 325%, at least 350%, at least 375% at least 400%, at least, 425%, at least 450%, at least 475%, at least 500%, at least 550%, at least 600%, at least 650%, at least 700%, at least 750%, at least 800%, at least 850%, at least 900%, at least 950% at least 1,000%, at least 1,100%, at least 1,200%, at least 1,300%, at least 1,400%, at least 1,500%, at least 1,600%, at least 1,700%, at least 1,800%, at least 1,900%, at least 2,000%, at least 2,250%, at least 2,500%, at least 2,750%, at least 3,000%, at least 3,500%, at least 4,000%, at least 4,500%, at least 5,000%, at least 6,000%, at least 7,000%, at least 8,000%, at least 9,000%, or even by at least 10,000%, including values and ranges therebetween, compared to cultures of cells in which glutamine synthesis is not increased by expression of GS as described herein.

In some embodiments, increased expression of GS using the methods described herein increases the concentration of glutamine in the culture medium to at least 0.001 mM, to at least 0.0025 mM, to at least 0.005 mM, to at least 0.0075 mM, to at least 0.01 mM, to at least 0.025 mM, to at least 0.05 mM, to at least 0.075 mM, to at least 0.1 mM, at least 0.25 mM, to at least 0.50 mM, to at least 0.75 mM, to at least 1.0 mM, to at least 1.5 mM, to at least 2.0 mM, to at least 3.0 mM, to at least 5.0 mM, to at least 10 mM, or even to at least 20 mM, including values and ranges therebetween, compared to cultures of cells in which the expression of GS is not increased.

Methods to measure the increase in the concentration of intracellular glutamine production include, but are not limited to assessment of the glutamine concentration in lysates of cell biomass or the ambient culture medium by HPLC (Chorili et. al., 2012. Validation of a HPLC Method for Determination of Glutamine in Food Additives Using Post-Column Derivatization, AJAC Vol. 3 No. 2) commercially available kits for absolute glutamine determination kits (Sigma-Aldrich #GLN1 and #GLN2), and trace-labeled ($H^3$ radiolabeled) glutamine monitoring.

In some embodiments, the protein synthesis in the cells is increased by at least 2.5%, by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or even by at least 95%.

In some embodiments, the concentration of ammonia is decreased by at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or even at least 95%. Methods to measure the decrease of extracellular ammonia concentrations in the cell media include, but are not limited to commercially available absolute ammonia detection kits such as (Sigma-Aldrich #AA0100), diffuse reflectance-based fiberoptic ammonia sensors (Non-enzymatic reversible colorimetric method such as diffuse reflectance-based fiberoptics (Spear, S. K., Rhiel, M., Murhammer, D. W. et al. Appl Biochem Biotechnol (1998) 75: 175), and use of a biochemistry analyzer (e.g. YSI Biochemistry Analyzer 2700).

In some embodiments, there is a delay in time for the cells to reach the ammonia concentration of otherwise not manipulated cultures (the wild-type cell ammonia concentration). For example, cells overexpressing GS may demonstrate at least a 1.5-fold, 2-fold, 3-fold, 4-fold, 5-fold, 6-fold, 7-fold, 8-fold, 9-fold, 10-fold, 15-fold, 20-fold, 25-fold, 30-fold, 40-fold, or even at least a 50-fold delay in time to achieve the wild type cell ammonia concentration.

In some embodiments, provided herein is a method of increasing the cell density of a culture comprising metazoan cells, comprising increasing the expression of glutamine synthetase (GS) protein by the cells, wherein the cells are of livestock, poultry, game or aquatic animal species. The culture density of cells may reach about $10^5$ cells/mL, about $10^6$ cells/mL, about $10^7$ cells/mL, about $10^8$ cells/mL, about $10^9$ cells/mL, or about $10^{10}$ cells/mL (cells in the cellular biomass/mL of cultivation infrastructure), including values and ranges therebetween.

In some embodiments, provided herein is a method of decreasing cell death comprising increasing the expression of glutamine synthetase in the cells. In some embodiments, the decrease in cell death is about 2.5%, about 5%, about 10%, about 20%, about 30%, about 40%, about 50%, about 60%, about 70%, about 80%, about 90%, or about 100%, including values and ranges therebetween, compared to the methods where the expression of GS is not increased.

Insulin-Like Growth Factor (IGF)

Provided herein are cells that overexpress an IGF protein.

Provided herein is a method of increasing the production and secretion of IGF by cells comprising increasing the expression of an IGF protein in cells. Also provided herein is a method of increasing the cell density of a culture comprising metazoan cells comprising increasing the expression of IGF in the cells in combination with other modifications described herein and culturing the cells in a cultivation infrastructure. Also provided is an in vitro method for producing a cultured edible product comprising increasing the expression of GS in the cells in combination with other modifications described herein.

In some embodiments, the cells are modified to overexpress the gene encoding an IGF protein. In some embodiments, cells ectopically express the IGF gene. In some embodiments, the cells are genetically modified and carry stable integrations of one or more copies of an IGF gene. In some embodiments, the cells overexpress the gene encoding the IGF protein at levels sufficient to increase production and/or secretion of IGF into the cell medium. The IGF gene can be of any metazoan species.

Increase of IGF expression may be achieved using different approaches. In some embodiments, the expression is inducible. In some embodiments, the method comprises expressing nucleotides that encode the IGF gene. In some embodiments, the nucleotides are ectopically expressed from constructs that are introduced into the cells, for example expressed from a plasmid, or other expression vector. In some embodiments, the constructs are integrated into the cell's genome, and the expression is driven in that manner (e.g. homologous recombination, introduction mediated by CRISPR-based technology). In some embodiments the expression of the IGF gene involves electroporating a DNA, delivering a DNA complexed with a transfection vehicle, using a viral vector (e.g. retrovirus, lentivirus, adenovirus, adeno-associated virus, herpes simplex virus), and the like, or combinations thereof. In some embodiments, the expression is constitutive. In some embodiments, the expression is conditional, e.g. inducible, e.g. under the control of an inducible promoter, e.g. an inducible Tet construct. In some embodiments, the expression of IGF is constitutive, but the expression of additional genes of interest is inducible. In some embodiments, the expression of IGF is inducible, but the expression of additional genes of interest is constitutive.

The IGF gene can be from any animal, such as vertebrate and invertebrate animal species. The IGF gene can be from any vertebrate animal species such as mammals, reptiles, birds, amphibians, and the like. The IGF gene can be from any mammalian species such as a human, murine, bovine, porcine, poultry, and the like.

In the methods described herein, a polynucleotide sequence encoding the IGF gene may encode any homolog of IGF, including IGF paralogs, such as IGF-1, IGF-2 or any other IGF paralogs, or an IGF protein translated from any splice variants of an IGF gene, or may comprise any mutations in the IGF gene sequence including, but not limited to nucleotide deletions, truncations, fusions, or substitutions. Mutations may be synthetic or naturally occurring. In one embodiment, the methods described herein comprise introducing into the cells a polynucleotide sequence encoding IGF-1. In another embodiment, the methods described herein comprise introducing into the cells a polynucleotide sequence encoding IGF-2. In some embodiments, methods described herein to overexpress IGF comprise introducing into the cells a polynucleotide sequence from Table 1B comprising an IGF gene.

In some embodiments, the cells are of a livestock, poultry, game or aquatic animal species. In an exemplary embodiment, the renewal capacity of the primary duck myoblasts is extended, and the myoblasts are engineered to stably overexpress IGF. In another exemplary embodiment, the renewal capacity of the primary duck myoblasts is extended, and the myoblasts are engineered to transiently overexpress IGF. In another exemplary embodiment, the renewal capacity of the primary duck myoblasts is extended, and the myoblasts are engineered to ectopically overexpress IGF.

In some embodiments, the concentration of IGF in the cell culture medium is increased by at least 0.001%, 0.005%, 0.01%, at least 0.02%, at least 0.03%, at least 0.04%, at least 0.05%, at least 0.075%, at least 0.1%, at least 0.5%, at least 0.75%, at least 1%, at least 1.25%, at least 1.5%, at least 1.75%, at least 2%, at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 225%, at least 250%, at least 275%, at least 300%, at least 325%, at least 350%, at least 375% at least 400%, at least, 425%, at least 450%, at least 475%, at least 500%, at least 550%, at least 600%, at least 650%, at least 700%, at least 750%, at least 800%, at least 850%, at least 900%, at least 950% at least 1,000%, at least 1,100%, at least 1,200%, at least 1,300%, at least 1,400%, at least 1,500%, at least 1,600%, at least 1,700%, at least 1,800%, at least 1,900%, at least 2,000%, at least 2,250%, at least 2,500%, at least 2,750%, at least 3,000%, at least 3,500%, at least 4,000%, at least 4,500%, at least 5,000%, at least 6,000%, at least 7,000%, at least 8,000%, at least 9,000%, or even by at least 10,000% including values and ranges therebetween, compared to cultures of cells in which the expression of IGF is not increased as described herein.

In some embodiments, increased expression of IGF using the methods described herein increases the concentration of IGF in the culture medium by at least 0.00001 ng/mL, to at least 0.000025 ng/mL, to at least 0.000075 ng/mL, to at least 0.0005 ng/mL, to at least 0.001 ng/mL, to at least 0.0025 ng/mL, to at least 0.005 ng/mL, to at least 0.0075 ng/mL, to at least 0.01 ng/mL, to at least 0.025 ng/mL, to at least 0.05 ng/mL, to at least 0.1 ng/mL, to at least 0.25 ng/mL, to at least 0.5 ng/mL, to at least 1 ng/mL, to at least 2.5 ng/mL, to at least 5 ng/mL, to at least 7.5 ng/mL, to at least 10 ng/mL, to at least 25 ng/mL, to at least 50 ng/mL, to at least 75 ng/mL, to at least 125 ng/mL, to at least 250 ng/mL, to at least 500 ng/mL, to at least 750 ng/mL, to at least 1,000 ng/mL, to at least 1,500 ng/mL, to at least 2,000 ng/mL, to at least 2,500 ng/mL, to at least 3,000 ng/mL, to at least 3,500 ng/mL, to at least 4,000 ng/mL, to at least 4,500 ng/mL, to at least 5,000 ng/mL to at least 6,000 ng/mL, to at least 7,000 ng/mL, to at least 8,000 ng/mL, to at least 9,000 ng/mL, or even to at least 10,000 ng/mL including values and ranges therebetween, compared to cultures of cells in which the expression of IGF is not increased as described herein.

Methods to measure the increase in the concentration of IGF include, but are not limited to, antibody-based methods such as immunoprecipitation, co-immunoprecipitation, Western blotting, Enzyme-linked immunosorbent assay (ELISA), and amino-acid based tagging, isolation, and separation (e.g., FLAG, GST, GFP, etc.).

In some embodiments, the rate of synthesis of IGF by cells is increased by about 0.000001 $\mu g/10^6$ cells/day, by about 0.00001 $\mu g/10^6$ cells/day, by about 0.0001 $\mu g/10^6$ cells/day, 0.001 $\mu g/10^6$ cells/day, by about 0.01 $\mu g/10^6$ cells/day, by about 0.1 $\mu g/10^6$ cells/day, by about 1.0 $\mu g/10^6$ cells/day, by about 10 $\mu g/10^6$ cells/day, by about 100 $\mu g/10^6$ cells/day, by about 10 $\mu g/10^6$ cells/day, by about 100 $\mu g/10^6$ cells/day, by about 1,000 $\mu g/10^6$ cells/day, or by even about 10,000 $\mu g/10^6$ cells/day, including values and ranges therebetween, compared to cells wherein the rate of IGF synthesis is not increased as described herein.

In some embodiments, provided herein is a method of increasing the proliferation rate of cells comprising increasing the expression of Insulin-like Growth Factor (IGF) protein by the cells, wherein the cells are of livestock, poultry, game or aquatic animal species. In some embodiments, the population doubling time of the cells is decreased by about by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, or by more than 95%, including values and ranges therebetween, compared to cells wherein the expression of IGF is not increased.

In some embodiments, provided herein is a method of increasing protein production in the cells comprising increasing the expression of Insulin-like Growth Factor (IGF) protein by the cells, wherein the cells are of livestock, poultry, game or aquatic animal species. In some embodiments, the protein produced by the cells in culture is measured as total cell protein per cell nucleus. In some embodiments, the total cell protein per nucleus is increased by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, by about 100%, by about 110%, by about 120%, by about 130%, by about 140%, by about 150%, by about 160%, by about 170%, by about 180%, by about 190%, by about 200%, by about 225%, by about 250%, by about 275%, by about 300%, by about 350%, by about 400%, by about 450%, by about 500%, by about 550%, by about 600%, by about 650%, by about 700%, by about 750%, by about 800%, by about 850%, by about 900%, by about 950%, by about 1,000%, by about 1,100%, by about 1,200%, by about 1,300%, by about 1,400%, by about 1,500%, by about 1,600%, by about, 1,700%, by about 1,800%, by about 1,900%, by about 2,000%, by about 2,100%, by about 2,200%, by about 2,300%, by about 2,400%, by about 2,500%, by more than 2,500%, including values and ranges therebetween, compared to the total cell protein production where the expression of IGF is not increased.

In some embodiments, the total cell protein per nucleus is increased by about 5 pg/nucleus; by about 10 pg/nucleus; by about 15 pg/nucleus; by about 20 pg/nucleus; by about 25 pg/nucleus; by about 30 pg/nucleus; by about 35 pg/nucleus; by about 40 pg/nucleus; by about 45 pg/nucleus, by about 50 pg/nucleus; by about 55 pg/nucleus, by about 60 pg/nucleus, by about 65 pg/nucleus, by about 70 pg/nucleus, by about 75 pg/nucleus, by about 80 pg/nucleus, by about 85 pg/nucleus, by about 90 pg/nucleus, by about 95 pg/nucleus, by about 100 pg/nucleus, by about 110 pg/nucleus, by about 120 pg/nucleus, by about 130 pg/nucleus, by about 140 pg/nucleus, by about by about 150 pg/nucleus, by about, by about 160 pg/nucleus, by about 170 pg/nucleus, by about 180 pg/nucleus, by about 190 pg/nucleus, by about 200 pg/nucleus, by about 225 pg/nucleus, by about 250 pg/nucleus, by about 275 pg/nucleus, by about 280 pg/nucleus, by about 290 pg/nucleus, by about 300 pg/nucleus, by about 350 pg/nucleus, by about 400 pg/nucleus, by about 450 pg/nucleus, by about 500 pg/nucleus, by about 550 pg/nucleus, by about 600 pg/nucleus, by about 650 pg/nucleus, by about 700 pg/nucleus, by about 750 pg/nucleus, by about 800 pg/nucleus, by about 850 pg/nucleus, by about 900 pg/nucleus, by by about 950 pg/nucleus, by about 1000 pg/nucleus, by about 1,100 pg/nucleus, by about 1,200 pg/nucleus, by about 1,300 pg/nucleus, by about 1,400 pg/nucleus, by about 1,500 pg/nucleus, by about 1,600 pg/nucleus, by about 1,700 pg/nucleus, by about 1,800 pg/nucleus, by about 1,900 pg/nucleus, by about 2,000 pg/nucleus, by about 2,100 pg/nucleus, by about 2,200 pg/nucleus, by about 2,300 pg/nucleus, by about 2,400 pg/nucleus, by about 2,500 pg/nucleus, by more than 2,500 pg/nucleus, including values and ranges therebetween.

In some embodiments, provided herein is a method for increasing the rate of proliferation of cells in a cultivation infrastructure, comprising increasing the expression of Insulin-like Growth Factor (IGF) protein in the cells, wherein the cells are of livestock, poultry, game or aquatic animal species. In some embodiments, increasing the expression of IGF comprises introducing a polynucleotide sequence encoding IGF into the cells. In some embodiments, the polynucleotide sequence encodes IGF1. In some embodiments, the polynucleotide sequence encodes IGF2. In some embodiments, the polynucleotide sequence comprises an IGF coding sequence from Tables 1A and 1B.

Albumin

Provided herein are cells that overexpress an albumin protein.

Provided herein is a method of increasing the production and secretion of albumin by cells comprising increasing the expression of an albumin protein in the cells. Also provided herein is a method of increasing the cell density of a culture comprising metazoan cells, comprising increasing the expression of albumin in the cells in combination with other modifications described herein and culturing the cells in a cultivation infrastructure. Also provided is an in vitro method for producing a cultured edible product comprising increasing the expression of albumin in the cells in combination with other modifications described herein.

In some embodiments, the cells are modified to overexpress the gene encoding albumin. In some embodiments, cells ectopically express the albumin gene. In some embodiments, the cells are genetically modified and carry stable integrations of one or more copies of the albumin gene. In some embodiments, the cells overexpress the gene encoding the albumin protein at levels sufficient to increase production and/or secretion of albumin into the cell culture medium.

Increase of albumin expression may be achieved using different approaches. In some embodiments, the expression is inducible. In some embodiments, the method comprises expressing nucleotides that encode the albumin gene. In some embodiments, the nucleotides are ectopically expressed from constructs that are introduced into the cells, for example expressed from a plasmid, or other expression vector. In some embodiments, the constructs are integrated into the cell's genome, and the expression is driven in that manner (e.g. homologous recombination, introduction mediated by CRISPR-based technology). In some embodiments, expression of the albumin gene involves electroporating a DNA, delivering a DNA complexed with a transfection vehicle, using a viral vector (e.g. retrovirus, lentivirus, adenovirus, adeno-associated virus, herpes simplex virus), and the like, or combinations thereof. In some embodiments, the expression is constitutive. In some embodiments, the expression is conditional, e.g. inducible, e.g. under the control of an inducible promoter, e.g. an inducible Tet construct. In some embodiments, the expression of albumin is constitutive, but the expression of additional genes of interest is inducible. In some embodiments, the expression of albumin is inducible, but the expression of additional genes of interest is constitutive.

The albumin gene can be from any animal, such as vertebrate and invertebrate animal species. In some embodiments, the albumin gene can be from any vertebrate animal species such as mammals, reptiles, birds, amphibians, and the like. In some embodiments, the albumin gene can be from any mammalian species, such as a human, murine, bovine, porcine, livestock, and the like.

In the methods described herein, a polynucleotide sequence encoding the albumin gene may encode any homolog of albumin, including any albumin paralogs, or an albumin protein translated from any splice variants of an albumin gene, or may comprise any mutations in the albumin gene sequence including, but not limited to nucleotide deletions, truncations, fusions, or substitutions. Mutations may be synthetic or naturally occurring. In some embodiments, methods described herein to overexpress albumin comprise introducing into the cells a polynucleotide sequence from Table 1B comprising an albumin gene.

In some embodiments, the cells are of a livestock, poultry, game or aquatic animal species. In an exemplary embodiment, the renewal capacity of the primary duck myoblasts is extended, and the myoblasts are engineered to stably overexpress albumin. In another exemplary embodiment, the renewal capacity of the primary duck myoblasts is extended, and the myoblasts are engineered to transiently overexpress albumin. In another exemplary embodiment, the renewal capacity of the primary duck myoblasts is extended, and the myoblasts are engineered to ectopically overexpress albumin.

In some embodiments, an increased expression of albumin using the methods described herein increases the concentration of albumin in the culture medium by at least 0.001%, 0.005%, 0.01%, at least 0.02%, at least 0.03%, at least 0.04%, at least 0.05%, at least 0.075%, at least 0.1%, at least 0.5%, at least 0.75%, at least 1%, at least 1.25%, at least 1.5%, at least 1.75%, at least 2%, at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 225%, at least 250%, at least 275%, at least 300%, at least 325%, at least 350%, at least 375% at least 400%, at least, 425%, at least 450%, at least 475%, at least 500%, at least 550%, at least 600%, at least 650%, at least 700%, at least 750%, at least 800%, at least 850%, at least 900%, at least 950% at least 1,000%, at least 1,100%, at least 1,200%, at least 1,300%, at least 1,400%, at least 1,500%, at least 1,600%, at least 1,700%, at least 1,800%, at least 1,900%, at least 2,000%, at least 2,250%, at least 2,500%, at least 2,750%, at least 3,000%, at least 3,500%, at least 4,000%, at least 4,500%, at least 5,000%, at least 6,000%, at least 7,000%, at least 8,000%, at least 9,000%, or even by at least 10,000% including values and ranges therebetween, compared to cultures of cells in which the albumin expression is not increased as described herein.

In some embodiments, an increased expression of albumin using the methods described herein increases the concentration of albumin in the culture medium to at least 0.0001 mg/mL, to at least 0.0002 mg/mL, to at least 0.0004 mg/mL, to at least 0.0005 mg/mL, to at least 0.0006 mg/mL, to at least 0.0007 mg/mL, to at least 0.0008 mg/mL, to at least 0.0009 mg/mL, to at least 0.001 mg/mL, to at least 0.002 mg/mL, to at least 0.003 mg/mL, to at least 0.004 mg/mL, to at least 0.005 mg/mL, to at least 0.006 mg/mL, to at least 0.007 mg/mL, to at least 0.008 mg/mL, to at least 0.009 mg/mL, to at least 0.01 mg/mL, to at least 0.05 mg/mL, to at least 0.075 mg/mL, to at least 0.1 mg/mL, to at least 0.25 mg/mL, to at least 0.5 mg/mL, to at least 0.75 mg/mL, to at least 1 mg/mL, to at least 1.25 mg/mL, to at least 1.5 mg/mL, to at least 1.75 mg/mL, to at least 2 mg/mL, to at least 3 mg/mL, to at least 5 mg/mL, to at least 10 mg/mL, to at least 20 mg/mL, to at least 25 mg/mL, to at least 50 mg/mL, to at least 75 mg/mL, or even to at least 100 mg/mL, including values and ranges therebetween, compared to cultures of cells in which the albumin expression is not increased as described herein.

Methods to measure the increase in the concentration of albumin include commercial kits, such as the BCG Albumin Assay Kit (Sigma-Aldrich #MAK124), BCP Albumin Assay Kit (Sigma-Aldrich #MAK125), and antibody-based methods, such as immunoprecipitation, co-immunoprecipitation, Western blotting, Enzyme-linked immunosorbent assay (ELISA), and amino-acid based tagging, isolation, and separation (e.g., FLAG, GST, GFP, etc.).

In some embodiments, provided herein is a method of increasing the rate of proliferation of cells in a cultivation infrastructure, comprising increasing the expression of albumin in the cells, wherein the cells are of livestock, poultry, game or aquatic animal species. In some embodiments, the population doubling time of the cells is decreased by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%, by more than 95%, including values and ranges therebetween, compared to cells in which the expression of albumin is not increased.

In one embodiment, provided herein is a method of decreasing cell death comprising increasing the expression of albumin in the cells. In some embodiments, the decrease in cell death provided is about 2.5%, about 5%, about 10%, about 20%, about 30%, about 40%, about 50%, about 60%, about 70%, about 80%, about 90%, or about 100%, including values and ranges therebetween, compared to the methods wherein the expression of albumin is not increased.

In some embodiments, provided herein are cells that overexpress any combination of GS, IGF, and albumin. For example, in one embodiment, provided herein are cells that overexpress a GS protein and an IGF protein. In one embodiment, provided herein are cells that overexpress an albumin protein and a GS protein. In one embodiment, provided herein are cells that overexpress an albumin protein and an IGF protein. In one embodiment, provided herein are cells that overexpress an albumin protein, a GS protein, and an IGF protein.

TERT and CKI Proteins

Provided herein are cells whose renewal capacity is extended, for e.g., by overexpressing a TERT protein and/or by inhibiting the activity of CM proteins. Exemplary methods to overexpress TERT and inhibit the activity of CM proteins are disclosed in U.S. Provisional Application No. 62/278,869, filed on Jan. 14, 2016, and 62/361,867, filed on Jul. 13, 2016, and a PCT Application No. PCT/US2017/013782, filed on Jan. 17, 2017, all of which are incorporated herein by reference in their entirety.

In some embodiments, provided herein is a method for increasing the density of cells in a culture or an in vitro method for producing a cultured edible product comprising increasing the expression of a TERT protein in the cells in combination with increasing the expression of GS, IGF, albumin, or a combination thereof. In some embodiments, provided herein is a method for increasing the density of cells in a culture or an in vitro method for producing a cultured edible product comprising inhibiting the activity of CM proteins in the cells in combination with increasing the expression of GS, IGF, albumin, or a combination thereof. In some embodiments, provided herein is a method for increasing the density of cells in a culture or an in vitro method for producing a cultured edible product comprising increasing the expression of a TERT protein in the cells, inhibiting the activity of CM proteins in the cells, and increasing the expression of GS, IGF, albumin, or a combination thereof.

In some embodiments, the cells are modified to overexpress a polynucleotide sequence encoding TERT. In some embodiments, cells ectopically express the TERT polynucleotide. In some embodiments, the cells are genetically modified and carry stable integrations of one or more copies of the TERT polynucleotide.

Increased expression of TERT may be achieved using different approaches. In some embodiments, increased expression of TERT may be achieved by ectopically expressing TERT. In some embodiments, increased expression of TERT may be achieved by introducing targeted mutations in the TERT promoter. In some embodiments, increased expression of TERT may be achieved by activating endogenous TERT expression by an engineered transcriptional activator. In some embodiments, increased expression of TERT may be achieved by transiently transfecting TERT mRNA.

In some embodiments, the expression of TERT is inducible. In some embodiments, the method comprises expressing nucleotides that encode the TERT protein. In some embodiments, the nucleotides are ectopically expressed from constructs that are introduced into the cells, for example expressed from a plasmid, or other expression vector. In some embodiments, the constructs are integrated into the cell's genome, and the expression is driven in that manner (e.g. homologous recombination, introduction mediated by CRISPR-based technology). In some embodiments, the expression of the TERT gene involves electroporating a DNA, delivering a DNA complexed with a transfection vehicle, using a viral vector (e.g. retrovirus, lentivirus, adenovirus, adeno-associated virus, herpes simplex virus), and the like, or combinations thereof. In some embodiments, the expression is constitutive. In some embodiments, the expression is conditional, e.g. inducible, e.g. under the control of an inducible promoter, e.g. an inducible Tet construct. In some embodiments, the expression of TERT is constitutive, but the expression of additional genes of interest is inducible. In some embodiments, the expression of TERT is inducible, but the expression of additional genes of interest is constitutive.

The polynucleotide encoding TERT can be from of any organism. The TERT polynucleotide can be from bacteria, plants, fungi, and archaea. The TERT polynucleotide can be from any animal, such as vertebrate and invertebrate animal species. The TERT polynucleotide can be from any vertebrate animal species such as mammals, reptiles, birds, amphibians, and the like. The TERT polynucleotide can be from any mammalian species, such as a human, murine, bovine, porcine, and the like.

In some embodiments, the methods of inhibiting CM proteins comprise introducing loss-of-function mutations, e.g., INDEL (insertion or deletion) mutations, into one or more genes encoding CM proteins in the cells. This can be accomplished using any gene based technologies, for example, using CRISPR-Cas (Clustered Regularly Interspersed Short Palindromic Repeats) based technology or TALEN based technology. In an exemplary embodiment, the genes encoding CM proteins are the genes encoding CM proteins p15, p16, paralogs, orthologs, or genetic variants thereof. In an exemplary embodiment, the methods of inhibiting CM proteins comprise introducing loss-of-function mutations in CDKN2B gene (p15) and/or in CDKN2A gene (p16).

In some embodiments, inhibiting the activity of CM proteins comprises activating a CDK4 protein, paralogs, orthologs or genetic variants thereof.

In some embodiments, the methods of inhibiting the CM function comprise introducing into the cells a vector expressing a polynucleotide that encodes a dominant negative mutant of one or more CM proteins. In some embodiments, the polynucleotide is ectopically expressed from a construct that is introduced into the cells of the biomass, for example expressed from a plasmid, or other vector. In some embodiments, the construct is integrated into the cell's genome, and the expression is driven in that manner (e.g. introduction mediated by CRISPR-based technology). In some embodiments, the expression of the polynucleotide involves electroporating a DNA, delivering a DNA complexed with a transfection vehicle, using a viral vector (e.g. retrovirus, lentivirus, adenovirus, adeno-associated virus, herpes simplex virus), and the like, or combinations thereof. In some embodiments, the expression is constitutive. In some embodiments, the expression is conditional, e.g. inducible, e.g. under the control of an inducible promoter, e.g. an inducible Tet construct.

In some embodiments, the methods of inhibiting comprise delivering dominant negative mutants of one or more CM proteins directly, e.g. purified proteins, synthetic proteins, or recombinantly expressed proteins, or combinations thereof, to the cells.

In some embodiments, the methods of inhibiting comprise transcriptional repression of the endogenous genes encoding one or more CM proteins in the cells. This can be accomplished, for example, by using nucleic acid sequence-directed transcriptional repressors. For example, an endonuclease-defective Cas9, dCas9, can be combined with a guide RNA that targets the promoter region of the genes encoding one or more CM proteins and reduces the transcriptional activation and concomitant gene expression.

In some embodiments, the cells are of a livestock, poultry, game or aquatic animal species. In an exemplary embodiment, the renewal capacity of the primary duck myoblasts is extended, and the myoblasts are engineered to stably overexpress GS, IGF, albumin, or any combination thereof. In another exemplary embodiment, the renewal capacity of the primary duck myoblasts is extended, and the myoblasts are engineered to transiently overexpress GS, IGF, albumin, or any combination thereof. In another exemplary embodiment, the renewal capacity of the primary duck myoblasts is extended, and the myoblasts are engineered to ectopically overexpress GS, IGF, albumin, or any combination thereof.

In some embodiments, provided herein are cells that overexpress a GS protein and an IGF protein. The cells may optionally be modified to extend renewal capacity, and may comprise activated TERT and/or inactivated CM protein, may comprise an antagonized HIPPO signaling pathway, e.g., activated YAP/TAZ, may be further differentiated, and the like.

In some embodiments, provided herein are cells that overexpress an albumin protein and a GS protein. The cells may optionally be modified to extend renewal capacity, and may comprise activated TERT and/or inactivated CM protein, may comprise an antagonized HIPPO signaling pathway, e.g., activated YAP/TAZ, may be further differentiated, and the like.

In some embodiments, provided herein are cells that overexpress an albumin protein and an IGF protein. The cells may optionally be modified to extend renewal capacity, and may comprise activated TERT and/or inactivated CM protein, may comprise an antagonized HIPPO signaling pathway, e.g., activated YAP/TAZ, may be further differentiated, and the like.

In some embodiments, provided herein are cells that overexpress an albumin protein, a GS protein, and an IGF protein. The cells may optionally be modified to extend renewal capacity, and may comprise activated TERT and/or inactivated CM protein, may comprise an antagonized HIPPO signaling pathway, e.g., activated YAP/TAZ, may be further differentiated, and the like.

Tables 1A and 1B show exemplary sequences used for ectopic overexpression in some exemplary embodiments provided herein. The cells may optionally be modified to extend renewal capacity, and may comprise activated TERT and/or inactivated CM protein, may comprise an antagonized HIPPO signaling, e.g., activated YAP/TAZ, may be further differentiated, and the like.

Table 1C shows exemplary amino acid sequences for GS, albumin, and IGF proteins that may be expressed in cells according to the methods described here.

TABLE 1A

| Gene | Species | NCBI # | Vendor | Eukaryotic selection marker | Prokaryotic selection marker | Tag | Backbone |
|---|---|---|---|---|---|---|---|
| Glutamine Synthetase (GS) | mouse | NM_008131 | Genscript OMu19897D | Neo | Amp | C terminal DYKDDDDK (SEQ ID NO: 57) tags | pcDNA3.1+/ C-(K)DYK (SEQ ID NO: 58) |
| IGF-1 | human | NM_000618.2 | Origene RG212527 | Neo | Kan | Myc-DDK | pCMV6-Entry |
| Albumin | human | NM_000477 | Genscript OHu18744 | Neo | Amp | C terminal DYKDDDDK (SEQ ID NO: 57) tags | |
| Albumin | Mouse | NM_009654 | Genscript OMu21640 | Neo | Amp | C terminal DYKDDDDK (SEQ ID NO: 57) tags | |

TABLE 1B

| Gene | Species | NCBI # | DNA Sequence |
|---|---|---|---|
| IGF1 + porcine albumin signal peptide | bovine | | ATGAAGTGGGTGACTTTTATTTCCCTTCTCTTTCTCTTCAGCTCT GCTTATTCCTTCTTGAAGCAGGTGAAGATGCCCATCACATCCT CCTCGCATCTCTTCTATCTGGCCCTGTGCTTGCTCGCCTTCACC AGCTCTGCCACGGCGGGACCCGAGACCCTCTGCGGGGCTGAGT TGGTGGATGCTCTCCAGTTCGTGTGCGGAGACAGGGGCTTTTA TTTCAACAAGCCCACGGGGTATGGCTCGAGCAGTCGGAGGGC GCCCCAGACAGGAATCGTGGATGAGTGCTGCTTCCGGAGCTGT GATCTGAGGAGGCTGGAGATGTACTGCGCGCCTCTCAAGCCCG CCAAGTCGGCCCGCTCAGTCCGTGCCCAGCGCCACACCGACAT GCCCAAGGCTCAGAAGGAAGTACATTTGAAGAACACAAGTAG AGGGAGTGCAGGAAACAAGAACTACAGAATGTAG (SEQ ID NO: 1) |
| IGF1 + porcine albumin signal peptide | chicken | | ATGAAGTGGGTGACTTTTATTTCCCTTCTCTTTCTCTTCAGCTCT GCTTATTCCTTCTTGAAGGTGAAGATGCACACTGTGTCCTACAT TCATTTCTTCTACCTTGGCCTGTGTTTGCTTACCTTAACCAGTTC TGCTGCTGCCGGCCCAGAAACACTGTGTGGTGCTGAGCTGGTT GATGCTCTTCAGTTCGTATGTGGAGACAGAGGCTTCTACTTCA GTAAGCCTACAGGGTATGGATCCAGCAGTAGACGCTTACACCA CAAGGGAATAGTGGATGAATGCTGCTTCCAGAGTTGTGACCTG AGGAGGCTGGAGATGTACTGTGCTCCAATAAAGCCACCTAAAT CTGCACGCTCTGTACGTGCTCAGCGCCACACTGATATGCCAAA AGCACAAAAGGAAGTGCATTTGAAGAATACAAGTAGAGGGAA CACAGGAAACAGAAACTACAGAATGTAA (SEQ ID NO: 2) |
| IGF1 + porcine albumin signal peptide | porcine | | ATGAAGTGGGTGACTTTTATTTCCCTTCTCTTTCTCTTCAGCTCT GCTTATTCCTTGGCCCTGTGCTTGCTCTCCTTCACCAGCTCTGC CACGGCTGGACCTGAGACCCTCTGTGGGGCTGAGCTGGTGGAC GCTCTTCAGTTCGTGTGCGGAGACAGGGGCTTTTATTTCAACA AGCCCACAGGGTACGGCTCCAGCAGTCGGAGGGCGCCACAGA CGGGCATCGTGGATGAGTGCTGCTTCCGGAGCTGTGATCTGAG GAGGCTGGAGATGTACTGTGCACCCCTCAAGCCTGCCAAGTCG GCCCGCTCCGTCCGTGCCCAGCGCCACACGGACATGCCCAAGG CTCAGAAGGAAGTACATTTGAAGAACACAAGTAGAGGGAGTT CAGGAAACAAGAACTACAGAATGTAG (SEQ ID NO: 3) |
| Wild Type IGF1 | chicken | NM_001004384 | ATGGAAAAAATCAACAGTCTTTCAACACAATTAGTTAAGTGCT GCTTTTGTGATTTCTTGAAGGTGAAGATGCACACTGTGTCCTAC ATTCATTTCTTCTACCTTGGCCTGTGTTTGCTTACCTTAACCAG TTCTGCTGCTGCCGGCCCAGAAACACTGTGTGGTGCTGAGCTG GTTGATGCTCTTCAGTTCGTATGTGGAGACAGAGGCTTCTACTT CAGTAAGCCTACAGGGTATGGATCCAGCAGTAGACGCTTACAC CACAAGGGAATAGTGGATGAATGCTGCTTCCAGAGTTGTGACC TGAGGAGGCTGGAGATGTACTGTGCTCCAATAAAGCCACCTAA ATCTGCACGCTCTGTACGTGCTCAGCGCCACACTGATATGCCA AAAGCACAAAAGGAAGTGCATTTGAAGAATACAAGTAGAGGG AACACAGGAAACAGAAACTACAGAATGTAA (SEQ ID NO: 4) |
| Wild Type IGF1 | bovine | NM_001077828 | ATGGGAAAAATCAGCAGTCTTCCAACCCAATTATTTAAGTGCT GCTTTTGTGATTTCTTGAAGCAGGTGAAGATGCCCATCACATC CTCCTCGCATCTCTTCTATCTGGCCCTGTGCTTGCTCGCCTTCA CCAGCTCTGCCACGGCGGGACCCGAGACCCTCTGCGGGGCTGA GTTGGTGGATGCTCTCCAGTTCGTGTGCGGAGACAGGGGCTTT TATTTCAACAAGCCCACGGGGTATGGCTCGAGCAGTCGGAGG GCGCCCCAGACAGGAATCGTGGATGAGTGCTGCTTCCGGAGCT |

TABLE 1B-continued

| Gene | Species | NCBI # | DNA Sequence |
|---|---|---|---|
| | | | GTGATCTGAGGAGGCTGGAGATGTACTGCGCGCCTCTCAAGCC<br>CGCCAAGTCGGCCCGCTCAGTCCGTGCCCAGCGCCACACCGAC<br>ATGCCCAAGGCTCAGAAGGAAGTACATTTGAAGAACACAAGT<br>AGAGGGAGTGCAGGAAACAAGAACTACAGAATGTAG (SEQ ID<br>NO: 5) |
| Wild Type<br>IGF1 | porcine | NM_214256 | ATGCACATCACATCCTCTTCGCATCTCTTCTACTTGGCCCTGTG<br>CTTGCTCTCCTTCACCAGCTCTGCCACGGCTGGACCTGAGACC<br>CTCTGTGGGGCTGAGCTGGTGGACGCTCTTCAGTTCGTGTGCG<br>GAGACAGGGGCTTTTATTTCAACAAGCCCACAGGGTACGGCTC<br>CAGCAGTCGGAGGGCGCCACAGACGGGCATCGTGGATGAGTG<br>CTGCTTCCGGAGCTGTGATCTGAGGAGGCTGGAGATGTACTGT<br>GCACCCCTCAAGCCTGCCAAGTCGGCCCGCTCCGTCCGTGCCC<br>AGCGCCACACGGACATGCCCAAGGCTCAGAAGGAAGTACATT<br>TGAAGAACACAAGTAGAGGGAGTTCAGGAAACAAGAACTACA<br>GAATGTAG (SEQ ID NO: 6) |
| Albumin +<br>porcine<br>albumin<br>signal<br>peptide | bovine | | ATGAAGTGGGTGACTTTTATTTCCCTTCTCTTTCTCTTCAGCTCT<br>GCTTATTCCAGGGGTGTGTTTCGTCGAGATACACACAAGAGTG<br>AGATTGCTCATCGGTTTAAAGATTTGGGAGAAGAACATTTTAA<br>AGGCCTGGTACTGATTGCCTTTTCTCAGTATCTCCAGCAGTGTC<br>CATTTGATGAGCATGTAAAATTAGTGAACGAACTAACTGAGTT<br>TGCAAAAACATGTGTTGCTGATGAGTCCCATGCCGGCTGTGAG<br>AAGTCACTTCACACTCTCTTTGGAGATGAATTGTGTAAAGTTG<br>CATCCCTTCGTGAAACCTATGGTGACATGGCTGACTGCTGTGA<br>GAAACAAGAACCTGAGAGAAATGAATGCTTCTTGTCACACAA<br>AGATGATAGCCCTGATCTACCTAAACTCAAACCTGACCCCAAT<br>ACTTTGTGTGACGAGTTTAAGGCCGATGAAAAGAAGTTTTGGG<br>GAAAATACCTATACGAAATTGCTAGAAGACATCCCTACTTTTA<br>TGCACCAGAACTCCTTTACTATGCTAATAAATATAATGGAGTT<br>TTTCAAGAATGCTGCCAAGCTGAAGATAAAGGTGCCTGCCTGC<br>TACCAAAGATTGAAACTATGAGGGAAAAGGTACTGACTTCATC<br>TGCCAGACAGAGACTCAGGTGTGCCAGTATTCAAAAATTTGGA<br>GAAAGAGCTTTAAAAGCATGGTCAGTAGCTCGCCTGAGCCAG<br>AAATTTCCCAAGGCTGAGTTTGTAGAAGTTACCAAGCTAGTGA<br>CAGATCTCACAAAAGTGCACAAGGAATGCTGCCATGGAGACC<br>TACTTGAATGCGCAGATGACAGGGCGGACCTTGCCAAGTACAT<br>ATGTGATAATCAAGATACAATCTCCAGTAAACTGAAGGAATGC<br>TGTGATAAGCCTTTGTTGGAAAAATCCCACTGCATTGCTGAGG<br>TAGAAAAAGATGCCATACCTGAAAACTTGCCCCCATTAACTGC<br>TGACTTTGCTGAAGATAAGGATGTATGCAAAAACTATCAAGAA<br>GCAAAGGATGCCTTCCTGGGCTCATTTCTTTATGAATATTCAA<br>GAAGGCATCCTGAATATGCTGTCTCAGTGCTATTGAGACTTGC<br>CAAGGAATATGAAGCCACACTGGAGGAATGCTGTGCCAAAGA<br>TGATCCACATGCATGCTATTCCACAGTGTTTGACAAACTTAAG<br>CATCTTGTGGATGAGCCTCAGAATTTAATTAAACAAAACTGTG<br>ACCAATTCGAAAAACTTGGAGAGTATGGATTCCAAAATGCGCT<br>CATAGTTCGTTACACCAGGAAAGTACCCCAAGTGTCAACTCCA<br>ACTCTCGTGGAGGTTTCAAGAAGCCTAGGAAAAGTGGGTACTA<br>GGTGTTGTACAAAACCGGAATCAGAAAGAATGCCCTGTACAG<br>AAGACTATCTGAGCTTGATCCTGAACCGGTTGTGCGTGCTGCA<br>TGAGAAGACACCAGTGAGTGAAAAAGTCACCAAGTGCTGCAC<br>AGAGTCATTGGTGAACAGACGGCCATGTTTCTCTGCTCTGACA<br>CCTGATGAAACATATGTACCCAAAGCCTTTGATGAGAAATTGT<br>TCACCTTCCATGCAGATATATGCACACTTCCCGATACTGAGAA<br>ACAAATCAAGAAACAAACTGCACTTGTTGAGCTGTTGAAACAC<br>AAGCCCAAGGCAACAGAGGAACAACTGAAAACCGTCATGGAG<br>AATTTTGTGGCTTTTGTAGACAAGTGCTGCGCAGCTGATGACA<br>AAGAAGCCTGCTTTGCTGTGGAGGGTCCAAAACTTGTTGTTTC<br>AACTCAAACAGCCTTAGCCTAA (SEQ ID NO: 7) |
| Albumin +<br>porcine<br>albumin<br>signal<br>peptide | chicken | | ATGAAGTGGGTGACTTTTATTTCCCTTCTCTTTCTCTTCAGCTCT<br>GCTTATTCCAGGAATCTGCAAAGATTTGCTCGTGATGCAGAGC<br>ACAAGAGTGAAATTGCCCATCGCTACAATGATTTGAAAGAAG<br>AAACATTTAAGGCAGTTGCCATGATCACATTTGCCCAGTATCT<br>CCAGAGGTGCTCTTATGAAGGACTGTCTAAGCTTGTGAAGGAT<br>GTTGTTGATCTGGCACAAAAATGTGTAGCCAATGAAGATGCTC<br>CTGAATGCTCAAAACCACTGCCTTCCATTATCCTGGATGAAAT<br>CTGCCAAGTGGAAAAGCTCCGTGACTCTTATGGTGCAATGGCC<br>GACTGCTGTAGCAAAGCTGATCCTGAAAGAAATGAGTGTTTCC<br>TGTCATTTAAAGTTTCCCAACCAGACTTCGTTCAGCCATACCA<br>AAGACCAGCTTCTGATGTGATATGCCAGGAATACCAGGACAA<br>CAGAGTGTCATTTCTGGGACATTTCATCTATTCTGTTGCAAGAA<br>GACACCCCTCTTGTATGCCCCTGCAATCCTTAGTTTTGCTGTT<br>GATTTTGAACATGCACTTCAAAGCTGTTGCAAAGAGAGTGATG<br>TCGGTGCTTGCCTGGACACCAAGGAAATTGTTATGAGAGAAAA<br>AGCCAAGGGAGTAAGTGTGAAGCAGCAGTATTTTTGTGGAATC<br>TTGAAGCAGTTCGGAGATAGAGTTTTCCAAGCACGACAACTTA |

TABLE 1B-continued

| Gene | Species | NCBI # | DNA Sequence |
|---|---|---|---|
| | | | TTTACCTAAGCCAAAAATACCCCAAGGCTCCATTCTCAGAGGT<br>TTCTAAATTTGTACATGATTCTATCGGCGTCCACAAAGAGTGC<br>TGTGAAGGGACATGGTGGAGTGCATGGATGACATGGCACGT<br>ATGATGAGCAATCTGTGCTCTCAACAAGATGTTTTCTCAGGTA<br>AAATCAAAGACTGCTGTGAGAAGCCTATTGTGGAACGAAGCC<br>AGTGCATTATGGAGGCAGAATTTGATGAGAAACCTGCAGATCT<br>TCCTTCATTAGTTGAAAAGTACATAGAAGATAAGGAAGTGTGT<br>AAAAGTTTTGAAGCAGGCCACGATGCATTCATGGCAGAGTTCG<br>TTTATGAATACTCACGAAGACACCCTGAGTTCTCCATACAGCT<br>TATTATGAGAATTGCCAAAGGATATGAATCACTTCTGGAAAAG<br>TGCTGCAAAACTGATAACCCTGCTGAGTGCTACGCAAATGCTC<br>AAGAGCAACTGAACCAACATATCAAAGAAACTCAGGATGTTG<br>TGAAGACAAACTGTGATCTTCTCCATGACCATGGCGAGGCAGA<br>CTTCCTCAAGTCCATCCTGATCCGCTACACTAAGAAAATGCCT<br>CAAGTACCAACTGATCTCCTGCTTGAAACTGGAAAGAAAATGA<br>CAACTATTGGTACTAAGTGCTGCCAGCTTCCTGAAGACAGACG<br>CATGGCTTGTTCTGAGGGTTATCTGAGCATTGTGATTCATGATA<br>CGTGCAGGAAACAGGAGACCACACCTATAAATGACAACGTTT<br>CACAATGCTGCAGCAGCTCCTATGCTAACAGAAGACCATGTTT<br>CACTGCTATGGGAGTAGATACCAAATATGTTCCTCCACCATTT<br>AATCCTGATATGTTCAGCTTTGATGAAAAATTGTGCAGTGCTC<br>CTGCTGAAGAACGAGAAGTAGGCCAGATGAAATTGCTAATCA<br>ACCTCATTAAACGCAAGCCCCAGATGACAGAAGAACAAATAA<br>AGACAATTGCTGATGGTTTCACTGCCATGGTTGACAAGTGCTG<br>CAAGCAGTCGGACATCAATACATGCTTTGGAGAAGAGGGTGC<br>CAACCTAATAGTCCAAAGCAGAGCCACATTAGGAATTGGTGCT<br>TAA (SEQ ID NO: 8) |
| Wild Type<br>Albumin | porcine | NM_001005208 | ATGAAGTGGGTGACTTTTATTTCCCTTCTCTTTCTCTTCAGCTCT<br>GCTTATTCCAGGGGTGTGTTTCGTCGAGATACATACAAGAGTG<br>AAATTGCTCATCGGTTTAAAGATTTGGGAGAACAATATTTCAA<br>AGGCCTAGTGCTGATTGCCTTTTCTCAGCATCTCCAGCAATGCC<br>CATATGAAGAGCATGTGAAATTAGTGAGGGAAGTAACTGAGT<br>TTGCAAAAACATGTGTTGCTGATGAGTCAGCTGAAAATTGTGA<br>CAAGTCAATTCACACTCTCTTTGGAGATAAATTATGTGCAATT<br>CCATCCCTTCGTGAACACTATGGTGACTTGGCTGACTGCTGTG<br>AAAAAGAAGAGCCTGAGAGAAACGAATGCTTCCTCCAACACA<br>AAAATGATAACCCCGACATCCCTAAATTGAAACCAGACCCTGT<br>TGCTTTATGCGCTGACTTCCAGGAAGATGAACAGAAGTTTTGG<br>GGAAAAATACCTATATGAAATTGCCAGAAGACATCCCTATTTCT<br>ACGCCCCAGAACTCCTTTATTATGCCATTATATATAAAGATGTT<br>TTTTCAGAATGCTGCCAAGCTGCTGATAAAGCTGCCTGCCTGT<br>TACCAAAGATTGAGCATCTGAGAGAAAAAGTACTGACTTCCGC<br>CGCCAAACAGAGACTTAAGTGTGCCAGTATCCAAAAATTCGG<br>AGAGAGAGCTTTCAAAGCATGGTCATTAGCTCGCCTGAGCCAG<br>AGATTTCCCAAGGCTGACTTTACAGAGATTTCCAAGATAGTGA<br>CAGATCTTGCAAAAGTCCACAAGGAATGCTGCCATGGTGACCT<br>GCTTGAATGTGCAGATGACAGGGCGGATCTTGCCAAATATATA<br>TGTGAAAATCAAGACACAATCTCCACTAAACTGAAGGAATGCT<br>GTGATAAGCCTCTGTTGGAAAAATCCCACTGCATTGCTGAGGC<br>AAAAAGAGATGAATTGCCTGCAGACCTGAACCCATTAGAACA<br>TGATTTTGTTGAAGATAAGGAAGTTTGTAAAAACTATAAAGAA<br>GCAAAGCATGTCTTCCTGGGCACGTTTTTGTATGAGTATTCAA<br>GAAGGCACCCAGACTACTCTGTCTCATTGCTGCTGAGAATTGC<br>CAAGATATATGAAGCCACACTGGAGGACTGCTGTGCCAAAGA<br>GGATCCTCCGGCATGCTATGCCACAGTGTTTGATAAATTTCAG<br>CCTCTTGTGGATGAGCCTAAGAATTTAATCAAACAAAACTGTG<br>AACTTTTTGAAAAACTTGGAGAGTATGGATTCCAAAATGCGCT<br>CATAGTTCGTTACACCAAGAAAGTACCCCAAGTGTCAACTCCA<br>ACTCTTGTGGAGGTCGCAAGAAAACTAGGACTAGTGGGCTCTA<br>GGTGTTGTAAGCGTCCTGAAGAAGAAAGACTGTCCTGTGCTGA<br>AGACTATCTGTCCCTGGTCCTGAACCGGTTGTGCGTGTTGCAC<br>GAGAAGACACCAGTGAGCGAAAAAGTTACCAAATGCTGCACA<br>GAGTCCTTGGTGAACAGACGGCCTTGCTTTTCTGCTCTGACAC<br>CAGACGAAACATACAAACCCAAAGAATTTGTTGAGGGAACCT<br>TCACCTTCCATGCAGACCTATGCACACTTCCTGAGGATGAGAA<br>ACAAATCAAGAAGCAAACTGCACTCGTTGAGTTGTTGAAACAC<br>AAGCCTCATGCAACAGAGGAACAACTGAGAACTGTCCTGGGC<br>AACTTTGCAGCCTTTGTACAAAAGTGCTGCGCCGCTCCTGACC<br>ATGAGGCCTGCTTTGCTGTGGAGGGTCCGAAATTTGTTATTGA<br>AATTCGAGGGATCTTAGCCTAA (SEQ ID NO: 9) |
| Wild Type<br>Albumin | chicken | NM_205261 | ATGAAGTGGGTAACATTAATTTCATTCATTTTCCTCTTCAGTTC<br>AGCAACATCCAGGAATCTGCAAAGATTTGCTCGTGATGCAGAG<br>CACAAGAGTGAAATTGCCCATCGCTACAATGATTTGAAAGAA<br>GAAACATTTAAGGCAGTTGCCATGATCACATTTGCCCAGTATC<br>TCCAGAGGTGCTCTTATGAAGGACTGTCTAAGCTTGTGAAGGA<br>TGTTGTTGATCTGGCACAAAAATGTGTAGCCAATGAAGATGCT |

TABLE 1B-continued

| Gene | Species | NCBI # | DNA Sequence |
|---|---|---|---|
| | | | CCTGAATGCTCAAAACCACTGCCTTCCATTATCCTGGATGAAA<br>TCTGCCAAGTGGAAAAGCTCCGTGACTCTTATGGTGCAATGGC<br>CGACTGCTGTAGCAAAGCTGATCCTGAAAGAAATGAGTGTTTC<br>CTGTCATTTAAAGTTTCCCAACCAGACTTCGTTCAGCCATACCA<br>AAGACCAGCTTCTGATGTGATATGCCAGGAATACCAGGACAA<br>CAGAGTGTCATTTCTGGGACATTTCATCTATTCTGTTGCAAGAA<br>GACACCCCTTCTTGTATGCCCCTGCAATCCTTAGTTTTGCTGTT<br>GATTTTGAACATGCACTTCAAAGCTGTTGCAAAGAGAGTGATG<br>TCGGTGCTTGCCTGGACACCAAGGAAATTGTTATGAGAGAAAA<br>AGCCAAGGGAGTAAGTGTGAAGCAGCAGTATTTTTGTGGAATC<br>TTGAAGCAGTTCGGAGATAGAGTTTTCCAAGCACGACAACTTA<br>TTTACCTAAGCCAAAAATACCCCAAGGCTCCATTCTCAGAGGT<br>TTCTAAATTTGTACATGATTCTATCGGCGTCCACAAAGAGTGC<br>TGTGAAGGGACATGGTGGAGTGCATGGATGACATGGCACGT<br>ATGATGAGCAATCTGTGCTCTCAACAAGATGTTTTCTCAGGTA<br>AAATCAAAGACTGCTGTGAGAAGCCTATTGTGGAACGAAGCC<br>AGTGCATTATGGAGGCAGAATTTGATGAGAAACCTGCAGATCT<br>TCCTTCATTAGTTGAAAAGTACATAGAAGATAAGGAAGTGTGT<br>AAAAGTTTTGAAGCAGGCCACGATGCATTCATGGCAGAGTTCG<br>TTTATGAATACTCACGAAGACACCCTGAGTTCTCCATACAGCT<br>TATTATGAGAATTGCCAAAGGATATGAATCACTTCTGGAAAAG<br>TGCTGCAAAACTGATAACCCTGCTGAGTGCTACGCAAATGCTC<br>AAGAGCAACTGAACCAACATATCAAAGAAACTCAGGATGTTTG<br>TGAAGACAAACTGTGATCTTCTCCATGACCATGGCGAGGCAGA<br>CTTCCTCAAGTCCATCCTGATCCGCTACACTAAGAAAATGCCT<br>CAAGTACCAACTGATCTCCTGCTTGAAACTGGAAAGAAAATGA<br>CAACTATTGGTACTAAGTGCTGCCAGCTTCCTGAAGACAGACG<br>CATGGCTTGTTCTGAGGGTTATCTGAGCATTGTGATTCATGATA<br>CGTGCAGGAAACAGGAGACCACACCTATAAATGACAACGTTT<br>CACAATGCTGCAGCAGCTCCTATGCTAACAGAAGACCATGTTT<br>CACTGCTATGGGAGTAGATACCAAATATGTTCCTCCACCATTT<br>AATCCTGATATGTTCAGCTTTGATGAAAAATTGTGCAGTGCTC<br>CTGCTGAAGAACGAGAAGTAGGCCAGATGAAATTGCTAATCA<br>ACCTCATTAAACGCAAGCCCCAGATGACAGAAGAACAAATAA<br>AGACAATTGCTGATGGTTTCACTGCCATGGTTGACAAGTGCTG<br>CAAGCAGTCGGACATCAATACATGCTTTGGAGAAGAGGGTGC<br>CAACCTAATAGTCCAAAGCAGAGCCACATTAGGAATTGGTGCT<br>TAA (SEQ ID NO: 10) |
| Wild Type<br>Albumin | Bovine | NM_180992 | ATGAAGTGGGTGACTTTTATTTCTCTTCTCCTTCTCTTCAGCTCT<br>GCTTATTCCAGGGGTGTGTTTCGTCGAGATACACACAAGAGTG<br>AGATTGCTCATCGGTTTAAAGATTTGGGAGAAGAACATTTTAA<br>AGGCCTGGTACTGATTGCCTTTTCTCAGTATCTCCAGCAGTGTC<br>CATTTGATGAGCATGTAAAATTAGTGAACGAACTAACTGAGTT<br>TGCAAAAACATGTGTTGCTGATGAGTCCCATGCCGGCTGTGAG<br>AAGTCACTTCACACTCTCTTTGGAGATGAATTGTGTAAAGTTG<br>CATCCCTTCGTGAAACCTATGGTGACATGGCTGACTGCTGTGA<br>GAAACAAGAACCTGAGAGAAATGAATGCTTCTTGTCACACAA<br>AGATGATAGCCCTGATCTACCTAAACTCAAACCTGACCCCAAT<br>ACTTTGTGTGACGAGTTTAAGGCCGATGAAAAGAAGTTTTGGG<br>GAAAATACCTATACGAAATTGCTAGAAGACATCCCTACTTTTA<br>TGCACCAGAACTCCTTTACTATGCTAATAAATATAATGGAGTT<br>TTTCAAGATGCTGCCAAGCTGAAGATAAAGGTGCCTGCCTGC<br>TACCAAAGATTGAAACTATGAGGGAAAAGGTACTGACTTCATC<br>TGCCAGACAGAGACTCAGGTGTGCCAGTATTCAAAAATTTGGA<br>GAAAGAGCTTTAAAAGCATGGTCAGTAGCTCGCCTGAGCCAG<br>AAATTTCCCAAGGCTGAGTTTGTAGAAGTTACCAAGCTAGTGA<br>CAGATCTCACAAAAGTGCACAAGGAATGCTGCCATGGAGACC<br>TACTTGAATGCGCAGATGACAGGGCGGACCTTGCCAAGTACAT<br>ATGTGATAATCAAGATACAATCTCCAGTAAACTGAAGGAATGC<br>TGTGATAAGCCTTTGTTGGAAAAATCCCACTGCATTGCTGAGG<br>TAGAAAAAGATGCCATACCTGAAAACTTGCCCCCATTAACTGC<br>TGACTTTGCTGAAGATAAGGATGTATGCAAAAACTATCAAGAA<br>GCAAAGGATGCCTTCCTGGGCTCATTTCTTTATGAATATTCAA<br>GAAGGCATCCTGAATATGCTGTCTCAGTGCTATTGAGACTTGC<br>CAAGGAATATGAAGCCACACTGGAGGAATGCTGTGCCAAAGA<br>TGATCCACATGCATGCTATTCCACAGTGTTTGACAAACTTAAG<br>CATCTTGTGGATGAGCCTCAGAATTTAATTAAACAAAACTGTG<br>ACCAATTCGAAAAACTTGGAGAGTATGGATTCCAAAATGCGCT<br>CATAGTTCGTTACACCAGGAAAGTACCCCAAGTGTCAACTCCA<br>ACTCTCGTGGAGGTTTCAAGAAGCCTAGGAAAAGTGGGTACTA<br>GGTGTTGTACAAAACCGGAATCAGAAAGAATGCCCTGTACAG<br>AAGACTATCTGAGCTTGATCCTGAACCGGTTGTGCGTGCTGCA<br>TGAGAAGACACCAGTGAGTGAAAAAGTCACCAAGTGCTGCAC<br>AGAGTCATTGGTGAACAGACGGCCATGTTTCTCTGCTCTGACA<br>CCTGATGAAACATATGTACCCAAAGCCTTTGATGAGAAATTGT<br>TCACCTTCCATGCAGATATATGCACACTTCCCGATACTGAGAA<br>ACAAATCAAGAAACAAACTGCACTTGTTGAGCTGTTGAAACAC |

TABLE 1B-continued

| Gene | Species | NCBI # | DNA Sequence |
|---|---|---|---|
| | | | AAGCCCAAGGCAACAGAGGAACAACTGAAAACCGTCATGGAG<br>AATTTTGTGGCTTTTGTAGACAAGTGCTGCGCAGCTGATGACA<br>AAGAAGCCTGCTTTGCTGTGGAGGGTCCAAAACTTGTTGTTTC<br>AACTCAAACAGCCTTAGCCTAA (SEQ ID NO: 11) |
| TERT | chicken | Modified<br>NM_001031007.1<br>(substitution<br>made at position<br>2667 T to C) | ATGGAGCGCGGGGCTCAGCCGGGAGTCGGTGTGCGGCGGCTC<br>CGCAATGTAGCGCGGGAGGAGCCCTTCGCCGCGGTCCTGGGC<br>GCGCTGCGGGGCTGCTACGCCGAGGCCACGCCGCTGGAGGCC<br>TTCGTCCGGCGGCTGCAGGAGGGTGGCACCGGGGAGGTCGAG<br>GTGCTGCGAGGCGACGACGCTCAGTGCTACCGGACCTTCGTGT<br>CGCAGTGCGTGGTGTGCGTCCCCCGCGGTGCTCGCGCCATCCC<br>CCGGCCCATCTGCTTCCAGCAGTTATCCAGTCAGAGCGAAGTC<br>ATCACAAGAATCGTTCAGAGGCTGTGTGAAAAGAAAAGAAG<br>AACATCCTTGCGTATGGATACTCCTTGCTGGATGAGAACAGTT<br>GTCACTTCAGAGTTTTGCCATCTTCGTGTATATACAGCTATCTG<br>TCCAATACTGTAACAGAAACGATTCGCATCAGTGGCCTCTGGG<br>AGATACTGCTGAGTAGGATAGGGGACGACGTGATGATGTACC<br>TGCTGGAGCACTGTGCACTCTTCATGCTGGTTCCCCCAAGTAA<br>CTGTTACCAGGTCTGCGGGCAACCAATTTATGAACTTATTTCG<br>CGTAACGTAGGGCCATCCCCAGGGTTTGTTAGACGACGGTACT<br>CAAGGTTTAAACATAATAGCTTGCTTGACTATGTGCGAAAAAG<br>GCTTGTGTTTCACAGGCACTATCTTTCCAAGTCGCAGTGGTGG<br>AAGTGCAGGCCGAGACGTCGAGGTCGTGTCTCCAGCAGGAGA<br>AAAAGAAGGAGCCATAGGATACAAAGCCTAAGGTCTGGTTAT<br>CAGCCTTCTGCAAAAGTGAACTTTCAAGCAGGTAGGCAGATCA<br>GCACAGTTACTGCACGTCTGGAAAAACAGAGCTGCTCCAGTTT<br>ATGTTTGCCAGCTAGAGCACCATCTTTAAAAAGGAAGCGTGAT<br>GGAGAACAGGTTGAAATCACAGCTAAGAGAGTGAAAATAATG<br>GAGAAAGAGATAGAGGAACAGGCTTGTAGTATCGTTCCTGAT<br>GTAAACCAAAGTAGCTCCCAGAGGCATGGAACCTCCTGGCAT<br>GTAGCACCACGTGCTGTAGGTCTTATTAAAGAACATTACATTT<br>CTGAAAGAAGTAACAGTGAGATGTCTGGTCCTTCTGTAGTTCA<br>CAGATCTCACCCTGGGAAGAGGCCTGTGGCAGACAAAAGCTC<br>TTTTCCACAAGGAGTTCAGGGTAACAAACGCATAAAGACCGGT<br>GCAGAAAAACGAGCAGAATCCAATAGAAGGGGCATAGAGATG<br>TATATAAACCCAATCCATAAACCCAATAGAAGGGGCATAGAG<br>AGGCGTATAAATCCAACCCACAAACCTGAGTTGAATTCTGTAC<br>AAACTGAACCAATGGAAGGTGCTTCTTCAGGGGACAGAAAGC<br>AGGAAAATCCCCCAGCTCATTTGGCAAAGCAGTTACCAAATAC<br>ATTGTCGCGCTCTACAGTGTACTTTGAGAAGAAATTTCTTCTGT<br>ATTCCCGCAGTTACCAAGAATATTTTCCTAAATCGTTCATACTG<br>AGCCGCCTGCAGGGTTGTCAGGCAGGTGGAAGGCGGCTTATA<br>GAAACTATATTCTTAAGCCAAAACCCATTAAAGGAACAGCAG<br>AACCAAAGCCTACCACAGCAAAAGTGGCAAAGAAGAGGTTG<br>CCCAAACGCTACTGGCAAATGAGAGAGATATTTCAGAAGCTG<br>GTAAAGAACCATGAGAAGTGCCCTTATTTAGTTTTCTTGAGGA<br>AAAATTGCCCTGTTTTGCTTTCTGAAGCATGTTTGAAAAAGAC<br>GGAGCTGACCTTGCAGGCGGCTCTGCCTGGGAAGCAAAGGT<br>TCACAAGCACACAGAACATGGGAAAGAGTCCACTGAGGGTAC<br>TGCACCGAACAGCTTCCTCGCTCCTCCCTCAGTGCTAGCATGT<br>GGGCAGCCAGAGAGAGGGGAACAGCACCCTGCAGAGGGGAG<br>TGATCCGCTCCTCAGGGAGCTGCTCAGGCAGCACAGCAGCCAC<br>TGGCAGGTGTATGGCTTTGTGAGGGAGTGCCTGGAGCGGGTGA<br>TCCCTGCTGAGCTGTGGGGTTCAAGCCATAACAAATGCCGGTT<br>CTTTAAAAACGTGAAAGCATTCATTTCCATGGGGAAGTATGCT<br>AAGCTTTCATTGCAGCAGCTGATGTGGAAGATGAGAGTGAATG<br>ACTGCGTATGGCTTCGTCTGGCCAAAGGTAATCACTCTGTTCCT<br>GCCTATGAACATTGTTACCGTGAAGAAATTCTGGCAAAATTCC<br>TATACTGGCTGATGGATTCCTATGTTATCGAGTTGCTCAAATCA<br>TTTTTCTATATCACCGAGACCATGTTCCAGAAAAACATGCTTTT<br>CTACTACCGAAAGTTTATCTGGGGCAAGTTACAGAACATTGGA<br>ATTAGAGACCATTTTGCCAAAGTACATCTACGTGCCTTGTCTTC<br>AGAGGAGATGGAAGTGATCCGTCAAAAAAGTATTTTCCTATT<br>GCATCAAGGCTCCGGTTCATTCCTAAAATGAATGGTTTAAGAC<br>CCGTAGTAAGACTAAGCCGTGTTGTTGAAGGACAGAAACTCA<br>GCAAGGAAAGCAGAGAAAGAAGATACAGCGCTATAACACTC<br>AGCTAAAAAATCTATTTAGTGTTTTAAACTATGAACGAACTGT<br>AAACACCAGTATCATTGGCTCCTCAGTATTCGGGAGAGATGAT<br>ATCTACAGGAAGTGGAAGGAGTTTGTTACAAAGGTTTTTGAAT<br>CAGGTGGTGAAATGCCTCATTTCTACTTTGTAAAGGGTGATGT<br>ATCCAGAGCTTTTGATACCATTCCTCACAAGAAACTTGTGGAA<br>GTGATATCACAGGTCTTGAAACCTGAGAGCCAAACTGTCTATG<br>GAATAAGGTGGTATGCAGTGATTATGATTACCCCAACTGGAAA<br>AGCCAGGAAACTCTATAAGAGACATGTTTCTACTTTCGAGGAT<br>TTTATTCCAGACATGAAGCAGTTTGTGTCCAAGCTTCAAGAGA<br>GAACTTCATTACGAAATGCAATAGTAGTTGAACAGTGCTTAAC<br>TTTTAATGAGAACAGTTCCACCCTGTTTACTTTCTTTCTTCAAA<br>TGTTACATAATAACATCCTGGAGATTGGGCACAGGTACTATAT |

TABLE 1B-continued

| Gene | Species | NCBI # | DNA Sequence |
|---|---|---|---|
| | | | ACAGTGCTCTGGAATCCCACAGGGCTCCATTTTGTCAACCTTA<br>CTTTGCAGCTTATGCTACGGAGACATGGAAAACAAATTACTCT<br>GTGGGATCCAGAAGGATGGAGTCCTAATACGTCTTATTGATGA<br>CTTTTTGCTGGTTACGCCACATTTAATGCAGGCAAGAACTTTTC<br>TAAGGACTATAGCAGCAGGTATTCCTGAGTATGGCTTTTTAAT<br>AAATGCCAAGAAGACTGTGGTGAATTTTCCTGTTGATGATATC<br>CCGGGATGTTCCAAGTTCAAACATCTGCCAGATTGTCGTTTGA<br>TCTCATGGTGTGGTTTATTATTGGATGTGCAGACACTTGAGGTT<br>TATTGTGATTACTCCAGTTATGCCTTTACTTCTATCAGATCAAG<br>TCTTTCCTTCAATTCAAGTAGAATAGCTGGGAAAAACATGAAA<br>TGCAAATTGACTGCAGTCCTCAAACTGAAATGCCATCCTTTAC<br>TTCTTGACTTAAAGATCAACAGCCTTCAGACAGTTCTAATTAA<br>CATCTACAAGATATTTTACTTCAGGCTTACAGGTTCCATGCCT<br>GTGTTCTTCAGCTTCCATTCAACCAGAAAGTTAGGAATAATCC<br>TGATTTCTTCCTAAGGATCATCTCTGATACTGCTTCATGCTGCT<br>ATTTTATCCTGAAAGCTAAAAATCCAGGAGTTTCTTTAGGTAG<br>CAAAGATGCATCTGGCATGTTCCCTTTTGAGGCAGCAGAATGG<br>CTGTGCTACCATGCCTTCATTGTCAAACTGTCCAACCACAAAG<br>TTATTTACAAATGCTTACTTAAGCCCCTTAAAGTCTATAAGATG<br>CATCTGTTTGGGAAGATCCCAAGGGATACTATGGAACTGCTGA<br>AGACGGTGACGGAACCATCGCTTTGTCAAGATTTCAAAACTAT<br>ACTGGACTAA (SEQ ID NO: 12) |
| cMyoDER | chicken | | ATGGACTTACTGGGCCCCATGGAAATGACGGAGGGCTCCCTCT<br>GCTCCTTCACGGCCGCCGATGACTTCTATGACGACCCGTGCTT<br>CAACACGTCGGACATGCACTTCTTCGAGGACCTGGACCCCCGG<br>CTGGTGCACGTGGGCGGGCTGCTGAAGCCCGAGGAGCACCCG<br>CACCACCACGGGCACCACCACGGGAACCCACACGAGGAGGAG<br>CACGTGCGGGCGCCCAGTGGGCACCACCAGGCCGGCCGCTGC<br>CTGCTGTGGGCGTGCAAGGCCTGCAAGAGGAAGACCACCAAC<br>GCTGACCGCCGCAAAGCCGCCACCATGAGGGAACGGCGGCGG<br>CTCAGCAAGGTCAACGAGGCCTTCGAGACCCTCAAGCGCTGCA<br>CTTCCACCAACCCCAACCAGCGCCTGCCCAAGGTGGAGATCCT<br>GCGCAACGCCATCCGCTACATCGAGAGCCTGCAGGCCCTGCTG<br>CGTGAGCAGGAGGGCGATTCTTCTACAGAGCTGCGAGCTCCAA<br>CCCTTTGGACAAGTCCACTGGTGGTTAAACATAACAAGAAGAA<br>CAGTCCGGCTCTGTCTCTGACAGCAGAACAGATGGTCAGTGCC<br>TTGCTGGAAGCTGAGCCACCTATAGTTTATTCTGAATATGACC<br>CCAATAGACCATTCAACGAAGCATCTATGATGACCCTGTTGAC<br>CAACCTTGCAGACAGAGAATTAGTGCACATGATCAACTGGGC<br>AAAGAGAGTTCCAGGATTTGTGGATTTAACACTCCATGATCAG<br>GTCCATCTGCTGGAATGTGCCTGGTTAGAGATATTGATGATCG<br>GCTTAGTCTGGCGCTCCATGGAACACCCAGGAAAGCTTTTATT<br>TGCACCTAATCTATTACTGGACAGGAATCAAGGGAAATGTGTA<br>GAGGGCATGGTGGAAATCTTTGACATGCTACTGGCTACTGCTG<br>CTCGGTTTCGGATGATGAACCTTCAAGGGAGGAATTTGTGTG<br>CCTTAAGTCCATCATCCTGCTCAATTCTGGTGTGTACACTTTTC<br>TTTCTAGCACCTTGAAATCTCTGGAAGAGAGGGACTATATCCA<br>CCGTGTTCTGGACAAAATCACAGATACTCTGATACACCTAATG<br>GCAAAGTCAGGTCTTTCTCTGCAGCAGCAACACCGGCGACTAG<br>CTCAGCTCCTCCTTATCCTCTCTCACATCAGGCATATGAGCAAC<br>AAAGGAATGGAGCACCTGTACAATATGAAGTGTAAAAATGTA<br>GTTCCGCTCTACGACCTCTTACTGGAGATGCTGGACGCTCACC<br>GCCTACATGCACCGGCAGCCAGGAGTGCTGCACCAATGGAAG<br>AGGAGAACCGAAACCAACTGACAACCGCACCAGCTTCATCTC<br>ATTCCCTGCAGTCCTTTTACATTAACAGCAAAGAAGAGGAGAG<br>TATGCAGAATACAGCTATCGCCGATGCATACTACCCAGTGCTG<br>GAGCACTACAGCGGGGAGTCAGATGCCTCCAGCCCTCGCTCCA<br>ACTGCTCCGACGGCATGATGGAGTACAGCGGGCCGCCCTGTAG<br>CTCTCGCAGGAGAAACAGCTACGACAGCAGCTACTACACGGA<br>ATCACCAAATGACCCAAAGCATGGGAAGAGTTCTGTTGTTTCC<br>AGCCTCGACTGCCTCTCAAGCATTGTGGAGAGGATTTCCACAG<br>ACAACTCCACATGTCCCATACTGCCTCCAGCTGAAGCTGTAGC<br>TGAAGGGAGTCCCTGTTCCCCCCAGGAAGGAGCAAACCTGAG<br>TGACAGTGGAGCCCAGATTCCTTCCCCCACCAACTGCACCCCT<br>CTTCCCCAGGAAAGCAGCAGCAGCAGCAGCAATCCAATC<br>TACCAAGTGCTATAA (SEQ ID NO: 13) |
| IGF2 | Cow<br>[Bos<br>Taurus] | NM_174087.3 | ATGGGGATCACAGCAGGAAAGTCGGTGCTGGTGCTTCTTGCCT<br>TCTTGGCCTTCGCCTCGTGCTGCTATGCTGCTTACCGCCCCAGC<br>GAGACTCTGTGCGGCGGGGAGCTGGTGGACACCCTCCAGTTTG<br>TCTGTGGGGACCGCGGCTTCTACTTCAGCCGACCATCCAGCCG<br>CATAAACCGACGCAGCCGTGGCATCGTGGAAGAGTGTTGCTTC<br>CGAAGCTGCGACCTGGCCCTGCTGGAGACTTACTGTGCCACCC<br>CCGCCAAGTCCGAGAGGGATGTGTCTGCCTCTACGACCGTGCT<br>TCCGGACGACGTCACCGCATACCCCGTGGGCAAGTTCTTCCAA<br>TATGACATCTGGAAGCAGTCCACCCAGCGCCTGCGCAGGGGCC<br>TGCCCGCCTTCCTGCGAGCACGCCGGGGTCGCACGCTCGCCAA |

TABLE 1B-continued

| Gene | Species | NCBI # | DNA Sequence |
|---|---|---|---|
| | | | GGAGCTGGAGGCGCTCAGAGAGGCCAAGAGTCACCGTCCGCT GATCGCCCTGCCCACCCAGGACCCTGCCACCCACGGGGGCGCC TCTTCCAAGGCATCCAGCGATTAG (SEQ ID NO: 15) |
| IGF1 | Zebrafish [*Danio rerio*] | NM_131825.2 | ATGTCTAGCGGTCATTTCTTCCAGGGGCATTGGTGTGATGTCTT TAAGTGTACCATGCGCTGTCTCCCGAGTACCCACACCCTCTCA CTGGTGCTGTGCGTCCTCGCGTTGACTCCCGCGACTCTGGAGG CGGGGCCGGAGACGCTGTGCGGGGCGGAGCTTGTAGACACGC TGCAGTTTGTGTGTGGAGACAGGGGCTTTTATTTCAGCAAACC GACAGGATATGGACCTAGTTCAAGAAGGTCACACAACCGTGG CATCGTGGACGAATGCTGCTTTCAGAGCTGTGAGCTACGGCGC CTCGAGATGTATTGTGCGCCTGTGAAGACAGGCAAATCTCCAC GATCTCTACGAGCACAACGACACACAGATATTCCCAGGACACC AAAGAAACCTATATCTGGGCATAGCCACTCTTCCTGTAAGGAG GTTCATCAGAAGAACTCGAGCCGAGGAAACACAGGGGGCAGA AACTATCGCATGTAG (SEQ ID NO: 16) |
| serum albumin 1 | Rainbow trout [*Oncorhynchus mykiss*] | XM_021614654.1 | ATGAGGAGACCCTGTATCCTGGCCATCCAGCCTGACACGGAGT TCATGCCCCCAGAGCTGGATGCCAGCAACTTCCACATGGGCCC TGAGCTCTGCACCAAGGACAGCAAGGAGCTGCTGCTCTCTGGG AAGAAACTACTGTATGGTGTGGTCAGACATAAGACCACCATCA CTGAGGAGCAGCTGAAGTCCATCTCTACTAAATATCACAGTAT GAAGGAGAAGTGCTGTGCTGCTGAGGACCAAGCAGCATGCTT CACTGAGGAGGCACCCAAGCTGGTTGCTGAGAGTGCAGAGCT GGTCAAGGCTTAA (SEQ ID NO: 17) |
| GLUL | Tilapia [*Oreochromis niloticus*] | NM_001279668.1 | ATGGCTACATCCGCCAGCGCCAGCTTGAGTAAAGCTGTCAAGC AGCAGTACATGGAGCTCCTCAGGGGACAAAGTCCAGGCCA TGTACATCTGGATCGACGGAACCGGAGAGGGGCTCCGATGCA AAACCAGGACGCTTGATTCTGAGCCCAAAAGCATCGAAGATCT TCCTGAATGGAACTTTGACGGATCCAGTACCTACCAGTCCGAA GGCTCCAACAGCGACATGTATCTGATCCCCTCAGCCATGTTCC GCGATCCATTCCGCAAAGACCCCAACAAGCTGGTGCTGTGTGA AGTCCTGAAGTACAACCGTAAACCTACAGAAACCAACCTTCGG CTCACCTGTAAGAAAGTGATGGATATGGTGGCGGATCAGCATC CTTGGTTTGGCATGGAGCAGGAGTACACCATCCTTGGAACGGA CGGGCATCCATTTGGCTGGCCATCTAATGGTTTCCCCGGACCA CAGGGGCCGTACTACTGTGGTGTTGGAGCTGACAAAGCCTATG GCAGGGACGTAGTCGAGGCCCATTACAAAGCTTGTTTGTACGC TGGAGTCCAGATTTGTGGCACAAATGCTGAAGTAATGCCTGCT CAGTGGGAGTTCCAGGTCGGACCTTGCGAAGGCATTGACATGG GCGATCATTTGTGGGTAGCGCGCTTCATCCTGCACCGTGTCTGT GAGGATTTTGGCGTCGTCGCCTCATTTGATCCCAAGCCAATCC CTGGAAACTGGAACGGTGCTGGCTGCCATACAAACTTCAGCAC GAAAGAGATGAGGGAAGACGGTGGATTGAAAGCTATTGAGGA TTCCATTGAGAAGCTTGGAAAGAGGCACAGCTACCACATTCGT GCCTACGACCCCAAAGGGGGGCTCGACAACGCCCGCCGTCTC ACTGGCCGCCATGAAACCTCAAACATCAACGAATTCTCTGCTG GTGTGGCCAACCGTGGTGCCAGCATTCGCATTCCTCGTAATGT TGGTCAGGAAGAAAGGCTACTTCGAAGACCGTCGCCCTTCA GCCAACTGTGACCCGTACAGTGTGACCGAGGCCCTGATCCGCA CCTGTCTGCTGAACGAGGAAGGAGATGAACCCGCGGATTACT AA (SEQ ID NO: 18) |
| IGF2 | Rainbow trout [*Oncorhynchus mykiss*] | NM_001124697.1 | ATGGAAACCCAGAAAAGACACGAATACCACTCAGTTTGTCAC ACCTGCCGGAGAACGGAAAACAAGAATGAAGGTCAAGATG ATGTCTTCGTCAAATCGAGTGCTGGTCATTGCGCTGGCACTTA CTCTGTACATTGTTGAAGTGGCTTCGGCAGAAACGCTATGTGG AGGAGAACTGGTGGACGCGCTGCAGTTCGTCTGTGAAGATAG AGGATTCTATTTCAGTAGGCCAACCAGCAGGTCTAACAGCAGA CGCTCCCAGAACCGTGGTATCGTGGAGGAGTGTTGTTTCCGTA GCTGTGACCTCAACCTGTTGGAGCAGTACTGTGCCAAACCTGC CAAGTCAGAGGGACGTGTCGGCCACCTCTCTACAGATCATT CCCATGGTGCCCACAATCAAACAGGATGTCCCAAGAAAACAT GTGACTGTGAAGTATTCCAAATATGAGGCGTGGCAGAGGAAG GCTGCTCAGCGGCTCCGGAGGGCGTCCCGGCCATCCTCAGGG CCCGGAAGTTCCGGAGGCAGGCGGTGAAGATCAAGGCCCAAG AGCAGGCGATGTTCCACCGGCCTCTGATCACCCTGCCCAGCAA GCTTCCCCCAGTCCTGCCCCCCACGGACAACTACGTCAGCCAC AATTGA (SEQ ID NO: 19) |
| IGF1 | Tropical clawed frog [*Xenopus tropicalis*] | XM_002936829.4 | ATGGAAAAAACAACAGTCTTTCAACACAATTATTTAAGTGCT ACTTTTGTGATTTCTTAAAGCTGAAGATGCACAAAATGTCCTA CATTCATCTGCTCTACCTGGCTTTGTGTTTCCTGACTTTAACCC ATTCAGCAGCTGCTGGACCAGAGACCCTCTGTGGAGCCGAACT GGTAGACACTCTTCAGTTTGTATGTGGAGACAGAGGCTTCTAT TTTAGCAAGCCAACAGGGTACGGATCCAGCAATCGAAGATCG CATCACAGAGGAATAGTAGATGAGTGCTGTTTCCAAAGCTGTG |

TABLE 1B-continued

| Gene | Species | NCBI # | DNA Sequence |
|---|---|---|---|
| | | | ATTTCAGAAGGCTGGAGATGTACTGCGCTCCTGCCAAGCCAGC<br>CAAATCAGCACGTTCTGTACGTGCTCAACGTCACACTGACATG<br>CCAAAAGCCCAGAAGGAAGTACACCTAAAGAATGCAAGTCGA<br>GGAAACACAGGGAGTCGAGGATTCCGAATGTAA (SEQ ID NO: 20) |
| GLUL | Tropical clawed frog [*Xenopus tropicalis*] | XM_004914038.3 | ATGGCAACCTCCGCCAGTGCTCAGTTGAGTAAGGCCATAAAGC<br>AGATGTATCTGGAACTGCCACAGGGAGATAAGGTGCAGGCTA<br>TGTACATCTGGGTTGATGGGACCGGGGAGGGTCTTCGCTGCAA<br>GACTCGCACTCTGGACAGTGAACCCAAGACCATAGAAGATCTT<br>CCTGAATGGAACTTCGATGGATCTAGCACATACCAATCCGAGG<br>GTTCCAACAGTGACATGTACCTGATTCCAGTTGCAATGTTTAG<br>AGACCCTTTTCGAAGGGACCCCAACAAGCTGGTACTCTGCGAG<br>GTGCTCAAATACAACCGAAAAACAGCTGAAACAAACTTGCGT<br>CATACATGTAACCAGATAATGGACATGATGGCCAATGAGCATC<br>CATGGTTTGGCATGGAACAGGAATACACATTGCTGGGTATGGA<br>TGGACACCCTTTTGGCTGGCCTTCAAATGGCTTCCCAGGACCA<br>CAAGGTCCCTATTACTGTGGAGTGGGTGCAGATAAGGCATATG<br>GTCGGGATATTGTGGAGGCTCATTATCGGGCTTGCCTTTATGCT<br>GGTGTGAAAATTGCAGGAACAAATGCAGAAGTTATGCCAGCA<br>CAGTGGGAGTTCCAAATTGGGCCATGTGAGGGAATAGAAATG<br>GGAGATCACCTTTGGATTGCTCGATTTATACTGCATAGAATTT<br>GTGAGGATTTTGGGATCATTGTTTCGTTTGACCCAAAGCCCAT<br>AACTGGAAACTGGAATGGAGCTGGATGTCACACCAATTTCAGC<br>ACAAAGTCAATGCGTGAAGAAGGAGGCCTTAAGGACATAGAA<br>GAATCCATTGAACGTCAAGCAAACGTCATGATTATCACATCA<br>GAATGTATGACCCAAGGGGTGGTAAAGACAATGCCCGTCGTCT<br>CACAGGTTTCCATGAGACCTCCAGCATCCATGAGTTCTCTGCA<br>GGAGTGGCAAACCGTGGTGCCAGTATCCGCATTCCCCGCAGTG<br>TAGGCCAGGAGAAGAAAGGCTATTTTGAAGATCGTCGTCCATC<br>AGCCAACTGTGATCCCTATGCTGTGACAGAAGCTATGATCAGA<br>ACCTGCCTACTGAATGAAACTGGAGACGAACCTCTTGAATACA<br>AGAACTAA (SEQ ID NO: 21) |
| ALB | Tropical clawed frog [*Xenopus tropicalis*] | BC075287.1 | ATGAACGCGTTGATGCGGCGTGCCTGCTGCGGGGCGCTATTCC<br>CCCTCTCATTCCGACTGGCCGCGCTGAGCCCTATGAAGGGAGC<br>TAGTAACTTTAGCTGCGGTAACGTGTGCGCCTCTCCTGCCGGA<br>TGTTGGGCGCCACCAAGTGGACACGACACGGGGATAAAAGTG<br>TACAACAGCCTTACTAGGAGGAAGGATCCACTTATTCTGGCAG<br>ATCCGACAGTAGCGACATGGTATAGCTGTGGACCTACAGTTTA<br>TGACCATGCACATCTTGGACATGCATGTTCTTATGTTAGATTTG<br>ACATAATTCGAAGGATTCTGCTCAAGGTTTTTGGGATTGATAC<br>AGTCGTGGTGATGGTAGTCACAGACATTGATGATAAGATAATC<br>AAGAGAGCAAAGGAGCTCAATATATCTCCTGTGGCCTTAGCTC<br>GTACTTACGAACAGGATTTTAAACAAGACATGACTGCGTTGAA<br>GGTCCTTCCACCAACAGTATACATGAGAGTTACTGAAAATATT<br>CCACAGATCATATCATTTATTGAACACATAATTGCCAATGGAT<br>ATGCATATGCTACCTCACAAGGAAATGTTTATTTTGATGTTCA<br>GTCGATTGGAGAGCGATATGGGAAATTTAATGATTCTTTCAGT<br>GATACAGCCAGCGAATCAGCATCACAAGATAAAAGGCATATC<br>CGAGATTTTGCTTTGTGGAAAACATCCAAGCCTGAGGAGCCTT<br>ACTGGGCTTCTCCTTGGGGCAAGGGAAGACCTGGCTGGCACAT<br>AGAGTGTTCCACAATTGCAAGTTCTGTATTTGGCAAACATCTA<br>GACATTCACACTGGTGGGATTGACCTTGCTTTCCCTCATCATGA<br>AAATGAAATTGCTCAGTGTGAGGCATATCACCAGAGCACACA<br>GTGGGGAAACTATTTCCTTCATACTGGACATTTACATTTGAAA<br>GGGAATGAAGAAAAATGTCAAAATCCCTGAGAAACTATCTG<br>ACAGTTAAGGAGTTTTTAAAGTCCTTTTCCCCTGACCAGTTTAG<br>AATGTTTTGTCTGCGCTCAAAATATAAATCAGCCGTGGAATAC<br>AGCAACGGGTCCATGCATGATGCAGTAAATACCCTACACACCA<br>TCTCTTCGTTTGTCGATGATGCAAAAGCCTATATGAAAGGTCA<br>GCTGATTTGCCAACCAGTCAGGAGGCTTTACTCTGGCAAAGG<br>CTGAATGAAACAAAGTAAATGTTAAGGCTGCGTTTTCAGATG<br>ACTTTGACACCCCACGAGCAGTTGATGCAGTTATGGACCTCAT<br>TCACCATGGCAACAGACAGCTTAAGGCTGTTTCCAAGGAGTCA<br>AACTCTCCCAGGAGCTCTGTAGTTTATGGTGCCATGATCTCTTA<br>CATTGAACAATTCTGGAGATATTGGGAATTTCCTTGAGCCAA<br>AACCAGGTCGCTGCAGAAGATAGACACTCGGCTGTTCTCTTTA<br>ATGTAGTAGAAGAAATGATCAGTTTTAGAAGTAAGGTGCGGA<br>ATTACGCCCTGGCTGCAGATGAATCACCAAATGCAATAGGACA<br>AGAGGAAAAACAGCAATACAAGGAGAGGGAAAGGCAGTTGTT<br>ACTGGAAAGGGAACCACTCCTACAGGCTTGTGACATAATGCGC<br>CAACATCTGGCTGTATATGGCATAAATGTAAAGGATCGTGGAA<br>ATACATCAACATGGGAACTACTTGACCGCAAAGAAGAAACCT<br>AG (SEQ ID NO: 22) |

TABLE 1B-continued

| Gene | Species | NCBI # | DNA Sequence |
| --- | --- | --- | --- |
| IGF2 | Tropical clawed frog [*Xenopus tropicalis*] | NM_001113672.1 | ATGAGGCATCTCCTCCTCCTCTCTATCACCTTCCTGGTATACAC<br>GCTAGACTCTGCTAAAGCCTATGGAGCAACGGAGACCCTGTGC<br>GGTGGGGAGCTGGTGGACACCCTGCAGTTTGTTTGTGGAGACA<br>GGGGCTTCTATTTCAGCAGGAATAATGGCCGCTCCAACCGCAG<br>GGCTAACAGGGGGATTGTGGAAGAATGTTGCTTCCGGAGCTGT<br>GATTTGGAACTGTTGGAAACGTACTGCGCAAAGCCAGCTAAG<br>AACGAGAGGGATGTCTCCACTGCACCCTCCACAGCAATACCAC<br>CACTGAACAAGCAGGACCTGTACCACAAACATCACCACACAA<br>AGAGCTCCAAGTATGACATTTGGCAGAGGAAGTCTATCCATCG<br>GCTGCGGAGAGGAGTCCCTGCCATTGTACGTGCTAGGCAGTAT<br>CGATTGCTAATGCAGCAGGCTGAAGAATCAGAGCAGGCACTA<br>TCACATCGGCCCCTTACCACCTTACCCATAACGCGGCCTCTCC<br>ATCTGCAACAAACCTCAGAACCTTCCCTCAATTGA (SEQ ID NO: 23) |
| GLUL | Chicken [*Gallus gallus*] | NM_205493.1 | ATGGCCACCTCGGCGAGCTCCCACCTGAGCAAAGCCATCAAGC<br>ACATGTACATGAAGCTGCCGCAGGGTGAGAAGGTCCAAGCCA<br>TGTACATCTGGATCGACGGGACTGGGGAGCACCTCCGCTGCAA<br>AACCCGCACTCTGGACCACGAACCCAAGAGCCTGGAAGATCT<br>CCCCGAGTGGAACTTTGATGGCTCCAGCACCTTCCAAGCCGAA<br>GGCTCCAACAGCGACATGTACCTGCGACCTGCTGCCATGTTCC<br>GGGACCCTTTTCGCAAGGATCCCAACAAATTAGTTCTCTGTGA<br>GGTCTTCAAATACAACCGCCAGTCTGCAGACACAAATCTTCGG<br>CACACCTGTAGGCGGATTATGGATATGGTGTCCAACCAGCACC<br>CCTGGTTTGGGATGGAGCAGGAGTACACCCTTCTGGGAACAGA<br>TGGTCATCCGTTTGGCTGGCCTTCCAATTGCTTCCCTGGACCCC<br>AAGGTCCGTACTACTGCGGTGTAGGAGCTGACAAAGCCTATGG<br>CAGAGACATTGTGGAGGCCCACTACCGAGCGTGCCTGTATGCT<br>GGTGTGAAAATTGGAGGAACCAACGCAGAAGTGATGCCAGCC<br>CAGTGGGAGTTCCAGGTGGGACCGTGCGAAGGGATTGAGATG<br>GGGGATCACCTCTGGATAGCACGTTTCATCCTCCACCGGGTGT<br>GCGAAGACTTTGGTGTCATTGTGTCCTTCGATCCCAAACCCAT<br>CCCTGGGAACTGGAACGGTGCTGGCTGTCACACCAACTTCAGC<br>ACCAAGAACATGAGGGAAGATGGAGGTCTCAAGCACATCGAG<br>GAGGCCATCGAGAAGCTGAGCAAGCGCCACCAGTACCACATC<br>CGTGCCTACGACCCCAAAGGAGGGCTGGACAACGCCCGGCGC<br>CTGACGGGCTTCCACGAGACGTCCAGCATCCACGAGTTCTCCG<br>CCGGCGTGGCCAACCGCGGCGCCAGCATCCGCATCCCACGCA<br>ACGTGGGCCATGAGAAGAAAGGCTACTTCGAGGACCGCGGGC<br>CTTCAGCCAACTGCGATCCCTACGCCGTGACGGAGGCCCTGGT<br>CCGTACGTGTCCTCAACGAAACCGGGGACGAGCCTTTTGAG<br>TACAAGAACTAa (SEQ ID NO: 24) |
| IGF2 | Chicken [*Gallus gallus*] | NM_001030342 | ATGTGTGCTGCCAGGCAGATACTGCTGCTACTGCTGGCCTTCC<br>TGGCCTATGCGTTGGATTCAGCTGCGGCGTATGGCACGGCGGA<br>GACCCTCTGCGGTGGGGAGCTGGTGGACACACTGCAGTTCGTC<br>TGTGGGGACAGGGGCTTCTACTTCAGTAGACCAGTGGGACGA<br>AATAACAGGAGGATCAACCGTGGCATTGTGGAGGAGTGCTGC<br>TTTCGGAGCTGTGACCTGGCTCTGCTGGAAACCTACTGTGCCA<br>AGTCCGTCAAGTCAGAGCGTGACCTCTCCGCCACCTCCCTCGC<br>GGGCCTCCCAGCCCTCAACAAGGAGAGCTTCCAGAAGCCATCT<br>CATGCCAAGTACTCCAAGTACAACGTGTGGCAGAAGAAGAGC<br>TCGCAGCGGCTGCAGCGGGAGGTGCCAGGCATCCTGCGTGCCC<br>GTCGGTACCGGTGGCAGGCGGAGGGGCTGCAAGCAGCTGAGG<br>AAGCCAGGGCGATGCATCGTCCCCTCATCTCCTTGCCCAGTCA<br>GCGGCCCCCAGCGCCGCGGGCATCCCCTGAAGCGACCGGCCC<br>CCAGGAATGA (SEQ ID NO: 25) |
| TERT | Cow [*Bos taurus*] | NM_001046242.1 | ATGCCGCGCGCGCCCAGGTGCCGGGCCGTGCGCGCCCTTCTGC<br>GGGCCAGCTACCGGCAGGTGCTGCCCCTGGCCGCCTTCGTACG<br>GCGCCTGCGGCCCCAGGGCCACCGGCTTGTGCGGCGCGGGGA<br>CCCGGCGGCCTTCCGCGCGCTGGTGGCTCAGTGCTTGGTGTGC<br>GTGCCCTGGGACGCGCAGCCGCCCCTGCCGCCCCGTCCTTCC<br>GCCAGGTGTCCTGCCTGAAGGAGCTGGTGGCCAGAGTCGTGCA<br>GAGGCTCTGCGAGCGCGGCGCGAGGAACGTGCTGGCCTTCGG<br>CTTCACGCTGCTGGCCGGGGCCCGCGGCGGGCCGCCCGTGGCC<br>TTCACGACCAGCGTACGCAGCTACCTGCCCAACACGGTAACCG<br>ACACGCTGCGCGGCAGCGCGCCGCCCTGGGGGCTGCTGCTGCACC<br>GCGTGGGCGACGACGTGCTCACCCACCTGCTGTCGCGCTGCGC<br>GCTCTACCTGCTGGTGCCCCCGACCTGCGCCTACCAGGTGTGT<br>GGGCCGCCGCTCTATGACCTCCGCGCCGCCGCCGCCGCCGCTC<br>GTCGGCCCACGCGGCAAGTGGGCGGGACCCGGCGGGCTTCG<br>GACTCCCGCGCCCGGCTCGTCGAACGGCGGCCACGGGGAGG<br>CCGAAGGACTCCTGGAGGCGCGGGCCCAGGGCGCGAGGCGGC<br>GTCGCAGTAGCGCGCGGGGACGACTGCCTCCAGCCAAGAGGC<br>CCAGGCGCGGCCTGGAGCCCGGGCGGGATCTCGAAGGGCAGG<br>TGGCCCGCAGCCCGCCCCGCGTGGTGACACCTACCCGAGACGC |

TABLE 1B-continued

| Gene | Species | NCBI # | DNA Sequence |
|---|---|---|---|
| | | | TGCGGAAGCCAAGTCTCGGAAGGGCGACGTGCCCGGGCCCTG CCGCCTCTTCCCGGGCGGCGAGCGGGGTGTCGGCTCCGCGTCC TGGCGGCTGTCACCCTCGGAGGGCGAGCCGGGTGCCGGAGCTT GCGCTGAGACCAAGAGGTTCCTTTACTGCTCCGGCGGTGGCGA ACAGCTGCGCCGCTCCTTCCTGCTCTGCTCCCTGCCTCCCAGCC TGGCCGGGGCGCGGACACTCGTGGAAACCATCTTTCTGGACTC GAAGCCCGGGCCGCCAGGGGCTCCCCGCCGGCCGCGCCGCCT GCCCGCGCGCTACTGGCAGATGCGGCCCCTGTTCCGGAAACTG CTTGGGAACCACGCGCGGAGCCCCTATGGCGCGCTGCTCAGGG CGCACTGCCCGCTGCCGGCCTCTGCGCCCCGGGCGGGGCCAGA CCATCAGAAGTGCCCTGGTGTTGGGGGCTGCCCCTCTGAGAGG CCGGCCGCTGCCCCCGAGGGCGAGGCGAACTCAGGGCGCCTG GTCCAGCTGCTCCGCCAGCACAGCAGCCCTGGCAGGTGTACG GGCTCCTGCGGGCCTGTCTTCGCCGCCTGGTGCCCGCCGGCCT CTGGGGCTCCCGGCACAACGAGCGGCGCTTCCTGCGGAACGTG AAGAAGCTCCTCTCCCTGGGGAAGCACGGCAGGCTCTCGCAGC AGGAGCTCACGTGGAAGATGAAGGTGCAGGACTGCGCCTGGC TGCGCGCGAGCCCAGGGGCTCGCTGCGTGCCCGCCGCGGAGC ACCGCCAGCGCGAGGCCGTCCTGGGTCGCTTCCTGCACTGGCT GATGGGCGCCTACGTGGTGGAGCTGCTCAGGAGCTTCTTCTAC GTCACAGAGACCACGTTCCAGAAGAACCGGCTCTTCTTCTTCC GGAAGCGCATCTGGAGCCAGCTGCAGCGCCTGGGCGTCAGAC AACACTTAGACCGTGTGCGGCTTCGAGAACTGTCAGAAGCAG AGGTCAGGCAGCACCAGGAGGCCAGGCCGGCTCTGCTGACAT CCAGGCTCCGTTTCGTCCCCAAGCCCGGCGGGCTGCGGCCCAT CGTGAACGTGGGCTGTGTTGAGGGCGCCCCGGCACCGCCCAG AGACAAGAAGGTGCAGCATCTCAGCTCACGGGTCAAGACGCT GTTCGCGGTGCTGAACTACGAGCGAGCTCGGCGGCCTGGCCTC CTGGGGGCCTCGGTGCTGGGCATGGACGACATCCACAGGGCCT GGCGGGCCTTCGTGCTGCCCCTGAGGGCCCGGGGCCCAGCCCC CCCGCTCTACTTCGTCAAGGTGGACGTGGTGGGGGCCTACGAT GCCCTCCCCCAGGATAAGCTGGCAGAGGTGATCGCTAACGTGC TGCAGCCGCAGGAGAATACGTACTGCGTGCGCCACTGCGCCAT GGTCCGGACTGCGCGCGGGCGCATGCGCAAGTCCTTCAAGAG ACACGTGTCCACCTTCTCGGACTTCCAGCCGTACCTGAGGCAG CTCGTGGAGCATCTGCAGGCGATGGGCTCCCTGAGGGACGCCG TGGTCATCGAGCAGAGCTGCTCCCTGAACGAGCCTGGCAGCAG CCTCTTCAACCTCTTCCTGCACCTGGTCCGCAGCCACGTCATCA GGATCGGGGCAGGTCCTACATCCAGTGTCAGGGGATCCCCCA GGGCTCCATCCTGTCCACCCTGCTCTGCAGCTTCTGCTATGGGG ACATGGAGAACAAGCTCTTCCCTGGAGTCCAGCAGGACGGGG TGCTTCTGCGCCTGGTGGACGACTTCCTGCTGGTCACCCCACA CCTGACGCGGGCCAGAGACTTCCTCAGGACGCTGGTGCGCGGT GTGCCTGAGTATGGCTGCCAGGTGAACCTGCGGAAGACGGTG GTGAACTTCCCCGTGGAGCCCGGGGCCCTGGGCGGCGCGGCG CCCCTGCAGCTGCCGGCCCACTGCCTGTTCCCCTGGTGCGGCC TGCTGCTGGATACCCGCACCCTGGAGGTGCATGGCGACCACTC CAGTTATGCCCGGACGTCCATCAGAGCGAGTCTCACCTTCACC CAGGGCTTCAAGCCCGGGAGGAACATGCGTCGCAAGCTGTTG GCGGTCTTGCAGCTCAAGTGCCATGGGCTCTTCCTGGACCTGC AGGTGAACAGTCTGCAGACGGTCTTCACAAACGTTTACAAGAT ATTCCTGCTGCAGGCCTACAGGTTCCACGCCTGCGTGCTGCAG CTGCCCTTCAGCCAGCCGGTCAGGAGCAGCCCCGCGTTCTTTC TCCAGGTCATCGCCGACACCGCATCCCGCGGCTACGCCCTCCT GAAAGCCAGGAACGCAGGGGCGTCACTGGGGGCCAGGGGCGC CGCCGGCCTGTTCCCGTCTGAAGCTGCGCAGTGGCTGTGTCTC CACGCCTTCCTGCTCAAGCTGGCTCGCCACCGTGTCACCTACA GCCGCCTGCTGGGGGCCCTCCGGACAGCCCGAGCACGGCTGC ACCGGCAGCTCCCGGGGCCCACACGGGCCGCCCTGGAGGCGG CGGCCGACCCCGCCCTGACCGCAGACTTCAAGACCATCTTGGA CTGA (SEQ ID NO: 39) |
| TERT | Porcine [Sus scrofa] | NM_001244300.2 | ATGCCGCGCGCGCCCCGGTGCCGGGCCGTGCGCTCCCTGCTCC GGGACCGCTACAGGCAGGTGCTGCCGCTGGCCACCTTCGTGCG GCGCCTGGGCCCTGAGGGCCGGCGGCTTGTTCGGCGCGGGGA CCCGGCGGCCTACCGCGCGTGGTGGCGCAGTGCCTGGTGTGC GTGCCCTGGGACGCGCAGCCGCCTCCTGCCTCCCCGTCCTTCC GCCAGGTGTCCTGCCTGAAGGAGCTGGTGGCCAGGGTCGTGCA GAGGCTCTGCGAGCGCGGCGCGGAGGAACGTGCTGGCCTTTGG CTTCGCGCTGCTGGACGGGGCTCGCGGCGGGCCGCCCGTGGCC TTCACGACCAGCGTGCGCAGCTACCTGCCCAACACCGTGACCG ACACACTGCGCGGGAGCGGCGCGTGGGGGCTGCTGCTGCGCC GCGTGGGCGACGTGCTCACCCACCTGTTGGCGCGCGTGCGC GCTGTACCTGCTGGTGCCCCCGAGTTGCGCCTACCAGGTGTGC GGGCCGCCACTCTATGACCTCTACACCGCAGCGGAGGCTCGGC CCATGCGACACAAGGGCCAGACCCCGACTGGCCTCGGACTCA CGCGCCCCGTTTGCAATGGGGAAGCCGGGCGACCCCAGGAGC AGAGGGCGCAAGGTGTGAGGCGACGTCGGGGCAGAGCGGGG |

TABLE 1B-continued

| Gene | Species | NCBI # | DNA Sequence |
|---|---|---|---|
| | | | GGACATCCACTTCCAGCCAAGAGGCCCAGGCACGTCCCGGAG<br>CCTGAACAGGGTCCCGAAGGGCAGGCGTCCCGGGCCCACCAG<br>GGCAGGGCGCCTGGGCCGAGCGACAGCGACCCCCCCGTGATG<br>ACACCTACCAGAGCCGCTGCGAAAGCCAAGTCTCGGGAGGGT<br>GAGGCGCCCGGAACCCGGCACCTTTCCCCTCAAGCAGGCGGTG<br>CGCGGGGTACCTGCCCCCCATCCTGGTGGCAGCCACACCTCCA<br>GGGCAAGCCCAGTCCTCATGTGTGCGCTGCCGAGACCAAGCGC<br>TTCCTCTACTGCTCGGGGAGCAAGGAAGGGCTGCGCCGCTCGT<br>TCCTGCTCTGCTCCCTGCCGCCCAGCCTGGCGGGGGCCGGGAG<br>GCTCGTGGAGGTCATCTTTCTGGCCTCAAAGCCCGGGCAGCCA<br>GGGGCGCGCCGCGTGCCCGCACGCTACTGGCGGATGAGGCCC<br>CTGTTCCGGGAGCTGCTTAAGAACCACGCGCGGTGCCCCTACA<br>AGGCGCTTCTCAGGGCGCACTGCCCGTTGCGGGCTGCGGCGAC<br>CCTCTCGGGGTCCGGCGGTCAGGTGTGCGACCACAAAGTGGGC<br>CCCCTCGCTCCAGAGCGGCTGGCAGCGGCCGCCGAGGGGGAC<br>TCGGCCTCGAGGCGCCTAGTCCAGCTGCTCCGCCAGCACAGCA<br>GCCCCTGGCAGGTGTACCGCCTCCTGCGGGCCTGTCTTCACCG<br>GCTGGTGCCCCCGGGCCTCTGGGGCTCCCCGCACAACAAGCGG<br>CGCTTTCTGAAGAATGTGAAGAAGCTCGTCTCCCTGGGGAAGC<br>ACGCCAGGCTCTCGCTGCAGGAGCTGATGTGGAAGATGAAAG<br>TGCAAGACTGCATCTGGCTGCGCCGGAGCCCGGACGCTCGCCA<br>TGTCCAGGCCGCCGAGCACCGTCTGAGAGAGGCCATTCTGGCC<br>AAGTTCCTGCGCTGGTTGATGGGCACGTACGTGGTCGAGCTGC<br>TCAGGTCGTTTTTTTATGTCACGGAGACCACGTTTCAGAAGAA<br>CCGGCTCTTCTTCTTCCGGAAGCGCATCTGGAGCCGGCTGCAG<br>AGCGCAGGCATCAGGCAACACTTAGATCGTGTGCGGCTTCGAG<br>AACTGTCGGAAGCAGAGATCAGGCGACGCCGGGAGGCCAGGC<br>CCGCTGTACTGACCTCCAAGCTCCGCTTCGTCCCCAAACCCGA<br>CGGGCTGCGGCCCATCGTGAACATGGCGAACGTCGTGCGAGC<br>CAGGACAGGCCCCGGAGACAAGAAGGTCCGGCGTCTCACGGG<br>GCAGGTCAAGACGCTGTTTGCTGTGCTGAACTACGAGCGGGCG<br>CGGCGCCCGCGCCTCCTGGGGGCCTCCGTGCTGGGCGTGGGTG<br>ACATCCACAGGGCCTGGCGGGCCTTTGTGCTGCCCCTGCGGGC<br>CCAGGACCCGGCCCCCCCGCTGTACTTTGTCAAGGTGGACGTG<br>ACGGGGGCCTACGACGCCCTCCCTCAGGACAGGCTGCTGGAG<br>GTGGTCGCCAACGTGATCCGGCCCCACGAGAGCACGTACTGCG<br>TGCGCCAGTGCGCCGTGCTCCGGAGGACCGCCCGCGGGCACGT<br>GCGCAAGTCCTTCCAAACCCACGTGTCCACCTTCGCAGACCTC<br>CAGCCTTACATGAGACAGTTTGTGGCACACCTGCAGGCAACCG<br>GCCCGCTGAGGGACGCCGTGGTCATCGAGCAGAGCTGCTCTCT<br>GAACGAGGCCGGCAGCCGTCTCCTGGAGCTTTTCCTGAGCCTG<br>CTGCGAAACCACGTCATCCGGATCGGGGGCAGGTCCTACGTCC<br>AGTGTCAGGGGATCCCACAGGGCTCCATTCTGTCCACGCTGCT<br>CTGCAGCCTGTGCTACGGGGACATGGAAAACAGACTCTTCCCC<br>GGGATCCAGCGTGACGGGGTGCTCCTGCGCTTGGTGGACGACT<br>TCCTGCTGGTGACCCCTCACCTGACACGAGCCAAAGCCTTTCT<br>CAGGACCCTGGTCCGCGGCGTGCCCGAGTACGGCTGCCTGGCC<br>AACTTGCGGAAGACGGCCGTGAACTTCCCTGTGGAGGACGGC<br>GCCCGGGGCGGCCCGGCCCCACTGCAGCTGCCGGCACACTGCC<br>TGTTCCCCTGGTGCGGGCTGCTGCTGGACACCCGCACGCTGGA<br>GGTGCACTGCGACTATGCCAGTTACGCCCGGACCTCGATCAGA<br>GCGAGTCTCACCTTCAACCAGGGCTTCAAGCCCGGGAGGAAC<br>ATGCGCCGCAAGCTCTTGGCGGTCTTGCGGCTAAAGTGCCACG<br>GGATCCTTCTGGACCTGCAGGTGAACAGTCTTCCGACGGTGCT<br>CGCCAACGTTTACAAGATCTTCCTGCTGCAGGCCTACAGGTTC<br>CACGCGTGTGTGCTGCAGCTGCCCTTCCGTCAGCCGCTTGCGA<br>GGAACCCCTCATTTTTCCTCCGGCTTGTCTCCGACACCGCGTCC<br>TGCTGCTACTCGCTCCTGAAAGCCAGAAACGCAGGGATGTCCC<br>TGGGAGCCAGGGGCGCCTCCGGCCCGTTTCCCTCTGAAGCCGC<br>AGAGTGGCTCTGCCTCCACGCCTTCCTGCTCAAGCTGGTTCGTC<br>ACCGCGTTACCTACAGCTGTCTTCTGGGGCGCTCCGGGCAGC<br>CAGAGAGCGATTGTGCCAGCGGCTCCCTGGGGCCACACTGGCC<br>GCCCTCGAGGCCGCCGCCGACCCAGCCCTGACTACAGACTTCC<br>GGACCATCCTGGACTGA (SEQ ID NO: 40) |
| TERT | Zebrafish<br>[Danio<br>rerio] | NM_001083866.1 | ATGTCTGGACAGTACTCGACAGATGGCGGATTTAGGCCGGTTT<br>TGGAGATTCTGCGCTCCTTATATCCGGTCGTGCAGACTTTGGA<br>GGAGTTCACCGACGGACTGCAATTCCCTGACGGCCGAAAGCC<br>GGTTCTGCTGGAGGAAACAGACGGCGCGCGCTTTAAAAAGCT<br>CCTCAGTGGACTTATTGTATGTGCGTACACGCCGCCGCAGCTG<br>CGCGTCCCCGCCCAGCTCAGCACCCTGCCGGAGGTCTTGGCGT<br>TCACTCTGAACCACATTAAACGTAAGAAACTGAGGAACGTCCT<br>GGGCTTCGGTTATCAATGCAGCGACGTGACGACCAGTTCGGAT<br>CCCTTCCGTTTCCATGGCGACGTTTCGCAGACGGCTGCCTCCAT<br>CAGCACCAGCGAGGTCTGGAAGCGTATCAACCAGCGTCTGGG<br>CACGGAGGTAACGCGGTACCTGCTGCAGGACTGTGCCGTTTTC<br>ACCACCGTCCCGCCATCGTGTGTTCTGCAGGTGTGCGGAGAAC<br>CTGTTTACGACTTGCTGATGCCGCGCTCATGGTCTGGCTTTTTC |

TABLE 1B-continued

| Gene | Species | NCBI # | DNA Sequence |
|---|---|---|---|
| | | | CTCAGTAACTCAGATAATGAACGAATCAGCGGCGCGATGCGG<br>AAATTCCCTGCTGTCCAGAAGACAGTCGCAATTTCCAAAAGA<br>GAACAAGAGATAACGAAAAATATATTTCGGTAAAGCGGCGGA<br>GGGTAAAGGAAACTGTGAATAATAATAACGGAAATTACAGAT<br>CTCTGTGTTTTGCAATTTCTAAAAAGAGAGCGATAGATAATGA<br>AGAAAATATTTCGTTAAAGCGACGGAGGATGGAGGAAACTGA<br>CCAAGTAGCGAAAATACGTAATGAAAATCACGAATCTCAGAG<br>TTTCGCAATTTCTAAAAAGAGAGCGAGAGATAATGAAGAAAA<br>TATTTCGTTAAAGCGACAAAGGATGGAGGAAATTGACCAAGT<br>AGCGAAAATACGTAACGAAAATCATGGATCTCAGAGTTGGAA<br>ACCAGCAGATCAGCGTCCTCCTCGACCCTCGCAATGTTCAATA<br>CGCGTTCTGAGCATGCTCTACAATGGGCGGGGCATGAAGAACT<br>TCCTGCTCAACAGGAAGTTGAAAGGAGTGGGCGGGGCCAGGC<br>GCATGCAAGGGGAGGATCTTGTCCGCATGATTTTCCTCCAATC<br>AGAATCCAACGACAGCAAACCGAAAAAACTTCCCAAACGATT<br>CTTCGCAATGGTGCCGCTATTCAGTCGGCTGTTGCGGCAGCAC<br>AGGAAGTGTCCGTATCGGCTGTTCCTGCAGAGGAAGTGTGCAG<br>GAAATCCAGACGTGAAGGATATGGAGTCTCTGCTGAAGTCAC<br>ACTCGTCTCCATATAGAGTTTATCTGTTCGTCAGGGAGTGTCTG<br>CGCCATATTATTCCCCACGAGCTCTGGGGCTGCCAGGAAAACC<br>AGCTCCACTTCCTGTCTAATGTAAAGAACTTCCTGCTTCTGGGG<br>AAGTTTGAGCGCCTCACGCTGGTCCAGCTGATGTGGAGGATGA<br>AGGTTCAGGCCTGCCATTGGCTGGGGCCCAAGAAACGTCAGTG<br>TGCGAGCGAGCACCGCTACCGTGAGTGGATGTTGGGTCAGTGT<br>ATGGGCTGGATGTTGAGTGGTTTTGTGGTCGGTCTGGTCAGAG<br>CTCAGTTCTACATCACGGAGAGTATGGGCCACAAACACACACT<br>GCGCTTCTACAGGGGAGATGTCTGGAGCAGACTGCAGGACCA<br>GGCCTTCAGGGCTCATCTGTGTAAGGGCCAGTGGAGGCCCCTG<br>TCTCCATCCCAGGCGCTGAAGGTCCCCAATAGTGCAGTGACAT<br>CCCGCATCCGCTTTATTCCCAAAACCAGCAGCATGAGGCCCAT<br>CACACGCCTCAGCGGCAGCAGAGACACACTGCAGTATTTTCAG<br>AGCTGTGTGCGTGTGCTGCAGAATGTGTTGAGTGTGTGTGTGC<br>GTGAGGCCCCGGGGCCCATGGGCTCCACCGTCTGGGGTTGGCA<br>GGACATTCACAGACGCCTGCAAGACTTCAGCCCTCAGCAGAA<br>GAGCTCGCCACGACCGCTCTACTTCGTCAAGGTGGATGTGAGC<br>GGAGCGTATGACAGTCTCCCGCACCTGAAGCTGGTGGAGGTGC<br>TGAAGGAAGTGTTGGGTCCGTTTGCAGAGCAGAGCTTCTTCCT<br>GCGTCAGTACAGCAGTGTGTGGAGCGACCCGACCCGCGGCCT<br>GCGCAAACGCTTCTGCACCAAAGCTGAGATGTCAGAGCCGCTC<br>AACATGAAGGGGTTTGTTGTGGATGAACAGGTCAGCGGGCGC<br>CTGCATGACGCTATATTAGTGGAGCGGCACTCGTCTGAGGTCA<br>GAGGTGGAGACGTCTTCCAGTTCTTCCAGAAGATGCTCTGCAG<br>TTACGTCATCCATTACGACCAGCAGATGTTCCGGCAGGTGTGT<br>GGGATCCCGCAGGGCTCTTCAGTGTCTTTCTCTGCTGTGTAATCT<br>GTGTTACGGACACATGGAGAAAGCCCTGCTGAAGGACATCGC<br>TAAAGGAGGGTGTCTGATGAGGCTGATTGATGATTTTTTGCTC<br>ATTACTCCTCATCTGAGTAAAGCCACAGAGTTCCTGACCACTC<br>TTCTGTCTGGAGTTCCAGATTACGGTTGCCAGATTAACCCTCA<br>GAAGGTGGCGGTGAACTTCCCCGTGTGTGTGTCCTGGGTAAAC<br>TCGGGCGTCTCTGTGCTGCCGTCCAGCTGCCTGTTCCCCTGGTG<br>CGGCTTGATGATACACACACACACGCTGGACGTCTATAAAGAC<br>TACTCACGGTATGACGGCCTATCACTGCGCTACAGCCTGACTC<br>TTGGCTCCGCCCACTCTCCATCTACAGTCATGAAGAAGCTGCT<br>GTCGGTGCTCAGCATCAAAAGCACGGACATCTTCTTAGACCTC<br>AGGCTGAACTCTGTGGAGGCCGTTTACAGGAGTCTGTATAAGC<br>TGATTCTGCTGCAGGCGCTCAGGTTTCATGCGTGCGTGAGGAG<br>TCTGCCGTTGGGTCAGAGTGTGAACAGAAACCCGTCGTTCTTC<br>CTGAAGATGATCTGGAGAATGACTCGAGTCACCAATAAACTCC<br>TCACACACATTAACAAAGGTCTGCCTGTGTGTTCTGTGGACAG<br>TGGTGGTGTTCTGCAGTCTGAGGCGGTTCAGCTTTTATTCTGTT<br>TGGCCTTCGAGACGCTTTTCAGACGGTTTCGCTCGGTTTACCAC<br>TGCCTGATCCCTGCACTGCACAAACGGAAGCGTGCTCTTCAGC<br>GTGAGCTCTGCGGGATCACTCTGGCTGGGTCCGTCAAGCTTC<br>CTCTCCCAGAATCCCCCTGGATTTCAGCATGCGGGTGTAA<br>(SEQ ID NO: 41) |
| TERT | Tilapia<br>[Oreochromis<br>niloticus] | XM_003458511.4 | ATGACGCGGGCCCTTAAAAGGTCAAACATAGCTAAATCCCAGT<br>GTAAAGTAGCTAACCTCCGTCCAAGTGCTCCGAACACAGTCGG<br>TATGTCTGCGACTGATATGTCCGGTGTGCTGGATATCCTTCGGT<br>TACTGTACCGGCACACGCAGACACTGGAGGAGTTTTCGGACAG<br>CATCCGTGTTCAGAGAAGGACAGAAAGCAGCTCTCATTGAGCA<br>GACAGATACAAACCGATTCAAATCTTTCGTTAGGAGTGTTTTT<br>GTGTGCTTTGACAAGGAGCTACAGCAGGTAGCGAGCTGTAAA<br>CAGATCTGCAGTCTGCCTGAACTACTGGCGTTTGTTCTCAACA<br>CTCTAAAAGAAAAGAAAAAGGAATGTCTTGGCACATGGCT<br>ATAACTTTCAGACCCTGGCTCAGGAGGATCGGGATGCAGACTT<br>CCTCAAATTCCAAGGCGACGTAACACAGAGTGCTGCCTACATC<br>CACGGCAGTGACCTGTGGAAAAAAGTCACAATGCGTCTGGGC |

TABLE 1B-continued

| Gene | Species | NCBI # | DNA Sequence |
|---|---|---|---|
| | | | ACAGACATCACGCAATATCTTCTGGAGAGCTGCTCTGTGTTTG
TGGCAGTTCCTCCTTCGTGTGTTTTCCAGGTGTGCGGCCCTCCA
GTCTATGACAGGGTGTCCATGACCATGGCCTCGAGTGGGTTTT
TTCTCCAGCCTGGAGTCAGGAAACATAATCGTACCAAGATTGA
GAGCTGTCGAGGGTCAGTGAGTTTGAAACAGAAACGCACAGT
TGTGAATCCTGCTGCAAGCAAGAAGATGAAAAGAAGGAATAA
AGGAGGGAAAAAAGGGAAAAGAAAACGGGAAACTGGTGAAG
AGGAGGAGGTGGCGGTTTGTTCAAGAAAGAGGCGGCGAGTAG
CGTCTATAGAACATCAACAGGCGATCCAACCAGTTGGCTCTGA
AAAGGAAGGACAGGTTGTGCCTGTGGAATCAGCACCGCCTGC
AGCTTTTCAAACAGCCTGTTGAAATGCCAACATTGGAGGGCGGT
CCTAGTTGGAGATCAGGGATTTTCCCCCCTTTACCACCCTCGCA
ATGTTTTATCCGCACCCTGGGATTCCTGTATGGGGGCAGGGGC
ATGCGTGGCTTTCTTCTTAACAGGAGGAAGAAGACTGCTCATG
GATCCAGAAGGCTTCAAGGACAAGATCTGGTAAGAATAGTCTT
CTTCGAGGGACTAGCGTATTTGAATGGAGTAGAGAGGAAGCC
TAAAAAACTCCCCCAGAGGTTCTTTGGCATGGTCCCCCTGTTT
AGGCAGCTCTTACAACAACACAGGAGCTGTTCCTACACCAAAA
TACTACAGAGGTTATGTCCATCAATAGAGGAGAGCAATGCAG
GACAGGGAGAACTAAACTCACTCTTACCTCAGCACTGTGCACC
GCACAGGGTTTACCTGTTTGTCCGGGAATGCCTCTCTTCTGTGA
TCCCGCAAGAACTGTGGGGCTCTGATCAAAACCGGCTGCATTT
CTTTGCCAGGGTCAGGACTTTCTTGCGAAGTGGCAAGTTTGAG
AGGCTCTCACTGGCTGAACTGATGTGGAAGATAAAGGTGAAT
GACTGTGATTGGTTGAAGAGGAGTAAAACAGGCTGTTTTCCAC
CCAGCGAGCTTGCGTATCGGACACAGGTCCTGGGTCAGTTCTT
GGCTTGGCTTCTGGATGGATATGTTACAGGCCTTGTGAGAGCC
TGTTTCTATGCAACAGAGAGTATTGGGCAAAAAAACGCCATCA
GGTTCTACAGGCAGGAAGTCTGGGCCAAACTGCAAGACTTGG
CCTTCAGAGGTCACCTTTCCAAAGGCCAGATGGAAGAGCTGAC
TCCAGCTCAGGTGGCATCCCTGCCCAAAGGCACCGTCATCTCC
CGCCTTCGCTTTATTCCCAAGACTGATGGCATGAGGCCCATCA
CACGAGTCATAGGAGCAGATGCCAAAACAAGGCTCTACCGAG
GCCGTGTCAGGGACTTGCTGGATATGCTGCGGGCCTGTGTGCG
TGCCACTCCATCACTGCTGGGGTCCACAGTGTGGGGGATGACT
GACATCCACAAGGTTTTGTGCTCTTTGGCACCAGCGCAGAAGG
AAAAACCACAACCCCTCTATTTTGTTAAGGTGGACGTGAGTGG
AGCCTATGAGAGTTTGCCGCATGACAAACTCATAGAGGTGATT
GGCCAAGCCCTGTCACCTGTCCACGATGAACTCTTTACCATCC
GCCGCTATGCCAAGATCTGGGCGGACTCCCACGAAGGCCTGA
AAAAGGCCTTTGTCAGACAGGCAGATTTCCTGGAGGATAACAT
GGGATCCACCAACATGAAGGGCTTTTTGACGTCACTGCAGAGA
AAAGGCAAAGTTCATCACGCCATCCTGGTTGAGCAGCACTTTT
GCTCAGATCTTCATGGCAGAGAGGCATTGCAGTTCTTTACCCA
AATGCTAACTGGCAGTGTTGTTCAGTATGGGAAAAAGACGTAC
CGTCAGTGCCGGGGGATTCCTCAGGGATCGGTTGTGTCTAGTC
TGCTCTGCTGCCTTTGCTACGGCCACATGGAGAATCTCCTGTTT
AAAGATATTCCTGGACACAAAGGGTGTTTGATGAGACTGGTGG
ATGACTTCCTTCTGATCACACCAGACCAACATGAAGCACAAGC
TTTTCTCAAGATCTTGCTGGCCGGAGTGCCACAGTATGGTCTG
GCGGTCAACCCGCAGAAGGTGGTTTTGAACTTTCAGGTATCGG
GAAGCGTGGCCTCCTGTCCCGACATTCGCATCCTGCCCCCTCA
CTGCCTCTTCCCCTGGTGTGGACTGCTGCTGGACACCCACAAG
CTGGACGTCTATAAAGACTATTCCAGCTATGCTGGACTGTCTC
TGCGCTACAGCCTTACTCTGGGTTCATCCCACTCTGCAGGACA
GCAGATGAAAAGGAAACTAATGGCTATCCTCAGGCTCAAGTG
TCATGCCCTGTTCTTCGACTTGAAGACTAATTCTCTTGAAGCGG
TCTACAAGAACATCTACAAGCTGGTGCTGCTGCATGCGTGCAG
GTTTCATGTCTGTGCCCAAAGCTTGCCCTTTGGTCAGACCGTTT
CCAAGAACCCCGTCTTCTTTCTGCAGTTGATATGGGAGATGGC
CCAGTACTGCAACAAGCTCATCAGACGCAGCAACAAAGGACT
GATTTTAGGTGATAAGGCCCAGACGGGGATCGTGCAGTACGA
AGCAGTGGAGCTGCTTTTCTGTCTGTGCTTCTTGCTGGTGCTGT
CACAACATCGTCTTCTCTATAAAGATCTGCTCGCACACTTGCA
CAAGCGAAAGCCAGTCTGGAGCGGCGTCTGGGGGACCTGAG
GCTGGCCAGGGTGCGGCAGGCTGCTAGCCCCAGGACTCCAGTC
GACTTCTTGGCCATTCAGACATAA (SEQ ID NO: 42) |
| TERT | Rainbow trout [Oncorhynchus mykiss] | XM_021559758.1 | ATGCCCAGTGGCGATATGACACGTGTGCTCGGCATACTCGGCT
CTCTGTATCGGCACGTCGAGACCCTGGAGGAGTTTGCAGACCA
TATTGTATTCAGAGAGGGACAGAGAGCGGTGCTCATCGAACC
GACAGATACAACGCGCTTCATATCGTTTGTCCGGGGAGTGTTG
GTCTGCACGGATAAAACCCTACAGGACGTCCCCAGCTGCAATC
AGATCAGCACCGTGCCTGAGCTGTGGCGTTCGTGTTGAACAA
CATCAAGAGGAAAAGAAAGGAATGTCCTGGCGCACGGTTA
CGGTTACACGTTCCAGGACCGCGACGCAGACCAGTTTAAGTTT
CATGGCGAGATCACTCAGAGTGCCATGTACATCCACTGCAGCG
ACTTATGGAAGAGGGCCTGCCAGCGCCTCGGCACGGACATCTC |

TABLE 1B-continued

| Gene | Species | NCBI # | DNA Sequence |
|------|---------|--------|--------------|
| | | | CAAGTACCTCCTGGAGAGCTGTTCTTTGTTCGTGACGGTGCCG |
| | | | CCGTCGTCCGCGTTCCAGGTGTGCGGCGTGCCTGTGTACGACC |
| | | | GCGTTTCCATGTCAACGGGTATCTCTAGGTTCCACCTGGGATA |
| | | | CAAACGGAATGGTACTACTAGGAACAGCAGAGGGAGAAGTAA |
| | | | GGAGGTCAGAAATGGGGATGGGAATTTCAGGGTTCTGCTGG |
| | | | GAGAAATAGGAGAAAGGATGGAGGTAGAGACACTGGGAAAA |
| | | | GGAAGGGAGACGAGGTCAGTTTGGGAGGGAAGAGGAAGAGG |
| | | | GAGAGGGAGGAGGTGGAAGGAGATGTGTGTTTGCCTGGAAAA |
| | | | AGGAGATGCACTCAAAGAGAAGCTCCCACAGTCTCCAGTGGG |
| | | | ACTAGCGATCGTAAGCACAGAACACTGGAAACAAATGGGGTC |
| | | | AAGAGACCAGTGGAGGTCATTTCTCTCACCAAGGGACCCACAC |
| | | | AGAGCCTACAGGTTTTCAATGGTTCTAGCAATGTGGAACAGGT |
| | | | GTCAGCAGAAATGGAACGTCTCAGGAAGCCAGTGGAGAAACT |
| | | | GGCTGGACCCGGAAGACCATTGGAGGCTGTGATGGTCACCAT |
| | | | AGCACCCGCTGAGAGCTCTAAACAGGTCTCCAACGGCACAGG |
| | | | TAATATCGAGCAGATGTCAATGAAAACAGGACATAGAAGGCC |
| | | | AGCGGCTGTAGTCCCAAGACCAGTAGAAGAACAGTCTGGACC |
| | | | TGTATCGGCCACCGTCCATGTAGAGGGGGGCCCTAGTTGGAGA |
| | | | ACAGGGTCGTTCCCACCGCTTCCCCACTCCCAGTGTTTCATCCG |
| | | | CACCCTGGGCATGCTCTACGGAGGGCGGGGCATGCGCCGCTTC |
| | | | CTACTAAACAGGAAGAGGAAAAGTAGGGACGAGGGGCCCAG |
| | | | GCGTCTGCAGGGGCGAGACTTAGTGAGACTGGTCTTCTTTGAA |
| | | | GGCGTGGCCTATCTGAACGGAACAGAAAGGAAGCCTGAGAGA |
| | | | CTTCCCAGAAGATTTTTCACCTTGGTGCCTCTGTTTTGTCAGTT |
| | | | GTTACGTCGACACAGGAGGTGTCCCTATTCTAAGATACTGCAG |
| | | | AGGGTTTGTCCAGCAGTGGGACAGGGGGATATGGCCTCCCTCC |
| | | | TGCCCCAGCACAGTGCACCTCACCGGGTGTACCTCTTTGTCAG |
| | | | AGAGTGCCTCAACGCGGTGGTCCCCTCGGAGTTCTGGGGGTCG |
| | | | GACCATAACCGATTCAAATTCCTGTCCGCAGTCAGGAACTTCC |
| | | | TGTCCATGGGCAAGTTTGAGAGGATGTCATTGGCTGAGCTGAT |
| | | | GTGGAAGATGAAGGTGAATGACTGTGATTGGCTGAAGATCAG |
| | | | CAAGACAGGCCGCTGCCCGCCCAGTGAGCTGTCGTATCGGACG |
| | | | CGGGTGCTAGGCCAGCTCCTGGCTTGGCTGCTGGATGGCTATG |
| | | | TGCTAGGCCTGGTGAGAGCTATGTTCTACGTCACAGAGAGCAT |
| | | | GGGACAGAAGAACGCACTGCGCTTCTACAGATACCAGGTCTG |
| | | | GGCCAAGCTGCAGGAGCTGGCTTTCAGTGGTCACCTCTCTAAA |
| | | | GGTCAGATGTCAGAGTTGACCCTGGCCCAGGTGACGTCGCTCC |
| | | | CCAAAACCACTGTCCCCTCCCGCCTCCGCTTCATCCCCAAGAC |
| | | | CGAAGGGATGAGACCCATCACACGGGTCATAGGGGCTGACGC |
| | | | CAAAACAAGGTTGTTCCAGACCCGTGTGAAGGAGCTGTTAGAT |
| | | | GTGCTAGGTGTCTGTGTACGGTCCTCTCCCTCTCTCCTGGGCTC |
| | | | TACAGTGTGGGGGTTGACCGACATCCACAGAGTCCTCTCTTCC |
| | | | ATCACCCCTGCTCAGAAAGACAAACCACAGCGGCTCTACTTTG |
| | | | TCAAGGTGGATGTGAGTGGGGCCTATGACAGTCTACCCCACAC |
| | | | TCAGCTCTTGGAGGTGATTGGTCAGGTCCTGTCACATGTGCAG |
| | | | CAAGAGCTTTTCTCGGTGCGACGCTATGCCAAGGTGTGGGCCG |
| | | | ACACCCACGAGGGCCTCAAGAAGACCTTTGTCAGACAGGCAG |
| | | | ACTTCACGGAAGACACTGTGTCGTCCACCAACATGAAAGGCTT |
| | | | TGTGATGTCACTGCAGAGAGAGGGCAAAGTTCACGATGCCAT |
| | | | ACTGGTGGAGCAGCATTTCTCCACAGATATTCATGGCAAAGAC |
| | | | GTCTTGGAGTTCTTCACCCAGATGCTCTCTAGCTGTGTTGTCCA |
| | | | GTTTGGGAAGAAATCGTTCCGTCAGTGTCAGGGGATTCCTCAG |
| | | | GGTTCCGCGGTGTCGTCTCTGCTGTGCTGCCTCTGTTACGGCCA |
| | | | CATGGAGAACCTTCTGTTTCCTAACGTCAGTCGGCGAGGAGGG |
| | | | TGTCTGATGAGACTGGTTGACGATTTCCTCCTCATCACTCCTGA |
| | | | CCTGAGCCAGGCACAGACCTTCCTCAAGACCCTGATGGCGGGG |
| | | | GTACCACGGTACGGGTGTGTGGTGAACCCCCAGAAGGTGGCT |
| | | | GTTAACTTCCCTTTGGGTGAGTGGGGGTCCTGTCCTGCTGGGG |
| | | | TACGCCTGCTGCCTTTACACTGTCTGTTCCCCTGGTGTGGACTA |
| | | | TTGCTGAATACACACACCCTGGACGTCCACAACAACTACGCCA |
| | | | GCTACGCTGGCCTATCCCTGCGCTACAGCCTGACGCTAGGCTC |
| | | | CGCCCACTGCGCGGGGCAGCAAATGAAGAGGAAGCTCATGTC |
| | | | CATCCTTAGATTCAAGTGCCACGCCCTCTTCCTGGACCTCAAA |
| | | | ACCAACTCCCTGGAGGCTGTCTATAGCAACGTCTACAAGTTAG |
| | | | TGTTGCTGCAGGCGTTCAGGTTCCATGCCTGTGCACAGAGTTT |
| | | | GCCGTTTGGTCAGAAAGTGGGCGGAAACCACTCGTACTTCCTC |
| | | | AATCTGATCTGGGACTTGGCGGAGTACACCAACCATCTAGTCA |
| | | | GACTCTGCAACAAAGGTGTGTCTCTAGGCTGTAAGGCTTTAAC |
| | | | AGGTAGCCTTCAGTATGAGGCAGTAGAACTGATATACTGTCTG |
| | | | GCCTTCCTGTTGGTTCTGTCCCGTCATCGCCCCCTCTACTACCA |
| | | | TCTCCTGCTCCGCTACGCACACGTAAGAGGAAGCTGGAGGGG |
| | | | AAGCTGGAGGGTTTGAGATTGGCCCGAATCAGACAGGCTGCC |
| | | | ACACCCAAAATGCCTGAAGACTTCAAGGCCATCCAGGCCTAG |
| | | | (SEQ ID NO: 43) |

TABLE 1B-continued

| Gene | Species | NCBI # | DNA Sequence |
|---|---|---|---|
| TERT | Tropical clawed frog [*Xenopus tropicalis*] | XM_018094976.1 | ATGACTCTGTGTACCGGAGGAGCTGAACTACTGAGCATTTTGC<br>ACAGCCTTTATGGCCAGGTCCTTGGGATTGTGGAATATATCGA<br>CTCACTGCATGTTCCCGGCGGCATTAAGGTGCCTGTGCTGCGA<br>GAGGGAGACCCGGAGAAGTTCAAGTCATTTGTTGCGGAACTG<br>ATGCTGTGCATTCCAAGAGGAACAAAGTCGCTTCCGTCCCCTG<br>TCTCCTTTCTTCAGCTATCAACTCAGAGAGAAGTAGTGGCGCG<br>AGTAATTCAGCGGATTTGTGAAAAGAAAAGAAAAAATGTTCTT<br>GCTTTTGGTTATGGCTTAGTTGATGAAAAAGCTCTCTGAATA<br>TTCGATTGACTCCAAATATTTGCAGTTATTTTCCTAATTCCACA<br>ACAACAACAATCAGCACAAGTATTCTTTGGGAAACTCTGCTTA<br>CTAGAGTAGGTGATGATGTTATGATGTATTGGCTGGAACAATG<br>CTCAGTTTTTGTATTTGTGCCACCTAGTTGTTGTTATCAAATCA<br>GTGGGCAGCCAATCTACACTTTACCCTATGATAGTATGTGTTC<br>ATTTCGATCTCAGTCATTTATGCATAGCAATGTTTTGTTGCAGT<br>ACATTAAAAGAAATGCCTTTTTCTTGCGGAAAAAATATCTGAA<br>GCCAAAAAGTGGTGGAAAACGGTGTTAAACAGCAAAGTAGA<br>AAAACATTCAAAGACTTCTCAAATGCTAACATGGCAAAATAA<br>AAAGTCCACATCAGCATTGCCTATTTGTAGTGAGTCATCTATG<br>AAAGTTACCACAAAAATACATTCCAAAAGGAAGATGTGTACT<br>ACAGATATTTGTGACATTCCAACTAAGAAACGCAGAGTCAACT<br>TGGACAAAGATGATAAAATGGACCACGTTTCCTTTACGTCTGC<br>ATGTCTTTCTTCCTTCTCAAATGTGTGCCCTGAAGCTAAAGTAC<br>AAGCAACGGAATTTATTACCTCAAGATATGGAAAAAAAACAA<br>AAATTCAATGTCCAAATCGACTTCATACTCAGTTGATGGTGA<br>ATTTAATGTAACTCTTCAAAATAATGCTAATACGTTTATTACCA<br>ATGCTTCTGTCCCTACAATACAAAGCAAAACTTCATTTTCAAA<br>TATTTTTATTGAAATTGGAAGAACATTGTATTCAAGTATTAGTT<br>TCAAGAAGGGCTTCTCTGAAAGTTTTATACTTAACAGTTTAGA<br>CTGTACCCCTTCTGGGAGCCAAAAATTAGTGGAAACCATATTT<br>CTAAACAACTTTTTAACTGAGCAAAATTTTGACCAGCCAAAAC<br>GGGATGAAAACTTTAGATCTAAACTTCCCAAACGTTATTGGAG<br>AATGAGAAAATATTTCCAAGAATTAATACAGAACCATAAGAA<br>TTTCCCTTATCTGGTATATTTGAATAAACACTGCCCTGTTAGGC<br>CTTCAATGGCTTGTTCACACAAACTGGCGTTGCAGAAAAAGAA<br>TAAATGTAAAATGGATAAATCAATTTGTGACTTAAGTAATACC<br>TCAGTTATGAAAACAAAATTGTAAATGATGAAAAGCCGCTA<br>AAACATGTTACAGCCGAAGCAACTTTTTTACCTCTTCTTAAAC<br>AACACAGCAGCAGTTGGCAAGTGTACATGTTTGTTAGAGAATG<br>TTTAAATAGTTTAGTGCCTGATTTCATATGGGGCTCCAGTCACA<br>ACAAGTGCCGTTTCCTTAGAAATGTAAAATCTTTTCTTTTTTTT<br>TCTGGCAAATTTGGCAAGGTCTCTTTATTAGAGCTTATGTGGA<br>AGATGAAAGTAGAAGACTGCTCTTGGATTCGTCTACGAAAAA<br>GTGATCACTTTGTTCCTGCTTCAGAACACTTGCTACGAGAGAG<br>AATCCTTGCCAAATTTATCTTTTGGCTAATGGACACCTATGTCA<br>TACAGTTGCTGAAATCATTTTTTTTGTCACGGAAACCATGTTT<br>CAGAAGAATAGACTTTTGTTCTACAGAAAAAGAATTTGGAAG<br>AAACTTCAAAATTTAGGTCTAAGAAAACATCTAGAGAAGGTG<br>AAATTGCGTCCATTGTCCTGCGATGAACTAGAAAAGATGCAAC<br>AATGGAAAAACATTCCACTGGTTTCCAGGCTCAGATTCATACC<br>AAAAACAAATGGACTACGTCCAATATCTAGAGTATCCAGTACT<br>TTGGGTAGCCAACAAAGCAAAGAAAACCAAGAGAAGAAGATT<br>CAACATTTTACCTCTCGGGTTCGAAACCTTTTTAGTGTTCTTAA<br>CTATGAATGGAATAGAAATTGCAGCCTAATTGGCTCATCTGTT<br>TTTGGCATGGATGATATATACAAACAGTGGAAAAAATTTGTGC<br>TAGATTTTGAAAAATCGAGAGCTGAAAAAGGCAAATTTTACTT<br>TGTGAAGACAGATGTTAAGGGAGCATATGATACCATTCCACAT<br>TCAAAGCTCGATGAAGTGATCTTAAAAGTAATTAATCCAAATG<br>CAAATGAAGTATATTGCATACGACGTTATGCCTCAGTTTCAGT<br>GGATTCAACTGGACGCATTATAAAATCTTTCAAAAGACATGTA<br>TCTGCATTAGCAGATGTTCTTCCAAATATGAAACAGTTTGTTTC<br>AAATCAACAAGAAAAAACTTGACACGTAACACAATTCTAGT<br>GGAACAGAGCCTTTATTGAATGAGAGCTCTGTCAAACTTCTT<br>GCTGTTTTTCAACAAATGATCAGATCCCATATTTTAAGAATAG<br>AAGATCGATATTCATGCAGTGCTGTGGAATACCACAGGGTTC<br>AATGTTATCTACAATCCTATGCAGTTTATGCTATGGAGACATG<br>GAAAATAAACTGTTTGGCGGAATACAGCAAATGGGGTACTA<br>ATGCGATTGATTGATGATTTTTGTTTGTAACACCTCATCTTAA<br>CCAGGCAAAAACATTTTTAAGGACTCTGGCAGAAGGAATTCCC<br>CAATATGGGTGCTCCATCAGCCCTCAAAAAACAGTGGTAAACT<br>TTCCTGTTGATGACATCCCAGCATGCTCTGAGGTGGAACAATT<br>ACCAGTTCACTGCTTGTTCCGGTGGTGTGGTCTTTTGCTGGACA<br>CTCAGACTTTGGATGTTTACTATGATTATTCAAGCTATGCCTGT<br>ACCTCAATCCGATCAAGTATGACATTTTGTCACAGTTCTGCAG<br>CAGGAAAAAACATGAAACAAAAACTTCTAAGAGTCCTTAAAT<br>TGAAGTGCCACAGTCTCTTTCTTGATTTACAGGTAAACAGTTTA<br>AGGACAGTTTTCATCAATACTTATAAGATATTCTTACTTCAAGC<br>TTACAGATTCCATGCTTGTGTTGTTCAGCTTCCATTTGGCCAGC |

TABLE 1B-continued

| Gene | Species | NCBI # | DNA Sequence |
|---|---|---|---|
| | | | GTGTAATGAATAATCCACCTTTTTTTCTTACTGTGATTTCTGAT<br>ATGGCACCTTGCTTTTACACTACTTTTAAGTCCAAAAACAAAG<br>ATGTCACACGTGGGTACAAGGATGTGAGCTGCCAGTTTAACTT<br>TGAAGCAGTCCAGTGGCTCAGTTATCAAGCTTTTCTTACTAAG<br>CTTCGCAATCACAAAATATTATACAAATGTCTTATTGGGCCAC<br>TGCAGAACTGTAAAATGCAGTTATCTAGAAGACTTTCGCAGTA<br>TACTATTGATCTTCTAAAAGCTGTCACAGATTCTTCCCTTCACA<br>AAGACTTTTCATGTATAATGGATTAG (SEQ ID NO: 44) |
| TERT | Chicken<br>[*Gallus<br>gallus*] | NM_001031007.1 | ATGGAGCGCGGGGCTCAGCCGGGAGTCGGCGTGCGGCGGCTC<br>CGCAATGTAGCGCGGGAGGAGCCCTTCGCCGCGGTCCTGGGC<br>GCGCTGCGGGGCTGCTACGCCGAGGCCACGCCGCTGGAGGCC<br>TTCGTCCGGCGGCTGCAGGAGGGTGGCACCGGGGAGGTCGAG<br>GTGCTGCGAGGCGACGACGCTCAGTGCTACCGGACCTTCGTGT<br>CGCAGTGCGTGGTGTGCGTCCCCCGCGGTGCTCGCGCCATCCC<br>CCGGCCCATCTGCTTCCAGCAGTTATCCAGTCAGAGCGAAGTC<br>ATCACAAGAATCGTTCAGAGGCTGTGTGAAAAGAAAAAGAAG<br>AACATCCTTGCGTATGGATACTCCTTGCTGGATGAGAACAGTT<br>GTCACTTCAGAGTTTTGCCATCTTCGTGTATATACAGCTATCTG<br>TCCAATACTGTAACAGAAACGATTCGCATCAGTGGCCTCTGGG<br>AGATACTGCTGAGTAGGATAGGGGACGACGTGATGATGTACC<br>TGCTGGAGCACTGTGCACTCTTCATGCTGGTTCCCCCAAGTAA<br>CTGTTACCAGGTCTGCGGGCAACCAATTTATGAACTTATTTCG<br>CGTAACGTAGGGCCATCCCCAGGGTTTGTTAGACGACGGTACT<br>CAAGGTTTAAACATAATAGCTTGCTTGACTATGTGCGAAAAAG<br>GCTTGTGTTCACAGGCACTATCTTTCCAAGTCACAGTGGTGG<br>AAGTGCAGGCCGAGACGTCGAGGTCGTGTCTCCAGCAGGAGA<br>AAAAGAAGGAGCCATAGGATACAAAGCCTAAGGTCTGGTTAT<br>CAGCCTTCTGCAAAAGTGAACTTTCAAGCAGGTAGGCAGATCA<br>GCACTGTTACTGCACGTCTGGAAAAACAGAGCTGCTCCAGTTT<br>ATGTTTGCCAGCTAGAGCACCATCTTTAAAAAGGAAGCGTGAT<br>GGAGAACAGGTTGAAATCACAGCTAAGAGAGTGAAAGTAATG<br>GAGAAAGAGATAGAGGAACAGGCTTGTAGTATCGTTCCTGAT<br>GTAAACCAAAGTAGCTCCCAGAGGCATGGAACCTCCTGGCAT<br>GTAGCACCACGTGCTGTAGGTCTTATTAAAGAACATTACATTT<br>CTGAAAGAAGTAACAGTGAGATGTCTGGTCCTTCTGTAGTTCG<br>CAGATCTCACCCTGGGAAGAGGCCTGTGGCAGACAAAAGCTC<br>TTTTCCACAAGGAGTTCAGGGTAACAAACGCATAAAGACCGGT<br>GCAGAAAAACGAGCAGAATCCAATAGAAGGGGCATAGAGATG<br>TATATAAACCCAATCCATAAACCCAATAGAAGGGGCATAGAG<br>AGGCGTATAAATCCAACCCACAAACCTGAGTTGAATTCTGTAC<br>AAACTGAACCAATGGAAGGTGCTTCTTCAGGGGACAGAAAGC<br>AGGAAAATCCCCCAGCTCATTTGGCAAAGCAGTTACCAAATAC<br>ATTGTCGCGCTCTACAGTGTACTTTGAGAAGAAATTTCTTCTGT<br>ATTCCCGCAGTTACCAAGAATATTTTCCTAAATCGTTCATACTG<br>AGCCGCCTGCAGGGTTGTCAGGCAGGTGGAAGGCGGCTTATA<br>GAAACTATATTCTTAAGCCAAAACCCATTAAAGGAACAGCAG<br>AACCAAAGCCTACCACAGCAAAAGTGGCAAAGAAGAGGTTG<br>CCCAAACGCTACTGGCAAATGAGAGAGATATTTCAGAAGCTG<br>GTAAAGAACCATGAGAAGTGCCCTTATTTAGTTTTCTTGAGGA<br>AAAATTGCCCTGTTTTGCTTTCTGAAGCATGTTTGAAAAAGAC<br>GGAGCTGACCTTGCAGGCGGCTCTGCCTGGGAAGCAAAGGT<br>TCACAAGCACACAGAACATGGGAAAGAGTCCACTGAGGGTAC<br>TGCACCGAACAGCTTCCTCGCTCCTCCCTCAGTGCTAGCGTGT<br>GGGCAGCCAGAGAGAGGGGAACAGCACCCTGCAGAGGGGAG<br>TGATCCGCTCCTCAGGGAGCTGCTCAGGCAGCACAGCAGCCAC<br>TGGCAGGTGTATGGCTTTGTGAGGGAGTGCCTGGAGCGGGTGA<br>TCCCTGCTGAGCTGTGGGGTTCAAGCCATAACAAATGCCGGTT<br>CTTTAAAAACGTGAAAGCATTCATTTCCATGGGGAAGTATGCT<br>AAGCTTTCATTGCAGCAGCTGATGTGGAAGATGAGAGTGAATG<br>ACTGCGTATGGCTTCGTCTGGCCAAAGGTAATCACTCTGTTCCT<br>GCCTATGAACATTGTTACCGTGAAGAAATTCTGGCAAAATTCC<br>TATACTGGCTGATGGATTCCTATGTTATCGAGTTGCTCAAATCA<br>TTTTTCTATATCACCGAGACCATGTTCCAGAAAAACATGCTTTT<br>CTACTACCGAAAGTTTATCTGGGGCAAGTTACAGAACATTGGA<br>ATTAGAGACCATTTTGCCAAAGTACATCTACGTGCCTTGTCTTC<br>AGAGGAGATGGAAGTGATCCGTCAAAAAAGTATTTTCCTATT<br>GCATCAAGGCTCCGGTTCATTCCTAAAATGAATGGTTTAAGAC<br>CCGTAGTAAGACTAAGCCGTGTTGTTGAAGGACAGAAACTCA<br>GCAAGGAAAGCAGAGAAAAGAAGATACAGCGCTATAACACTC<br>AGCTAAAAAATCTATTTAGTGTTTAAACTATGAACGAACTGT<br>AAACACCAGTATCATTGGCTCTTCAGTATTCGGGAGAGATGAT<br>ATCTACAGGAAGTGGAAGGAGTTTGTTACAAAGGTTTTTGAAT<br>CAGGTGGTGAAATGCCTCATTTCTACTTTGTAAAGGGTGATGT<br>ATCCAGAGCTTTTGATACCATTCCTCACAAGAAACTTGTGGAA<br>GTGATATCACAGGTCTTGAAACCTGAGAGCCAAACTGTCTATG<br>GAATAAGGTGGTATGCAGTGATTATGATTACCCCAACTGGAAA<br>AGCCAGGAAACTCTATAAGAGACATGTTTCTACTTTCGAGGAT |

TABLE 1B-continued

| Gene | Species | NCBI # | DNA Sequence |
|---|---|---|---|
| | | | TTTATTCCAGACATGAAGCAGTTTGTGTCCAAGCTTCAAGAGA<br>GAACTTCATTACGAAATGCAATAGTAGTTGAACAGTGCTTAAC<br>TTTTAATGAGAACAGTTCCACCCTGTTTACTTTCTTTCTTCAAA<br>TGTTACATAATAACATCCTGGAGATTGGGCACAGGTACTATAT<br>ACAGTGCTCTGGAATCCCACAGGGCTCCATTTTGTCAACCTTA<br>CTTTGCAGCTTATGCTACGGAGACATGGAAAACAAATTACTCT<br>GTGGGATCCAGAAGGATGGAGTCCTAATACGTCTTATTGATGA<br>CTTTTTGCTGGTTACGCCACATTTAATGCAGGCAAGAACTTTTC<br>TAAGGACTATAGCAGCAGGTATTCCTGAGTATGGCTTTTTAAT<br>AAATGCCAAGAAGACTGTGGTGAATTTTCCTGTTGATGATATC<br>CCGGGATGTTCCAAGTTCAAACATCTGCCAGATTGTCGTTTGA<br>TCTCATGGTGTGGTTTATTATTGGATGTGCAGACACTTGAGGTT<br>TATTGTGATTACTCCAGTTATGCCTTTACTTCTATCAGATCAAG<br>TCTTTCCTTCAATTCAAGTAGAATAGCTGGAAAAAACATGAAA<br>TGCAAATTGACTGCAGTCCTCAAACTGAAATGCCATCCTTTAC<br>TTCTTGACTTAAAGATCAACAGCCTTCAGACAGTTCTAATTAA<br>CATCTACAAGATATTTTTACTTCAGGCTTACAGGTTCCATGCCT<br>GTGTTCTTCAGCTTCCATTCAACCAGAAAGTTAGGAATAATCC<br>TGATTTCTTCCTAAGGATCATCTCTGATACTGCTTCATGCTGCT<br>ATTTTATCCTGAAAGCTAAAAATCCAGGAGTTTCTTTAGGTAG<br>CAAAGATGCATCTGGCATGTTCCCTTTTGAGGCAGCAGAATGG<br>CTGTGCTACCATGCCTTCATTGTCAAACTGTCCAACCACAAAG<br>TTATTTACAAATGCTTACTTAAGCCCCTTAAAGTCTATAAGATG<br>CATCTGTTTGGGAAGATCCCAAGGGATACTATGGAACTGCTGA<br>AGACGGTGACGAACCATCGCTTTGTCAAGATTTCAAAACTAT<br>ACTGGACTAA (SEQ ID NO: 45) |
| TERT | Turkey<br>[Meleagris<br>gallopavo] | XM_019613879.1 | ATGTCTGGGGCTCGGGGGCTCGTCTGGTGCGACGAGCGAGCGT<br>GGCTGTTATCCAGTCAGAGCGAAGTCATCACAAGAATCGTTCA<br>GAGACTATGTGAAAAGAAAAGAAGAACATCCTTGCGTATGG<br>ATACTCCTTGCTGGATGAAAACAGTTGTCACTTCAGGATTTTG<br>CCATCTTCGTGCATATACAGCTATCTGCCCAATACTGTAACAG<br>AAACGATTCGCATCAGTGGCCTCTGGGAGATACTGCTGAGCAG<br>GATAGGGGACGATGTGATGATGTACCTGCTGGAGCACTGTGCA<br>CTCTTCATGCTGGTTCCCCCAAGTAACTGTTACCAGGTCTGCGG<br>GCAACCAATTTATGAACTTATTTCGCGTAACATAGGGCCGTCC<br>CCAGGGTTCGTTAGACGACGATATTCAAGGTTTAAACATAATA<br>ACTTGCTTAACTATGTGCGAAAAAGACTTGTGTTTCATAGGCA<br>CTATCTTTCCAAGTCACAGTGGTGGAAGTGCGGGCCGAGACGT<br>CAAGGTCGTGTCTCCAGCAGAAGAAAAAGAAGGACCCATAGG<br>ATACAAAGCCCAAGGTCTGGTTACCAGTCTTCTGCAAAAGTGA<br>ACTTTCAAGCAGGCATGCGGATCAGCACAGTTACTGCACATCT<br>GGAAAAACAGAACTGCTCCAGTTTATGTTTGCCAGCTAGAACA<br>CCATCTTTAAAAAGGAAGCGTGATGGAGAACAGGTTGAAACC<br>ACAGCTAAGAGAGTGAAAGTAATGGAGAGAGAGGAACAGGCT<br>TGTAGTATCGTTCCTGATGTAAATCGAAGTAGCTCCCGGAGGC<br>ATGGAGTTTGGCATGTAGCACCACGTGCTGTAGGTCTTATTAA<br>AGAACGTTACGTTTCTGAAAGAAGTTACAGTGAGATGTCTGGT<br>CCTTCTGTAGTTCACAGATCTCACCCTGGGAAGAGGCCTGTAG<br>CAGACAAAAGCTCTTTTCCAAGAGGAGTTCAGGGTAACAAAC<br>ACATAAAGACCGGTGCAGAAAAACGAGCAGAATCCAATAAAA<br>GGGGCATAGAGATGTATATAAACCCAATCTGTAAACCCAATA<br>GAAGGGGTATAGAGAGGCATATAAATCCAACCCATAAACCTG<br>GGTTGAATTCTGTACAAACTGAACCAATGGAAAGTGCTTCTTC<br>GGGGGACAGAAAGCAGGAAAATCCCCCAGCTCATTTGGCAAA<br>GCAGTTACCAAATACATTCTTGCGCTCTGCAGTGTACTTTGAG<br>AAGAAATTTCTTCTGTATTCCCGTAGTTACCAAGAATATTTTCC<br>TAAATCGTTCATACTGAGCCGCCTGCAGGGTTGTCAGGCAGGT<br>GGAAGGCAGCTTATAGAAACTATATTTTTAAGCCAAAACCCAT<br>TAAAGGAAAAGCAGAACCAAAGCCTAAAACAGCAAAAGTGG<br>AGAAAGAAGAGGTTGCCCAAACGCTACTGGCAAATGAGAGAG<br>ATATTTCAGAAGCTGTTAAAAAACCACGAGAAGTGCCCTTATT<br>TAGTTTTCTTGAGAAAAAATTGCCCTGTTTTGCTTTCTGAAGCA<br>TGTTTGAAAAAAACGGAGCTGACCTTGCAGGCAGCTCTGCCTG<br>GGGAAGCAAAGGTTCACAAGCACACAGAACATGGGGAAGAG<br>ACCACTGAGGGTACTGCACCGAACAGCTTCTACACTCCTCCCT<br>CAATGCCATTGTGTGGGCAGACAGAGAGAGGAGCAGCACC<br>TTGCAGAGGGGAGTGATCCGCTCCTCAGGGAGCTGCTCAGGCA<br>GCACAGCAGCCACTGGCAGGTGTATGGCTTTGTGAGGGAGTGC<br>CTGGAGCGGGTGATTCCTGCCGAGCTGTGGGGTTCAAGCCATA<br>ACAAATGCCGGTTCTTTAAAAACGTGAAAGCATTCATTTCCAT<br>GGGGAAGTATGCTAAGCTTTCATTGCAGCAGCTGATGTGGAAG<br>ATGAGAGTGAATGACTGCGTATGGCTTCGTCTGGCCAAAGGTA<br>ATCATTCTGTTCCTGCCTATGAACATTGTTACCGTGAAGAAATT<br>TTGGCAAATTCCTATACTGGCTGATGGATTCCTATGTTATCGA<br>GTTGCTCAAATCATTTTTCTATATCACCGAGACCATGTTCCAGA<br>AAAACATGCTTTTCTACTACCGAAAGTTTATCTGGGGCAAGTT<br>ACAGAACATTGGAATTAGAAACCATTTTGCCAAAGTACATCTA |

TABLE 1B-continued

| Gene | Species | NCBI # | DNA Sequence |
|---|---|---|---|
| | | | CGTGCTTTATCTTCAGAGGAGATGGAAGTGATCCATCAAAAAA<br>AGTATTTTCCTATTGCATCAAGGCTCCGGTTCATTCCTAAAATC<br>AATGGTTTAAGACCCGTAGTAAGACTAAGCCGTGTTGTTGAAG<br>GACAGAAACTCAGCAAGGAAAGCAGAGAAAAGAAGATACAG<br>CGCTATAACACTCAGCTAAAAAATCTATTTAGTGTGTTAAATT<br>ATGAACGAACTGTAAACACCAGTATCATTGGCTCTTCAGTATT<br>CGGGAGAGATGATATCTACAGGAAGTGGAAGGAGTTTGTTAC<br>AAAGGTTTTTGAATCAGGTGGTGAAATGCCTCATTTCTACTTTG<br>TGAAGGGTGATGTGTCCAGAGCTTTTGATACTATTCCTCACAA<br>GAAACTTGTGGAAGTGATCTCACAGGTCTTGAAACCTGAGAGC<br>CAAACTGTATATGGAATAAGGTGGTATGCTGTGATTATGATTA<br>CCCCAACTGGAAAAGCCAGGAAGCTCTATAAGAGACACGTTT<br>CTACTTTTGAGGATTTTATTCCAGACATGAAGCAGTTTGTGTCC<br>AAGCTTCAAGAGAGAACTTCATTACGAAATGCAATAGTAGTTG<br>AACAGTGCTTAACTTTTAATGAGAACAGTTCCACCCTGTTTACT<br>TTCTTTCTTCAAATGTTACATAATAACATCCTGGAGATTGGGCA<br>CAGGTACATATACAGTGCTCTGGAATCCCACAGGGCTCCATT<br>TTGTCAACCTTACTTTGCAGCTTATGCTATGGAGACATGGAAA<br>ACAAATTACTTTGTGGAATCCAGAAGGATGGAATCCTAATACG<br>TCTTATTGATGACTTTTTGCTGGTTACACCACATTTAATGCAGG<br>CAAAAACTTTTCTAAGGACTATAGCAGCAGGTATTCCTGAGTA<br>TGGCTTTTTAATAAATGCCAAGAAGACAGTGGTGAATTTTCCT<br>GTTGATGATATTCCGGGATGTTCTAAGTTCAAACAGCTGCCAG<br>ATTGTCGTTTGATCTCATGGTGCGGTTTATTACTGGATATGCAG<br>ACACTTGAGGTTTATTGTGATTACTCCAGTTATGCCTTTACTTC<br>TATCAGATCAAGTCTTTCCTTCAATTCAAGTAGAATAGCTGGA<br>AAAAACATGAAATGCAAATTGACTGCAGTCCTCAAACTGAAA<br>TGCCATCCTTTATTTCTTGACTTAAAGATCAACAGCCTTAAAAC<br>AGTTTTAATTAACATCTACAAGATATTTTTACTTCAGGCTTACA<br>GATTCCATGCCTGTGTTCTTCAGCTTCCATTCAACCAGAAAGTT<br>AGGAATAATCCTTATTTCTTTGTAAGGATCATCTCTGATACTGC<br>TTCATGCTGCTATTTTATCCTGAAAGCTAAAAATCCAGGGGTTT<br>GTTTAGGTTGCAAAGATGCATCTGGCATGTTCCCTTTTGAGGC<br>AGCAGAATGGCTCTGCTACCATGCTTTCATTGTCAAACTGTCC<br>AACCACAAAGTTATTTACAAATGCTTACTTAAGCCCCTTAAAG<br>TCTATAAGATGCATCTGTTTGGGAAGATACCAAGGGATACTAT<br>GGTACTGCTGAAGACAGTGACGGAACCATCTCTTTGTCAAGAT<br>TTCAAAACTATACTGGACTAA (SEQ ID NO: 46) |
| TERT | Duck<br>[Anas<br>platyrhynchos] | XM_013104503.2 | ATGCAGAGGCTGTGTGGGAAAAAGAAGAAGAACATCCTCACG<br>TATGGATACTCCTTGCTGGATGAAAACAGTTCTCACTTCCAAA<br>TCATGCCGCTCTCAAACGTGTACAGCTACCTGCCCAACACCGC<br>AACAGAAACCATGCGTATCAGTGGCCTCTGGGAAACGCTGCTG<br>AGCAGGATAGGGGATGACGTGATGATGTATTTATTGGAACACT<br>GTGCGATCTTTATGCTGGTTCCCCCTAGTAACTGTTACCAAGTC<br>TGTGGGCAACCAATTTATGAACTTATTCGCAAAATGTAGAAT<br>CAGCCCCAGCGTTTGTTAAACAACGGCTTTCAAAGCACAAACG<br>TAGTAGCTTGCTTAAGTATACCCAGAAAAAGGCTAACGTTTCAC<br>AGACAGTATCTTTCAAAGTCACGTCAGTCGAAACGCAGGCAA<br>AGACTTGAAGCTAATGTCTCCAGCGTGAGAAATAAAACCAGC<br>AATAATATACAAAGCCTAGGGTCCGCTGCTCTGGAAAAACAG<br>AGTAGCTCCAATGCAGGTTTGTCAGCTACAGCACCGTCCTTAA<br>AAAGGAAGCTTGCTAGGGAGCAACTGGAAGTCACGGCTAAGA<br>GAGCAAGATTAGAAGAGAAAGAGAGGGAGGAACAGGCATGT<br>AATACTGCTCCTAATGTAAACCAGAGCATTCCCAAGAGGTATG<br>GAACCGGCTGTGTAGCATCACGTTCTGTAAGTCTGACTAAAGA<br>AAAAAACATTTCTCAAAGAAGTAACAGTGATATGCCTCGTCCT<br>TCTTTAGTTCACAATTCTCATCGCGGGAAGAAGTCTGTGGCAG<br>ACAAAAGCTCTTTCCTGCAAGGAGCTGAGAGTAACAGACATTT<br>AAAGCCCAGCATTGAAATGCAAGCAGGATCCAGCAGGAAGGG<br>AGTGGAGACACGCAGGCCTATACCTCGGTTGGATTGGGTACCA<br>ATCGAACCGGCGGAAAGTAGTTCTTCAGGACACAAAAAGCAG<br>GAAGGTCCCTAGCTCATCTGGCAGAGGAGGTACCAAATAGG<br>GTTTTGCCATCTACAATATACATTGACAGGAAGTTTCTGTATTC<br>TCGCAGATACTGGGGGAGCGTTTCCCGAAATCCTTCCTATTG<br>AATCGCCTGAAGGGTAGCCAGGCAGGTGTAAAGCGGCTAATA<br>GAAACGATATTCTTAAGCCAAAATCCGTTTGGGCAAAAGTGCA<br>ACCAAGGTCTGCCACAGAAAAAACGGAGAAAGAAGAAGCTTC<br>CCAAACGCTTCTGGAGAATGAGAAGTATATTTCAACAACTCTT<br>AAAGAATCATGGAAAGTTCCCTTACGTAGCTTTCTTGAGACAA<br>AATTGCCCTCTTCGGATATCTGACACCATTTTGGGAAAAGCCA<br>AGCTGCTCAGTCGGGCACCTTTGCCTGGGCAAGCAGAGGCTCG<br>CAAGCAAGCAGAACAGCTTGGGAAGGAGCCTGCTGAGCGTGT<br>GGCAAGCAGCAGATGTGAATCTGGTCACACCAACGTGCCCAG<br>CAGCGTACGCGTCCTCTCGCAGCATCTGCGTGTGGGGAGCCG<br>GGGGGTGAGGAGCAGATCCCTGCAGAGGCGTCTGATTCAGTC<br>CTCAGGGAGCTTCTCAAGGAGCACTGCAGCCACTTCCAGGTGT<br>ACCTCTTTGTGAGGGAGTGCGTGGAGAGGGTGATCCCCACCGA |

TABLE 1B-continued

| Gene | Species | NCBI # | DNA Sequence |
|---|---|---|---|
| | | | GCTCTGGGGTTCAAACCATAACAAGCGCCGGTTCTTCAAGAAC
GTGAAAGCGTTCATTTCCATGGGGAAGTACGCTAAGCTTTCCT
TGCAGGTGTTGATGTGGAAGATGAGAGTAAATGACTGCATGTG
GCTTCGTCTGGCCAAAGGTAATCACTTTGTTCCTGCCTCTGAAC
ACCTTTACCGTGAAGAAATTTTGGCTAAATTCCTATACTGGCT
GATGGATACGTATGTTGTTCAGTTGCTCAGATCATTTTTCTATG
TCACCGAGACCATGTTCCAGAAAAACATGCTCTTCTACTACCG
AAAGTGTATTTGGGCAAGTTACAGGACATTGGAATTAGAAA
GCATTTTTCCAAAGTGAAGCTACGTCCTTTAACTGCAGAGGAG
ATGGAAGCGATCCATCAAAAAAAATACCTTCCTATGGCGTCAA
AGCTCCGTTTCATTCCCAAAGTCACTGGACTAAGACCCCATCGT
CAGAATGAGCGGTGTTGTTGAAGCACAAACGTTGAGCAAGGA
AAGCAGAGCAAAGAAGGCCGATGTGTCCAGGGCTTTTGATAG
CATTCCTCACAATAAACTTGTGGAAGTGATTTCACAGGTCTTA
AAACCCGAGAAAAAAACTGTCTACTGCATACGGCGCTATGCA
GTGGTTATGATCACTGGAAGTGGAAAAAACCAGGAAGTTATAT
AAGAGACATGTTTCTACTTTCAAGGATTTTATGCCAGACATGA
AGCAGTTTGTGTCCCGGCTTCATGAGAGTACCTCATTGCGAGA
TGCAATAATAGTTGAACAGAGCCTAACTTTCAATGAGACAAGT
GCCAGTCTATTTAATTTTTTTCTTCAAATGCTAAATAATAACAT
CCTGGAAATTGAGCGCAGTTACTACTTACAGTGCTCTGGAATT
CCACAGGGCTCCCTTTTGTCAACCTTGCTTTGCAGCTTGTGCTA
TGGAGACATGGAAAACAAATTATTCAGTGGGGTACAGAAGGA
TGGAGTCCTGATCCGTCTCATTGATGACTTTTTGCTGGTTACAC
CACATTTAATGCATGCAAGAACTTTTCTAAGGACTCTAGCAAT
GGGCATTCCTGAGTATGGCTTTTTGATAAACCCCAAAAAGACA
GTGGTGAATTTTTCTGCTGACGATATCCCAGAATGTTCTGAATT
TAAACAGCTGCCAAACTGTCGTTTGATCCCATGGTGTGGCTTA
TTATTGGATACACAGACACTTGAGGTTTACTGCGATTACTCCA
GCTATTCCTGTACTTCTATCAGATCAAGTCTTTCCTTCAATTCA
AACAGAACAGCTGGGAAAAACATGAAACACAAATTGCTTGCA
GTCCTTAAACTGAAATGCCATGGCTTGTTTCTCGATTTACAGAT
CAATAGCCTTAAAACAGTTTTCATTAACGTCTACAAGATATTTT
TACTTCAGGCTTACAGGTTCCATGCCTGTGTTATTCAACTTCCA
TTCAACCAGAAAGTTAGGAACAATCCTGATTTCTTCCTCAGAG
TCATCGCTGAGAATGCATCGTGCTGCTATTCTATGCTAAAAGC
TAAAAATCCAGGGTTTACTTTAGGTAACAGAGGTGCATCTGGC
ATGTTTCCTTCTGAGGCAGCAGAGTGGCTCTGCTATCATGCCTT
CACTGTCAAACTGTCAAACCACAAAGTTGTTTACAAATGCTTG
CTGAAGCCCCTGAAGTTCTGTATGATGCAGCTATTCCGGAAGA
TCCCAAAGGATACTAAGGCACTACTGAAGACAGTGACAGAAC
CATCTATTTGTAAAGATTTCAAATCTATCCTGGACTGA (SEQ ID
NO: 47) |

TABLE 1C

| Gene | Species | NCBI # | Amino Acid Sequence |
|---|---|---|---|
| IGF2 | Cow [Bos Taurus] | NP_776512.2 | MGITAGKSVLVLLAFLAFASCCYAAYRPSETLCGGELV
DTLQFVCGDRGFYFSRPSSRINRRSRGIVEECCFRSCDL
ALLETYCATPAKSERDVSASTTVLPDDVTAYPVGKFFQ
YDIWKQSTQRLRRGLPAFLRARRGRTLAKELEALREA
KSHRPLIALPTQDPATHGGASSKASSD (SEQ ID NO: 26) |
| IGF1 | Zebrafish [Danio rerio] | NP_571900.1 | MSSGHFFQGHWCDVFKCTMRCLPSTHTLSLVLCVLAL
TPATLEAGPETLCGAELVDTLQFVCGDRGFYFSKPTGY
GPSSRRSHNRGIVDECCFQSCELRRLEMYCAPVKTGKS
PRSLRAQRHTDIPRTPKKPISGHSHSSCKEVHQKNSSRG
NTGGRNYRM (SEQ ID NO: 27) |
| serum albumin 1 | Rainbow trout [Oncorhynchus mykiss] | XP_021470329.1 | MRRPCILAIQPDTEFMPPELDASNFHMGPELCTKDSKEL
LLSGKKLLYGVVRHKTTITEEQLKSISTKYHSMKEKCC
AAEDQAACFTEEAPKLVAESAELVKA (SEQ ID NO: 28) |
| GLUL | Tilapia [Oreochromis niloticus] | NP_001266597.1 | MATSASASLSKAVKQQYMELPQGDKVQAMYIWIDGT
GEGLRCKTRTLDSEPKSIEDLPEWNFDGSSTYQSEGSNS
DMYLIPSAMFRDPFRKDPNKLVLCEVLKYNRKPTETNL
RLTCKKVMDMVADQHPWFGMEQEYTILGTDGHPFGW
PSNGFPGPQGPYYCGVGADKAYGRDVVEAHYKACLY
AGVQICGTNAEVMPAQWEFQVGPCEGIDMGDHLWVA
RFILHRVCEDFGVVASFDPKPIPGNWNGAGCHTNFSTK
EMREDGGLKAIEDSIEKLGKRHSYHIRAYDPKGGLDNA
RRLTGRHETSNINEFSAGVANRGASIRIPRNVGQEKKG
YFEDRRPSANCDPYSVTEALIRTCLLNEEGDEPADY
(SEQ ID NO: 29) |

TABLE 1C-continued

| Gene | Species | NCBI # | Amino Acid Sequence |
|------|---------|--------|---------------------|
| IGF2 | Rainbow trout [Oncorhynchus mykiss] | NP_001118169.1 | METQKRHEYHSVCHTCRRTENTRMKVKMMSSSNRVL VIALALTLYIVEVASAETLCGGELVDALQFVCEDRGFY FSRPTSRSNSRRSQNRGIVEECCFRSCDLNLLEQYCAKP AKSERDVSATSLQIIPMVPTIKQDVPRKHVTVKYSKYE AWQRKAAQRLRRGVPAILRARKFRRQAVKIKAQEQA MFHRPLITLPSKLPPVLPPTDNYVSHN (SEQ ID NO: 30) |
| IGF1 | Tropical clawed frog [Xenopus tropicalis] | XP_002936875.1 | MEKNNSLSTQLFKCYFCDFLKLKMHKMSYIHLLYLAL CFLTLTHSAAAGPETLCGAELVDTLQFVCGDRGFYFSK PTGYGSSNRRSHHRGIVDECCFQSCDFRRLEMYCAPAK PAKSARSVRAQRHTDMPKAQKEVHLKNASRGNTGSR GFRM (SEQ ID NO: 31) |
| GLUL | Tropical clawed frog [Xenopus tropicalis] | XP_004914095.1 | MATSASAQLSKAIKQMYLELPQGDKVQAMYIWVDGT GEGLRCKTRTLDSEPKTIEDLPEWNFDGSSTYQSEGSNS DMYLIPVAMFRDPFRRDPNKLVLCEVLKYNRKTAETN LRHTCNQIMDMMANEHPWFGMEQEYTLLGMDGHPFG WPSNGFPGPQGPYYCGVGADKAYGRDIVEAHYRACL YAGVKIAGTNAEVMPAQWEFQIGPCEGIEMGDHLWIA RFILHRICEDFGIIVSFDPKPITGNWNGAGCHTNFSTKSM REEGGLKDIEESIERLSKRHDYHIRMYDPRGGKDNARR LTGFHETSSIHEFSAGVANRGASIRIPRSVGQEKKGYFE DRRPSANCDPYAVTEAMIRTCLLNETGDEPLEYKN (SEQ ID NO: 32) |
| ALB | Tropical clawed frog [Xenopus tropicalis] | AAH75287.1 | MNALMRRACCGALFPLSFRLAALSPMKGASNFSCGNV CASPAGCWAPPSGHDTGIKVYNSLTRRKDPLILADPTV ATWYSCGPTVYDHAHLGHACSYVRFDIIRRILLKVFGI DTVVVMVVTDIDDKIIKRAKELNISPVALARTYEQDFK QDMTALKVLPPTVYMRVTENIPQIISFIEHIIANGYAYA TSQGNVYFDVQSIGERYGKFNDSFSDTASESASQDKRH IRDFALWKTSKPEEPYWASPWGKGRPGWHIECSTIASS VFGKHLDIHTGGIDLAFPHHENEIAQCEAYHQSTQWGN YFLHTGHLHLKGNEEKMSKSLRNYLTVKEFLKSFSPDQ FRMFCLRSKYKSAVEYSNGSMHDAVNTLHTISSFVDD AKAYMKGQLICQPVQEALLWQRLNETKVNVKAAFSD DFDTPRAVDAVMDLIHHGNRQLKAVSKESNSPRSSVV YGAMISYIEQFLEILGISLSQNQVAAEDRHSAVLFNVVE EMISFRSKVRNYALAADESPNAIGQEEKQQYKERRQL LLEREPLLQACDIMRQHLAVYGINVKDRGNTSTWELL DRKEET (SEQ ID NO: 33) |
| IGF2 | Tropical clawed frog [Xenopus tropicalis] | NP_001107144.1 | MRHLLLLSITFLVYTLDSAKAYGATETLCGGELVDTLQ FVCGDRGFYFSRNNGRSNRRANRGIVEECCFRSCDLEL LETYCAKPAKNERDVSTAPSTAIPPLNKQDLYHKHHHT KSSKYDIWQRKSIHRLRRGVPAIVRARQYRLLMQQAEE SEQALSHRPLTTLPITRPLHLQQTSEPSLN (SEQ ID NO: 34) |
| GLUL | Chicken [Gallus gallus] | NP_990824.1 | MATSASSHLSKAIKHMYMKLPQGEKVQAMYIWIDGTG EHLRCKTRTLDHEPKSLEDLPEWNFDGSSTFQAEGSNS DMYLRPAAMFRDPFRKDPNKLVLCEVFKYNRQSADTN LRHTCRRIMDMVSNQHPWFGMEQEYTLLGTDGHPFG WPSNCFPGPQGPYYCGVGADKAYGRDIVEAHYRACLY AGVKIGGTNAEVMPAQWEFQVGPCEGIEMGDHLWIAR FILHRVCEDFGVIVSFDPKPIPGNWNGAGCHTNFSTKN MREDGGLKHIEEAIEKLSKRHQYHIRAYDPKGGLDNA RRLTGFHETSSIHEFSAGVANRGASIRIPRNVGHEKKGY FEDRGPSANCDPYAVTEALVRTCLLNETGDEPFEYKN (SEQ ID NO: 35) |
| ALB | Chicken [Gallus gallus] | NP_990592.2 | MKWVTLISFIFLFSSATSRNLQRFARDAEHKSEIAHRYN DLKEETFKAVAMITFAQYLQRCSYEGLSKLVKDVVDL AQKCVANEDAPECSKPLPSIILDEICQVEKLRDSYGAM ADCCSKADPERNECFLSFKVSQPDFVQPYQRPASDVIC QEYQDNRVSFLGHFIYSVARRHPFLYAPAILSFAVDFEH ALQSCCKESDVGACLDTKEIVMREKAKGVSVKQQYFC GILKQFGDRVFQARQLIYLSQKYPKAPFSEVSKFVHDSI GVHKECCEGDMVECMDDMARMMSNLCSQQDVFSGKI KDCCEKPIVERSQCIMEAEFDEKPADLPSLVEKYIEDKE VCKSFEAGHDAFMAEFVYEYSRRHPEFSIQLIMRIAKG |

TABLE 1C-continued

| Gene | Species | NCBI # | Amino Acid Sequence |
|---|---|---|---|
| | | | YESLLEKCCKTDNPAECYANAQEQLNQHIKETQDVVK<br>TNCDLLHDHGEADFLKSILIRYTKKMPQVPTDLLLETG<br>KKMTTIGTKCCQLPEDRRMACSEGYLSIVIHDTCRKQE<br>TTPINDNVSQCCSSSYANRRPCFTAMGVDTKYVPPPFN<br>PDMFSFDEKLCSAPAEEREVGQMKLLINLIKRKPQMTE<br>EQIKTIADGFTAMVDKCCKQSDINTCFGEEGANLIVQS<br>RATLGIGA (SEQ ID NO: 36) |
| IGF1 | Chicken [Gallus gallus] | NP_001004384.1 | MEKINSLSTQLVKCCFCDFLKVKMHTVSYIHFFYLGLC<br>LLTLTSSAAAGPETLCGAELVDALQFVCGDRGFYFSKP<br>TGYGSSSRRLHHKGIVDECCFQSCDLRRLEMYCAPIKP<br>PKSARSVRAQRHTDMPKAQKEVHLKNTSRGNTGNRN<br>YRM (SEQ ID NO: 37) |
| IGF2 | Chicken [Gallus gallus] | NP_001025513 | MCAARQILLLLLAFLAYALDSAAAYGTAETLCGGELV<br>DTLQFVCGDRGFYFSRPVGRNNRRINRGIVEECCFRSC<br>DLALLETYCAKSVKSERDLSATSLAGLPALNKESFQKP<br>SHAKYSKYNVWQKKSSQRLQREVPGILRARRYRWQA<br>EGLQAAEEARAMHRPLISLPSQRPPAPRASPEATGPQE<br>(SEQ ID NO: 38) |

Provided herein are expression vectors comprising any one of the sequences selected from Tables 1A and 1B, and cells comprising any one of such expression vectors, for example a cell is from a livestock, poultry, game, or aquatic species.

Exemplary Methods and Compositions

Provided herein are methods of increasing the efficiency of maintaining cells in culture.

In some embodiments, provided herein is a method of decreasing the concentration of ammonia in the culture medium of cells comprising increasing the expression of glutamine synthetase (GS) protein in the cells, wherein the cells are of livestock, poultry, game or aquatic animal species, and wherein the concentration of ammonia in the culture medium is decreased by at least 2.5%.

In some embodiments, provided herein is a method of increasing the production of glutamine in cells comprising increasing the expression of glutamine synthetase (GS) protein in the cells, wherein the cells are of livestock, poultry, game or aquatic animal species, and wherein the concentration of glutamine in the cells is increased by at least 2.5%.

In some embodiments, provided herein is a method of increasing the concentration of Insulin-like growth factor (IGF) in the medium of cells in culture comprising increasing the expression of IGF protein secreted by the cells, wherein the cells are of livestock, poultry, game or aquatic animal species, and wherein the concentration of IGF in the ambient medium, or within the cell, is increased by at least 2.5%.

In some embodiments, provided herein is a method of increasing the concentration of albumin in the medium of cells in culture comprising increasing the expression of albumin in the cells, wherein the cells are of livestock, poultry, game or aquatic animal species, and wherein the concentration of albumin in the ambient medium, or within the cell, is increased by increased by at least 2.5%.

In some embodiments, provided herein are methods for increasing the cell density of a culture comprising metazoan cells comprising introducing any combination of the following cellular modifications: increased expression of GS, increased expression of IGF, increased expression of albumin, increased expression of telomerase reverse transcriptase (TERT), loss-of-function mutations in cyclin-dependent kinase inhibitor (CM) proteins, increased expression of YAP, increased expression of TAZ, increased expression of myogenic transcription factors.

In some embodiments, provided herein is a method for increasing the cell density of a culture comprising metazoan cells, the method comprising (a) introducing into the cells one or more polynucleotide sequences encoding glutamine synthetase (GS), insulin-like growth factor (IGF), and albumin; and (b) culturing the cells in a cultivation infrastructure.

In some embodiments, provided herein is a method for increasing the cell density of a culture comprising metazoan cells, the method comprising (a) introducing into the cells one or more polynucleotide sequences encoding glutamine synthetase (GS), insulin-like growth factor (IGF), albumin or combinations (GS+IGF; GS+albumin; IGF+albumin; GS+IGF+albumin) thereof; and (b) culturing the cells in a cultivation infrastructure.

In some embodiments, provided herein is a method for increasing the cell density of a culture comprising metazoan cells, the method comprising (a) introducing into the cells one or more polynucleotide sequences encoding glutamine synthetase (GS), insulin-like growth factor (IGF), albumin or combinations (GS+IGF; GS+albumin; IGF+albumin; GS+IGF+albumin) thereof; (b) introducing into the cells a polynucleotide sequence encoding a telomerase reverse transcriptase (TERT); and (c) culturing the cells expressing GS, IGF, albumin or combinations thereof and TERT in a cultivation infrastructure.

As provided herein, the density of cells in a culture or cultivation infrastructure is determined by calculating the cell number per unit volume of the cultivation infrastructure, by determining the biomass per unit volume of the cultivation infrastructure, by determining the biomass DNA content per unit volume of the cultivation infrastructure, by determining the biomass RNA content per unit volume of the cultivation infrastructure, by determining the biomass protein content per unit volume of the cultivation infrastructure, or by visual, electronic, metabolic, spectroscopic, or microscopic, measurement of the biomass density.

In some embodiments, an increase in the cell density of a culture using the methods described herein is about 1.025 fold, 1.05 fold, 1.10-fold, 1.15-fold, 1.20-fold, 1.25-fold, 1.30 fold, 1.35-fold, 1.40-fold, 1.45-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold, compared to the density of a culture comprising cells that do not include one or more cellular modifications described herein.

In some embodiments, an increase in the density of cells in a culture using the methods described herein is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, at least 1000%, compared to the cell density of a culture comprising cells that do not include one or more cellular modifications described herein.

In some embodiments, using the methods described herein, there is an increased yield of cellular biomass harvestable per unit volume of the cultivation infrastructure. In some embodiments, the increase is at least about 1.0-fold, 1.25-fold, 1.5-fold, 2-fold, 2.5-fold, 3-fold, 3.5-fold, 4-fold, 4.5-fold, 5-fold, 7.5-fold, 10-fold, 15-fold, 20-fold, 25-fold, 30-fold, 40-fold, or even about 50-fold, 75-fold, 100-fold, 150-fold, or is even about 200-fold compared to the yield of cellular biomass harvestable per unit volume of the cultivation infrastructure in the absence of one or more cellular modifications described herein.

In some embodiments, methods described herein increase the density of cells in a culture by increasing the rate of proliferation of cells in the culture. In some embodiments, the increase in the rate of cell proliferation is at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 250%, at least 300%, at least 350%, at least 400%, at least 450%, at least 500%, at least 550%, at least 600%, at least 650%, at least 700%, at least 750%, at least 800%, at least 850%, at least 900%, at least 950%, or at least 1000%, including values and ranges therebetween, compared to the rate of proliferation of cells that do not include one or more cellular modifications described herein. In some embodiments, the increase in the rate of cell proliferation is about 25-1000%, about 25-750%, about 25-500%, about 50-1000%, about 50-750%, about 50-500%, about 100-1000%, about 100-750%, or about 100-500%, including values and ranges therebetween, compared to the rate of proliferation of cells that do not include one or more cellular modifications described herein.

In some embodiments, methods described herein increase the cell density of a culture by decreasing cell death within the cellular biomass. In some embodiments, the decrease in cell death is at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, including values and ranges therebetween, compared to the rate of cell death in cells that do not include one or more cellular modifications described herein. In some embodiments, a decrease in the rate of cell death within the cellular biomass is about 2.5-10%, about 2.5-75%, about 2.5-50%, about 5.0-100%, about 5.0-75%, about 5.0-50%, about 10-100%, about 10-75%, or about 10-50%, including values and ranges therebetween, compared to the rate of cell death in cells that do not include one or more cellular modifications described herein.

In some embodiments, using the methods described herein, the density of cells in a culture may reach about $10^5$ cells/mL, about $10^6$ cells/mL, about $10^7$ cells/mL, about $10^8$ cells/mL, about $10^9$ cells/mL, or about $10^{10}$ cells/mL (cells in the cellular biomass/mL of cultivation infrastructure), including values and ranges therebetween.

In some embodiments, using the methods described herein, the density of cells in a culture may reach about 1 g/L, 5 g/L, 10 g/L, 25 g/L, 50 g/L, 75 g/L, 100 g/L, 150 g/L, 200 g/L, 250 g/L, 300 g/L, 350 g/L, 400 g/L, 450 g/L, 500 g/L, 550 g/L, 600 g/L, 650 g/L, 700 g/L, 750 g/L, 800 g/L, 850 g/L, 900 g/L, or 1000 g/L (g of cellular biomass/L of cultivation infrastructure), including values and ranges therebetween. In some embodiments, the density of cells in a culture may range from about 1 g/L to about 5 g/L, about 1 g/L to about 750 g/L, about 1 g/L to about 500 g/L, about 1 g/L to about 250 g/L, about 1 g/L to about 100 g/L, about 1 g/L to about 50 g/L, about 5 g/L to about 1000 g/L, about 5 g/L to about 750 g/L, about 5 g/L to about 500 g/L, about 5 g/L to about 250 g/L, about 5 g/L to about 100 g/L, about 5 g/L to about 50 g/L, about 25 g/L to about 1000 g/L, about 25 g/L to about 750 g/L, about 25 g/L to about 500 g/L, about 25 g/L to about 300 g/L, about 25 g/L to about 250 g/L, about 25 g/L to about 100 g/L, about 50 g/L to about 1000 g/L, about 50 g/L to about 750 g/L, about 50 g/L to about 500 g/L, about 50 g/L to about 300 g/L, about 50 g/L to about 250 g/L, about 100 g/L to 1000 g/L, about 100 g/L to about 750 g/L, about 100 g/L to about 500 g/L, about 200 g/L to about 1000 g/L, about 200 g/L to about 750 g/L, about 200 g/L to about 500 g/L, about 300 g/L to about 1000 g/L, about 300 g/L to about 800 g/L, about 400 g/L to about 1000 g/L, or about 500 g/L to about 1000 g/L including values and ranges therebetween.

In some embodiments, provided herein is an in vitro method for producing a cultured edible product (e.g. cultured poultry, cultured livestock, cultured game, cultured fish), the method comprising: (a) introducing one or more polynucleotide sequences encoding glutamine synthetase (GS), insulin-like growth factor (IGF), albumin or combinations (GS+IGF; GS+albumin; IGF+albumin; GS+IGF+albumin) thereof into myogenic metazoan cells; (b) optionally introducing a polynucleotide sequence encoding a telomerase reverse transcriptase (TERT) into the myogenic metazoan cells; (c) inducing myogenic differentiation of the cells, wherein the differentiated cells form myocytes and multinucleated myotubes; and (d) culturing the myocytes and myotubes to generate skeletal muscle fibers, thereby producing a cultured edible product. In one embodiment, myogenic cells are natively myogenic. In another embodiment, myogenic cells are not natively myogenic and are modified to become myogenic cells by expressing one or more myogenic transcription factors.

In some embodiments, provided herein is an in vitro method for producing a cultured edible product, the method comprising: (a) overexpressing GS, IGF, albumin, or a combination thereof in a self-renewing cell line, wherein the cell line is a myogenic transcription factor-modified cell line, and wherein the cell line is of a livestock, poultry, game or aquatic animal species; (b) inducing myogenic differentiation of the cell line, wherein the differentiated cell line forms myocytes and multinucleated myotubes; and (c) culturing the myocytes and myotubes to generate skeletal muscle fibers, thereby producing a cultured edible product.

In some embodiments, provided herein is cultured edible product produced by the in vitro methods.

In the methods for producing a cultured edible product provided herein, myogenic differentiation can be induced in a variety of ways. In some embodiments, cellular biomass with increased cell density can be differentiated into a phenotype of interest by contacting the cells with a differentiation agent. For example, if the phenotype of interest for the expanded cellular biomass is skeletal muscle and the cellular biomass comprises non-myogenic cells (e.g., non-myogenic stem cells or fibroblasts), the expanded cellular biomass can be contacted with a differentiation agent that would induce the skeletal muscle phenotype into the cells of the biomass. Exemplary differentiation agents that may induce skeletal muscle phenotype include myogenic transcription factors such as MYOD1, MYOG, MYF5, MYF6, PAX3, PAX7, paralogs, orthologs, and genetic variants thereof. A PCT publication, WO/2015/066377, discloses exemplary methods for differentiating cells into a skeletal muscle phenotype and is incorporated by reference herein in its entirety. Accordingly, in some embodiments, the expanded cellular biomass may be differentiated into the skeletal muscle phenotype using the methods described in WO/2015/066377.

In some embodiments, cells of the expanded biomass can be differentiated into a phenotype of interest without a differentiation agent. For example, if the phenotype of interest for the expanded biomass is a skeletal muscle and the cellular biomass comprises cells of the skeletal muscle lineage, then these cells may differentiate into the skeletal muscle phenotype on their own without a need for an external differentiation agent. However, in some embodiments, an external differentiation agent such as one or more myogenic transcription factors can be used to differentiate cells of the skeletal muscle lineage into the skeletal muscle phenotype.

Induction of myogenic differentiation in cells overexpressing any one of the cellular modifications described herein would result in the formation of differentiated myocytes and multinucleated myotubes. These myocytes and myotubes are cultured to generate skeletal muscle fibers thereby producing a cultured edible biomass or a cultured edible product.

The cultured edible biomass/product can be processed as a raw, uncooked edible product (cultured meat) or as a cooked edible product or as a cooked/uncooked food ingredient. In some embodiments, processing comprises withdrawal of the culture medium that supports the viability, survival, growth, expansion and differentiation of the cellular biomass. Withdrawal may comprise physical removal of the culture medium or altering the composition of the culture medium, for example, by addition of components that would reduce or prevent further expansion and/or differentiation of the biomass or by depletion of components that support expansion and/or differentiation of the biomass.

In some embodiments, processing comprises exposing the cultured edible biomass to sub-physiological temperatures that would not support the expansion and/or differentiation of the biomass. Sub-physiological temperatures include a temperature of about 15° C. (about 59° F.) or lower, about 10° C. (about 50° F.) or lower, about 0° C. to about 15° C. (about 32° F. to about 59° F.), about 0° C. to −15° C. (about 32° F. to about 5° F.), about −15° C. to about 15° C. (about 5° F. to about 59° F.), about 0° C. to −213° C. (about 32° F. to about −350° F.), about −30° C. to about −100° C. (about −22° F. to about −148° F.), about −50° C. to about −90° C. (about −58° F. to about −130° F.), or about −170° C. to about −190° C. (about −274° F. to about −310° F.). For example, in one embodiment, the expanded and/or differentiated biomass can be cooled to a temperature of about 2° C. to about 8° C. (about 35° F. to about 46.5° F.). In another embodiment, the expanded and/or differentiated biomass can be frozen, for example, by cooling to a temperature of about 32° F. or lower, e.g. about 32° F. to about 0° F., about 32° F. to about −10° F., about 32° F. to about −20° F., about 32° F. to about −30° F., about 32° F. to about −40° F., about 32° F. to about −50° F., about 32° F. to about −60° F., about 32° F. to about −70° F., about 32° F. to about −80° F., and the like. In some embodiments, the expanded and/or differentiated biomass can be exposed to sub-physiological temperatures as low as about −300° F. to about −350° F., such as the liquid nitrogen temperature of about −321° F.

In some embodiments, processing comprises exposing the biomass to superphysiological temperatures that would not support the viability, survival, expansion and/or differentiation of the biomass. In one embodiment, exposing the biomass to superphysiological temperatures comprises fully or partially cooking the biomass, for example, by heating the biomass to a temperature of about 100° F. to about 600° F., about 100° F. to about 550° F., about 100° F. to about 500° F., about 100° F. to about 450° F., about 100° F. to about 400° F., about 100° F. to about 350° F., about 100° F. to about 300° F., about 100° F. to about 250° F., about 100° F. to about 200° F. or about 100° F. to about 150° F.

In some embodiments, provided herein is an edible metazoan biomass product (cultured edible product) comprising cells having any combination of the following cellular modifications: increased expression of GS, increased expression of IGF, increased expression of albumin, increased expression of telomerase reverse transcriptase (TERT), loss-of-function mutations in cyclin-dependent kinase inhibitor (CM) proteins, increased expression of YAP, increased expression of TAZ, increased expression of myogenic transcription factors.

Cultivation Infrastructure

As referred to herein, a cultivation infrastructure refers to the environment in which metazoan cells are cultured, i.e. the environment in which the cellular biomass is cultivated.

A cultivation infrastructure may be a tube, a cylinder, a flask, a petri-dish, a multi-well plate, a dish, a vat, an incubator, a bioreactor, an industrial fermenter and the like. A cultivation infrastructure may be a culture medium in which metazoan cells are cultured.

A cultivation infrastructure can be of any scale, and support any volume of cellular biomass and culturing reagents. In some embodiments, the cultivation infrastructure ranges from about 10 μL to about 100,000 L. In exemplary embodiments, the cultivation infrastructure is about 10 μL, about 100 μL, about 1 mL, about 10 mL, about 100 mL, about 1 L, about 10 L, about 100 L, about 1000 L, about 10,000 L, or even about 100,000 L.

In some embodiments, the cultivation infrastructure comprises a substrate. A cultivation infrastructure may comprise a permeable substrate (e.g. permeable to physiological solutions) or an impermeable substrate (e.g. impermeable to physiological solutions).

In some embodiments, the cultivation infrastructure comprises a primary substrate, which can be a flat, concave, or convex substrate. In some embodiments, the cultivation infrastructure further comprises a secondary substrate, either introduced, or autologous, to direct cellular growth between the substrates, e.g. to direct attachment, proliferation and hypertrophy of cells on a plane perpendicular to the primary substrate.

In some embodiments, the cultivation infrastructure comprises a hydrogel, a liquid cell culture media, or soft agar.

In some embodiments, the cultivation infrastructure does not comprise a substrate to which cells can adhere. In some embodiments, the cultivation infrastructure comprises a suspension culture, e.g. supporting the growth of a self-adhering biomass, or single-cell suspension in a liquid medium.

In some embodiments, the cultivation infrastructure comprises adherent cells (i.e. those cells that adhere to a substrate). In some embodiments, the cultivation infrastructure comprises non-adherent cells (i.e. those cells that do not adhere to a substrate). In some embodiments, the cultivation infrastructure comprises both adherent and non-adherent cells.

Kits and Articles of Manufacture

The present application also provides kits for engineering cells of interest to increase production of glutamine, increase production of IGF, increase production of albumin, and/or decrease the production of ammonia.

In some embodiments, the kits comprise a GS DNA construct, an IGF construct, and/or an albumin construct for transfection. The kits optionally may further comprise tools for immortalization or extending cell self-renewal capacity, activating YAP/TAZ pathways, and myogenic differentiation.

The present application also provides articles of manufacture comprising any one of the compositions or kits described herein.

It is to be understood that the terminology employed herein is used for the purpose of describing particular embodiments only and is not intended to be limiting since the scope of the present invention will be limited only by the appended claims and equivalents thereof. The following examples are for illustrative purposes. These are intended to show certain aspects and embodiments of the present invention but are not intended to limit the invention in any manner.

EXAMPLES

Example 1: The Effects of Ectopic Expression of Glutamine Synthetase (GS) in Primary Duck Fibroblasts and Myoblasts This example describes the effects of ectopic expression of GS on ammonia concentration in ambient media from primary duck fibroblast and myoblast cultures.

Methods

Measurement of Ammonia Concentration

Following the manufacturer's instructions (Sigma-Aldrich #AA0100), the absolute ammonia concentration (in μg/mL) was determined for each time point and treatment group (in biological triplicate). Results were reported as the mean of the treatment group bounded by the 95% confidence interval. Measurements of the ammonia detection assay were performed on a spectrophotometer (Spectramax 250). All statistical analyses and visualizations were performed in Microsoft Excel 2010.

Primary Duck Fibroblast and Myoblast Cultures

A peptide-coated (peptides mimicking extracellular matrix) T-150 flask was prepared for cell seeding by adding 10 mL of an aqueous peptide solution to the T-150 flask and incubated for at least 1 hour at 37° C. The aqueous peptide solution was aspirated from the T-150 flask and the flask washed with PBS. 25 mL of culture medium specific to the targeted cell type was added to the flask and the flask incubated and equilibrated at 37° C. in 5% atmospheric $CO_2$.

Under aseptic conditions the targeted tissue was excised with dissection instruments. Tissue sections were minced into approximately 2 mm×2 mm sections. 150 mg tissue sections were weighed and then transferred to a sterile 50 mL centrifuge tube containing 8 mL of enzymatic cell dissociation solution consisting of 0.17% trypsin and 0.085% collagenase in Hanks Balanced Salt Solution pH 7.4. The centrifuge tube was closed tightly and incubated on ice. Following overnight incubation, the tube was then incubated at 37° C. for 15 minutes. The enzymatic tissue digest was triturated with a sterile 5 mL serological pipet for 1 minute. The cell suspension was passed through a sterile 70 μm strainer into a sterile 50 mL centrifuge tube. 20 mL of cold basal medium was flowed through the strainer. The strainer was discarded and the tube capped. The centrifuge tube was centrifuged at 300×g for 5 minutes. The supernatant was aspirated, and the cell pellet was resuspended in culture medium before transfer to the T-150 flask prepared for seeding. The flask was incubated at 37° C. in 5% atmospheric $CO_2$. The cells were checked daily for growth and contamination. Culture medium was changed every two to three days. After the cultures reached a confluence of 70% to 90%, the cells were dissociated and either cryopreserved or passaged using standard cell culture technique.

Transfection

The primary duck fibroblast and myoblast cultures were routinely sub-cultured under 5% atmospheric $CO_2$ at 37° C. (i.e. incubation conditions) until 80% confluent on gelatin-coated dishes. Cells were dissociated to single cells and counted to determine the number of cells. In a gelatin-coated 12-well tissue culture plate, $5 \times 10^4$ cells were seeded into each well. Growth culture medium was added to each well to a total final volume of 1 ml per well. The cells were incubated overnight at 37° C.

Cells were washed with PBS and transfection media added. 1 μg of plasmid DNA containing the murine GS coding sequence (pcDNA3.1+/C–(K)DYK (SEQ ID NO: 58), Genscript OMu19897D, Table 1A) driven by a CMV promoter was complexed using the Lipofectamine 3000 system (Thermo Fisher Scientific #L3000001). The complexed DNA was added dropwise to each well in biological triplicate. Vehicle control cells received an equivalent treatment absent the DNA. The cells were shaken gently and incubated for 48 hours; the media was then changed to proliferation media supplemented with 10% FBS and either the combination of 434 μg/mL (2 mM) L-alanyl-L-glutamine and 584 μg/mL (4 mM) L-glutamine or no supplemented glutamine (0 mM glutamine, "glutamine absent"). The cells were then returned to incubation conditions.

Conditioned Media Collection

Cells were washed with PBS, and 1 mL of either glutamine-supplemented or glutamine-absent proliferation medium was added to each well. Cells were then returned to incubation.

200 μL media samples were collected from each well and stored in sterile tubes at −80° C. In a gelatin-coated 12-well plate, proliferation medium was incubated in wells devoid of cells (i.e. acellular) in parallel experimental wells containing cells as a background control for ammonia accumulation.

Following each 24-hour period through day seven, 200 μL samples of media were collected from each well stored at −80° C. 200 μL of fresh medium were then added to each of the wells to a total volume of 1 mL. Following sample collection, the plates were then returned to incubation conditions.

Results

As demonstrated in FIG. 1, concentration of ammonia in media spontaneously increased in the absence of cells over the course of seven days. The rate at which ammonia increased differed between the three media conditions shown in the figure. Initial concentration of ammonia was largely dependent on whether or not the media had been supplemented with glutamine.

Figure 2B:
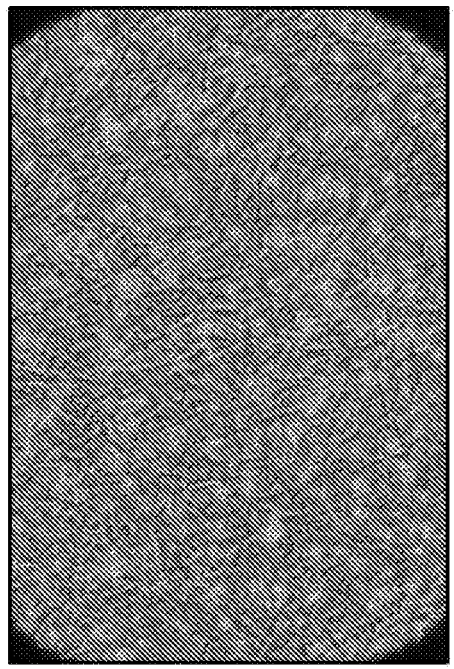
FIGS. 2A-D show morphology of wild type duck fibroblast cells following transfection with a glutamine synthetase (GS) gene.
Figure 2D:
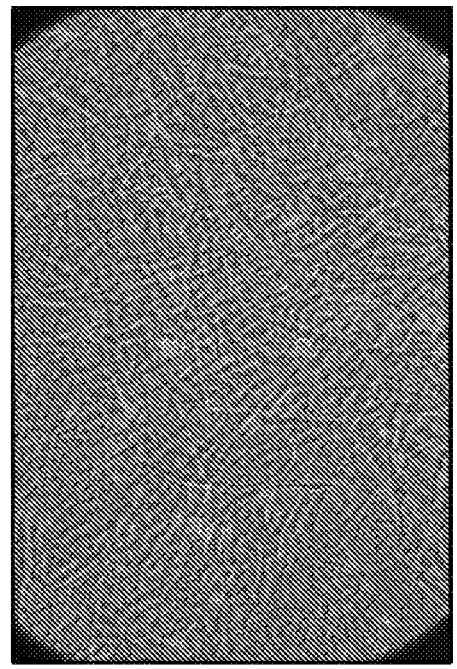
Figure 2A:
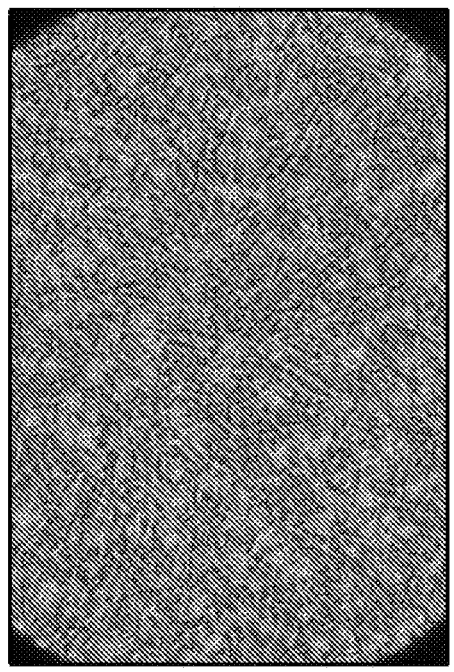
Figure 2C:
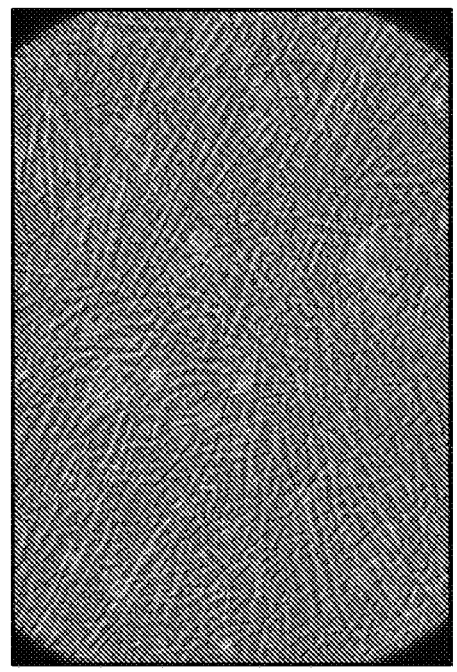

FIG. 2A-D shows that fibroblasts transfected with expression vectors coding for glutamine synthetase exhibited morphology similar to vehicle-only control transfected fibroblasts. Transfected fibroblasts remained viable and stable as evidenced by their continued adherence to substrate following a seven day incubation. FIG. 2A shows fibroblasts transfected with vehicle-only and grown in media with supplemented glutamine; FIG. 2B shows fibroblasts transfected with mouse GS and grown in media with supplemented glutamine; FIG. 2C shows fibroblasts transfected with vehicle-only and grown in media without supplemented glutamine; and FIG. 2D shows fibroblasts transfected with mouse GS and grown in media without supplemented glutamine.

Figure 3:
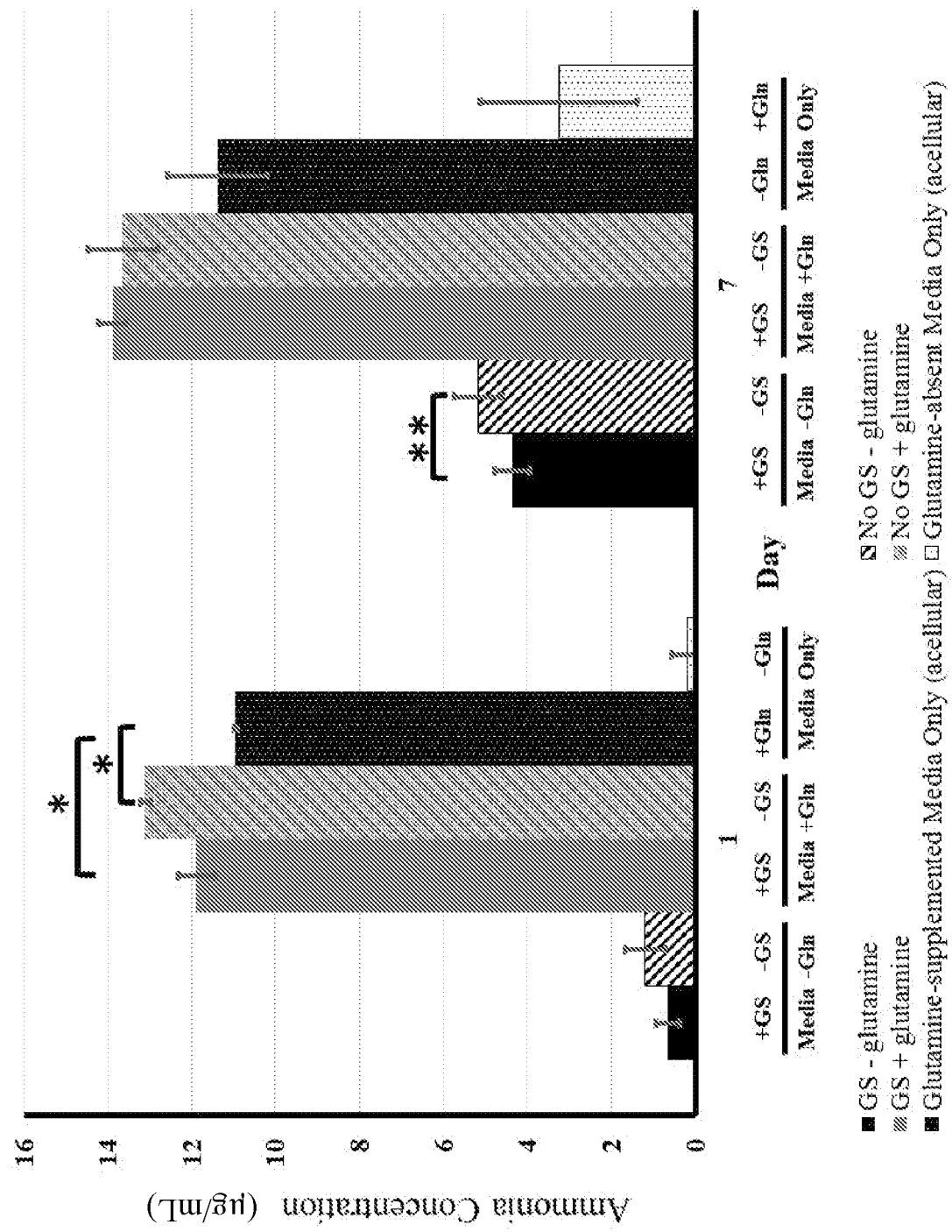
FIG. 3 demonstrates quantification of ammonia levels in media following transfection of wild type duck fibroblast cells with a GS gene.

As demonstrated in FIG. 3, following a one day incubation post transfection, fibroblasts expressing GS and grown in a culture medium supplemented with glutamine showed a smaller increase in extracellular ammonia than cells transfected with vehicle-only and grown in a culture medium supplemented with glutamine compared to a culture medium supplemented with glutamine in which no cells were grown. Within glutamine treatment groups, two-way ANOVA revealed a statistically significant difference ($p<0.001$) between ammonia concentration over time, dependent upon GS transfection and dependent on which day the measurement was made. The glutamine-supplemented culture medium in which no cells were grown showed an increase in ammonia concentration of 0.072 μg/mL/day, and the culture medium not supplemented with glutamine in which no cells were grown showed an increase in ammonia concentration of 0.51 μg/mL/day. It was observed on Day 3 that fibroblasts grown without supplemental ammonia and transfected with GS exhibited a statistically lower ammonia concentration compared to fibroblasts transfected with vehicle-only. Seven days following transfection, there was a significant difference ($p<0.001$, two-way ANOVA) in the amount of ammonia in glutamine absent growth media between cells transfected with GS and cells transfected with vehicle-only. Error bars in FIG. 3 indicate 95% confidence intervals. One asterisk indicates $p<0.05$; two asterisks indicate $p<0.01$.

Figure 4:
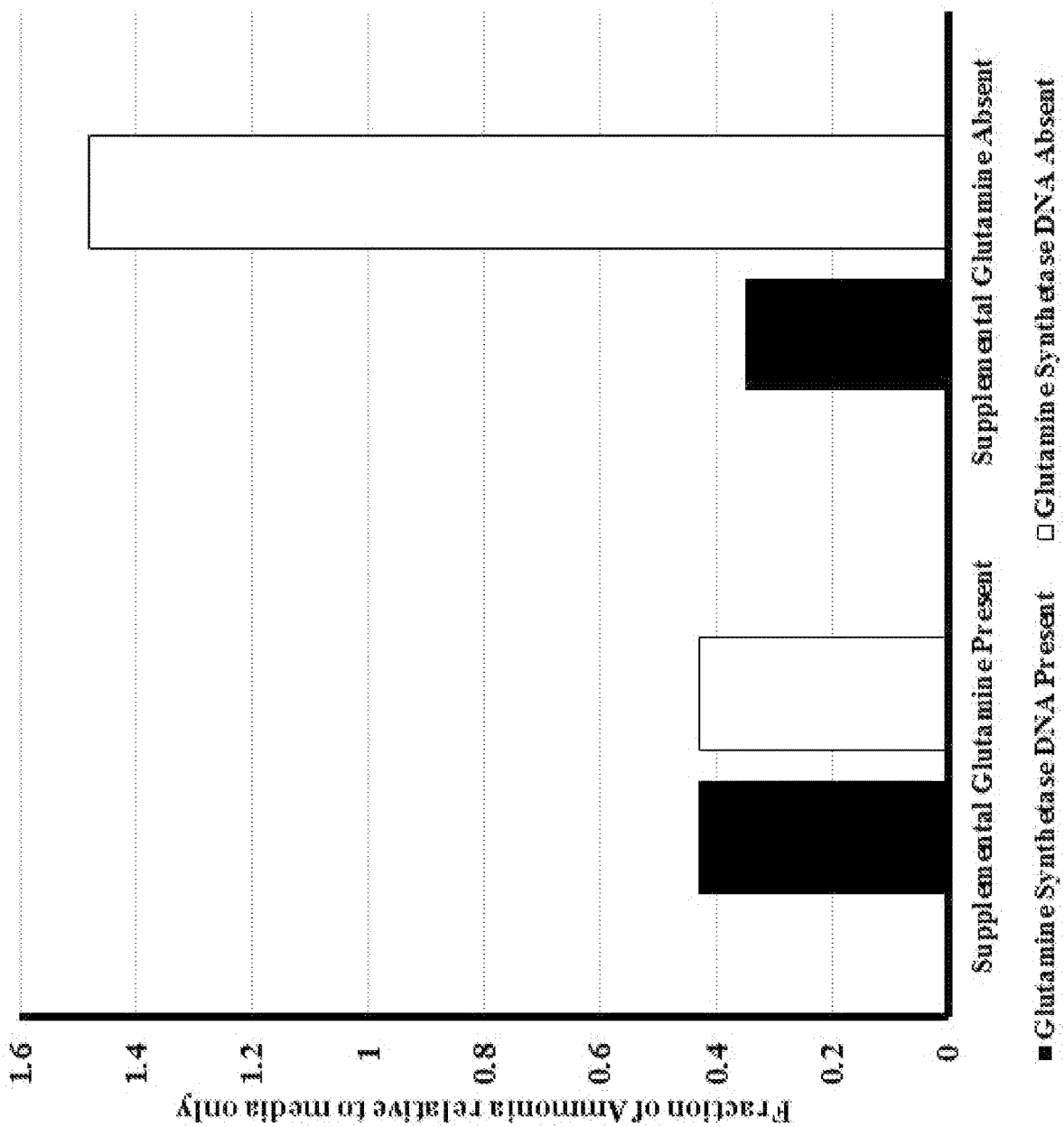
FIG. 4 shows an increase in glutamine in culture media from duck fibroblast cell cultures normalized to culture medium in which no cells were present.
Figure 5B:
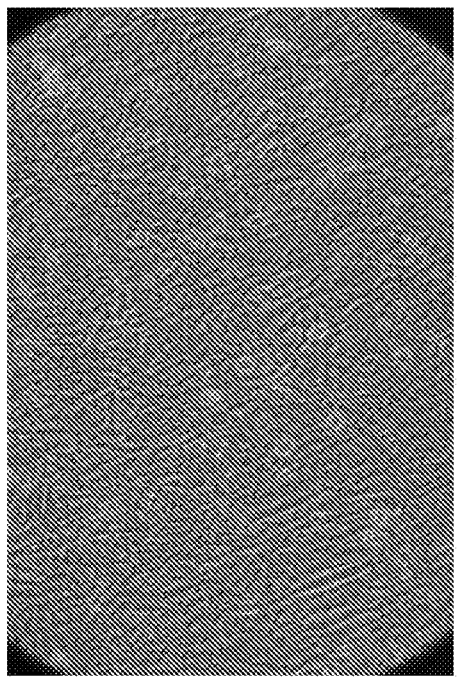
FIGS. 5A-D show morphology of wild-type duck myoblast cells following transfection with GS.
Figure 5D:
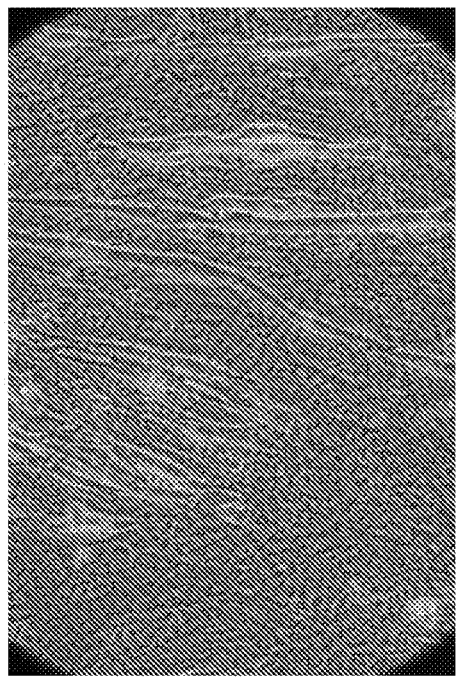
Figure 5A:
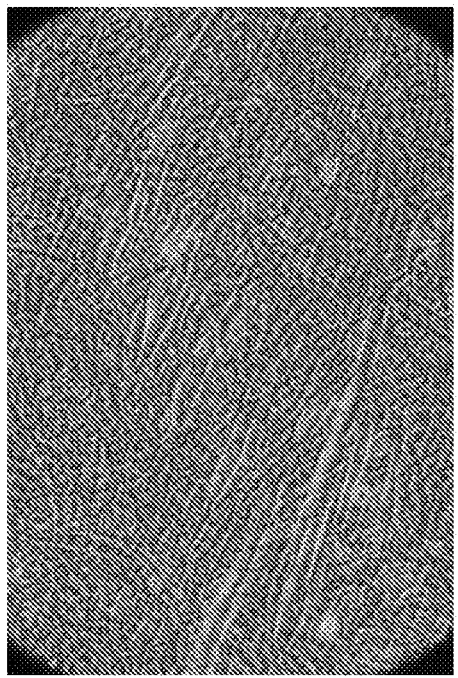
Figure 5C:
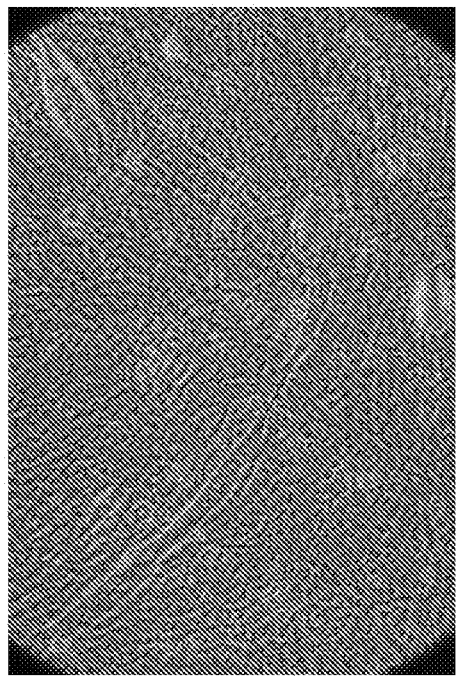

FIG. 4 and Table 2 show normalized data from FIG. 3 to present a percent increase in ammonia relative to the extracellular ammonia concentration. After seven days in media without supplemented glutamine, fibroblasts transfected with GS showed a smaller increase in ammonia than cells transfected with vehicle-only.

TABLE 2

Percent Increase of Ammonia Relative to Media-Only Ammonia Concentration

|  | +Glutamine Media | −Glutamine Media |
|---|---|---|
| Glutamine Synthetase | 43% | 35% |
| Vehicle | 43% | 148% |

As shown in FIG. 5, myoblasts transfected with expression vectors coding for GS exhibited morphology similar to vehicle treated myoblasts. Transfected cells remain viable and capable of normal differentiation as evidenced by spontaneous myotube formation. FIG. 5A shows myoblasts transfected with vehicle and grown in media with supplemented glutamine; FIG. 5B shows myoblasts transfected with a mouse GS gene and grown in a medium with supplemented glutamine; FIG. 5C shows myoblasts transfected with vehicle-only and grown in media without supplemented glutamine; and FIG. 5D shows myoblasts transfected with a mouse GS gene and grown in a medium without supplemented glutamine.

Figure 6:
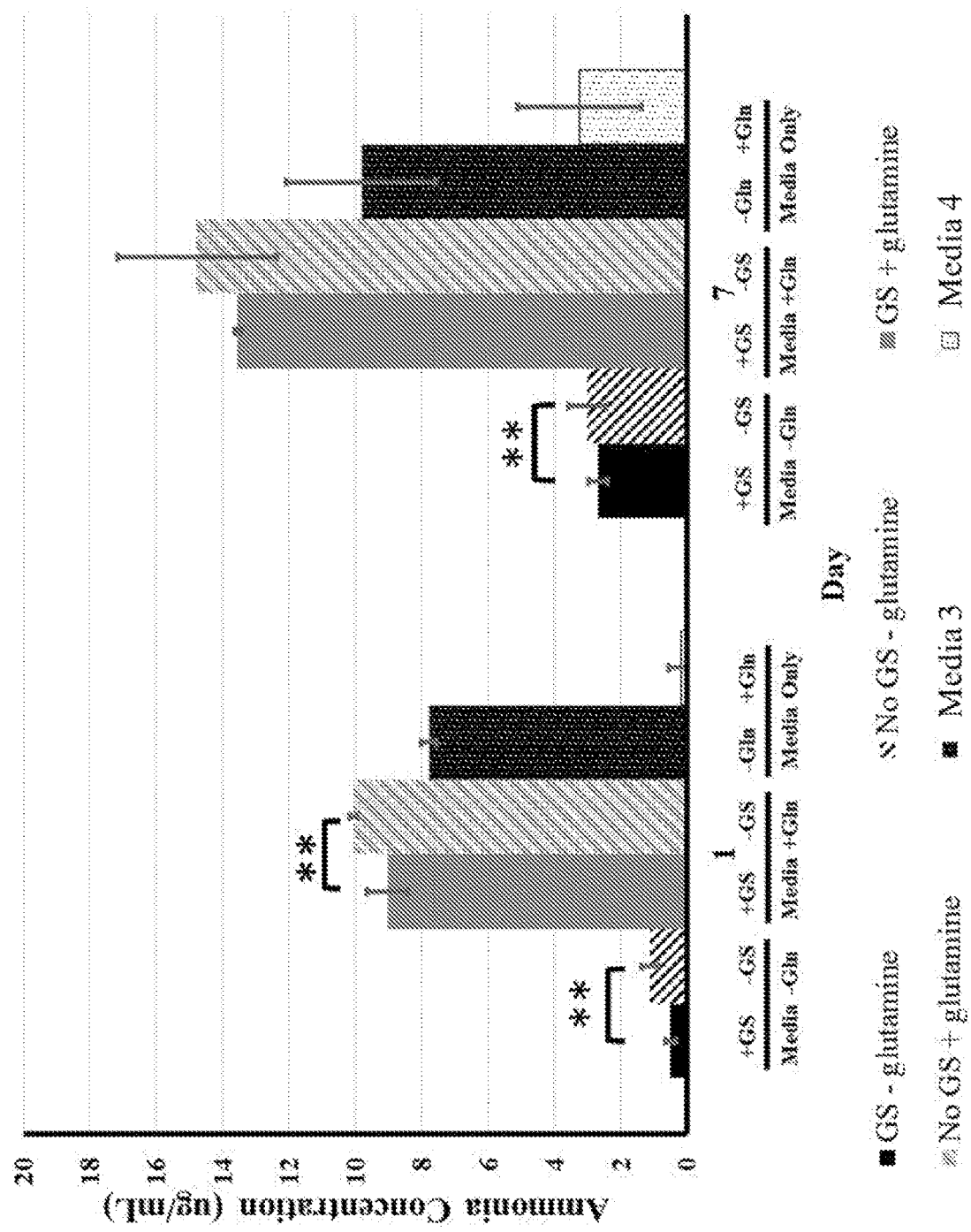
FIG. 6 demonstrates quantification of ammonia levels in media following transfection of wild type duck myoblast cells with a GS gene.
Figure 7:
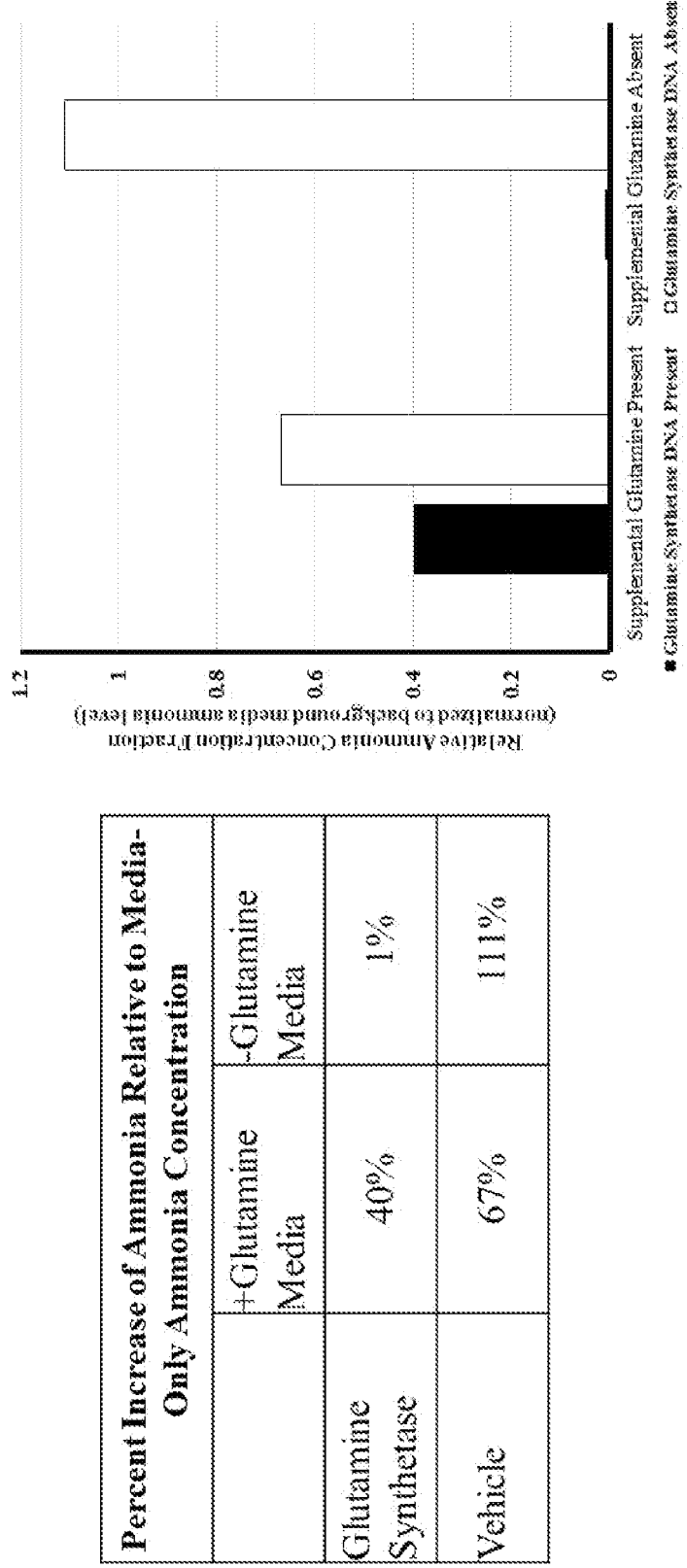
FIG. 7 shows an increase in glutamine in in culture media from myoblast cultures normalized to culture medium in which no cells were present.

As demonstrated in FIG. 6, following a one-day incubation post transfection, myoblasts expressing GS and grown in media not supplemented with glutamine show less increase in ammonia in the media than myoblasts transfected with vehicle and grown in media not supplemented with glutamine compared to acellular control medium supplemented with glutamine. Additionally, following a one-day incubation post transfection, myoblasts expressing GS and grown in media supplemented with glutamine show less increase in ammonia in the media than myoblasts transfected with vehicle and grown in a medium supplemented with glutamine compared to a medium supplemented with glutamine in which no cells were grown. Glutamine-supplemented medium in which no cells were grown showed an increase in ammonia concentration of 0.34 μg/mL/day, and medium in which no cells were grown and not supplemented with glutamine increased by 0.51 μg/mL/day. It was observed on Day 3 that myoblasts grown without supplemental ammonia and transfected with GS exhibited a statistically lower ammonia concentration compared to fibroblasts transfected with vehicle. Seven days following transfection, there is a significant difference in the amount of ammonia in growth media between myoblasts transfected with GS and myoblasts transfected with vehicle. Two-way ANOVA revealed a statistically significant difference ($p<0.001$) between ammonia concentrations over time, dependent upon the presence or absence of glutamine, revealing that the effect of GS was statistically significant ($p<0.001$) only when glutamine was absent. Error bars in FIG. 6 indicate 95% confidence intervals. One asterisk indicates $p<0.05$; two asterisks indicate $p<0.01$. FIG. 7 and Table 3 normalize the data from FIG. 6 to show a percent increase in ammonia relative to the medium-only (medium without cells—control) concentration of ammonia. After seven days in media with or without supplemented glutamine, myoblasts transfected with GS show a smaller increase in ammonia than myoblasts transfected with vehicle.

TABLE 3

Percent Increase of Ammonia Relative to Media-Only Ammonia Concentration

|  | +Glutamine Media | −Glutamine Media |
|---|---|---|
| Glutamine Synthetase | 40% | 1% |
| Vehicle | 67% | 111% |

Figure 8:
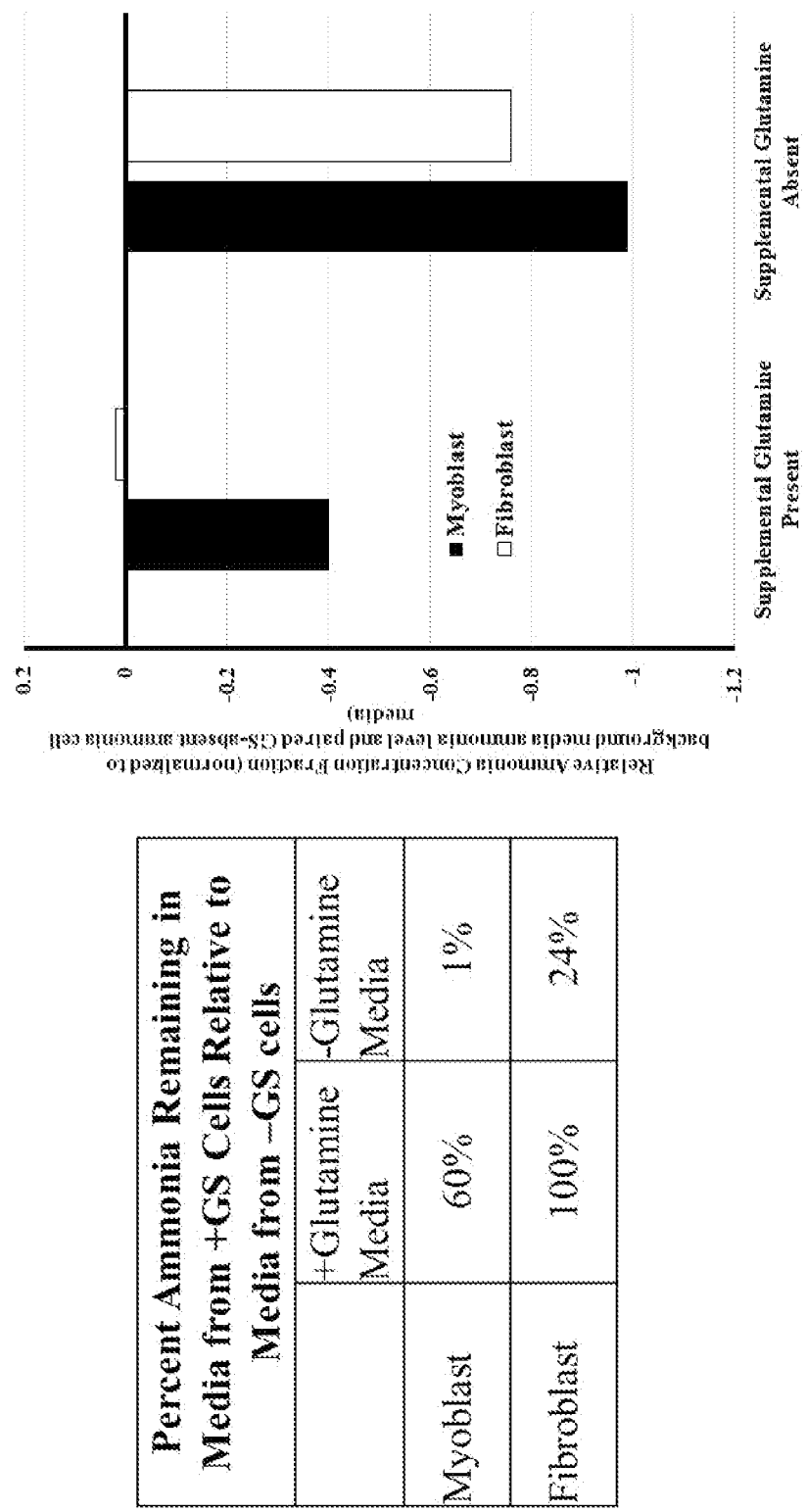
FIG. 8 shows a comparison of normalized ammonia levels between culture media from myoblast cultures and culture media from fibroblast cultures.

FIG. 8 and Table 4 demonstrate that myoblast cultures show a reduction in ammonia in glutamine supplemented medium and an even larger percentage decrease in medium not supplemented with glutamine. Fibroblast cultures do not show a decrease in ammonia in glutamine supplemented media, but do exhibit a decrease in ammonia in media without supplemented glutamine.

TABLE 4

Percent Ammonia Remaining in Media from +GS Cells Relative to Media from −GS cells

|  | +Glutamine Media | −Glutamine Media |
|---|---|---|
| Myoblast | 60% | 1% |
| Fibroblast | 100% | 24% |

In both fibroblasts and myoblasts, transfection of GS resulted in statistically significant reduction of observed ammonia concentration compared to background ammonia generation ($p<0.001$, two-way ANOVA). In both cell types, there was a significant difference between ammonia concentrations in groups that were supplemented with glutamine compared to those that were not supplemented with glutamine ($P<0.001$). There was a statistically significant difference in cells transfected with GS compared to those transfected with vehicle alone when media was not supplemented with glutamine ($p<0.001$). The presence or absence of glutamine in cell culture media exhibits a significantly different effect between treatment groups ($p<0.01$, two-way ANOVA). Regression analysis reveals that the presence or absence of glutamine accounts for 72-98% of the variance of the data ($p<0.001$). Covariance analysis reveals strong positive interactions between systems where glutamine is present (4-12 fold greater than without glutamine), and a moderate interaction when cells are transfected with a GS gene or vehicle-only control, regardless of whether glutamine is present or not.

Figure 9:
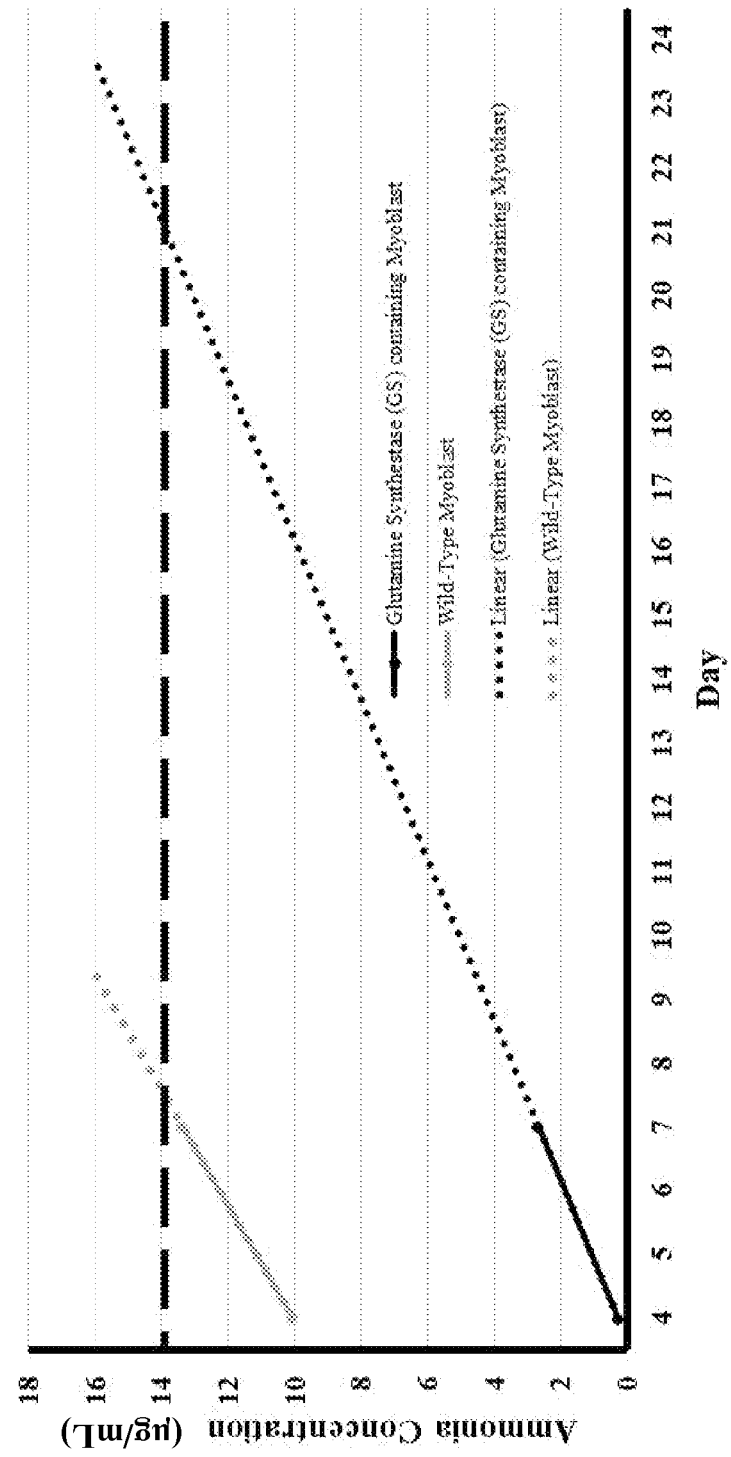
FIG. 9 depicts predicted extension of growth period before media reaches growth-limiting ammonia concentration.

Based on data presented in FIG. 3, FIG. 9 illustrates cells transfected with a GS gene demonstrate a 6.8-fold delay in the time to achieve wild-type, primary cell ammonia concentration (in this instance, 14 µg/mL was observed on average and is indicated by horizontal dashed line). When controlled for the absence of supplemented glutamine, transfection of a GS gene accounts for 31% of this delay. Solid lines depict experimental data while dotted lines are extrapolated values based on a linear fit of the experimental data.

Example 2: The Effects of Ectopic Expression of IGF-1 and Albumin Expression in Primary Duck Fibroblasts and Myoblasts This example describes the effects of ectopic expression of IGF-1 and albumin expression on the concentration of IGF-1 and albumin in media in primary duck fibroblasts and myoblasts.

Primary duck myoblast and fibroblast cells were isolated and cultured as described in Example 1. Cells were washed with PBS and transfection medium was added. 1 µg of plasmid DNA comprising a human serum albumin gene (Genscript OHu18744, Table 1A), a murine serum albumin gene (Genscript OMu21640, Table 1A) or human insulin-like growth factor 1 (IGF-1) (Origene RG212527, Table 1A) gene coding sequence fused to a nucleotide coding sequence encoding a FLAG-tag peptide (DYKDDDDK (SEQ ID NO: 57)) driven by a CMV promoter was complexed using the Lipofectamine 3000 system as a transfection vehicle (Thermo Fisher Scientific #L3000001). For transfection, the complexed DNA was added dropwise to each well in biological triplicate. Vehicle-only control cells received an equivalent treatment absent the DNA. The cell cultures were shaken gently and incubated for 48 hours; the transfection medium was then changed to growth medium and the cells were returned to incubation. Conditioned medium was collected as described in Example 1.

Figure 10B:
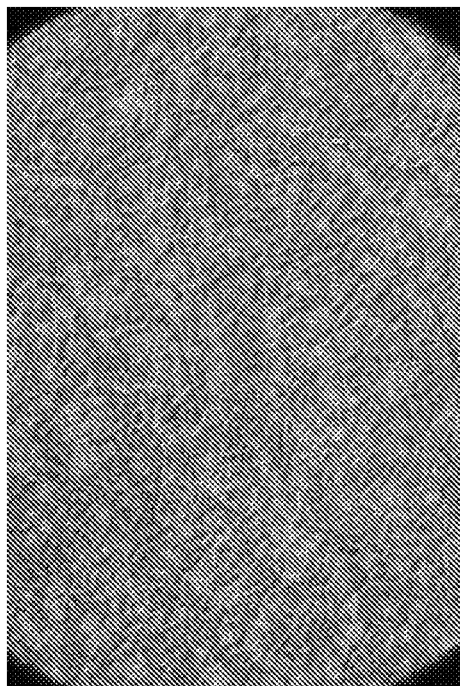
FIGS. 10A-D show morphology of wild type duck fibroblast cells following transfection with IGF-1, mouse albumin, or human albumin genes.
Figure 10D:
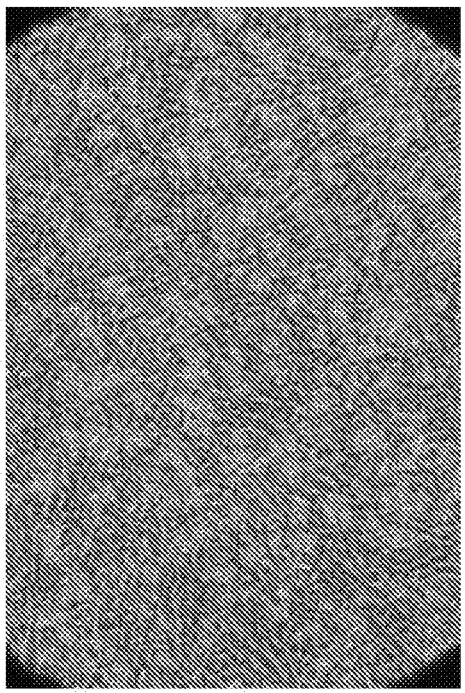
Figure 10A:
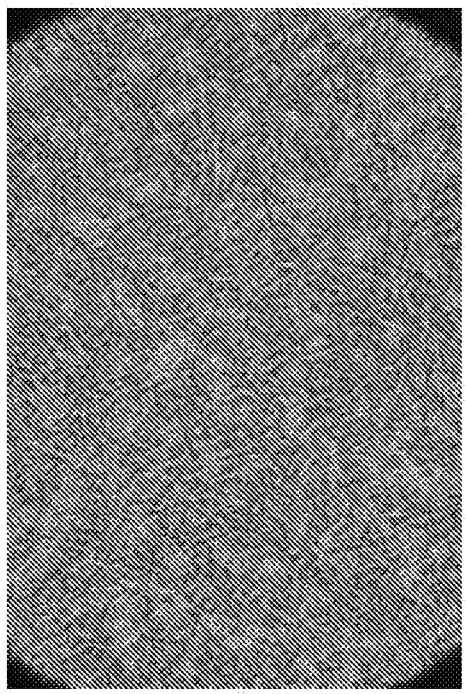
Figure 10C:
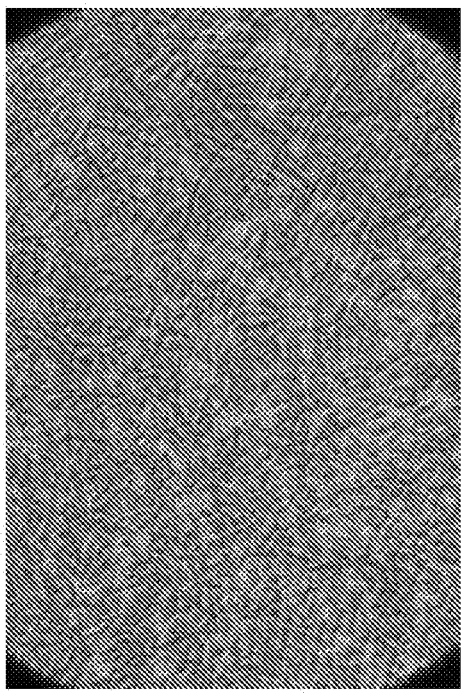

FIG. 10A-D show that fibroblasts transfected with a IGF-1 or albumin gene show morphology similar to cells transfected with vehicle-only (FIG. 10A Fibroblasts transfected with vehicle-only; FIG. 10B Fibroblasts transfected with a human IGF-1 gene; FIG. 10C Fibroblasts transfected with a mouse albumin gene; FIG. 10D Fibroblasts transfected with a human albumin gene).

Figure 11A:
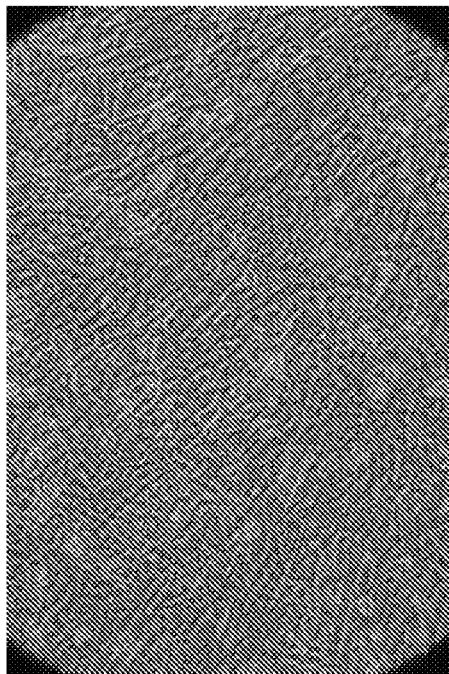
FIGS. 11A-D show morphology of duck myoblasts following transfection with IGF-1, mouse albumin, or human albumin genes.
Figure 11B:
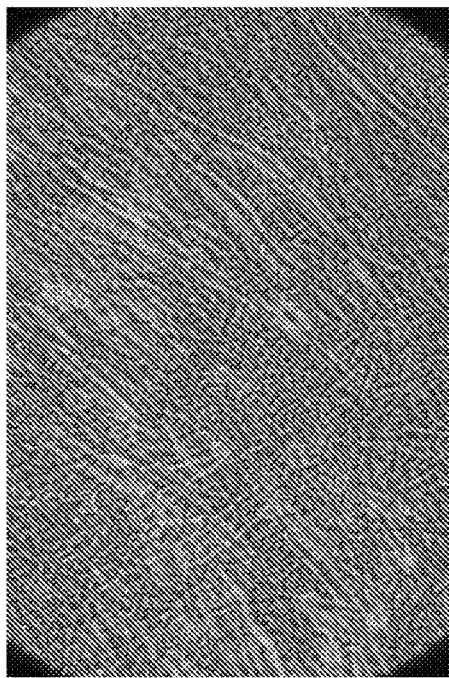
Figure 11C:
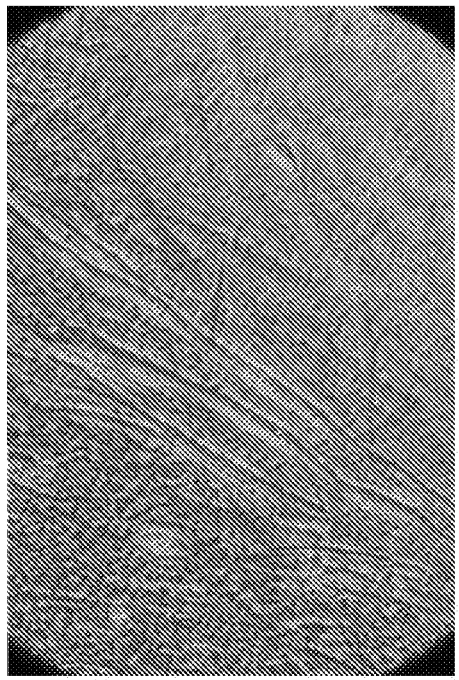
Figure 11D:

FIG. 11A-D show that myoblasts transfected with an IGF-1 or albumin gene show morphology similar to cells transfected with vehicle-only (FIG. 11A Myoblasts transfected with vehicle-only; FIG. 11B Myoblasts transfected with a human IGF-1 gene; FIG. 11C Myoblasts transfected with a mouse albumin gene; FIG. 11D Myoblasts transfected with a human albumin gene).

Figure 12:
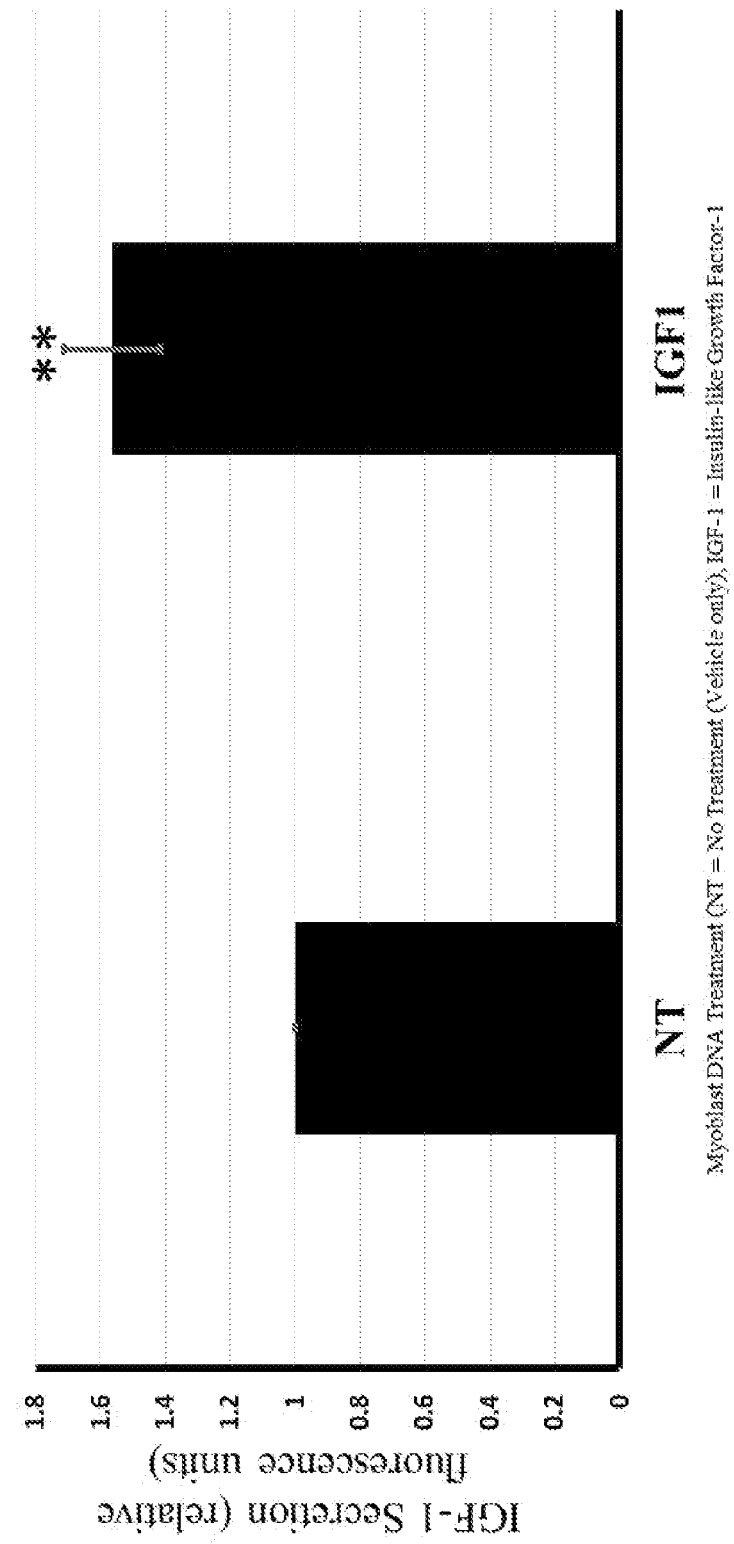
FIG. 12 shows IGF-1 levels secreted in myoblast cell culture media.

Indirect ELISA detection assays were used to measure the secretion of IGF-1 into the ambient medium by the cells. Ambient culture media samples were thawed and maintained on ice until use. Total protein concentration in media samples was determined by absorbance measurement on a spectrophotometer (Spectramax 250) using a BCA serial dilution method (Thermo Fisher Scientific #22325). Using untreated black walled, black-bottomed polystyrene 96-well plates, 1 µg of total protein from each treatment was adsorbed to the plate using 1× coating buffer (Abcam #ab210899). Following coating, the wells were washed and blocked using a 5% solution of non-fat dry milk (NFDM) in 1×PBS. Primary antibody (murine anti-DDK monoclonal, Origene #OTI4C5) was incubated at 1:5000 dilution in 5% NFDM/PBS at 4° C. for 18 hours. Wells were washed with PBS for three cycles of shaking for five minutes per cycle. Secondary antibody (goat anti-mouse-HRP conjugate, Sigma AP130P) was applied at a 1:10000 dilution in 5% NFDM/PBS for 1.5 hours at 22° C. A second PBS wash/shake cycle was applied to remove excess secondary antibody. QuantaRed kit detection was applied as per manufacturer's instructions (Thermo Fisher Scientific #15159). Fluorescence emission values were obtained by a fluorometer (Tecan Infinite F200). Data was analyzed and visualized using Microsoft Excel 2010. Transfection with a plasmid encoding an IGF-1 protein resulted in a statistically significant 53% increase in secretion of IGF-1 into the ambient medium (FIG. 12) compared to vehicle-only transfected cells ($p<0.001$, one-way ANOVA) as measured by ELISA.

Example 3: Edible Metazoan Biomass Manufacturing Methods

The manufacturing of an edible metazoan biomass, in one exemplary protocol, can comprise three steps:

Step 1 is expanding cell populations overexpressing containing a GS gene, an IGF gene, an albumin gene, or a combination thereof in a cell line capable of self-renewal, wherein the cell line is a myogenic transcription factor-modified cell line, and wherein the cell line is of from a livestock, poultry, game or an aquatic animal species. Selected cell populations overexpressing targeted genes are seeded onto a substrate consisting of peptide-coated tissue-culture treated plastic, in a standard growth medium at a density of $7.5\times10^3$ cells/cm² and cultured at 37° C. under 5% $CO_2$ atmospheric conditions. As cultures approach 80% confluence, cells are enzymatically dissociated and the expanded quantity of cells are seeded at $7.5\times10^3$ cells/cm².

This process is repeated until the total number of cells harvested following dissociation exceeds $1.0 \times 10^8$ cells.

Step 2 is cryopreserving and storing the expanded cell populations in a cryopreserved cell bank. Cells harvested in quantities equal to or exceeding $1.0 \times 10^8$ following expansion of selected cells are pelleted by centrifugation for 5 minutes at 300×g. The cell pellet is suspended in a standard cryopreservation medium at $2.5 \times 10^6$ cells/mL and aliquoted at 1.0 mL per cryovial. Cryovials are cooled to −80° C. at −1° C./minute using an insulated container and transferred to a dewar containing liquid nitrogen for long-term storage. As cells stocks are depleted from this bank, remaining vials of cells are expanded and cryopreserved to replenish the cryopreserved cell bank inventory.

Step 3 is seeding and cultivating cells from a master cell bank in an ex vivo milieu: In accordance with the cultivation scale desired, one or more vials from the master cell bank is rapidly thawed to room temperature. The cryopreservation medium is removed from the cells by a 5 minute, 300×g centrifugation step. Cells are suspended in standard growth medium and seeded onto a gelatin-coated cultivation substrate in standard growth medium as before, except that, on the final passage prior to harvest, the cells are permitted to proliferate to 100% confluence on the cell culture substrate. The growth medium is next exchanged for differentiation medium specific to the myogenic transcription factor-modified cell line, and the cultures are permitted to differentiate for up to 6 days inducing myogenic differentiation of the cell line, wherein the differentiated cell line forms myocytes and multinucleated myotubes; and the myocytes and myotubes are cultured to generate skeletal muscle fibers.

The cultivation scale for proliferative biomass is outlined according to Table 5, where the predicted average cell mass is $2.0 \times 10^{-9}$ grams, and the predicted average cell doubling time is 24 hours (h).

TABLE 5

Biomass Production Scale Cultivation Estimates During Cell Proliferation.
Masses are shown in grams. 1 vial is equivalent to $2.5 \times 10^6$ cells.

| # hours | 1 vial | 2 vials | 3 vials | 4 vials | 5 vials | 6 vials | 7 vials | 8 vials | 9 vials | 10 vials |
|---|---|---|---|---|---|---|---|---|---|---|
| 0 h | 0.005 | 0.01 | 0.015 | 0.02 | 0.025 | 0.03 | 0.035 | 0.04 | 0.045 | 0.05 |
| 24 h | 0.01 | 0.02 | 0.03 | 0.04 | 0.05 | 0.06 | 0.07 | 0.08 | 0.09 | 0.1 |
| 48 h | 0.02 | 0.04 | 0.06 | 0.08 | 0.1 | 0.12 | 0.14 | 0.16 | 0.18 | 0.2 |
| 72 h | 0.04 | 0.08 | 0.12 | 0.16 | 0.2 | 0.24 | 0.28 | 0.32 | 0.36 | 0.4 |
| 96 h | 0.08 | 0.16 | 0.24 | 0.32 | 0.4 | 0.48 | 0.56 | 0.64 | 0.72 | 0.8 |
| 120 h | 0.16 | 0.32 | 0.48 | 0.64 | 0.8 | 0.96 | 1.12 | 1.28 | 1.44 | 1.6 |
| 144 h | 0.32 | 0.64 | 0.96 | 1.28 | 1.6 | 1.92 | 2.24 | 2.56 | 2.88 | 3.2 |
| 168 h | 0.64 | 1.28 | 1.92 | 2.56 | 3.2 | 3.84 | 4.48 | 5.12 | 5.76 | 6.4 |
| 192 h | 1.28 | 2.56 | 3.84 | 5.12 | 6.4 | 7.68 | 8.96 | 10.24 | 11.52 | 12.8 |
| 216 h | 2.56 | 5.12 | 7.68 | 10.24 | 12.8 | 15.36 | 17.92 | 20.48 | 23.04 | 25.6 |
| 240 h | 5.12 | 10.24 | 15.36 | 20.48 | 25.6 | 30.72 | 35.84 | 40.96 | 46.08 | 51.2 |
| 264 h | 10.24 | 20.48 | 30.72 | 40.96 | 51.2 | 61.44 | 71.68 | 81.92 | 92.16 | 102.4 |
| 288 h | 20.48 | 40.96 | 61.44 | 81.92 | 102.4 | 122.88 | 143.36 | 163.84 | 184.32 | 204.8 |
| 312 h | 40.96 | 81.92 | 122.88 | 163.84 | 204.8 | 245.76 | 286.72 | 327.68 | 368.64 | 409.6 |
| 336 h | 81.92 | 163.84 | 245.76 | 327.68 | 409.6 | 491.52 | 573.44 | 655.36 | 737.28 | 819.2 |

Step 4 is harvesting cultivated cell biomass for dietary consumption. After the cells have proliferated to confluence, the culture medium is removed, and the adherent cell cultures are rinsed with phosphate buffered saline. Next, the confluent biomass of adherent cells mechanically dissociated from the substrate by means of a scraping device. The dissociated biomass is collected into centrifuge tubes, pelleted at 400×g for 5 minutes to remove excess liquid, and processed for food product preparation. Harvested yield of differentiated cell biomass are estimated by multiplying the projected biomass of the proliferative culture by four to account for biomass accumulation during cell differentiation.

Numbered Embodiments

1. A method for increasing the cell density of a culture comprising metazoan cells, the method comprising:
   a. introducing into the cells one or more polynucleotide sequences encoding glutamine synthetase (GS), insulin-like growth factor (IGF), and albumin; and
   b. culturing the cells in a cultivation infrastructure.
2. A method for increasing the cell density of a culture comprising metazoan cells, the method comprising:
   a. introducing into the cells one or more polynucleotide sequences encoding glutamine synthetase (GS), insulin-like growth factor (IGF), albumin or a combination thereof; and
   b. culturing the cells in a cultivation infrastructure.
3. A method for increasing the cell density of a culture comprising metazoan cells, the method comprising:
   a. introducing into the cells one or more polynucleotide sequences encoding glutamine synthetase (GS), insulin-like growth factor (IGF), albumin or a combination thereof;
   b. introducing into the cells a polynucleotide sequence encoding a telomerase reverse transcriptase (TERT); and
   c. culturing the cells in a cultivation infrastructure.
4. The method of any one of embodiments 1-3, wherein the cells comprise a loss-of-function mutation in one or more genes encoding cyclin-dependent kinase inhibitor (CM) proteins.
5. The method of embodiment 1 or 2, comprising introducing into the cells a polynucleotide sequence encoding a telomerase reverse transcriptase (TERT).
6. The method of embodiment 4, wherein the CM proteins are p15, p16, paralogs, orthologs, or genetic variants thereof
7. The method of any one of embodiments 1-6, wherein the cells are from a self-renewing cell line.
8. The method of embodiment 7, wherein the self-renewing cell line is selected from the group consisting of an embryonic stem cell line, induced pluripotent stem cell line, extraembryonic cell line, and somatic cell line.
9. The method of any one of embodiments 1-8, wherein the cells are modified with a myogenic transcription factor.

10. The method of embodiment 9, wherein the myogenic transcription factor is MYOD1, MYOG, MYF5, MYF6, PAX3, PAX7, paralogs, orthologs, or genetic variants thereof 11. The method of any one of embodiments 1-10, wherein:
    a. the concentration of glutamine in the culture medium is increased to at least 0.001 mM, to at least 0.0025 mM, to at least 0.005 mM, to at least 0.0075 mM, to at least 0.01 mM, to at least 0.025 mM, to at least 0.05 mM, to at least 0.075 mM, to at least 0.1 mM, to at least 0.25 mM, to at least 0.50 mM, to at least 0.75 mM, to at least 1.0 mM, to at least 1.5 mM, to at least 2.0 mM, to at least 3.0 mM, to at least 5.0 mM, to at least 10 mM, or to at least 20 mM;
    b. the concentration of IGF in the culture medium is increased to at least 0.00001 ng/mL, to at least 0.000025 ng/mL, to at least 0.000075 ng/mL, to at least 0.0005 ng/mL, to at least 0.001 ng/mL, to at least 0.0025 ng/mL, to at least 0.005 ng/mL, to at least 0.0075 ng/mL, to at least 0.01 ng/mL, to at least 0.025 ng/mL, to at least 0.05 ng/mL, to at least 0.1 ng/mL, to at least 0.25 ng/mL, to at least 0.5 ng/mL, to at least 1 ng/mL, to at least 2.5 ng/mL, to at least 5 ng/mL, to at least 7.5 ng/mL, to at least 10 ng/mL, to at least 25 ng/mL, to at least 50 ng/mL, to at least 75 ng/mL, to at least 125 ng/mL, to at least 250 ng/mL, to at least 500 ng/mL, to at least 750 ng/mL, to at least 1,000 ng/mL, to at least 1,500 ng/mL, to at least 2,000 ng/mL, to at least 2,500 ng/mL, to at least 3,000 ng/mL, to at least 3,500 ng/mL, to at least 4,000 ng/mL, to at least 4,500 ng/mL, to at least 5,000 ng/mL to at least 6,000 ng/mL, to at least 7,000 ng/mL, to at least 8,000 ng/mL, to at least 9,000 ng/mL, or even by at least 10,000 ng/mL; and/or
    c. the concentration of albumin in the culture medium is increased to at least 0.0001 mg/mL, to at least 0.0002 mg/mL, to at least 0.0004 mg/mL, to at least 0.0005 mg/mL, to at least 0.0006 mg/mL, to at least 0.0007 mg/mL, to at least 0.0008 mg/mL, to at least 0.0009 mg/mL, to at least 0.001 mg/mL, to at least 0.002 mg/mL, to at least 0.003 mg/mL, to at least 0.004 mg/mL, to at least 0.005 mg/mL, to at least 0.006 mg/mL, to at least 0.007 mg/mL, to at least 0.008 mg/mL, to at least 0.009 mg/mL, to at least 0.01 mg/mL, to at least 0.05 mg/mL, to at least 0.075 mg/mL, to at least 0.1 mg/mL, to at least 0.25 mg/mL, to at least 0.5 mg/mL, to at least 0.75 mg/mL, to at least 1 mg/mL, to at least mg/mL, to at least 1.5 mg/mL, to at least 1.5 mg/mL, to at least 1.75 mg/mL, to at least 2 mg/mL, to at least 3 mg/mL, to at least 5 mg/mL, to at least 10 mg/mL, to at least 20 mg/mL, to at least 25 mg/mL, to at least 50 mg/mL, to at least 75 mg/mL, or to at least 100 mg/mL,
    compared to cultures of cells in which the expression of GS, IGF, albumin or a combination thereof is not increased.

12. The method of any one of embodiments 1-11, comprising inhibiting the HIPPO signaling pathway.

13. The method of embodiment 12, wherein inhibiting the HIPPO signaling pathway comprises activating Yes-Associated Protein 1 (YAP1), Transcriptional co-Activator with PDZ-binding motif (TAZ), or a combination thereof in the cells.

14. The method of any one of embodiments 1-13, wherein the cells are the cells of livestock, poultry, game or aquatic animal species.

15. The method of any one of embodiments 1-14, wherein the cells are of a chicken, duck, or turkey.

16. The method of any one of embodiments 1-14, wherein the cells are of a fish.

17. The method of any one of embodiments 1-14, wherein the cells are of a livestock species.

18. The method of embodiment 17, wherein the livestock species is porcine or bovine.

19. The method of any one of embodiments 1-14, wherein the cells are from any animal species intended for human or non-human dietary consumption.

20. The method of any one of embodiments 1-6, wherein the cells are myogenic cells.

21. The method of embodiment 20, wherein the myogenic cells are myoblasts, myocytes, satellite cells, side population cells, muscle derived stem cells, mesenchymal stem cells, myogenic pericytes, or mesoangioblasts.

22. The method of any one of embodiments 1-6, wherein the cells are non-myogenic cells.

23. The method of any one of embodiments 1-6, wherein the cells are non-myogenic cells modified to express one or more myogenic transcription factors.

24. The method of embodiment 23, wherein the myogenic transcription factor is MYOD1, MYOG, MYF5, MYF6, PAX3, PAX7, paralogs, orthologs, or genetic variants thereof 25. The method of any one of embodiments 1-24, wherein the polynucleotide sequence encoding GS comprises a GS gene sequence from Tables 1A and 1B.

26. The method of any one of embodiments 1-24, wherein the polynucleotide sequence encoding IGF comprises an IGF gene sequence from Tables 1A and 1B.

27. The method of any one of embodiments 1-24, wherein the polynucleotide sequence encoding albumin comprises an albumin gene sequence from Tables 1A and 1B.

28. An in vitro method for producing a cultured edible product, the method comprising:
    a. introducing one or more polynucleotide sequences encoding glutamine synthetase (GS), insulin-like growth factor (IGF), albumin or a combinations thereof into myogenic cells;
    b. optionally introducing a polynucleotide sequence encoding a telomerase reverse transcriptase (TERT) into the cells;
    c. inducing myogenic differentiation of the cells expressing GS, IGF, albumin or combinations thereof and optionally TERT, wherein the differentiated cells form myocytes and multinucleated myotubes;
    d. culturing the myocytes and myotubes to generate skeletal muscle fibers, thereby producing a cultured edible product.

29. The method of embodiment 28, wherein the myogenic cells are natively myogenic.

30. The method of embodiment 28, wherein the myogenic cells are not natively myogenic and are modified to express one or more myogenic transcription factors.

31. The method of embodiment 28 or 29, wherein the myogenic cells are myoblasts, myocytes, satellite cells, side population cells, muscle derived stem cells, mesenchymal stem cells, myogenic pericytes, or mesoangioblasts.

32. The method of embodiment 30, wherein the myogenic transcription factor is MYOD1, MYOG, MYF5, MYF6, PAX3, PAX7, paralogs, orthologs, or genetic variants thereof 33. The method of any one of embodiments 28-32, wherein the step of inducing myogenic differentiation comprises activating the expression of one or more myogenic transcription factors.
34. The method of any one of embodiments 28-33, comprising inhibiting the HIPPO signaling pathway.
35. The method of embodiment 34, wherein inhibiting the HIPPO signaling pathway comprises activating Yes-Associated Protein 1 (YAP1) and/or Transcriptional co-Activator with PDZ-binding motif (TAZ) in the cells.
36. The method of any one of embodiments 28-35, wherein the cells comprise a loss-of-function mutation in one or more genes encoding cyclin-dependent kinase inhibitor (CM) proteins.
37. The method of embodiment 36, wherein the CM proteins are p15, p16, paralogs, orthologs, or genetic variants thereof
38. The method of embodiment 30, wherein the myogenic cells are from an embryonic stem cell line, induced pluripotent stem cell line, extraembryonic cell line, or a somatic cell line, modified to express one or more myogenic transcription factors.
39. The method of any one of embodiments 28-38, wherein:
    a. the concentration of glutamine in the culture medium is increased to at least 0.001 mM, to at least 0.0025 mM, to at least 0.005 mM, to at least 0.0075 mM, to at least 0.01 mM, to at least 0.025 mM, to at least 0.05 mM, to at least 0.075 mM, to at least 0.1 mM, to at least 0.25 mM, to at least 0.50 mM, to at least 0.75 mM, to at least 1.0 mM, to at least 1.5 mM, to at least 2.0 mM, to at least 3.0 mM, to at least 5.0 mM, to at least 10 mM, or to at least 20 mM;
    b. the concentration of IGF in the culture medium is increased to at least 0.00001 ng/mL, to at least 0.000025 ng/mL, to at least 0.000075 ng/mL, to at least 0.0005 ng/mL, to at least 0.001 ng/mL, to at least 0.0025 ng/mL, to at least 0.005 ng/mL, to at least 0.0075 ng/mL, to at least 0.01 ng/mL, to at least 0.025 ng/mL, to at least 0.05 ng/mL, to at least 0.1 ng/mL, to at least 0.25 ng/mL, to at least 0.5 ng/mL, to at least 1 ng/mL, to at least 2.5 ng/mL, to at least 5 ng/mL, to at least 7.5 ng/mL, to at least 10 ng/mL, to at least 25 ng/mL, to at least 50 ng/mL, to at least 75 ng/mL, to at least 125 ng/mL, to at least 250 ng/mL, to at least 500 ng/mL, to at least 750 ng/mL, to at least 1,000 ng/mL, to at least 1,500 ng/mL, to at least 2,000 ng/mL, to at least 2,500 ng/mL, to at least 3,000 ng/mL, to at least 3,500 ng/mL, to at least 4,000 ng/mL, to at least 4,500 ng/mL, to at least 5,000 ng/mL to at least 6,000 ng/mL, to at least 7,000 ng/mL, to at least 8,000 ng/mL, to at least 9,000 ng/mL, or even by at least 10,000 ng/mL; and/or
    c. the concentration of albumin in the culture medium is increased to at least 0.0001 mg/mL, to at least 0.0002 mg/mL, to at least 0.0004 mg/mL, to at least 0.0005 mg/mL, to at least 0.0006 mg/mL, to at least 0.0007 mg/mL, to at least 0.0008 mg/mL, to at least 0.0009 mg/mL, to at least 0.001 mg/mL, to at least 0.002 mg/mL, to at least 0.003 mg/mL, to at least 0.004 mg/mL, to at least 0.005 mg/mL, to at least 0.006 mg/mL, to at least 0.007 mg/mL, to at least 0.008 mg/mL, to at least 0.009 mg/mL, to at least 0.01 mg/mL, to at least 0.05 mg/mL, to at least 0.075 mg/mL, to at least 0.1 mg/mL, to at least 0.25 mg/mL, to at least 0.5 mg/mL, to at least 0.75 mg/mL, to at least 1 mg/mL, to at least mg/mL, to at least 1.5 mg/mL, to at least 1.5 mg/mL, to at least 1.75 mg/mL, to at least 2 mg/mL, to at least 3 mg/mL, to at least 5 mg/mL, to at least 10 mg/mL, to at least 20 mg/mL, to at least 25 mg/mL, to at least 50 mg/mL, to at least 75 mg/mL, or to at least 100 mg/mL,
    compared to cultures of cells in which the expression of GS, IGF, albumin or a combination thereof is not increased.
40. The method of any one of embodiments 28-39, wherein the cells are from livestock, poultry, game or aquatic animal species.
41. The method of any one of embodiments 28-40, wherein the cells are from a chicken, duck, or turkey.
42. The method of any one of embodiments 28-40, wherein the cells are from a fish.
43. The method of any one of embodiments 28-40, wherein the cells are from a livestock species.
44. The method of embodiment 43, wherein the livestock species is porcine or bovine.
45. The method of any one of embodiments 28-44, wherein the cells are from any animal species intended for human or non-human dietary consumption.
46. The method of any one of embodiments 28-45, wherein the polynucleotide sequence encoding GS comprises a GS coding sequence from Tables 1A and 1B.
47. The method of any one of embodiments 28-45, wherein the polynucleotide sequence encoding IGF comprises an IGF coding sequence from Tables 1A and 1B.
48. The method of any one of embodiments 28-45, wherein the polynucleotide sequence encoding albumin comprises an albumin coding sequence from Tables 1A and 1B.
49. The method of any one of embodiments 1-48, wherein the cells express the GS protein at levels sufficient to decrease the ammonia production, increase the production of glutamine, or any combination thereof
50. A method of decreasing the concentration of ammonia and/or ammonium hydroxide in the medium of cells in culture comprising increasing the expression of a glutamine synthetase (GS) protein in the cells, wherein the cells are of livestock, poultry, game or aquatic animal species, and wherein the concentration of ammonia (i.e. ammonium hydroxide) in the medium is decreased by at least 2.5%.
51. A method of increasing the production of glutamine in cells comprising increasing the expression of a glutamine synthetase (GS) protein in the cells, wherein the cells are of livestock, poultry, game or aquatic animal species, and wherein the concentration of glutamine in the cells is increased by at least 2.5%.
52. The method of any one of embodiments 50-51, wherein the cells are modified to overexpress a gene encoding the GS protein.
53. The method of any one of embodiments 50-52, wherein the cells overexpress the gene encoding the GS protein at levels sufficient to decrease the ammonia production, increase the production of glutamine, or any combination thereof
54. A method of increasing the concentration of Insulin-like growth factor (IGF) in the medium of cells in culture comprising increasing the expression of an IGF protein in the cells, wherein the cells are of livestock, poultry, game or aquatic animal species, and wherein the concentration of the IGF protein in the medium is increased by at least 2.5% or is increased to at least 0.001 ng/mL.
55. The method of embodiment 54, wherein the cells are modified to overexpress a gene encoding the IGF protein.

56. The method of any one of embodiments 54-55, wherein the cells overexpress the gene encoding the IGF protein at levels sufficient to increase the concentration of IGF in the medium.

57. The method of any one of embodiments 54-56, wherein the IGF protein is an IGF-1 protein.

58. The method of any one of embodiments 54-56, wherein the IGF protein is an IGF-2 protein.

59. A method of increasing the concentration of albumin in the medium of cells in culture comprising increasing the expression of albumin in the cells, wherein the cells are of livestock, poultry, game or aquatic animal species, and wherein the concentration of albumin in the medium is increased at least 2.5% or is increased to at least 0.1 µg/mL.

60. The method of embodiment 59, wherein the cells are modified to overexpress a gene encoding the albumin protein.

61. The method of any one of embodiments 59-60, wherein the cells overexpress the gene encoding the albumin protein at levels sufficient to increase the concentration of albumin in the medium.

62. The method of any one of embodiments 50-61, wherein the cells are a self-renewing cell line.

63. The method of embodiment 62, wherein the self-renewing cell line is selected from the group consisting of an embryonic stem cell line, induced pluripotent stem cell line, extraembryonic cell lines, and somatic cell lines.

64. The method of any one of embodiments 50-63, wherein the cell line is a myogenic transcription factor-modified cell line.

65. The method of embodiment 64, wherein the myogenic transcription factor is MYOD1, MYOG, MYF5, MYF6, PAX3, PAX7, paralogs, orthologs, or genetic variants thereof 66. The method of any one of embodiments 50-65, wherein the renewal capacity of the cells is extended.

67. The method of any one of embodiments 50-65, further comprising activating Telomerase reverse transcriptase (TERT) in the cells.

68. The method of any one of embodiments 50-67, wherein the cells comprise a loss-of-function mutation in one or more genes encoding cyclin-dependent kinase inhibitor (CM) proteins.

69. The method of embodiment 68, wherein the CM proteins are p15, p16, paralogs, orthologs, or genetic variants thereof 70. The method of any one of embodiments 50-67, comprising inhibiting the HIPPO signaling pathway in the cells.

71. The method of embodiment 70, wherein inhibiting the HIPPO signaling pathway comprises activating Yes-Associated Protein 1 (YAP1), Transcriptional co-Activator with PDZ-binding motif (TAZ), or a combination thereof in the cells.

72. The method of any one of embodiments 50-71, wherein the cell line is of a game species.

73. The method of any one of embodiments 50-71, wherein the cell line is of a poultry species.

74. The method of embodiment 73, wherein the poultry species is a duck.

75. The method of any one of embodiments 50-71, wherein the cell line is of an aquatic species.

76. The method of any one of embodiments 50-71, wherein the cell line is of a livestock species.

77. The method of embodiment 76, wherein the livestock species is porcine or bovine.

78. The method of any one of embodiments 50-71, wherein the cell line is from any animal species intended for human or non-human dietary consumption.

79. An in vitro method for producing a cultured edible product, the method comprising:
   a. overexpressing a GS, IGF, albumin protein, or a combination thereof in a self-renewing cell line, wherein the cell line is a myogenic transcription factor-modified cell line, and wherein the cell line is of a livestock, poultry, game or aquatic animal species;
   b. inducing myogenic differentiation of the cell line, wherein the differentiated cell line forms myocytes and multinucleated myotubes; and
   c. culturing the myocytes and myotubes to generate skeletal muscle fibers, thereby producing a cultured edible product.

80. The method of embodiment 79, wherein the cell line is modified to overexpress a gene encoding the GS protein.

81. The method of embodiment 80, wherein the cell line is engineered to overexpress the gene encoding the GS protein at levels sufficient to decrease the ammonia production, increase the production of glutamine, or any combination thereof 82. The method of embodiment 79, wherein the cell line is modified to overexpress a gene encoding the IGF protein.

83. The method of embodiment 82, wherein the cells overexpress the gene encoding the IGF protein at levels sufficient to increase the production of IGF by the cells.

84. The method of any one of embodiments 79-83, wherein the IGF protein is an IGF-1 protein.

85. The method of any one of embodiments 79-83, wherein the IGF protein is an IGF-2 protein 86. The method of embodiment 79, wherein the cell line is modified to overexpress a gene encoding the albumin protein.

87. The method of embodiment 86, wherein the cells overexpress the gene encoding the albumin protein at levels sufficient to increase the concentration of albumin in cells.

88. The method of any one of embodiments 79-87, wherein the self-renewing cell line is selected from the group consisting of embryonic stem cells, induced pluripotent stem cells, extraembryonic cell lines, and somatic cell lines.

89. The method of any one of embodiments 79-88, wherein the myogenic transcription factor is the MYOD1, MYOG, MYF5, MYF6, PAX3, PAX7, paralogs, orthologs, or genetic variants thereof 90. The method of any one of embodiments 79-89, wherein the renewal capacity of the cells is extended.

91. The method of any one of embodiments 79-89, further comprising activating Telomerase reverse transcriptase (TERT) in the cells.

92. The method of any one of embodiments 79-91, wherein the cells comprise a loss-of-function mutation in one or more genes encoding cyclin-dependent kinase inhibitor (CM) proteins.

93. The method of embodiment 92, wherein the CM proteins are p15, p16, paralogs, orthologs, or genetic variants thereof 94. The method of any one of embodiment 79-93, comprising inhibiting the HIPPO signaling pathway in the cells.

95. The method of embodiment 94, wherein the inhibition of the HIPPO signaling pathway comprises activating Yes-Associated Protein 1 (YAP1) and/or Transcriptional co-Activator with PDZ-binding motif (TAZ) in the cells.

96. The method of any one of embodiments 79-95, wherein the cell line is of a game species.

97. The method of any one of embodiments 79-95, wherein the cell line is of a poultry species.
98. The method of embodiment 97, wherein the poultry species is a duck.
99. The method of any one of embodiment 79-95, wherein the cell line is of an aquatic species.
100. The method of any one of embodiments 79-95, wherein the cell line is of a livestock species.
101. The method of embodiment 100, wherein the livestock species is porcine or bovine.
102. The method of any one of embodiments 79-95, wherein the cell line is from any animal species intended for human or non-human dietary consumption.
103. A cultured edible product produced by the in vitro method of any one of embodiments 28-49 and 79-102.
104. A cultured edible product comprising cells having increased expression of GS, increased expression of IGF, increased expression of albumin, and/or increased expression of TERT.
105. A construct comprising any one of the sequences selected from Table 1B.
106. An expression vector comprising any one of the sequences selected from Table 1B.
107. A cell comprising the expression vector of embodiment 106.
108. The cell of embodiment 107, wherein the cell is from a livestock, poultry, game, or aquatic species.
109. A method for increasing the secretion of glutamine by cells into a culture medium, the method comprising increasing the expression of a glutamine synthetase (GS) protein in the cells, wherein the cells are from livestock, poultry, game or aquatic animal species, and wherein the concentration of glutamine secreted into the culture medium is increased by at least 2.5%.
110. The method of embodiment 109, wherein the cells are modified to overexpress a gene encoding the GS protein.
111. The method of embodiment 109 or 110, comprising introducing into the cells a polynucleotide comprising a GS coding sequence from Table 1B.
112. The method of any one of embodiments 109-111, wherein the secretion of glutamine by cells into the culture medium is increased by at least 2.5% compared to cells in which the expression of GS is not increased.
113. A method for increasing the rate of proliferation of cells in a cultivation infrastructure, comprising:
    a. introducing into the cells one or more polynucleotide sequences encoding glutamine synthetase (GS), insulin-like growth factor (IGF), albumin or a combination thereof; and
    b. culturing the cells in a cultivation infrastructure, wherein the cells are from livestock, poultry, game or aquatic animal species.
114. The method of embodiment 113, wherein the polynucleotide sequence encoding GS comprises a GS coding sequence from Tables 1A and 1B.
115. The method of embodiment 113, wherein the polynucleotide sequence encoding IGF comprises an IGF coding sequence from Tables 1A and 1B.
116. The method of embodiment 113, wherein the polynucleotide sequence encoding albumin comprises an albumin coding sequence from Tables 1A and 1B.
117. The method of any one of embodiments 113-116, wherein the rate of proliferation of cells is increased by at least 5% compared to cells in which the expression of GS, IGF, albumin, or a combination thereof is not increased.
118. A method for decreasing death of cells in a cultivation infrastructure, comprising:
    a. introducing into the cells one or more polynucleotide sequences encoding glutamine synthetase (GS), insulin-like growth factor (IGF), albumin or a combination thereof; and
    b. culturing the cells in a cultivation infrastructure, wherein the cells are from livestock, poultry, game or aquatic animal species.
119. The method of embodiment 118, wherein the polynucleotide sequence encoding GS comprises a GS coding sequence from Tables 1A and 1B.
120. The method of embodiment 118, wherein the polynucleotide sequence encoding IGF comprises an IGF coding sequence from Tables 1A and 1B.
121. The method of embodiment 118, wherein the polynucleotide sequence encoding albumin comprises an albumin coding sequence from Tables 1A and 1B.
122. The method of any one of embodiment 118-121, wherein the cell death is decreased by at least 10% compared to cells in which the expression of GS, IGF, albumin, or a combination thereof is not increased.
123. A method for increasing protein production in cells in a cultivation infrastructure, comprising:
    a. introducing into the cells a polynucleotide sequence encoding insulin-like growth factor (IGF); and
    b. culturing the cells in a cultivation infrastructure, wherein the cells are from livestock, poultry, game or aquatic animal species.
124. The method of embodiment 123, wherein the polynucleotide sequence encoding IGF comprises an IGF coding sequence from Tables 1A and 1B.
125. The method of embodiment 123 or 124, wherein the IGF is IGF-1 or IGF-2.
126. The method of any one of embodiment 123-125, wherein the protein production measured as total cell protein per cell nucleus is increased by at least 5% compared to cells in which the expression of IGF is not increased.
127. The method of any one of embodiments 3, 28, 67, and 91, wherein the polynucleotide encoding TERT comprises a TERT coding sequence from Table 1B.

The invention claimed is:

1. A method for increasing the cell density of a culture comprising metazoan cells having myogenic or fibroblastic capacity, the method comprising:
   a) introducing into the cells one or more polynucleotide sequences encoding glutamine synthetase (GS), insulin-like growth factor (IGF), albumin or a combination thereof,
   b) introducing into the cells a polynucleotide sequence encoding a telomerase reverse transcriptase (TERT), and
   c) culturing the cells in a cultivation infrastructure.

2. The method of claim 1, wherein the cells comprise a loss-of-function mutation in one or more genes encoding cyclin-dependent kinase inhibitor (CKI) proteins.

3. The method of claim 2, wherein the CKI proteins are p15, p16, paralogs, orthologs, or genetic variants thereof.

4. The method of claim 1, wherein the cells are from a self-renewing cell line.

5. The method of claim 1, wherein the cells are further modified to express a myogenic transcription factor.

6. The method of claim 1, wherein:
   a) when the polynucleotide encoding GS is introduced into the cells, the concentration of glutamine in the culture medium is increased when compared to cultures of cells in which the polynucleotide encoding GS is not introduced into the cells;
   b) when the polynucleotide encoding IGF is introduced into the cells, the concentration of IGF in the culture medium is increased when compared to cultures of cells in which the polynucleotide encoding IGF is not introduced into the cells; and/or
   c) when the polynucleotide encoding albumin is introduced into the cells, the concentration of albumin in the culture medium is increased when compared to cultures of cells in which the polynucleotide encoding albumin is not introduced into the cells.

7. The method of claim 1, wherein the cells are further modified to inhibit the HIPPO signaling pathway.

8. The method of claim 7, wherein inhibiting the HIPPO signaling pathway comprises activating Yes-Associated Protein 1 (YAP1), Transcriptional co-Activator with PDZ-binding motif (TAZ), or a combination thereof in the cells.

9. The method of claim 1, wherein the cells are from a livestock, poultry, game or aquatic animal species.

10. The method of claim 1, wherein the cells are from a chicken, duck, or turkey.

11. The method of claim 1, wherein the cells are from a fish.

12. The method of claim 1, wherein the cells are from a livestock species.

13. The method of claim 12, wherein the livestock species is porcine or bovine.

14. The method of claim 1, wherein the cells are from any animal species intended for human or non-human dietary consumption.

15. The method of claim 1, wherein the cells are myogenic cells.

16. The method of claim 1, wherein the cells are non-myogenic cells modified to become myogenic cells through expression of one or more myogenic transcription factors.

17. The method of claim 1, wherein the polynucleotide sequence encoding GS comprises a GS coding sequence selected from SEQ ID NOs: 18, 21, and 24, wherein the polynucleotide sequence encoding IGF comprises an IGF coding sequence selected from SEQ ID NOs: 1-6, 15, 16, 19, 20, 23 and 25, or wherein the polynucleotide sequence encoding albumin comprises an albumin coding sequence selected from SEQ ID NOs: 7-11, 17, and 22.

18. The method of claim 1, wherein the cells further have the capacity for skeletal muscle tissue specification.

\* \* \* \* \*